United States Patent
Seymour et al.

(10) Patent No.: US 12,203,094 B2
(45) Date of Patent: Jan. 21, 2025

(54) ADENO-ASSOCIATED VIRUS COMPOSITIONS FOR RESTORING PAH GENE FUNCTION AND METHODS OF USE THEREOF

(71) Applicant: HOMOLOGY MEDICINES, INC., Bedford, MA (US)

(72) Inventors: Albert Barnes Seymour, Westborough, MA (US); Seemin Seher Ahmed, Worcester, MA (US); Jason Boke Wright, Concord, MA (US); Serena Nicole Dollive, Waltham, MA (US); James Anthony McSwiggen, Arlington, MA (US); Jaime Michelle Prout, Hudson, NH (US); Danielle Lauren Sookiasian, Quincy, MA (US)

(73) Assignee: Homology Medicines, Inc., Bedford, MA (US)

( * ) Notice: Subject to any disclaimer, the term of this patent is extended or adjusted under 35 U.S.C. 154(b) by 1130 days.

(21) Appl. No.: 17/073,862

(22) Filed: Oct. 19, 2020

(65) Prior Publication Data

US 2021/0130794 A1 May 6, 2021

Related U.S. Application Data

(63) Continuation of application No. PCT/US2019/016354, filed on Feb. 1, 2019.

(60) Provisional application No. 62/672,377, filed on May 16, 2018, provisional application No. 62/625,149, filed on Feb. 1, 2018.

(51) Int. Cl.
   *C12N 7/00* (2006.01)
   *A61K 35/761* (2015.01)
   *C12N 15/90* (2006.01)

(52) U.S. Cl.
   CPC .......... *C12N 15/907* (2013.01); *A61K 35/761* (2013.01); *C12N 7/00* (2013.01); *C12N 2710/10033* (2013.01); *C12N 2710/10052* (2013.01); *C12N 2750/14121* (2013.01); *C12N 2750/14143* (2013.01)

(58) Field of Classification Search
   None
   See application file for complete search history.

(56) References Cited

U.S. PATENT DOCUMENTS

| | | |
|---|---|---|
| 5,252,479 A | 10/1993 | Srivastava |
| 5,474,935 A | 12/1995 | Chatterjee et al. |
| 5,589,377 A | 12/1996 | Lebkowski et al. |
| 5,622,856 A | 4/1997 | Natsoulis |
| 5,650,309 A | 7/1997 | Wong-Staal et al. |
| 5,753,500 A | 5/1998 | Shenk et al. |
| 5,780,447 A | 7/1998 | Nienhuis |
| 5,895,759 A | 4/1999 | Strauss et al. |
| 6,025,195 A | 2/2000 | Sandig et al. |
| 6,153,436 A | 11/2000 | Hermonat et al. |
| 6,156,303 A | 12/2000 | Russell et al. |
| 6,180,613 B1 | 1/2001 | Kaplitt et al. |
| 6,238,914 B1 | 5/2001 | Boyce |
| 6,268,212 B1 | 7/2001 | Simonet |
| 6,329,181 B1 | 12/2001 | Xiao et al. |
| 6,338,962 B1 | 1/2002 | Boyce |
| 6,387,670 B1 | 5/2002 | Leblois-Prehaud et al. |
| 6,610,906 B1 | 8/2003 | Kurachi et al. |
| 6,759,237 B1 | 7/2004 | Wilson et al. |
| 6,919,209 B1 | 7/2005 | Chatterjee et al. |
| 6,924,128 B2 | 8/2005 | Allen |
| 6,936,243 B2 | 8/2005 | Snyder et al. |
| 6,936,466 B2 | 8/2005 | Feldhaus |
| 6,953,690 B1 | 10/2005 | Gao et al. |
| 6,984,517 B1 | 1/2006 | Chiorini et al. |
| 7,001,764 B2 | 2/2006 | Little et al. |
| 7,022,519 B2 | 4/2006 | Gao et al. |
| 7,056,502 B2 | 6/2006 | Hildinger et al. |
| 7,091,029 B2 | 8/2006 | Hwang |
| 7,094,604 B2 | 8/2006 | Snyder et al. |
| 7,148,341 B2 | 12/2006 | Kleinschmidt et al. |
| 7,157,571 B2 | 1/2007 | Wang et al. |
| 7,172,893 B2 | 2/2007 | Rabinowitz et al. |
| 7,179,903 B2 | 2/2007 | McArthur et al. |
| 7,198,951 B2 | 4/2007 | Gao et al. |
| 7,220,577 B2 | 5/2007 | Zolotukhin |

(Continued)

FOREIGN PATENT DOCUMENTS

| | | |
|---|---|---|
| EP | 126544 A2 | 11/1984 |
| EP | 161788 A1 | 11/1985 |

(Continued)

OTHER PUBLICATIONS

Chen H. Exploiting the Intron-splicing Mechanism of Insect Cells to Produce Viral Vectors Harboring Toxic Genes for Suicide Gene Therapy. Mol Ther Nucleic Acids. Nov. 27, 2012;1(11): e57. doi: 10.1038/mtna.2012.48. PMID: 23187456; PMCID: PMC3511675. (Year: 2012).*

Hacein-Bey-Abina et al., "Insertional oncogenesis in 4 patients after retrovirus-mediated gene therapy of SCID-X1," J Clin Invest. 2008; 118(9):3132-42.

Kramer et al., "In vitro and in vivo comparative study of chimeric liver-specific promoters," Mol Therapy. 2003; 7(3):375-85.

Lu et al., "A mini-intronic plasmid (MIP): a novel robust transgene expression vector in vivo and in vitro," Mol Ther. 2013;21(5):954-63.

(Continued)

Primary Examiner — Allison M Fox
Assistant Examiner — Qinhua Gu
(74) Attorney, Agent, or Firm — Dechert LLP; Andrew T. Wilkins; David M. Lee

(57) ABSTRACT

Provided herein are adeno-associated virus (AAV) compositions that can restore phenylalanine hydroxylase (PAH) gene function in cell. Also provided are methods of use of the AAV compositions, and packaging systems for making the AAV compositions.

20 Claims, 28 Drawing Sheets

Specification includes a Sequence Listing.

(56) References Cited

U.S. PATENT DOCUMENTS

| | | | |
|---|---|---|---|
| 7,235,393 B2 | 6/2007 | Gao et al. |
| 7,259,151 B2 | 8/2007 | Arbetman et al. |
| 7,282,199 B2 | 10/2007 | Gao et al. |
| 7,351,813 B2 | 4/2008 | Miao et al. |
| 7,465,583 B2 | 12/2008 | Samulski et al. |
| 7,482,156 B2 | 1/2009 | Arroyo et al. |
| 7,588,772 B2 | 9/2009 | Kay et al. |
| 7,749,492 B2 | 7/2010 | Bartlett et al. |
| 7,790,154 B2 | 9/2010 | Samulski et al. |
| 7,906,111 B2 | 3/2011 | Wilson et al. |
| 8,030,065 B2 | 10/2011 | Gray |
| 8,067,156 B2 | 11/2011 | Kaplitt et al. |
| 8,163,543 B2 | 4/2012 | Urabe et al. |
| 8,168,425 B2 | 5/2012 | Gray |
| 8,241,622 B2 | 8/2012 | Englehardt et al. |
| 8,283,151 B2 | 10/2012 | Schmidt et al. |
| 8,298,818 B2 | 10/2012 | Boye et al. |
| 8,476,418 B2 | 7/2013 | Mueller et al. |
| 8,524,446 B2 | 9/2013 | Gao et al. |
| 8,628,966 B2 | 1/2014 | Chatterjee et al. |
| 8,632,764 B2 | 1/2014 | Xiao et al. |
| 8,716,461 B2 | 5/2014 | Delwart et al. |
| 8,846,387 B2 | 9/2014 | Russell et al. |
| 8,846,389 B2 | 9/2014 | Chiorini et al. |
| 8,926,958 B2 | 1/2015 | Shah et al. |
| 8,999,678 B2 | 4/2015 | Vandenberghe et al. |
| 8,999,948 B2 | 4/2015 | Tubert et al. |
| 9,114,161 B2 | 8/2015 | Barkats |
| 9,150,882 B2 | 10/2015 | Kay et al. |
| 9,169,299 B2 | 10/2015 | Lisowski et al. |
| 9,169,494 B2 | 10/2015 | Hewitt et al. |
| 9,193,956 B2 | 11/2015 | Schaffer et al. |
| 9,217,155 B2 | 12/2015 | Gao et al. |
| 9,222,105 B2 | 12/2015 | Cost et al. |
| 9,402,919 B2 | 8/2016 | Roeth et al. |
| 9,408,904 B2 | 8/2016 | Wright et al. |
| 9,409,953 B2 | 8/2016 | Asokan et al. |
| 9,441,244 B2 | 9/2016 | Schaffer et al. |
| 9,617,548 B2 | 4/2017 | Chuah et al. |
| 9,623,120 B2 | 4/2017 | Chatterjee et al. |
| 9,764,045 B2 | 9/2017 | Nathwani et al. |
| 9,783,824 B2 | 10/2017 | Kay et al. |
| 9,840,719 B2 | 12/2017 | High et al. |
| 9,890,396 B2 | 2/2018 | Chatterjee et al. |
| 9,926,574 B2 | 3/2018 | Barkats |
| 2003/0129203 A1 | 7/2003 | Vega et al. |
| 2003/0130221 A1 | 7/2003 | High et al. |
| 2003/0198620 A1 | 10/2003 | Ozawa et al. |
| 2004/0086485 A1 | 5/2004 | Aguilar-Cordova |
| 2004/0142416 A1 | 7/2004 | Laipis et al. |
| 2004/0235174 A1 | 11/2004 | Grimm et al. |
| 2005/0112765 A1 | 5/2005 | Li et al. |
| 2009/0191597 A1 | 7/2009 | Samulski et al. |
| 2009/0215879 A1 | 8/2009 | Diprimio et al. |
| 2010/0297084 A1 | 11/2010 | Bennett et al. |
| 2011/0294218 A1* | 12/2011 | Chatterjee ............ C07K 14/005 530/350 |
| 2012/0046349 A1 | 2/2012 | Bell et al. |
| 2012/0093772 A1 | 4/2012 | Horsager et al. |
| 2012/0244127 A1 | 9/2012 | Lipschutz et al. |
| 2013/0023033 A1 | 1/2013 | Wilson et al. |
| 2013/0189225 A1 | 7/2013 | Voit et al. |
| 2013/0280222 A1 | 10/2013 | Kay et al. |
| 2013/0287736 A1 | 10/2013 | Passini et al. |
| 2013/0310443 A1 | 11/2013 | Srivastava et al. |
| 2013/0323226 A1 | 12/2013 | Wilson et al. |
| 2014/0037585 A1 | 2/2014 | Wright et al. |
| 2014/0050701 A1 | 2/2014 | Zhong et al. |
| 2014/0107185 A1 | 4/2014 | Maclaren et al. |
| 2014/0271550 A1 | 9/2014 | Rabinowitz et al. |
| 2014/0336245 A1 | 11/2014 | Mingozzi et al. |
| 2014/0359799 A1 | 12/2014 | Wang et al. |
| 2015/0023924 A1 | 1/2015 | High et al. |
| 2015/0024467 A1 | 1/2015 | Sheldon et al. |
| 2015/0065562 A1 | 3/2015 | Yazicioglu et al. |
| 2015/0079038 A1 | 3/2015 | Deverman et al. |
| 2015/0110762 A1 | 4/2015 | Holmes et al. |
| 2015/0111955 A1 | 4/2015 | High et al. |
| 2015/0184197 A1 | 7/2015 | Davidson et al. |
| 2015/0232836 A1* | 8/2015 | Krieg ..................... A61P 35/02 530/358 |
| 2015/0238550 A1 | 8/2015 | McCown et al. |
| 2015/0252384 A1 | 9/2015 | Kaspar et al. |
| 2015/0315610 A1 | 11/2015 | Nishie et al. |
| 2015/0352228 A1 | 12/2015 | Torbett et al. |
| 2015/0374803 A1 | 12/2015 | Wolfe |
| 2015/0376240 A1 | 12/2015 | Cronin et al. |
| 2015/0376650 A1 | 12/2015 | Auerbach et al. |
| 2016/0000887 A1 | 1/2016 | Wilson et al. |
| 2016/0017295 A1 | 1/2016 | Schaffer et al. |
| 2016/0032319 A1 | 2/2016 | Wright et al. |
| 2016/0123990 A1 | 5/2016 | High et al. |
| 2016/0175365 A1 | 6/2016 | Golden |
| 2016/0229904 A1 | 8/2016 | Xiao et al. |
| 2017/0088856 A1 | 3/2017 | Barzel et al. |
| 2017/0119906 A1 | 5/2017 | Riley |
| 2017/0145439 A1 | 5/2017 | Gao et al. |
| 2017/0326256 A1 | 11/2017 | Doering et al. |
| 2018/0298380 A1 | 10/2018 | Gao et al. |

FOREIGN PATENT DOCUMENTS

| | | |
|---|---|---|
| EP | 746624 A1 | 12/1996 |
| EP | 1497436 A1 | 1/2005 |
| WO | WO-1996008560 A1 | 3/1996 |
| WO | WO-1998009524 A1 | 3/1998 |
| WO | WO-1998021349 A1 | 5/1998 |
| WO | WO-1998027207 A1 | 6/1998 |
| WO | WO-1998028417 A1 | 7/1998 |
| WO | WO-1999003981 A1 | 1/1999 |
| WO | WO-1999018227 A1 | 4/1999 |
| WO | WO-1999055564 A1 | 11/1999 |
| WO | WO-1999064569 A1 | 12/1999 |
| WO | WO-2000049160 A1 | 8/2000 |
| WO | WO-2001036620 A2 | 5/2001 |
| WO | WO-2002066611 A2 | 8/2002 |
| WO | WO-2003052051 A2 | 6/2003 |
| WO | WO-2003087383 A1 | 10/2003 |
| WO | WO-2003093436 A2 | 11/2003 |
| WO | WO-2005111220 A2 | 11/2005 |
| WO | WO-2006096815 A2 | 9/2006 |
| WO | WO-2007019646 A1 | 2/2007 |
| WO | WO-2008021140 A2 | 2/2008 |
| WO | WO-2009000552 A2 | 12/2008 |
| WO | WO-2009130208 A1 | 10/2009 |
| WO | WO-2009134681 A2 | 11/2009 |
| WO | WO-2010124180 A1 | 10/2010 |
| WO | WO-2011038187 A1 | 3/2011 |
| WO | WO-2014064277 A1 | 5/2014 |
| WO | WO-2014089212 A1 | 6/2014 |
| WO | WO-2014193716 A2 | 12/2014 |
| WO | WO-2015061491 A1 | 4/2015 |
| WO | WO-2015143177 A1 | 9/2015 |
| WO | WO-2015164723 A1 | 10/2015 |
| WO | WO-2016049230 A1 | 3/2016 |
| WO | WO-2016097218 A1 | 6/2016 |
| WO | WO-2016097219 A1 | 6/2016 |
| WO | WO-2016100575 A1 | 6/2016 |
| WO | WO-2016146757 A1 | 9/2016 |
| WO | WO-2017015154 A1 | 1/2017 |
| WO | WO-2017100551 A1 | 6/2017 |
| WO | WO-2017106345 A1 | 6/2017 |
| WO | WO-2017136202 A1 | 8/2017 |
| WO | WO-2017149292 A1 | 9/2017 |
| WO | WO-2018046737 A1 | 3/2018 |
| WO | WO-2018126112 A1 | 7/2018 |
| WO | WO-2018126116 A1 | 7/2018 |
| WO | WO-2018129586 A1 | 7/2018 |
| WO | WO-2018167621 A1 | 9/2018 |
| WO | WO-2018187231 A2 | 10/2018 |

(56) References Cited

FOREIGN PATENT DOCUMENTS

| WO | WO-2018206168 A1 | 11/2018 |
| WO | WO-2018222925 A1 | 12/2018 |

OTHER PUBLICATIONS

Lu et al., "A 5' Noncoding Exon Containing Engineered Intron Enhances Transgene Expression from Recombinant AAV Vectors in vivo," Hum Gene Ther. 2017;28(1):125-34.

PCT International Search Report from PCT/US2019/016354 dated Apr. 30, 2019.

Regier et al., "Phenylalanine Hydroxylase Deficiency," GeneReviews. Jan. 10, 2000; Seattle (WA): University of Washington, Seattle; 1993-2019. Available from: <URL:https://www.ncbi.nlm.nih.gov/books/NBK1504>; Genbank supplement, pp. 1-3.

Savy et al., "Impact of Inverted Terminal Repeat Integrity on rAAV8 Production Using the Baculovirus/Sf9 Cells System," Human Gene Therapy Methods. 2017;28(5):277-89.

Sibley et al., "Lessons from non-canonical splicing," Nat Rev Gen. 2016;17(7):407-21.

Thöny, "Long-term correction of murine phenylketonuria by viral gene transfer: liver versus muscle," J Inherit Metab Dis. 2010;33(6):677-80.

\* cited by examiner

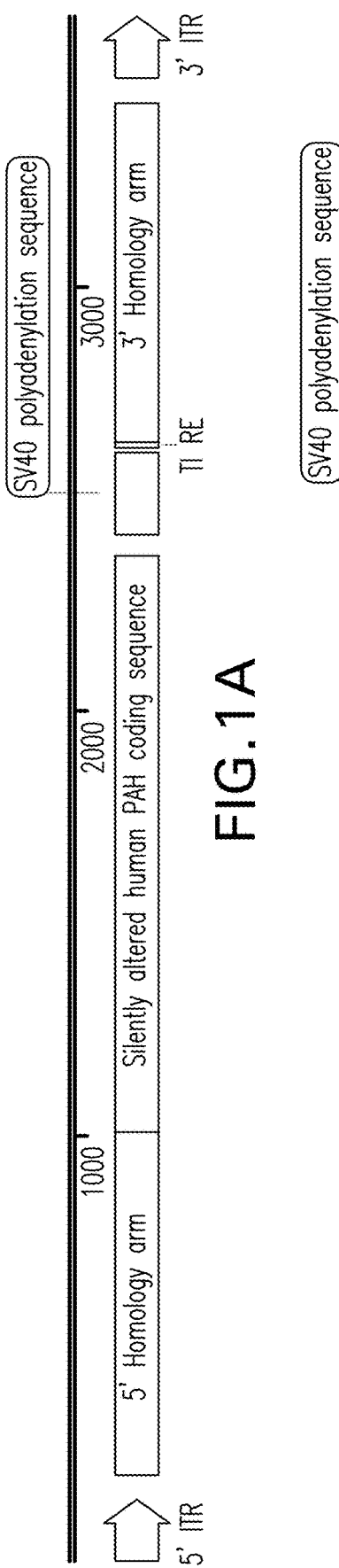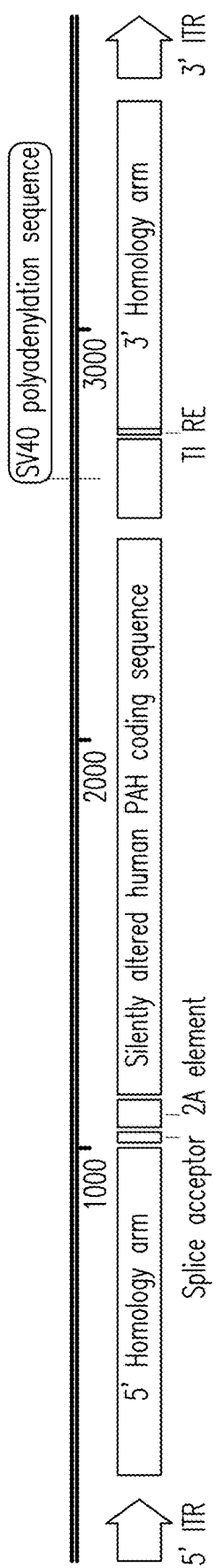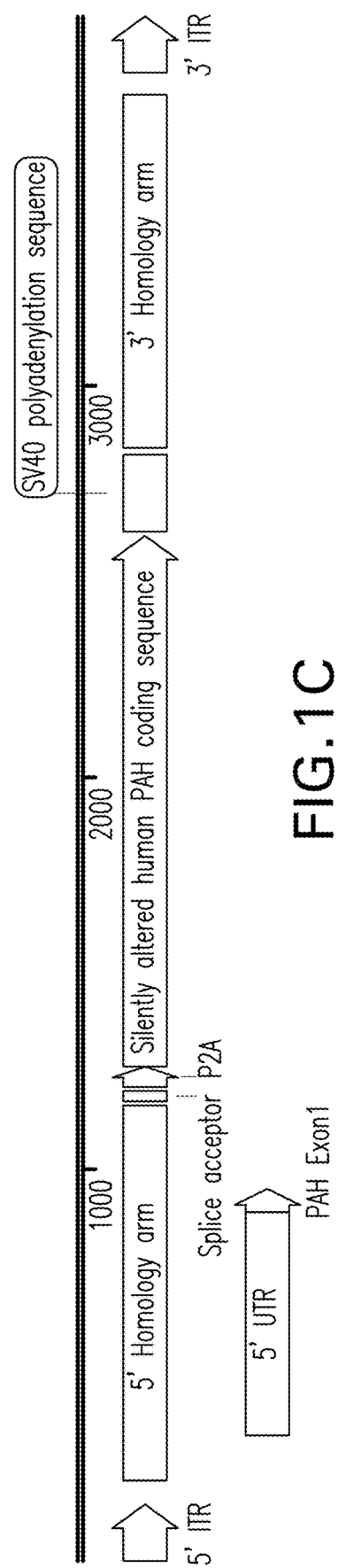
FIG. 1A
FIG. 1B
FIG. 1C

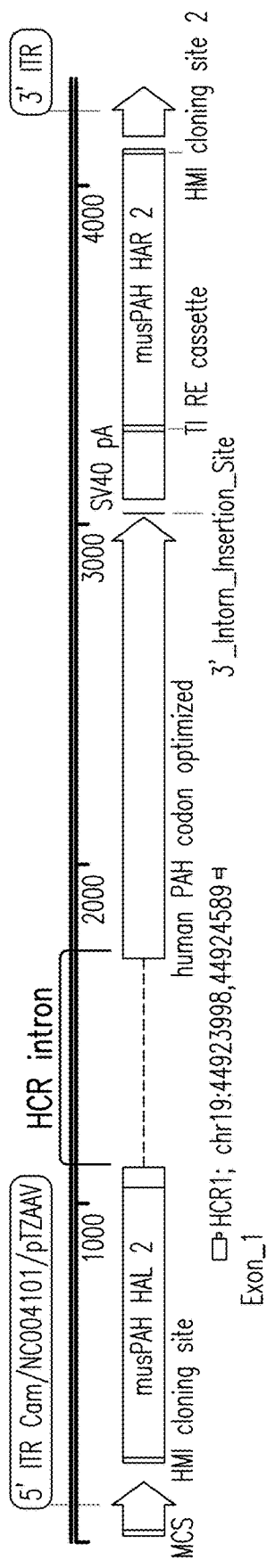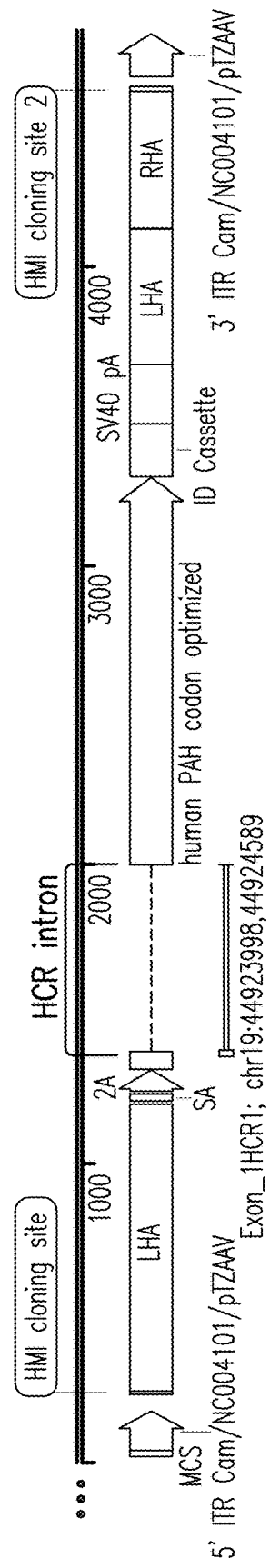
FIG. 17A
FIG. 17B

SEQUENCE LISTING

<160> NUMBER OF SEQ ID NOS: 153

<210> SEQ ID NO 1
<211> LENGTH: 736
<212> TYPE: PRT
<213> ORGANISM: Artificial Sequence
<220> FEATURE:
<223> OTHER INFORMATION: adeno-associated AAV9

<400> SEQUENCE: 1

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
```

-continued

```
            355                 360                 365
Ala Asp Val Phe Met Ile Pro Gln Tyr Gly Tyr Leu Thr Leu Asn Asp
        370                 375                 380
Gly Ser Gln Ala Val Gly Arg Ser Ser Phe Tyr Cys Leu Glu Tyr Phe
385                 390                 395                 400
Pro Ser Gln Met Leu Arg Thr Gly Asn Asn Phe Gln Phe Ser Tyr Glu
                405                 410                 415
Phe Glu Asn Val Pro Phe His Ser Ser Tyr Ala His Ser Gln Ser Leu
                420                 425                 430
Asp Arg Leu Met Asn Pro Leu Ile Asp Gln Tyr Leu Tyr Tyr Leu Ser
                435                 440                 445
Lys Thr Ile Asn Gly Ser Gly Gln Asn Gln Gln Thr Leu Lys Phe Ser
        450                 455                 460
Val Ala Gly Pro Ser Asn Met Ala Val Gln Gly Arg Asn Tyr Ile Pro
465                 470                 475                 480
Gly Pro Ser Tyr Arg Gln Gln Arg Val Ser Thr Thr Val Thr Gln Asn
                485                 490                 495
Asn Asn Ser Glu Phe Ala Trp Pro Gly Ala Ser Ser Trp Ala Leu Asn
                500                 505                 510
Gly Arg Asn Ser Leu Met Asn Pro Gly Pro Ala Met Ala Ser His Lys
                515                 520                 525
Glu Gly Glu Asp Arg Phe Phe Pro Leu Ser Gly Ser Leu Ile Phe Gly
530                 535                 540
Lys Gln Gly Thr Gly Arg Asp Asn Val Asp Ala Asp Lys Val Met Ile
545                 550                 555                 560
Thr Asn Glu Glu Glu Ile Lys Thr Thr Asn Pro Val Ala Thr Glu Ser
                565                 570                 575
Tyr Gly Gln Val Ala Thr Asn His Gln Ser Ala Gln Ala Gln Ala Gln
                580                 585                 590
Thr Gly Trp Val Gln Asn Gln Gly Ile Leu Pro Gly Met Val Trp Gln
                595                 600                 605
Asp Arg Asp Val Tyr Leu Gln Gly Pro Ile Trp Ala Lys Ile Pro His
        610                 615                 620
Thr Asp Gly Asn Phe His Pro Ser Pro Leu Met Gly Gly Phe Gly Met
625                 630                 635                 640
Lys His Pro Pro Pro Gln Ile Leu Ile Lys Asn Thr Pro Val Pro Ala
                645                 650                 655
Asp Pro Pro Thr Ala Phe Asn Lys Asp Lys Leu Asn Ser Phe Ile Thr
                660                 665                 670
Gln Tyr Ser Thr Gly Gln Val Ser Val Glu Ile Glu Trp Glu Leu Gln
                675                 680                 685
Lys Glu Asn Ser Lys Arg Trp Asn Pro Glu Ile Gln Tyr Thr Ser Asn
        690                 695                 700
Tyr Tyr Lys Ser Asn Asn Val Glu Phe Ala Val Asn Thr Glu Gly Val
705                 710                 715                 720
Tyr Ser Glu Pro Arg Pro Ile Gly Thr Arg Tyr Leu Thr Arg Asn Leu
                725                 730                 735
```

<210> SEQ ID NO 2
<211> LENGTH: 736
<212> TYPE: PRT
<213> ORGANISM: Artificial Sequence
<220> FEATURE:
<223> OTHER INFORMATION: novel AAV isolate

```
<400> SEQUENCE: 2

Met Thr Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
            115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
            195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
    275                 280                 285

Phe His Cys His Phe Ser Pro Arg Asp Trp Gln Arg Leu Ile Asn Asn
290                 295                 300

Asn Trp Gly Phe Arg Pro Lys Gln Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
    355                 360                 365

Ala Asp Val Phe Met Ile Pro Gln Tyr Gly Tyr Leu Thr Leu Asn Asp
370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415
```

```
Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
            435                 440                 445

Lys Thr Ile Asn Gly Ser Gly Gln Asn Gln Gln Thr Leu Lys Phe Ser
450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
            515                 520                 525

Glu Gly Glu Asp Arg Phe Phe Pro Leu Ser Gly Ser Leu Ile Phe Gly
            530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
            595                 600                 605

Asp Arg Asp Val Tyr Leu Gln Gly Pro Ile Trp Ala Lys Ile Pro His
            610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
            690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735
```

<210> SEQ ID NO 3
<211> LENGTH: 736
<212> TYPE: PRT
<213> ORGANISM: Artificial Sequence
<220> FEATURE:
<223> OTHER INFORMATION: novel AAV isolate

<400> SEQUENCE: 3

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45
```

```
Gly Tyr Lys Tyr Leu Gly Pro Gly Asn Gly Leu Asp Lys Gly Glu Pro
 50                  55                  60

Val Asn Ala Ala Asp Ala Ala Leu Glu His Asp Lys Ala Tyr Asp
 65                  70                  75                  80

Gln Gln Leu Lys Ala Gly Asp Asn Pro Tyr Leu Lys Tyr Asn His Ala
                 85                  90                  95

Asp Ala Glu Phe Gln Glu Arg Leu Lys Glu Asp Thr Ser Phe Gly Gly
                100                 105                 110

Asn Leu Gly Arg Ala Val Phe Gln Ala Lys Lys Arg Leu Leu Glu Pro
            115                 120                 125

Leu Gly Leu Val Glu Glu Ala Ala Lys Thr Ala Pro Gly Lys Lys Arg
        130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
450                 455                 460
```

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
            485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
            515                 520                 525

Glu Gly Glu Asp Arg Phe Phe Pro Leu Ser Gly Ser Leu Ile Phe Gly
530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
                580                 585                 590

Thr Gly Trp Val Gln Asn Gln Gly Ile Leu Pro Gly Met Val Trp Gln
            595                 600                 605

Asp Arg Asp Val Tyr Leu Gln Gly Pro Ile Trp Ala Lys Ile Pro His
610                 615                 620

Thr Gly Gly Asn Phe His Pro Ser Pro Leu Met Gly Gly Phe Gly Met
625                 630                 635                 640

Lys His Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
690                 695                 700

Tyr Tyr Lys Ser Asn Asn Val Glu Phe Ala Val Asn Thr Gly Gly Val
705                 710                 715                 720

Tyr Ser Glu Pro Arg Pro Ile Gly Thr Arg Tyr Leu Thr Arg Asn Leu
                725                 730                 735

<210> SEQ ID NO 4
<211> LENGTH: 736
<212> TYPE: PRT
<213> ORGANISM: Artificial Sequence
<220> FEATURE:
<223> OTHER INFORMATION: novel AAV isolate

<400> SEQUENCE: 4

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Ile Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

-continued

```
Asp Ala Glu Phe Gln Glu Arg Leu Lys Glu Asp Thr Ser Phe Gly Gly
                100                 105                 110
Asn Leu Gly Arg Ala Val Phe Gln Ala Lys Lys Arg Leu Leu Glu Pro
            115                 120                 125
Leu Gly Leu Val Glu Glu Ala Ala Lys Thr Ala Pro Gly Lys Lys Arg
        130                 135                 140
Pro Val Glu Gln Ser Pro Gln Glu Pro Asp Ser Ser Ala Gly Ile Gly
145                 150                 155                 160
Lys Ser Gly Ala Gln Pro Ala Lys Lys Arg Leu Asn Phe Gly Gln Thr
                165                 170                 175
Gly Asp Thr Glu Ser Val Pro Asp Pro Gln Pro Ile Gly Glu Pro Pro
            180                 185                 190
Ala Ala Pro Ser Gly Val Gly Ser Leu Thr Met Ala Ser Gly Gly Gly
        195                 200                 205
Ala Pro Val Ala Asp Asn Asn Glu Gly Ala Asp Gly Val Gly Ser Ser
210                 215                 220
Ser Gly Asn Trp His Cys Asp Ser Gln Trp Leu Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Asn Ser Thr Ser Gly Gly Ser Ser Asn Asp Asn
            260                 265                 270
Ala Tyr Phe Gly Tyr Ser Thr Pro Trp Gly Tyr Phe Asp Phe Asn Arg
        275                 280                 285
Phe His Cys His Phe Ser Pro Arg Asp Trp Gln Arg Leu Ile Asn Asn
        290                 295                 300
Asn Trp Gly Phe Arg Pro Lys Arg Leu Asn Phe Lys Leu Phe Asn Ile
305                 310                 315                 320
Gln Val Lys Glu Val Thr Asp Asn Asn Gly Val Lys Thr Ile Ala Asn
                325                 330                 335
Asn Leu Thr Ser Thr Val Gln Val Phe Thr Asp Ser Asp Tyr Gln Leu
            340                 345                 350
Pro Tyr Val Leu Gly Ser Ala His Glu Gly Cys Leu Pro Pro Phe Pro
        355                 360                 365
Ala Asp Val Phe Met Ile Pro Gln Tyr Gly Tyr Leu Thr Leu Asn Asp
370                 375                 380
Gly Ser Gln Ala Val Gly Arg Ser Ser Phe Tyr Cys Leu Glu Tyr Phe
385                 390                 395                 400
Pro Ser Gln Met Leu Arg Thr Gly Asn Asn Phe Gln Phe Ser Tyr Glu
                405                 410                 415
Phe Glu Asn Val Pro Phe His Ser Ser Tyr Ala His Ser Gln Ser Leu
            420                 425                 430
Asp Arg Leu Met Asn Pro Leu Ile Asp Gln Tyr Leu Tyr Tyr Leu Ser
        435                 440                 445
Lys Thr Ile Asn Gly Ser Gly Gln Asn Gln Gln Thr Leu Lys Phe Ser
        450                 455                 460
Val Ala Gly Pro Ser Asn Met Ala Val Gln Gly Arg Asn Tyr Ile Pro
465                 470                 475                 480
Gly Pro Ser Tyr Arg Gln Gln Arg Val Ser Thr Thr Val Thr Gln Asn
                485                 490                 495
Asn Asn Ser Glu Phe Ala Trp Pro Gly Ala Ser Ser Trp Ala Leu Asn
            500                 505                 510
Gly Arg Asn Ser Leu Met Asn Pro Gly Pro Ala Met Ala Ser His Lys
```

```
                515                 520                 525
Glu Gly Glu Asp Arg Phe Phe Pro Leu Ser Gly Ser Leu Ile Phe Gly
530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Tyr Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 5
<211> LENGTH: 736
<212> TYPE: PRT
<213> ORGANISM: Artificial Sequence
<220> FEATURE:
<223> OTHER INFORMATION: novel AAV isolate

<400> SEQUENCE: 5

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp Gln
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Asp
```

```
            145                 150                 155                 160
Lys Ser Gly Ala Gln Pro Ala Lys Lys Arg Leu Asn Phe Gly Gln Thr
                165                 170                 175
Gly Asp Thr Glu Ser Val Pro Asp Pro Gln Pro Ile Gly Glu Pro Pro
            180                 185                 190
Ala Ala Pro Ser Gly Val Gly Ser Leu Thr Met Ala Ser Gly Gly Gly
            195                 200                 205
Ala Pro Val Ala Asp Asn Asn Glu Gly Ala Asp Gly Val Gly Ser Ser
            210                 215                 220
Ser Gly Asn Trp His Cys Asp Ser Gln Trp Leu Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Asn Ser Thr Ser Gly Gly Ser Ser Asn Asp Asn
                260                 265                 270
Ala Tyr Phe Gly Tyr Ser Thr Pro Trp Gly Tyr Phe Asp Phe Asn Arg
            275                 280                 285
Phe His Cys His Phe Ser Pro Arg Asp Trp Gln Arg Leu Ile Asn Asn
        290                 295                 300
Asn Trp Gly Phe Arg Pro Lys Arg Leu Asn Phe Lys Leu Phe Asn Ile
305                 310                 315                 320
Gln Val Lys Glu Val Thr Asp Asn Asn Gly Val Lys Thr Ile Ala Asn
                325                 330                 335
Asn Leu Thr Ser Thr Val Gln Val Phe Thr Asp Ser Asp Tyr Gln Leu
            340                 345                 350
Pro Tyr Val Leu Gly Ser Ala His Glu Gly Cys Leu Pro Pro Phe Pro
            355                 360                 365
Ala Asp Val Phe Met Ile Pro Gln Tyr Gly Tyr Leu Thr Leu Asn Asp
            370                 375                 380
Gly Ser Gln Ala Val Gly Arg Ser Ser Phe Tyr Cys Leu Glu Tyr Phe
385                 390                 395                 400
Pro Ser Gln Met Leu Arg Thr Gly Asn Asn Phe Gln Phe Ser Tyr Glu
                405                 410                 415
Phe Glu Asn Val Pro Phe His Ser Ser Tyr Ala His Ser Gln Ser Leu
                420                 425                 430
Asp Arg Leu Met Asn Pro Leu Ile Asp Gln Tyr Leu Tyr Tyr Leu Ser
            435                 440                 445
Lys Thr Ile Asn Gly Ser Gly Gln Asn Gln Gln Thr Leu Lys Phe Ser
            450                 455                 460
Val Ala Gly Pro Ser Asn Met Ala Val Gln Gly Arg Asn Tyr Ile Pro
465                 470                 475                 480
Gly Pro Ser Tyr Arg Gln Gln Arg Val Ser Thr Thr Val Thr Gln Asn
                485                 490                 495
Asn Asn Ser Glu Phe Ala Trp Pro Gly Ala Ser Ser Trp Ala Leu Asn
            500                 505                 510
Gly Arg Asn Ser Leu Met Asn Pro Gly Pro Ala Met Ala Ser His Lys
            515                 520                 525
Glu Gly Glu Asp Arg Phe Phe Pro Leu Ser Gly Ser Leu Ile Phe Gly
            530                 535                 540
Lys Gln Gly Thr Gly Arg Asp Asn Val Asp Ala Asp Lys Val Met Ile
545                 550                 555                 560
Thr Asn Glu Glu Glu Ile Lys Thr Thr Asn Pro Val Ala Thr Glu Ser
                565                 570                 575
```

```
Tyr Gly Gln Val Ala Thr Asn His Gln Ser Ala Gln Ala Gln
            580                 585                 590
Thr Gly Trp Val Gln Asn Gly Ile Leu Pro Gly Met Val Trp Gln
            595                 600                 605
Asp Arg Asp Val Tyr Leu Gln Gly Pro Ile Trp Ala Lys Ile Pro His
610                 615                 620
Thr Asp Gly Asn Phe His Pro Ser Pro Leu Met Gly Gly Phe Gly Met
625                 630                 635                 640
Lys His Pro Pro Pro Gln Ile Leu Ile Lys Asn Thr Pro Val Pro Ala
                    645                 650                 655
Asp Pro Pro Thr Ala Phe Asn Lys Asp Lys Leu Asn Ser Phe Ile Thr
                660                 665                 670
Gln Tyr Ser Thr Gly Gln Val Ser Val Glu Ile Glu Trp Glu Leu Gln
            675                 680                 685
Lys Glu Asn Ser Lys Arg Trp Asn Pro Glu Ile Gln Tyr Thr Ser Asn
690                 695                 700
Tyr Tyr Lys Ser Asn Asn Val Glu Phe Ala Val Asn Thr Glu Gly Val
705                 710                 715                 720
Tyr Ser Glu Pro Arg Pro Ile Gly Thr Arg Tyr Leu Thr Arg Asn Leu
                    725                 730                 735
```

<210> SEQ ID NO 6
<211> LENGTH: 736
<212> TYPE: PRT
<213> ORGANISM: Artificial Sequence
<220> FEATURE:
<223> OTHER INFORMATION: novel AAV isolate

<400> SEQUENCE: 6

```
Met Ala Ala Asp Gly Tyr Leu Pro Asp Trp Leu Glu Asp Asn Leu Ser
1               5                   10                  15
Glu Gly Ile Arg Glu Trp Trp Ala Leu Lys Pro Gly Ala Pro Gln Pro
            20                  25                  30
Lys Ala Asn Gln Gln His Gln Asp Asn Ala Arg Gly Leu Val Leu Pro
        35                  40                  45
Gly Tyr Lys Tyr Leu Gly Pro Gly Asn Gly Leu Asp Lys Gly Glu Pro
    50                  55                  60
Val Asn Ala Ala Asp Ala Ala Ala Leu Glu His Asp Lys Ala Tyr Asp
65                  70                  75                  80
Gln Gln Leu Lys Ala Gly Asp Asn Pro Tyr Leu Lys Tyr Asn His Ala
                85                  90                  95
Asp Ala Glu Phe Gln Glu Arg Leu Lys Glu Asp Thr Ser Phe Gly Gly
            100                 105                 110
Asn Leu Gly Arg Ala Val Leu Gln Ala Lys Lys Arg Leu Leu Glu Pro
        115                 120                 125
Leu Gly Leu Val Glu Glu Ala Ala Lys Thr Ala Pro Gly Lys Lys Arg
    130                 135                 140
Pro Val Glu Gln Ser Pro Gln Glu Pro Asp Ser Ser Ala Gly Ile Gly
145                 150                 155                 160
Lys Ser Gly Ala Gln Pro Ala Lys Lys Arg Leu Asn Phe Gly Gln Thr
                165                 170                 175
Gly Asp Thr Glu Ser Val Pro Asp Pro Gln Pro Ile Gly Glu Pro Pro
            180                 185                 190
Ala Ala Pro Ser Gly Val Gly Ser Leu Thr Met Ala Ser Gly Gly Gly
        195                 200                 205
```

```
Ala Pro Val Ala Asp Asn Asn Glu Gly Ala Asp Gly Val Gly Ser Ser
    210                 215                 220
Ser Gly Asn Trp His Cys Asp Ser Gln Trp Leu Gly Asp Arg Val Ile
225                 230                 235                 240
Thr Thr Ser Thr Arg Thr Trp Ala Leu Pro Thr Tyr Asn Asn His Leu
            245                 250                 255
Tyr Lys Gln Ile Ser Asn Ser Thr Ser Gly Ser Ser Asn Asp Asn
        260                 265                 270
Ala Tyr Phe Gly Tyr Ser Thr Pro Trp Gly Tyr Phe Asp Phe Asn Arg
        275                 280                 285
Phe His Cys His Phe Ser Pro Arg Asp Trp Gln Arg Leu Ile Asn Asn
    290                 295                 300
Asn Trp Gly Phe Arg Pro Lys Arg Leu Asn Phe Lys Leu Phe Asn Ile
305                 310                 315                 320
Gln Val Lys Glu Val Thr Asp Asn Asn Gly Val Lys Thr Ile Ala Asn
                325                 330                 335
Asn Leu Thr Ser Thr Val Gln Val Phe Thr Asp Ser Asp Tyr Gln Leu
            340                 345                 350
Pro Tyr Val Leu Gly Ser Ala His Glu Gly Cys Leu Pro Pro Phe Pro
        355                 360                 365
Ala Asp Val Phe Met Ile Pro Gln Tyr Gly Tyr Leu Thr Leu Asn Asp
    370                 375                 380
Gly Ser Gln Ala Val Gly Arg Ser Ser Phe Tyr Cys Leu Glu Tyr Phe
385                 390                 395                 400
Pro Ser Gln Met Leu Arg Thr Gly Asn Asn Phe Gln Phe Ser Tyr Glu
                405                 410                 415
Phe Glu Asn Val Pro Phe His Ser Ser Tyr Ala His Ser Gln Ser Leu
            420                 425                 430
Asp Arg Leu Met Asn Pro Leu Ile Asp Gln Tyr Leu Tyr Tyr Leu Ser
        435                 440                 445
Lys Thr Ile Asn Gly Ser Gly Gln Asn Gln Gln Thr Leu Lys Phe Ser
    450                 455                 460
Val Ala Gly Ser Ser Asn Met Ala Val Gln Gly Arg Asn Tyr Ile Pro
465                 470                 475                 480
Gly Pro Ser Tyr Arg Gln Gln Arg Val Ser Thr Thr Val Thr Gln Asn
                485                 490                 495
Asn Asn Ser Glu Phe Ala Trp Pro Gly Ala Ser Ser Trp Ala Leu Asn
            500                 505                 510
Gly Arg Asn Ser Leu Met Asn Pro Gly Pro Ala Met Ala Ser His Lys
        515                 520                 525
Glu Gly Glu Asp Arg Phe Phe Pro Leu Ser Gly Ser Leu Ile Phe Gly
    530                 535                 540
Lys Gln Gly Thr Gly Arg Asp Asn Val Asp Ala Asp Lys Val Met Ile
545                 550                 555                 560
Thr Asn Glu Glu Glu Ile Lys Thr Thr Asn Pro Val Ala Thr Glu Ser
                565                 570                 575
Tyr Gly Gln Val Ala Thr Asn His Gln Ser Ala Gln Ala Gln
            580                 585                 590
Thr Gly Trp Val Gln Asn Gln Gly Ile Leu Pro Gly Met Val Trp Gln
        595                 600                 605
Asp Arg Asp Val Tyr Leu Gln Gly Pro Ile Trp Ala Lys Ile Pro His
    610                 615                 620
```

-continued

```
Thr Asp Gly Asn Phe His Pro Ser Pro Leu Met Gly Gly Phe Gly Met
625                 630                 635                 640

Lys His Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 7
<211> LENGTH: 736
<212> TYPE: PRT
<213> ORGANISM: Artificial Sequence
<220> FEATURE:
<223> OTHER INFORMATION: novel AAV isolate

<400> SEQUENCE: 7

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255
```

```
Tyr Lys Gln Ile Ser Asn Ser Thr Ser Gly Ser Ser Asn Asp Asn
                260                 265                 270

Ala Tyr Phe Gly Tyr Ser Thr Pro Trp Gly Tyr Phe Asp Phe Asn Arg
            275                 280                 285

Phe His Cys His Phe Ser Pro Arg Asp Trp Gln Arg Leu Ile Asn Asn
        290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Arg Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
```

```
                675                 680                 685
Lys Glu Asn Ser Lys Arg Trp Asn Pro Glu Ile Gln Tyr Thr Ser Asn
            690                 695                 700
Tyr Tyr Lys Ser Asn Asn Val Glu Phe Ala Val Asn Thr Glu Gly Val
705                 710                 715                 720
Tyr Ser Glu Pro Arg Pro Ile Gly Thr Arg Tyr Leu Thr Arg Asn Leu
                725                 730                 735

<210> SEQ ID NO 8
<211> LENGTH: 736
<212> TYPE: PRT
<213> ORGANISM: Artificial Sequence
<220> FEATURE:
<223> OTHER INFORMATION: novel AAV isolate

<400> SEQUENCE: 8

Met Ala Ala Asp Gly Tyr Leu Pro Asp Trp Leu Glu Asp Asn Leu Ser
1               5                   10                  15
Glu Gly Ile Arg Glu Trp Trp Ala Leu Lys Pro Gly Ala Pro Gln Pro
            20                  25                  30
Lys Ala Asn Gln Gln His Gln Asp Asn Ala Arg Gly Leu Val Leu Pro
        35                  40                  45
Gly Tyr Lys Tyr Leu Gly Pro Gly Asn Gly Leu Asp Lys Gly Glu Pro
    50                  55                  60
Val Asn Ala Val Asp Ala Ala Leu Glu His Asp Lys Ala Tyr Asp
65                  70                  75                  80
Gln Gln Leu Lys Ala Gly Asp Asn Pro Tyr Leu Lys Tyr Asn His Ala
                85                  90                  95
Asp Ala Glu Phe Gln Glu Arg Leu Lys Glu Asp Thr Ser Phe Gly Gly
            100                 105                 110
Asn Leu Gly Arg Ala Val Phe Gln Ala Lys Lys Arg Leu Leu Glu Pro
        115                 120                 125
Leu Gly Leu Val Glu Glu Ala Ala Lys Thr Ala Pro Gly Lys Lys Arg
    130                 135                 140
Pro Val Glu Gln Ser Pro Gln Glu Pro Asp Ser Ser Ala Gly Ile Gly
145                 150                 155                 160
Lys Ser Gly Ala Gln Pro Ala Lys Lys Arg Leu Asn Phe Gly Gln Thr
                165                 170                 175
Gly Asp Thr Glu Ser Val Pro Asp Pro Gln Pro Ile Gly Glu Pro Pro
            180                 185                 190
Ala Ala Pro Ser Gly Val Gly Ser Leu Thr Met Ala Ser Gly Gly Gly
        195                 200                 205
Ala Pro Val Ala Asp Asn Asn Glu Gly Ala Asp Gly Val Gly Ser Ser
    210                 215                 220
Ser Gly Asn Trp His Cys Asp Ser Gln Trp Leu Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Asn Ser Thr Ser Gly Gly Ser Ser Asn Asp Asn
            260                 265                 270
Ala Tyr Phe Gly Tyr Ser Thr Pro Trp Gly Tyr Phe Asp Phe Asn Arg
        275                 280                 285
Phe His Cys His Phe Ser Pro Arg Asp Trp Gln Arg Leu Ile Asn Asn
    290                 295                 300
Asn Trp Gly Phe Arg Pro Lys Arg Leu Asn Phe Lys Leu Phe Asn Ile
```

-continued

```
            305                 310                 315                 320
Gln Val Lys Glu Val Thr Asp Asn Asn Gly Val Lys Thr Ile Ala Asn
                    325                 330                 335
Asn Leu Thr Ser Thr Val Gln Val Phe Thr Asp Ser Asp Tyr Gln Leu
                340                 345                 350
Pro Tyr Val Leu Gly Ser Ala His Glu Gly Cys Leu Pro Phe Pro
            355                 360                 365
Ala Asp Val Phe Met Ile Pro Gln Tyr Gly Tyr Leu Thr Leu Asn Asp
370                 375                 380
Gly Ser Gln Ala Val Gly Arg Ser Ser Phe Tyr Cys Leu Glu Tyr Phe
385                 390                 395                 400
Pro Ser Gln Met Leu Arg Thr Gly Asn Asn Phe Gln Phe Ser Tyr Glu
                405                 410                 415
Phe Glu Asn Val Pro Phe His Ser Ser Tyr Ala His Ser Gln Ser Leu
                420                 425                 430
Asp Arg Leu Met Asn Pro Leu Ile Asp Gln Tyr Leu Tyr Tyr Leu Ser
            435                 440                 445
Lys Thr Ile Asn Gly Ser Gly Gln Asn Gln Gln Thr Leu Lys Phe Ser
        450                 455                 460
Val Ala Gly Pro Ser Asn Met Ala Val Gln Gly Arg Asn Tyr Ile Pro
465                 470                 475                 480
Gly Pro Ser Tyr Arg Gln Gln Arg Val Ser Thr Thr Val Thr Gln Asn
                485                 490                 495
Asn Asn Ser Glu Phe Ala Trp Pro Gly Ala Ser Ser Trp Ala Leu Asn
                500                 505                 510
Gly Arg Asn Ser Leu Met Asn Pro Gly Pro Ala Met Ala Ser His Lys
            515                 520                 525
Glu Gly Glu Asp Arg Phe Phe Pro Leu Ser Gly Ser Leu Ile Phe Gly
        530                 535                 540
Lys Gln Gly Thr Gly Arg Asp Asn Val Asp Ala Asp Lys Val Met Ile
545                 550                 555                 560
Thr Asn Glu Glu Glu Ile Lys Thr Thr Asn Pro Val Ala Thr Glu Ser
                565                 570                 575
Tyr Gly Gln Val Ala Thr Asn His Gln Ser Ala Gln Ala Gln Ala Gln
                580                 585                 590
Thr Gly Trp Val Gln Asn Gln Gly Ile Leu Pro Gly Met Val Trp Gln
            595                 600                 605
Asp Arg Asp Val Tyr Leu Gln Gly Pro Ile Trp Ala Lys Ile Pro His
        610                 615                 620
Thr Asp Gly Asn Phe His Pro Ser Pro Leu Met Gly Gly Phe Gly Met
625                 630                 635                 640
Lys His Pro Pro Pro Gln Ile Leu Ile Lys Asn Thr Pro Val Pro Ala
                645                 650                 655
Asp Pro Pro Thr Ala Phe Asn Lys Asp Lys Leu Asn Ser Phe Ile Thr
                660                 665                 670
Gln Tyr Ser Thr Gly Gln Val Ser Val Glu Ile Glu Trp Glu Leu Gln
            675                 680                 685
Lys Glu Asn Ser Lys Arg Trp Asn Pro Glu Ile Gln Tyr Thr Ser Asn
        690                 695                 700
Tyr Tyr Lys Ser Asn Asn Val Glu Phe Ala Val Asn Thr Glu Gly Val
705                 710                 715                 720
Tyr Ser Glu Pro Arg Pro Ile Gly Thr Arg Tyr Leu Thr Arg Asn Leu
                725                 730                 735
```

<210> SEQ ID NO 9
<211> LENGTH: 736
<212> TYPE: PRT
<213> ORGANISM: Artificial Sequence
<220> FEATURE:
<223> OTHER INFORMATION: novel AAV isolate

<400> SEQUENCE: 9

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Arg Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365
```

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
                420                 425                 430

Asp Arg Leu Met Asn Pro Leu Ile Asp Gln Tyr Leu Tyr Tyr Leu Ser
            435                 440                 445

Lys Thr Ile Asn Gly Ser Gly Gln Asn Gln Gln Thr Leu Lys Phe Ser
450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
                500                 505                 510

Gly Arg Asn Ser Leu Met Asn Pro Gly Pro Ala Met Ala Ser His Lys
            515                 520                 525

Glu Gly Glu Asp Arg Phe Phe Pro Leu Ser Gly Ser Leu Ile Phe Gly
530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
                580                 585                 590

Thr Gly Trp Val Gln Asn Gln Gly Ile Leu Pro Gly Met Val Trp Gln
            595                 600                 605

Asp Arg Asp Val Tyr Leu Gln Gly Pro Ile Trp Ala Lys Ile Pro His
610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
                660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 10
<211> LENGTH: 736
<212> TYPE: PRT
<213> ORGANISM: Artificial Sequence
<220> FEATURE:
<223> OTHER INFORMATION: novel AAV isolate

<400> SEQUENCE: 10

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65              70                  75                  80

Gln Gln Leu Lys Ala Gly Asp Asn Pro Tyr Leu Lys Tyr Asn His Ala
            85                  90                  95

Asp Ala Glu Phe Gln Glu Arg Leu Lys Glu Asp Thr Ser Phe Gly Gly
                100                 105                 110

Asn Leu Gly Arg Ala Val Phe Gln Ala Lys Lys Arg Leu Leu Glu Pro
            115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Cys Gly Gly
            195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
            245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
    275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
    355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415
```

Phe Glu Asn Val Pro Phe His Ser Ser Tyr Ala His Ser Gln Ser Leu
                420                 425                 430

Asp Arg Leu Met Asn Pro Leu Ile Asp Gln Tyr Leu Tyr Tyr Leu Ser
            435                 440                 445

Lys Thr Ile Asn Gly Ser Gly Gln Asn Gln Gln Thr Leu Lys Phe Ser
        450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 11
<211> LENGTH: 736
<212> TYPE: PRT
<213> ORGANISM: Artificial Sequence
<220> FEATURE:
<223> OTHER INFORMATION: novel AAV isolate

<400> SEQUENCE: 11

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

-continued

```
Gly Tyr Lys Tyr Leu Gly Pro Gly Asn Gly Leu Asp Lys Gly Glu Pro
            50                  55                  60

Val Asn Ala Ala Asp Ala Ala Leu Glu His Asp Arg Ala Tyr Asp
 65                  70                  75                  80

Gln Gln Leu Lys Ala Gly Asp Asn Pro Tyr Leu Lys Tyr Asn His Ala
                    85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
            115                 120                 125

Leu Gly Leu Val Glu Glu Ala Ala Lys Thr Ala Pro Gly Lys Lys Arg
        130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                    165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
            195                 200                 205

Ala Pro Val Ala Asp Asn Asn Glu Gly Ala Asp Gly Val Gly Ser Ser
        210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                    245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
            275                 280                 285

Phe His Cys His Phe Ser Pro Arg Asp Trp Gln Arg Leu Ile Asn Asn
        290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                    325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
            355                 360                 365

Ala Asp Val Phe Met Ile Pro Gln Tyr Gly Tyr Leu Thr Leu Asn Asp
        370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                    405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
            435                 440                 445

Lys Thr Ile Asn Gly Ser Gly Gln Asn Gln Gln Thr Leu Lys Phe Ser
        450                 455                 460

Val Ala Gly Pro Ser Asn Met Ala Val Gln Gly Arg Asn Tyr Ile Pro
```

```
            465                 470                 475                 480
        Gly Pro Ser Tyr Arg Gln Gln Arg Val Ser Thr Thr Val Thr Gln Asn
                        485                 490                 495

Asn Asn Ser Glu Phe Ala Trp Pro Gly Ala Ser Ser Trp Ala Leu Asn
                        500                 505                 510

Gly Arg Asn Ser Leu Met Asn Pro Gly Pro Ala Met Ala Ser His Lys
                        515                 520                 525

Glu Gly Glu Asp Arg Phe Phe Pro Leu Ser Gly Ser Leu Ile Phe Gly
                        530                 535                 540

Lys Gln Gly Thr Gly Arg Asp Asn Val Asp Ala Asp Lys Val Met Ile
        545                 550                 555                 560

Thr Asn Glu Glu Glu Ile Lys Thr Thr Asn Pro Val Ala Thr Glu Ser
                        565                 570                 575

Tyr Gly Gln Val Ala Thr Asn His Gln Ser Ala Gln Ala Gln Ala Gln
                        580                 585                 590

Thr Gly Trp Val Gln Asn Gln Gly Ile Leu Pro Gly Met Val Trp Gln
                        595                 600                 605

Asp Arg Asp Val Tyr Leu Gln Gly Pro Ile Trp Ala Lys Ile Pro His
                        610                 615                 620

Thr Asp Gly Asn Phe His Pro Ser Pro Leu Met Gly Gly Phe Gly Met
        625                 630                 635                 640

Lys His Pro Pro Pro Gln Ile Leu Ile Lys Asn Thr Pro Val Pro Ala
                        645                 650                 655

Asp Pro Pro Thr Ala Phe Asn Lys Asp Lys Leu Asn Ser Phe Ile Thr
                        660                 665                 670

Gln Tyr Ser Thr Gly Gln Val Ser Val Glu Ile Glu Trp Glu Leu Gln
                        675                 680                 685

Lys Lys Asn Ser Lys Arg Trp Asn Pro Glu Ile Gln Tyr Thr Ser Asn
                        690                 695                 700

Tyr Tyr Lys Ser Asn Asn Val Glu Phe Ala Val Asn Thr Glu Gly Val
        705                 710                 715                 720

Tyr Ser Glu Pro Arg Pro Ile Gly Thr Arg Tyr Leu Thr Arg Asn Leu
                        725                 730                 735

<210> SEQ ID NO 12
<211> LENGTH: 736
<212> TYPE: PRT
<213> ORGANISM: Artificial Sequence
<220> FEATURE:
<223> OTHER INFORMATION: novel AAV isolate

<400> SEQUENCE: 12

Met Ala Ala Asp Gly Tyr Leu Pro Asp Trp Leu Glu Asp Asn Leu Ser
1               5                  10                  15

Glu Gly Ile Arg Glu Trp Trp Ala Leu Lys Pro Gly Ala Pro Gln Pro
                20                  25                  30

Lys Ala Asn Gln Gln His Gln Asp Asn Ala Arg Gly Leu Val Leu Pro
            35                  40                  45

Gly Tyr Lys Tyr Leu Gly Pro Gly Asn Gly Leu Asp Lys Gly Glu Pro
        50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
```

```
            100                 105                 110
Asn Leu Gly Arg Ala Val Phe Gln Ala Lys Lys Arg Leu Leu Glu Pro
            115                 120                 125

Leu Gly Leu Val Glu Glu Ala Ala Lys Thr Ala Pro Gly Lys Lys Arg
            130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
            195                 200                 205

Ala Pro Val Ala Asp Asn Asn Glu Gly Ala Asp Gly Val Gly Ser Ser
            210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
            275                 280                 285

Phe His Cys His Phe Ser Pro His Asp Trp Gln Arg Leu Ile Asn Asn
            290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
            355                 360                 365

Ala Asp Val Phe Met Ile Pro Gln Tyr Gly Tyr Leu Thr Leu Asn Asp
            370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
            435                 440                 445

Lys Thr Ile Asn Gly Ser Gly Gln Asn Gln Gln Thr Leu Lys Phe Asn
            450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Arg Ala Ser Ser Trp Ala Leu Asn
            500                 505                 510

Gly Arg Asn Ser Leu Met Asn Pro Gly Pro Ala Met Ala Ser His Lys
            515                 520                 525
```

```
Glu Gly Glu Asp Arg Phe Phe Pro Leu Ser Gly Ser Leu Ile Phe Gly
            530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
            595                 600                 605

Asp Arg Asp Val Tyr Leu Gln Gly Pro Ile Trp Ala Lys Ile Pro His
            610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
                660                 665                 670

Gln Tyr Ser Thr Gly Gln Val Ser Met Glu Ile Glu Trp Glu Leu Gln
            675                 680                 685

Lys Glu Asn Ser Lys Arg Trp Asn Pro Glu Ile Gln Tyr Thr Ser Asn
690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 13
<211> LENGTH: 736
<212> TYPE: PRT
<213> ORGANISM: Artificial Sequence
<220> FEATURE:
<223> OTHER INFORMATION: novel AAV isolate

<400> SEQUENCE: 13

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160
```

```
Lys Ser Gly Ala Gln Pro Ala Lys Lys Arg Leu Asn Phe Gly Gln Thr
                165                 170                 175
Gly Asp Thr Glu Ser Val Pro Asp Pro Gln Pro Ile Gly Glu Pro Pro
            180                 185                 190
Ala Ala Pro Ser Gly Val Gly Ser Leu Thr Met Ala Ser Gly Gly Gly
            195                 200                 205
Ala Pro Val Ala Asp Asn Asn Glu Gly Ala Asp Gly Val Gly Ser Ser
        210                 215                 220
Ser Gly Asn Trp His Cys Asp Ser Gln Trp Leu Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Asn Ser Thr Ser Gly Gly Ser Ser Asn Asp Asn
                260                 265                 270
Ala Tyr Phe Gly Tyr Ser Thr Pro Trp Gly Tyr Phe Asp Phe Asn Arg
            275                 280                 285
Phe His Cys His Phe Ser Pro Arg Asp Trp Gln Arg Leu Ile Asn Asn
        290                 295                 300
Asn Trp Gly Phe Arg Pro Lys Arg Leu Asn Phe Lys Leu Phe Asn Ile
305                 310                 315                 320
Gln Val Lys Glu Val Thr Asp Asn Asn Gly Val Lys Thr Ile Ala Asn
                325                 330                 335
Asn Leu Thr Ser Thr Val Gln Val Phe Thr Asp Ser Asp Tyr Gln Leu
                340                 345                 350
Pro Tyr Val Leu Gly Ser Ala His Glu Gly Cys Leu Pro Pro Phe Pro
            355                 360                 365
Ala Asp Val Phe Met Ile Pro Gln Tyr Gly Tyr Leu Thr Leu Asn Asp
        370                 375                 380
Gly Ser Gln Ala Val Gly Arg Ser Ser Phe Tyr Cys Leu Glu Tyr Phe
385                 390                 395                 400
Pro Ser Gln Met Leu Arg Thr Gly Asn Asn Phe Gln Phe Ser Tyr Glu
                405                 410                 415
Phe Glu Asn Val Pro Phe His Ser Ser Tyr Ala His Ser Gln Ser Leu
                420                 425                 430
Asp Arg Leu Met Asn Pro Leu Ile Asp Gln Tyr Leu Tyr Tyr Leu Ser
            435                 440                 445
Lys Thr Ile Asn Gly Ser Gly Gln Asn Gln Gln Thr Leu Lys Phe Ser
        450                 455                 460
Val Ala Gly Pro Ser Asn Met Ala Val Gln Gly Arg Asn Tyr Ile Pro
465                 470                 475                 480
Gly Pro Ser Tyr Arg Gln Gln Arg Val Ser Thr Thr Val Thr Gln Asn
                485                 490                 495
Asn Asn Ser Glu Phe Ala Trp Pro Arg Ala Ser Ser Trp Ala Leu Asn
                500                 505                 510
Gly Arg Asn Ser Leu Met Asn Pro Gly Pro Ala Met Ala Ser His Lys
            515                 520                 525
Glu Gly Glu Asp Arg Phe Phe Pro Leu Ser Gly Ser Leu Ile Phe Gly
        530                 535                 540
Lys Gln Gly Thr Gly Arg Asp Asn Val Asp Ala Asp Lys Val Met Ile
545                 550                 555                 560
Thr Asn Glu Glu Glu Ile Lys Thr Thr Asn Pro Val Ala Thr Glu Ser
                565                 570                 575
```

```
Tyr Gly Gln Val Ala Thr Asn His Gln Ser Ala Gln Ala Gln
                580                 585                 590

Thr Gly Trp Val Gln Asn Gln Gly Ile Leu Pro Gly Met Val Trp Gln
    595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
    660                 665                 670

Gln Tyr Ser Thr Gly Gln Val Ser Val Glu Ile Glu Trp Glu Leu Gln
    675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 14
<211> LENGTH: 26
<212> TYPE: DNA
<213> ORGANISM: Artificial Sequence
<220> FEATURE:
<223> OTHER INFORMATION: splice acceptor

<400> SEQUENCE: 14
ctgacctctt ctcttcctcc cacagg                                          26

<210> SEQ ID NO 15
<211> LENGTH: 736
<212> TYPE: PRT
<213> ORGANISM: Artificial Sequence
<220> FEATURE:
<223> OTHER INFORMATION: novel AAV isolate

<400> SEQUENCE: 15

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
                20                  25                  30

Lys Ala Asn Gln Gln His Gln Asp Asn Ala Arg Gly Leu Val Leu Pro
            35                  40                  45

Gly Tyr Lys Tyr Leu Gly Pro Gly Asn Gly Leu Asp Lys Gly Glu Pro
        50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140
```

-continued

```
Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
            165                 170                 175

Gly Asp Thr Glu Ser Val Pro Asp Pro Gln Pro Ile Gly Glu Pro Pro
                180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
                260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
                340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
                420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Arg Ala Ser Ser Trp Ala Leu Asn
                500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
```

```
                565                 570                 575
Tyr Gly Gln Val Ala Thr Asn His Gln Ser Ala Gln Ala Gln
            580                 585                 590

Thr Gly Trp Val Gln Asn Gln Gly Ile Leu Pro Gly Met Val Trp Gln
            595                 600                 605

Asp Arg Asp Val Tyr Leu Gln Gly Pro Ile Trp Ala Lys Ile Pro His
            610                 615                 620

Thr Asp Gly Asn Phe His Pro Ser Pro Leu Met Gly Gly Phe Gly Met
625                 630                 635                 640

Lys His Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Arg Gln
            675                 680                 685

Lys Glu Asn Ser Lys Arg Trp Asn Pro Glu Ile Gln Tyr Thr Ser Asn
            690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 16
<211> LENGTH: 736
<212> TYPE: PRT
<213> ORGANISM: Artificial Sequence
<220> FEATURE:
<223> OTHER INFORMATION: novel AAV isolate

<400> SEQUENCE: 16

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
```

-continued

```
            195                 200                 205
Ala Pro Val Ala Asp Asn Asn Glu Gly Ala Asp Gly Val Gly Ser Ser
210                 215                 220
Ser Gly Asn Trp His Cys Asp Ser Gln Trp Leu Gly Asp Arg Val Ile
225                 230                 235                 240
Thr Thr Ser Thr Arg Thr Trp Ala Leu Pro Thr Tyr Asn Asn His Leu
            245                 250                 255
Tyr Lys Gln Ile Ser Asn Ser Thr Ser Gly Ser Ser Asn Asp Asn
            260                 265                 270
Ala Tyr Phe Gly Tyr Ser Thr Pro Trp Gly Tyr Phe Asp Phe Asn Arg
            275                 280                 285
Phe His Cys His Phe Ser Pro Arg Asp Trp Gln Arg Leu Ile Asn Asn
            290                 295                 300
Asn Trp Gly Phe Arg Pro Lys Arg Leu Asn Phe Lys Leu Phe Asn Ile
305                 310                 315                 320
Gln Val Lys Glu Val Thr Asp Asn Asn Gly Val Lys Thr Ile Ala Asn
            325                 330                 335
Asn Leu Thr Ser Thr Val Gln Val Phe Ala Asp Ser Asp Tyr Gln Leu
            340                 345                 350
Pro Tyr Val Leu Gly Ser Ala His Glu Gly Cys Leu Pro Pro Phe Pro
            355                 360                 365
Ala Asp Val Phe Met Ile Pro Gln Tyr Gly Tyr Leu Thr Leu Asn Asp
370                 375                 380
Gly Ser Gln Ala Val Gly Arg Ser Ser Phe Tyr Cys Leu Glu Tyr Phe
385                 390                 395                 400
Pro Ser Gln Met Leu Arg Thr Gly Asn Asn Phe Gln Phe Ser Tyr Glu
            405                 410                 415
Phe Glu Asn Val Pro Phe His Ser Ser Tyr Ala His Ser Gln Ser Leu
            420                 425                 430
Asp Arg Leu Met Asn Pro Leu Ile Asp Gln Tyr Leu Tyr Tyr Leu Ser
            435                 440                 445
Lys Thr Ile Asn Gly Ser Gly Gln Asn Gln Gln Thr Leu Lys Phe Ser
            450                 455                 460
Val Ala Gly Pro Ser Asn Met Ala Val Gln Gly Arg Asn Tyr Ile Pro
465                 470                 475                 480
Gly Pro Ser Tyr Arg Gln Gln Arg Val Ser Thr Thr Val Thr Gln Asn
            485                 490                 495
Asn Asn Ser Glu Phe Ala Trp Pro Arg Ala Ser Ser Trp Ala Leu Asn
            500                 505                 510
Gly Arg Asn Ser Leu Met Asn Pro Gly Pro Ala Met Ala Ser His Lys
            515                 520                 525
Glu Gly Glu Asp Arg Phe Phe Pro Leu Ser Gly Ser Leu Ile Phe Gly
            530                 535                 540
Lys Gln Gly Thr Gly Arg Asp Asn Val Asp Ala Asp Lys Val Met Ile
545                 550                 555                 560
Thr Asn Glu Glu Glu Ile Lys Thr Thr Asn Pro Val Ala Thr Glu Ser
            565                 570                 575
Tyr Gly Gln Val Ala Thr Asn His Gln Ser Ala Gln Ala Gln Ala Gln
            580                 585                 590
Thr Gly Trp Val Gln Asn Gln Gly Ile Leu Pro Gly Met Val Trp Gln
            595                 600                 605
Asp Arg Asp Val Tyr Leu Gln Gly Pro Ile Trp Ala Lys Ile Pro His
610                 615                 620
```

```
Thr Asp Gly Asn Phe His Pro Ser Pro Leu Met Gly Phe Gly Met
625                 630                 635                 640

Lys His Pro Pro Gln Ile Leu Ile Lys Asn Thr Pro Val Pro Ala
            645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
            690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
            725                 730                 735
```

<210> SEQ ID NO 17
<211> LENGTH: 736
<212> TYPE: PRT
<213> ORGANISM: Artificial Sequence
<220> FEATURE:
<223> OTHER INFORMATION: novel AAV isolate

<400> SEQUENCE: 17

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255
```

```
Tyr Lys Gln Ile Ser Asn Ser Thr Ser Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Ile Ala Trp Pro Arg Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670
```

```
Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
        690                 695                 700

Tyr Cys Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 18
<211> LENGTH: 145
<212> TYPE: DNA
<213> ORGANISM: Artificial Sequence
<220> FEATURE:
<223> OTHER INFORMATION: AAV2 5' ITR

<400> SEQUENCE: 18
ttggccactc cctctctgcg cgctcgctcg ctcactgagg ccgggcgacc aaaggtcgcc      60
cgacgcccgg gctttgcccg gcggcctca  gtgagcgagc gagcgcgcag agagggagtg     120
gccaactcca tcactagggg ttcct                                           145

<210> SEQ ID NO 19
<211> LENGTH: 145
<212> TYPE: DNA
<213> ORGANISM: Artificial Sequence
<220> FEATURE:
<223> OTHER INFORMATION: AAV2 3' ITR

<400> SEQUENCE: 19
aggaacccct agtgatggag ttggccactc cctctctgcg cgctcgctcg ctcactgagg      60
ccgggcgacc aaaggtcgcc cgacgcccgg gctttgcccg gcggcctca  gtgagcgagc     120 gagcgcgcag agagggagtg gccaa                                           145

<210> SEQ ID NO 20
<211> LENGTH: 167
<212> TYPE: DNA
<213> ORGANISM: Artificial Sequence
<220> FEATURE:
<223> OTHER INFORMATION: AAV5 5' ITR

<400> SEQUENCE: 20
ctctcccccc tgtcgcgttc gctcgctcgc tggctcgttt ggggggggtgg cagctcaaag     60 agctgccaga cgacggccct ctggccgtcg cccccccaaa cgagccagcg agcgagcgaa    120
cgcgacaggg gggagagtgc cacactctca agcaagggg  ttttgta                   167

<210> SEQ ID NO 21
<211> LENGTH: 167
<212> TYPE: DNA
<213> ORGANISM: Artificial Sequence
<220> FEATURE:
<223> OTHER INFORMATION: AAV5 3' ITR

<400> SEQUENCE: 21
tacaaaacct ccttgcttga gagtgtggca ctctcccccc tgtcgcgttc gctcgctcgc      60
tggctcgttt ggggggggtgg cagctcaaag agctgccaga cgacggccct ctggccgtcg    120
cccccccaaa cgagccagcg agcgagcgaa cgcgacaggg gggagag                   167

<210> SEQ ID NO 22
<211> LENGTH: 621
```

<212> TYPE: PRT
<213> ORGANISM: Artificial Sequence
<220> FEATURE:
<223> OTHER INFORMATION: AAV2 Rep

<400> SEQUENCE: 22

```
Met Pro Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Asp Phe Leu
    50                  55                  60

Thr Glu Trp Arg Arg Val Ser Lys Ala Pro Glu Ala Leu Phe Phe Val
65                  70                  75                  80

Gln Phe Glu Lys Gly Glu Ser Tyr Phe His Met His Val Leu Val Glu
                85                  90                  95

Thr Thr Gly Val Lys Ser Met Val Leu Gly Arg Phe Leu Ser Gln Ile
            100                 105                 110

Arg Glu Lys Leu Ile Gln Arg Ile Tyr Arg Gly Ile Glu Pro Thr Leu
        115                 120                 125

Pro Asn Trp Phe Ala Val Thr Lys Thr Arg Asn Gly Ala Gly Gly Gly
    130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Gln Tyr Leu
                165                 170                 175

Ser Ala Cys Leu Asn Leu Thr Glu Arg Lys Arg Leu Val Ala Gln His
            180                 185                 190

Leu Thr His Val Ser Gln Thr Gln Glu Gln Asn Lys Glu Asn Gln Asn
        195                 200                 205

Pro Asn Ser Asp Ala Pro Val Ile Arg Ser Lys Thr Ser Ala Arg Tyr
    210                 215                 220

Met Glu Leu Val Gly Trp Leu Val Asp Lys Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Gly Lys
            260                 265                 270

Ile Met Ser Leu Thr Lys Thr Ala Pro Asp Tyr Leu Val Gly Gln Gln
        275                 280                 285

Pro Val Glu Asp Ile Ser Ser Asn Arg Ile Tyr Lys Ile Leu Glu Leu
    290                 295                 300

Asn Gly Tyr Asp Pro Gln Tyr Ala Ala Ser Val Phe Leu Gly Trp Ala
305                 310                 315                 320

Thr Lys Lys Phe Gly Lys Arg Asn Thr Ile Trp Leu Phe Gly Pro Ala
                325                 330                 335

Thr Thr Gly Lys Thr Asn Ile Ala Glu Ala Ile Ala His Thr Val Pro
            340                 345                 350

Phe Tyr Gly Cys Val Asn Trp Thr Asn Glu Asn Phe Pro Phe Asn Asp
        355                 360                 365

Cys Val Asp Lys Met Val Ile Trp Trp Glu Glu Gly Lys Met Thr Ala
    370                 375                 380
```

-continued

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
            405                 410                 415

Ile Val Thr Ser Asn Thr Asn Met Cys Ala Val Ile Asp Gly Asn Ser
            420                 425                 430

Thr Thr Phe Glu His Gln Gln Pro Leu Gln Asp Arg Met Phe Lys Phe
            435                 440                 445

Glu Leu Thr Arg Arg Leu Asp His Asp Phe Gly Lys Val Thr Lys Gln
450                 455                 460

Glu Val Lys Asp Phe Phe Arg Trp Ala Lys Asp His Val Val Glu Val
465                 470                 475                 480

Glu His Glu Phe Tyr Val Lys Lys Gly Gly Ala Lys Lys Arg Pro Ala
                485                 490                 495

Pro Ser Asp Ala Asp Ile Ser Glu Pro Lys Arg Val Arg Glu Ser Val
            500                 505                 510

Ala Gln Pro Ser Thr Ser Asp Ala Glu Ala Ser Ile Asn Tyr Ala Asp
            515                 520                 525

Arg Tyr Gln Asn Lys Cys Ser Arg His Val Gly Met Asn Leu Met Leu
530                 535                 540

Phe Pro Cys Arg Gln Cys Glu Arg Met Asn Gln Asn Ser Asn Ile Cys
545                 550                 555                 560

Phe Thr His Gly Gln Lys Asp Cys Leu Glu Cys Phe Pro Val Ser Glu
                565                 570                 575

Ser Gln Pro Val Ser Val Val Lys Lys Ala Tyr Gln Lys Leu Cys Tyr
            580                 585                 590

Ile His His Ile Met Gly Lys Val Pro Asp Ala Cys Thr Ala Cys Asp
            595                 600                 605

Leu Val Asn Val Asp Leu Asp Asp Cys Ile Phe Glu Gln
            610                 615                 620

<210> SEQ ID NO 23
<211> LENGTH: 452
<212> TYPE: PRT
<213> ORGANISM: Homo sapiens

<400> SEQUENCE: 23

Met Ser Thr Ala Val Leu Glu Asn Pro Gly Leu Gly Arg Lys Leu Ser
1               5                   10                  15

Asp Phe Gly Gln Glu Thr Ser Tyr Ile Glu Asp Asn Cys Asn Gln Asn
            20                  25                  30

Gly Ala Ile Ser Leu Ile Phe Ser Leu Lys Glu Glu Val Gly Ala Leu
            35                  40                  45

Ala Lys Val Leu Arg Leu Phe Glu Glu Asn Asp Val Asn Leu Thr His
        50                  55                  60

Ile Glu Ser Arg Pro Ser Arg Leu Lys Lys Asp Glu Tyr Glu Phe Phe
65                  70                  75                  80

Thr His Leu Asp Lys Arg Ser Leu Pro Ala Leu Thr Asn Ile Ile Lys
            85                  90                  95

Ile Leu Arg His Asp Ile Gly Ala Thr Val His Glu Leu Ser Arg Asp
            100                 105                 110

Lys Lys Lys Asp Thr Val Pro Trp Phe Pro Arg Thr Ile Gln Glu Leu
        115                 120                 125

Asp Arg Phe Ala Asn Gln Ile Leu Ser Tyr Gly Ala Glu Leu Asp Ala
    130                 135                 140

Asp His Pro Gly Phe Lys Asp Pro Val Tyr Arg Ala Arg Arg Lys Gln
145                 150                 155                 160

Phe Ala Asp Ile Ala Tyr Asn Tyr Arg His Gly Gln Pro Ile Pro Arg
                165                 170                 175

Val Glu Tyr Met Glu Glu Lys Lys Thr Trp Gly Thr Val Phe Lys
            180                 185                 190

Thr Leu Lys Ser Leu Tyr Lys Thr His Ala Cys Tyr Glu Tyr Asn His
            195                 200                 205

Ile Phe Pro Leu Leu Glu Lys Tyr Cys Gly Phe His Glu Asp Asn Ile
    210                 215                 220

Pro Gln Leu Glu Asp Val Ser Gln Phe Leu Gln Thr Cys Thr Gly Phe
225                 230                 235                 240

Arg Leu Arg Pro Val Ala Gly Leu Leu Ser Arg Asp Phe Leu Gly
                245                 250                 255

Gly Leu Ala Phe Arg Val Phe His Cys Thr Gln Tyr Ile Arg His Gly
                260                 265                 270

Ser Lys Pro Met Tyr Thr Pro Glu Pro Asp Ile Cys His Glu Leu Leu
            275                 280                 285

Gly His Val Pro Leu Phe Ser Asp Arg Ser Phe Ala Gln Phe Ser Gln
        290                 295                 300

Glu Ile Gly Leu Ala Ser Leu Gly Ala Pro Asp Glu Tyr Ile Glu Lys
305                 310                 315                 320

Leu Ala Thr Ile Tyr Trp Phe Thr Val Glu Phe Gly Leu Cys Lys Gln
                325                 330                 335

Gly Asp Ser Ile Lys Ala Tyr Gly Ala Gly Leu Leu Ser Ser Phe Gly
                340                 345                 350

Glu Leu Gln Tyr Cys Leu Ser Gly Lys Pro Lys Leu Leu Pro Leu Glu
            355                 360                 365

Leu Glu Lys Thr Ala Ile Gln Asn Tyr Thr Val Thr Glu Phe Gln Pro
370                 375                 380

Leu Tyr Tyr Val Ala Glu Ser Phe Asn Asp Ala Lys Glu Lys Val Arg
385                 390                 395                 400

Asn Phe Ala Ala Thr Ile Pro Arg Pro Phe Ser Val Arg Tyr Asp Pro
                405                 410                 415

Tyr Thr Gln Arg Ile Glu Val Leu Asp Asn Thr Gln Gln Leu Lys Ile
            420                 425                 430

Leu Ala Asp Ser Ile Asn Ser Glu Ile Gly Ile Leu Cys Ser Ala Leu
            435                 440                 445

Gln Lys Ile Lys
    450

<210> SEQ ID NO 24
<211> LENGTH: 1359
<212> TYPE: DNA
<213> ORGANISM: Homo sapiens

<400> SEQUENCE: 24
atgtccactg cggtcctgga aacccaggc ttgggcagga aactctctga ctttggacag    60
gaaacaagct atattgaaga caactgcaat caaaatggtg ccatatcact gatcttctca   120
ctcaaagaag aagttggtgc attggccaaa gtattgcgct atttgagga gaatgatgta   180 aacctgaccc acattgaatc tagaccttct cgtttaaaga agatgagtta tgaattttc    240 acccatttgg ataaacgtag cctgcctgct ctgacaaaca tcatcaagat cttgaggcat   300

```
gacattggtg ccactgtcca tgagctttca cgagataaga agaaagacac agtgccctgg    360
ttcccaagaa ccattcaaga gctggacaga tttgccaatc agattctcag ctatggagcg    420
gaactggatg ctgaccaccc tggttttaaa gatcctgtgt accgtgcaag acggaagcag    480
tttgctgaca ttgcctacaa ctaccgccat gggcagccca tccctcgagt ggaatacatg    540
gaggaagaaa agaaaacatg ggcacagtg  ttcaagactc tgaagtcctt gtataaaacc    600
catgcttgct atgagtacaa tcacattttt ccacttcttg aaaagtactg tggcttccat    660
gaagataaca ttccccagct ggaagacgtt tctcaattcc tgcagacttg cactggtttc    720
cgcctccgac ctgtggctgg cctgctttcc tctcgggatt tcttgggtgg cctggccttc    780
cgagtcttcc actgcacaca gtacatcaga catggatcca agcccatgta taccccgaa     840
cctgacatct gccatgagct gttgggacat gtgcccttgt tttcagatcg cagctttgcc    900
cagttttccc aggaaattgg ccttgcctct ctgggtgcac ctgatgaata cattgaaaag    960
ctcgccacaa tttactggtt tactgtggag tttgggctct gcaaacaagg agactccata   1020
aaggcatatg gtgctgggct cctgtcatcc tttggtgaat acagtactg  cttatcagag   1080
aagccaaagc ttctcccccct ggagctggag aagacagcca tccaaaatta cactgtcacg   1140
gagttccagc ccctgtatta cgtggcagag agttttaatg atgccaagga gaaagtaagg   1200
aactttgctg ccacaatacc tcggcccttc tcagttcgct acgacccata cacccaaagg   1260
attgaggtct tggacaatac ccagcagctt aagattttgg ctgattccat taacagtgaa   1320
attggaatcc tttgcagtgc cctccagaaa ataaagtaa                          1359

<210> SEQ ID NO 25
<211> LENGTH: 1359
<212> TYPE: DNA
<213> ORGANISM: Artificial Sequence
<220> FEATURE:
<223> OTHER INFORMATION: Silently altered PAH coding sequence

<400> SEQUENCE: 25
atgtccaccg ctgtgctgga gaaccctggg ctggggagga aactgtcaga cttcgggcag     60
gagacttcat acattgagga taactgtaac cagaatggcg ccatctctct gatcttcagc    120
ctgaaggagg aagtgggcgc cctggcaaag gtgctgcgcc tgtttgagga gaacgacgtg    180
aatctgaccc acatcgagtc ccggccttct agactgaaga aggacgagta cgagttcttt    240
acccacctgg ataagcggtc cctgccagcc ctgacaaaca tcatcaagat cctgaggcac    300
gacatcggag caaccgtgca cgagctgtct cgggacaaga gaaggatac  cgtgccctgg    360
ttccctcgga caatccagga gctggataga tttgccaacc agatcctgtc ttacggagca    420
gagctggacg cagatcaccc tggcttcaag gacccagtgt atcgggcccg agaaaagcag    480
tttgccgata tcgcctacaa ttataggcac ggacagccaa tccctcgcgt ggagtatatg    540
gaggaggaga agaagacctg ggcacagtg  ttcaagaccc tgaagagcct gtacaagaca    600
cacgcctgct acgagtataa ccacatcttc cccctgctgg agaagtattg tggcttttcac   660
gaggacaata tccctcagct ggaggacgtg agccagttcc tgcagacctg cacaggcttt    720
aggctgagge cagtggcagg actgctgagc tcccgggact tcctgggagg actggccttc    780
agagtgtttc actgcaccca gtacatcagg cacggctcca agccaatgta taccccagag    840
cccgacatct gtcacgagct gctgggccac gtgcccctgt ttagcgatag atccttcgcc    900
cagttttccc aggagatcgg actggcatct ctggagcac  ctgacgagta catcgagaag    960
ctggccacca tctattggtt cacagtggag tttggcctgt gcaagcaggg cgatagcatc   1020
```

```
aaggcctacg gagcaggact gctgtctagc ttcggcgagc tgcagtattg tctgtccgag    1080
aagccaaagc tgctgcccct ggagctggag aagaccgcca tccagaacta caccgtgaca    1140
gagttccagc ccctgtacta tgtggccgag tcttttaacg atgccaagga gaaggtgaga    1200
aatttcgccg ccacaatccc taggcccttc agcgtgcggt acgacccta  tacccagagg    1260 atcgaggtgc tggataatac acagcagctg aagatcctgg ctgactcaat caatagcgaa    1320
atcggaatcc tgtgctccgc cctgcagaaa atcaaatga                          1359

<210> SEQ ID NO 26
<211> LENGTH: 106
<212> TYPE: DNA
<213> ORGANISM: Artificial Sequence
<220> FEATURE:
<223> OTHER INFORMATION: truncated AAV2 5'ITR

<400> SEQUENCE: 26
ctgcgcgctc gctcgctcac tgaggccgcc cgggcaaagc ccgggcgtcg ggcgaccttt    60
ggtcgcccgg cctcagtgag cgagcgagcg cgcagagagg gagtgg                  106

<210> SEQ ID NO 27
<211> LENGTH: 143
<212> TYPE: DNA
<213> ORGANISM: Artificial Sequence
<220> FEATURE:
<223> OTHER INFORMATION: modified AAV2 3'ITR

<400> SEQUENCE: 27
aggaacccct agtgatggag ttggccactc cctctctgcg cgctcgctcg ctcactgagg    60
ccgggcgacc aaaggtcgcc cgacgcccgg gctttgcccg gcggcctca  gtgagcgagc    120 gagcgcgcag agagggagtg gcc                                           143

<210> SEQ ID NO 28
<211> LENGTH: 130
<212> TYPE: DNA
<213> ORGANISM: Homo sapiens

<400> SEQUENCE: 28
gttggtatca aggttacaag acaggtttaa ggagaccaat agaaactggg catgtggaga    60
cagagaagac tcttgggttt ctgataggca ctgactctct ctgcctattg gtctattttc    120
ccacccttag                                                           130

<210> SEQ ID NO 29
<211> LENGTH: 116
<212> TYPE: DNA
<213> ORGANISM: Mus musculus

<400> SEQUENCE: 29
gttggtatcc aggttacaag gcagctcaca agaagaagtt gggtgcttgg agacagaggt    60
ctgctttcca gcagacacta actttcagtg tcccctgtct atgtttccct ttttag       116

<210> SEQ ID NO 30
<211> LENGTH: 92
<212> TYPE: DNA
<213> ORGANISM: Artificial Sequence
<220> FEATURE:
<223> OTHER INFORMATION: Minute virus in mice

<400> SEQUENCE: 30
```

```
aagaggtaag ggtttaaggg atggttggtt ggtggggtat taatgtttaa ttacctggag    60
cacctgcctg aaatcacttt ttttcaggtt gg                                 92

<210> SEQ ID NO 31
<211> LENGTH: 198
<212> TYPE: DNA
<213> ORGANISM: Simian virus 40

<400> SEQUENCE: 31
gatccagaca tgataagata cattgatgag tttggacaaa ccacaactag aatgcagtga    60
aaaaaatgct ttatttgtga aatttgtgat gctattgctt tatttgtaac cattataagc   120
tgcaataaac aagttaacaa caacaattgc attcatttta tgtttcaggt tcaggggag   180 gtgtgggagg ttttttaa                                                 198

<210> SEQ ID NO 32
<211> LENGTH: 122
<212> TYPE: DNA
<213> ORGANISM: Simian virus 40

<400> SEQUENCE: 32
aacttgttta ttgcagctta taatggttac aaataaagca atagcatcac aaatttcaca    60
aataaagcat ttttttcact gcattctagt tgtggtttgt ccaaactcat caatgtatct   120
ta                                                                  122

<210> SEQ ID NO 33
<211> LENGTH: 133
<212> TYPE: DNA
<213> ORGANISM: Simian virus 40

<400> SEQUENCE: 33
tgctttattt gtgaaatttg tgatgctatt gctttatttg taaccattat aagctgcaat    60
aaacaagtta acaacaacaa ttgcattcat tttatgtttc aggttcaggg ggaggtgtgg   120
gaggtttttt aaa                                                      133

<210> SEQ ID NO 34
<211> LENGTH: 135
<212> TYPE: DNA
<213> ORGANISM: Simian virus 40

<400> SEQUENCE: 34
gatccagaca tgataagata cattgatgag tttggacaaa ccacaactag aatgcagtga    60
aaaaaatgct ttatttgtga aatttgtgat gctattgctt tatttgtaac cattataagc   120
tgcaataaac aagtt                                                    135

<210> SEQ ID NO 35
<211> LENGTH: 1654
<212> TYPE: DNA
<213> ORGANISM: Artificial Sequence
<220> FEATURE:
<223> OTHER INFORMATION: pHMIA-hPAH-hI1C-032.1 editing element

<400> SEQUENCE: 35
ctgacctctt ctcttcctcc cacagggcag cggagctact aacttcagcc tgctgaagca    60
ggctggagac gtggaggaga accctggacc tatgtccacc gctgtgctgg agaaccctgg   120
gctggggagg aaactgtcag acttcgggca ggagacttca tacattgagg ataactgtaa   180
ccagaatggc gccatctctc tgatcttcag cctgaaggag gaagtgggcg ccctggcaaa   240
```

```
ggtgctgcgc ctgtttgagg agaacgacgt gaatctgacc cacatcgagt cccggccttc    300
tagactgaag aaggacgagt acgagttctt tacccacctg gataagcggt ccctgccagc    360
cctgacaaac atcatcaaga tcctgaggca cgacatcgga gcaaccgtgc acgagctgtc    420
tcgggacaag aagaaggata ccgtgccctg gttccctcgg acaatccagg agctggatag    480
atttgccaac cagatcctgt cttacggagc agagctggac gcagatcacc ctggcttcaa    540
ggacccagtg tatcgggccc ggagaaagca gtttgccgat atcgcctaca attataggca    600
cggacagcca atccctcgcg tggagtatat ggaggaggag aagaagacct ggggcacagt    660
gttcaagacc ctgaagagcc tgtacaagac acacgcctgc tacgagtata ccacatcttt    720 cccctgctg gagaagtatt gtggctttca cgaggacaat atccctcagc tggaggacgt    780
gagccagttc ctgcagacct gcacaggctt taggctgagg ccagtggcag gactgctgag    840
ctcccgggac ttcctgggag actggcctt cagagtgttt cactgcaccc agtacatcag    900
gcacggctcc aagccaatgt ataccaccaga gcccgacatc tgtcacgagc tgctgggcca    960
cgtgcccctg tttagcgata gatccttcgc ccagttttcc caggagatcg gactggcatc   1020
tctgggagca cctgacgagt acatcgagaa gctggccacc atctattggt tcacagtgga   1080
gtttggcctg tgcaagcagg gcgatagcat caaggcctac ggagcaggac tgctgtctag   1140
cttcggcgag ctgcagtatt gtctgtccga gaagccaaag ctgctgcccc tggagctgga   1200
gaagaccgcc atccagaact acaccgtgac agagttccag cccctgtact atgtggccga   1260
gtcttttaac gatgccaagg agaaggtgag aaatttcgcc gccacaatcc ctaggcccctt   1320 cagcgtgcgg tacgacccctt atacccagag gatcgaggtg ctggataata cacagcagct   1380
gaagatcctg gctgactcaa tcaatagcga atcggaatc ctgtgctccg ccctgcagaa   1440
aatcaaatga ggtaccgatc cagacatgat aagatacatt gatgagtttg acaaaccac   1500 aactagaatg cagtgaaaaa aatgctttat ttgtgaaatt tgtgatgcta ttgctttatt   1560
tgtaaccatt ataagctgca ataaacaagt taacaacaac aattgcattc attttatgtt   1620
tcaggttcag ggggaggtgt gggaggtttt ttaa                                1654
```

<210> SEQ ID NO 36
<211> LENGTH: 960
<212> TYPE: DNA
<213> ORGANISM: Homo sapiens

<400> SEQUENCE: 36

```
gcttcaggag cagttgtgcg aatagctgga gaacaccagg ctggatttaa acccagatcg     60
ctcttacatt tgctctttac ctgctgtgct cagcgttcac gtgccctcta gctgtagttt    120
tctgaagtca gcgcacagca aggcagtgtg cttagaggtt aacagaaggg aaaacaacaa    180
caacaaaaat ctaaatgaga atcctgactg tttcagctgg gggtaagggg ggcggattat    240
tcatataatt gttataccag acggtcgcag gcttagtcca attgcagaga actcgcttcc    300
caggcttctg agagtcccgg aagtgcctaa acctgtctaa tcgacggggc ttgggtggcc    360
cgtcgctccc tggcttcttc cctttaccca gggcgggcag cgaagtggtg cctcctgcgt    420
cccccacacc ctccctcagc ccctccctc cggcccgtcc tgggcaggtg acctggagca    480
tccggcaggc tgccctggcc tcctgcgtca ggacaacgcc cacgaggggc gttactgtgc    540
ggagatgcac cacgcaagag acacccttg taactctctt ctcctcccta gtgcgaggtt    600
aaaaccttca gccccacgtg ctgtttgcaa acctgcctgt acctgaggcc ctaaaaagcc    660
```

```
agagacctca ctcccgggga gccagcatgt ccactgcggt cctggaaaac ccaggcttgg      720
gcaggaaact ctctgacttt ggacaggtga gccacggcag cctgagctgc tcagttaggg      780
gaatttgggc ctccagagaa agagatccga agactgctgg tgcttcctgg tttcataagc      840
tcagtaagaa gtctgaattc gttggaagct gatgagaata tccaggaagt caacagacaa      900
atgtcctcaa caattgtttc taagtaggag aacatctgtc ctcggtggct ttcacaggaa      960
```

<210> SEQ ID NO 37
<211> LENGTH: 960
<212> TYPE: DNA
<213> ORGANISM: Artificial Sequence
<220> FEATURE:
<223> OTHER INFORMATION: 32.2 vector 5' homology arm

<400> SEQUENCE: 37

```
gcttcaggag cagttgtgcg aatagctgga gaacaccagg ctggatttaa acccagatcg       60
ctcttacatt tgctctttac ctgctgtgct cagcgttcac gtgccctcta gctgtagttt      120
tctgaagtca gcgcacagca aggcagtgtg cttagaggtt aacagaaggg aaaacaacaa      180
caacaaaaat ctaaatgaga atcctgactg tttcagctgg gggtaagggg ggcggattat      240
tcatataatt gttataccag acggtcgcag gcttagtcca attgcagaga actcgcttcc      300
caggcttctg agagtcccgg aagtgcctaa acctgtctaa tcgacggggc ttgggtggcc      360
cgtcgctccc tggcttcttc cctttaccca ggggcgggcag cgaagtggtg cctcctgcgt      420
cccccacacc ctccctcagc ccctcccctc cggcccgtcc tgggcaggtg acctggagca      480
tccggcaggc tgcctggcc tcctgcgtca ggacaacgcc cacgaggggc gttactgtgc      540
ggagatgcac cacgcaagag acacccttg taactctctt ctcctcccta gtgcgaggtt      600
aaaaccttca gccccacgtg ctgtttgcaa acctgcctgt acctgaggcc ctaaaaagcc      660
agagacctca ctcccgggga gccaccatgg cggcggcggt cctggaaaac ccaggcttgg      720
gcaggaaact ctctgacttt ggacaggtga gccacggcag cctgagctgc tcagttaggg      780
gaatttgggc ctccagagaa agagatccga agactgctgg tgcttcctgg tttcataagc      840
tcagtaagaa gtctgaattc gttggaagct gatgagaata tccaggaagt caacagacaa      900
atgtcctcaa caattgtttc taagtaggag aacatctgtc ctcggtggct ttcacaggaa      960
```

<210> SEQ ID NO 38
<211> LENGTH: 960
<212> TYPE: DNA
<213> ORGANISM: Artificial Sequence
<220> FEATURE:
<223> OTHER INFORMATION: 32.3 vector 5' homology arm

<400> SEQUENCE: 38

```
gcttcaggag cagttgtgcg aatagctgga gaacaccagg ctggatttaa acccagatcg       60
ctcttacatt tgctctttac ctgctgtgct cagcgttcac gtgccctcta gctgtagttt      120
tctgaagtca gcgcacagca aggcagtgtg cttagaggtt aacagaaggg aaaacaacaa      180
caacaaaaat ctaaatgaga atcctgactg tttcagctga gagtaagggg ggcggattat      240
tcatataatt gttataccag acggtcgcag gcttagtcca attgcagaga actcgcttcc      300
caggcttctg agagtcccgg aagtgcctaa acctgtctaa tcgacggggc ttgggtggcc      360
cgtcgctccc tggcttcttc cctttaccca ggggcgggcag cgaagtggtg cctcctgcgt      420
cccccacacc ctccctcagc ccctcccctc cggcccgtcc tgggcaggtg acctggagca      480
tccggcaggc tgcctggcc tcctgcgtca ggacaacgcc cacgaggggc gttactgtgc      540
```

| ggagatgcac cacgcaagag acacccttg taactctctt ctcctcccta gtgcgaggtt | 600 |
| aaaaccttca gccccacgtg ctgtttgcaa acctgcctgt acctgaggcc ctaaaaagcc | 660 |
| agagacctca ctcccgggga gccagcatgt ccactgcggt cctggaaaac ccaggcttgg | 720 |
| gcaggaaact ctctgacttt ggacaggtga gccacggcag cctgagctgc tcagttaggg | 780 |
| gaatttgggc ctccagagaa agagatccga agactgctgg tgcttcctgg tttcataagc | 840 |
| tcagtaagaa gtctgaattc gttggaagct gatgagaata tccaggaagt caacagacaa | 900 |
| atgtcctcaa caattgtttc taagtaggag aacatctgtc ctcggtggct ttcacaggaa | 960 |

<210> SEQ ID NO 39
<211> LENGTH: 960
<212> TYPE: DNA
<213> ORGANISM: Artificial Sequence
<220> FEATURE:
<223> OTHER INFORMATION: 32.4 vector 5' homology arm

<400> SEQUENCE: 39

| gcttcaggag cagttgtgcg aatagctgga gaacaccagg ctggatttaa acccagatcg | 60 |
| ctcttacatt tgctctttac ctgctgtgct cagcgttcac gtgccctcta gctgtagttt | 120 |
| tctgaagtca gcgcacagca aggcagtgtg cttagaggtt aacagaaggg aaaacaacaa | 180 |
| caacaaaaat ctaatgaga atcctgactg tttcagctgg gggtaagggg ggcggattat | 240 |
| tcatataatt gttataccag acggtcgcag gcttagtcca attgcagaga actcgcttcc | 300 |
| caggcttctg agagtcccgg aagtgcctaa acctgtctaa tcgacggggc ttgggtggcc | 360 |
| cgtcgctccc tggcttcttc cctttaccca gggcgggcag cgaagtggtg cctcctgcgt | 420 |
| cccccacacc ctccctcagc ccctcccctc cggcccgtcc tgggcaggtg acctggagca | 480 |
| tccggcaggc tgcctggcc tcctgagtca ggacaacgcc cacgagggc gttactgtgc | 540 |
| ggagatgcac cacgcaagag acacccttg taactctctt ctcctcccta gtgcgaggtt | 600 |
| aaaaccttca gccccacgtg ctgtttgcaa acctgcctgt acctgaggcc ctaaaaagcc | 660 |
| agagacctca ctcccgggga gccagcatgt ccactgcggt cctggaaaac ccaggcttgg | 720 |
| gcaggaaact ctctgacttt ggacaggtga gccacggcag cctgagctgc tcagttaggg | 780 |
| gaatttgggc ctccagagaa agagatccga agactgctgg tgcttcctgg tttcataagc | 840 |
| tcagtaagaa gtctgaattc gttggaagct gatgagaata tccaggaagt caacagacaa | 900 |
| atgtcctcaa caattgtttc taagtaggag aacatctgtc ctcggtggct ttcacaggaa | 960 |

<210> SEQ ID NO 40
<211> LENGTH: 960
<212> TYPE: DNA
<213> ORGANISM: Artificial Sequence
<220> FEATURE:
<223> OTHER INFORMATION: 32.5 vector 5' homology arm

<400> SEQUENCE: 40

| gcttcaggag cagttgtgcg aatagctgga gaacaccagg ctggatttaa acccagatcg | 60 |
| ctcttacatt tgctctttac ctgctgtgct cagcgttcac gtgccctcta gctgtagttt | 120 |
| tctgaagtca gcgcacagca aggcagtgtg cttagaggtt aacagaaggg aaaacaacaa | 180 |
| caacaaaaat ctaatgaga atcctgactg tttcagctgg gggtaagggg ggcggattat | 240 |
| tcatataatt gttataccag acggtcgcag gcttagtcca attgcagaga actcgcttcc | 300 |
| caggcttctg agagtcccgg aagtgcctaa acctgtctaa tcgacggggc ttgggtggcc | 360 |

```
cgtcgctccc tggcttcttc cctttaccca gggcgggcag cgaagtggtg cctcctgcgt      420
cccccacacc ctccctcagc ccctcccctc cggcccgtcc tgggcaggtg acgtcaagca      480
tccggcaggc tgccctggcc tcctgagtca ggacaacgcc cacgagggc gttactgtgc       540 ggagatgcac cacgcaagag acacccttg taactctctt ctcctcccta gtgcgaggtt       600
aaaaccttca gccccacgtg ctgtttgcaa acctgcctgt acctgaggcc ctaaaaagcc      660
agagacctca ctcccgggga gccagcatgt ccactgcgt cctggaaaac ccaggcttgg       720
gcaggaaact ctctgacttt ggacaggtga gccacggcag cctgagctgc tcagttaggg      780
gaatttgggc ctccagagaa agagatccga agactgctgg tgcttcctgg tttcataagc     840
tcagtaagaa gtctgaattc gttggaagct gatgagaata tccaggaagt caacagacaa      900
atgtcctcaa caattgtttc taagtaggag aacatctgtc ctcggtggct ttcacaggaa      960
```

<210> SEQ ID NO 41
<211> LENGTH: 960
<212> TYPE: DNA
<213> ORGANISM: Artificial Sequence
<220> FEATURE:
<223> OTHER INFORMATION: 32.6 vector 5' homology arm

<400> SEQUENCE: 41

```
gcttcaggag cagttgtgcg aatagctgga gaacaccagg ctggatttaa acccagatcg       60
ctcttacatt tgctctttac ctgctgtgct cagcgttcac gtgccctcta gctgtagttt      120
tctgaagtca gcgcacagca aggcagtgtg cttagaggtt aacagaaggg aaaacaacaa      180
caacaaaaat ctaaatgaga atcctgactg tttcagctgg gggtaagggg ggcggattat      240
tcatataatt gttataccag acggtcgcag gcttagtcca attgcagaga actcgcttcc      300
caggcttctg agagtcccgg aagtgcctaa acctgtctaa tcgacggggc ttgggtggcc      360
cgtcgctccc tggcttcttc cctttaccca gggcgggcag cgaagtggtg cctcctgcgt      420
cccccacacc ctccctcagc ccctcccctc cggcccgtcc tgggcaggtg acctggagca     480
tccggcaggc tgccctggcc tcctgcgtca ggacaacgcc cacgagggc gttactgtgc       540 ggagatgcac cacgcaagag acacccttg taactctctt ctcctcccta gtgcgaggtt       600
aaaaccttca gccccacgtg ctgtttgcaa acctgcctgt acctgaggcc ctaaaaagcc      660
agagacctca ctcccgggga gccagcatgt ccactgcgt cctggaaaac ccaggcttgg       720
gcaggaaact ctctgacttt ggacaggtga gccacggcag cctgagctgc tcagttaggg      780
gaatttgggc ctccagagaa agagatccga agactgctgg tgcttcctgg tttcataagc     840
tcagtaagaa gtctgaattc gttggaagct gatgagaatg tccaggaagt caacagacaa      900
atgtcctcaa caattgtttc taagtaggag aacatctgtc ctcggtggct ttcacaggaa      960
```

<210> SEQ ID NO 42
<211> LENGTH: 960
<212> TYPE: DNA
<213> ORGANISM: Artificial Sequence
<220> FEATURE:
<223> OTHER INFORMATION: 32.7 vector 5' homology arm

<400> SEQUENCE: 42

```
gcttcaggag cagttgtgcg aatagctgga gaacaccagg ctggatttaa acccagatcg       60
ctcttacatt tgctctttac ctgctgtgct cagcgttcac gtgccctcta gctgtagttt      120
tctgaagtca gcgcacagca aggcagtgtg cttagaggtt aacagaaggg aaaacaacaa      180
caacaaaaat ctaaatgaga atcctgactg tttcagctgg gggtaagggg ggcggattat      240
```

```
tcatataatt gttccaccag acggtcgcag gcttagtcca attgcagaga actcgcttcc      300
caggcttctg agagtcccgg aagtgcctaa acctgtctaa tcgacggggc ttgggtggcc      360
cgtcgctccc tggcttcttc cctttaccca gggcgggcag cgaagtggtg cctcctgcgt      420
cccccacacc ctccctcagc ccctcccctc cggcccgtcc tgggcaggtg acctggagca      480
tccggcaggc tgccctggcc tctgcgtcag gacaacgcc cacgaggggc gttactgtgc       540
ggagatgcac cacgcaagag acaccctttg taactctctt ctcctcccta gtgcgaggtt      600
aaaaccttca gccccacgtg ctgtttgcaa acctgcctgt acctgaggcc ctaaaaagcc      660
agagacctca ctcccgggga gccagcatgt ccactgcggt cctggaaaac ccaggcttgg      720
gcaggaaact ctctgacttt ggacaggtga gccacggcag cctgagctgc tcagttaggg      780
gaatttgggc ctccagagaa agagatccga agactgctgg tgcttcctgg tttcataagc      840
tcagtaagaa gtctgaattc gttggaagct gatgagaata tccaggaagt caacagacaa      900
atgtcctcaa caattgtttc taagtaggag aacatctgtc ctcggtggct ttcacaggaa      960
```

<210> SEQ ID NO 43
<211> LENGTH: 968
<212> TYPE: DNA
<213> ORGANISM: Artificial Sequence
<220> FEATURE:
<223> OTHER INFORMATION: 32.8 vector 5' homology arm

<400> SEQUENCE: 43

```
gcttcaggag cagttgtgcg aatagctgga gaacaccagg ctggatttaa acccagatcg       60
ctcttacatt tgctctttac ctgctgtgct cagcgttcac gtgccctcta gctgtagttt      120
tctgaagtca gcgcacagca aggcagtgtg cttagaggtt aacagaaggg aaaacaacaa      180
caacaaaaat ctaaatgaga atcctgactg tttcagctgg gggtaagggg ggcggattat      240
tcatataatt gttccaccag acggtcgcag gcttagtcca attgcagaga acacgctgtt      300
cttcgcccca ggcttctgag agtcccggaa gtgcctaaac ctgtctaatc gacggggctt      360
gggtggcccg tcgctccctg gcttcttccc tttacccagg gcgggcagcg aagtggtgcc      420
tcctgcgtcc cccacaccct ccctcagccc ctcccctccg gcccgtcctg ggcaggtgac      480
ctggagcatc cggcaggctg ccctggcctc tgcgtcagg acaacgccca cgagggggcgt      540 tactgtgcgg agatgcacca cgcaagagac ccctttgta actctcttct cctcccctagt      600 gcgaggttaa aaccttcagc cccacgtgct gtttgcaaac ctgcctgtac ctgaggccct      660
aaaaagccag agacctcact cccggggagc cagcatgtcc actgcggtcc tggaaaaccc      720
aggcttgggc aggaaactct ctgactttgg acaggtgagc cacggcagcc tgagctgctc      780
agttagggga atttgggcct ccagagaaag agatccgaag actgctggtg cttcctggtt      840
tcataagctc agtaagaagt ctgaattcgt tggaagctga tgagaatatc caggaagtca      900
acagacaaat gtcctcaaca attgtttcta agtaggagaa catctgtcct cggtggcttt      960
cacaggaa                                                             968
```

<210> SEQ ID NO 44
<211> LENGTH: 960
<212> TYPE: DNA
<213> ORGANISM: Artificial Sequence
<220> FEATURE:
<223> OTHER INFORMATION: 32.9 vector 5' homology arm

<400> SEQUENCE: 44

```
gcttcaggag cagttgtgcg aatagctgga gaacaccagg ctggatttaa acccagatcg    60
ctcttacatt tgctctttac ctgctgtgct cagcgttcac gtgccctcta gctgtagttt   120
tctgaagtca gcgcacagca aggcagtgtg cttagaggtt aacagaaggg aaaacaacaa   180
caacaaaaat ctaaatgaga atcctgactg tttcagctga gagtaagggg ggcggattat   240
tcatataatt gttataccag acggtcgcag gcttagtcca attgcagaga actcgcttcc   300
caggcttctg agagtcccgg aagtgcctaa acctgtctaa tcgacagagc ttgggtggcc   360
cgtcgctccc tggcttcttc cctttaccca gggcgggcag cgaagtggtg cctcctgcgt   420
cccccacacc ctccctcagc ccctcccctc cggcccgtcc taggcaggtg acctgaagca   480
tccagcaggc tgccctggcc tcctgcgtca ggacaacgcc cacgaggggc gttactgtgc   540
ggagatgcac cacgcaagag acacccttg taactctctt ctcctcccta gtgcgaggtt   600
aaaaccttca gccccacgtg ctgtttgcaa acctgcctgt acctgaggcc ctaaaaagcc   660
agagacctca ctcccgggga gccagcatgt ccactgcggt cctggaaaac ccaggcttgg   720
gcaggaaact ctctgacttt ggacaggtga gccacgcag cctgagctgc tcagttaggg   780
gaatttgggc tccagagaa agagatccga agactgctgg tgcttcctgg tttcataagc   840
tcagtaagaa gtctgaattc gttggaagct gatgagaata tccaggaagt caacagacaa   900
atgtcctcaa caattgtttc taagtaggag aacatctgtc ctcggtggct ttcacaggaa   960
```

<210> SEQ ID NO 45
<211> LENGTH: 911
<212> TYPE: DNA
<213> ORGANISM: Homo sapiens

<400> SEQUENCE: 45

```
ctgggatggg atgtggaatc cttctagatt tcttttgtaa tatttataaa gtgctctcag    60
caaggtatca aaatggcaaa attgtgagta actatcctcc tttcattttg ggaagaagat   120
gaggcatgaa gagaattcag acagaaactt actcagacca ggggaggcag aaactaagca   180
gagaggaaaa tgaccaagag ttagccctgg gcatggaatg tgaaagaacc ctaaacgtga   240
cttggaaata tgcccaagg tatattccat tctccgggat ttgttggcat tttcttgagg   300
tgaagaattg cagaatacat tctttaatgt gacctacata tttacccatg ggaggaagtc   360
tgctcctgga ctcttgagat tcagtcataa agcccaggcc agggaaataa tgtaagtctg   420
caggcccctg tcatcagtag gattagggag aagagttctc agtagaaaac agggaggctg   480
gagagaaaag aatggttaat gttaacgtta atataactag aaagactgca gaacttagga   540 ctgatttta tttgaatcct taaaaaaaaa aatttcttat gaaaatagta catggctctt   600
aggagacaga acttattgta cagaggaaca gcgtgagagt cagagtgatc ccagaacagg   660
tcctggctcc atcctgcaca tagttttggt gctgctggca atacggtccc cacaactgtg   720 ggaagggggtt aggggcaggg atctcatcag gaaagcatag gggtttaaag ttctttatag   780
agcacttaga agattgagaa tccacaaatt atattaataa caaacaaagt agtgtcgtgt   840
tatatagtaa atgtgaattt gcagacacat ttagggaaaa gttataatta aaaaaatagg   900
ctgtatatat a                                                         911
```

<210> SEQ ID NO 46
<211> LENGTH: 3537
<212> TYPE: DNA
<213> ORGANISM: Artificial Sequence
<220> FEATURE:
<223> OTHER INFORMATION: 32.1 vector correction genome

<400> SEQUENCE: 46

```
gcttcaggag cagttgtgcg aatagctgga gaacaccagg ctggatttaa acccagatcg      60
ctcttacatt tgctctttac ctgctgtgct cagcgttcac gtgccctcta gctgtagttt     120
tctgaagtca gcgcacagca aggcagtgtg cttagaggtt aacagaaggg aaaacaacaa     180
caacaaaaat ctaaatgaga atcctgactg tttcagctgg gggtaagggg ggcggattat     240
tcatataatt gttataccag acggtcgcag gcttagtcca attgcagaga actcgcttcc     300
caggcttctg agagtcccgg aagtgcctaa acctgtctaa tcgacggggc ttgggtggcc     360
cgtcgctccc tggcttcttc cctttaccca gggcgggcag cgaagtggtg cctcctgcgt     420
cccccacacc ctccctcagc ccctcccctc cggcccgtcc tgggcaggtg acctggagca     480
tccggcaggc tgccctggcc tcctgcgtca ggacaacgcc cacgaggggc gttactgtgc     540
ggagatgcac cacgcaagag acacccttttg taactctctt ctcctcccta gtgcgaggtt     600
aaaaccttca gccccacgtg ctgtttgcaa acctgcctgt acctgaggcc ctaaaaagcc     660
agagacctca ctcccgggga gccagcatgt ccactgcggt cctggaaaac ccaggcttgg     720
gcaggaaact ctctgacttt ggacaggtga gccacggcag cctgagctgc tcagttaggg     780
gaatttgggc ctccagagaa agagatccga agactgctgg tgcttcctgg tttcataagc     840
tcagtaagaa gtctgaattc gttggaagct gatgagaata tccaggaagt caacagacaa     900
atgtcctcaa caattgtttc taagtaggag aacatctgtc ctcggtggct ttcacaggaa     960
aagcttctga cctcttctct tcctcccaca gggcagcgga gctactaact tcagcctgct    1020
gaagcaggct ggagacgtgg aggagaaccc tggacctatg tccaccgctg tgctggagaa    1080
ccctgggctg gggaggaaac tgtcagactt cgggcaggag acttcataca ttgaggataa    1140
ctgtaaccag aatggcgcca tctctctgat cttcagcctg aaggaggaag tgggcgccct    1200
ggcaaaggtg ctgcgcctgt ttgaggaaa cgacgtgaat ctgacccaca tcgagtcccg    1260
gccttctaga ctgaagaagg acgagtacga gttctttacc cacctggata gcgggtccct    1320
gccagccctg acaaacatca tcaagatcct gaggcacgac atcggagcaa ccgtgcacga    1380
gctgtctcgg gacaagaaga aggataccgt gccctggttc cctcgacaa tccaggagct    1440
ggatagattt gccaaccaga tcctgtctta cggagcagag ctggacgcag atcaccctgg    1500
cttcaaggac ccagtgtatc gggcccggag aaagcagttt gccgatatcg cctacaatta    1560
taggcacgga cagccaatcc ctcgcgtgga gtatatggag gaggagaaga agacctgggg    1620
cacagtgttc aagaccctga agagcctgta caagacacac gcctgctacg agtataacca    1680
catcttcccc ctgctggaga agtattgtgg cttttcacgag gacaatatcc ctcagctgga    1740
ggacgtgagc cagttcctgc agacctgcac aggctttagg ctgaggccag tggcaggact    1800
gctgagctcc cgggacttcc tgggaggact ggccttcaga gtgtttcact gcacccagta    1860
catcaggcac ggctccaagc caatgtatac accagagccc gacatctgtc acgagctgct    1920
gggccacgtg cccctgttta gcgatagatc cttcgcccag ttttcccagg agatcggact    1980
ggcatctctg ggagcacctg acgagtacat cgagaagctg gccaccatct attggttcac    2040
agtggagttt ggcctgtgca agcagggcga tagcatcaag gcctacgag caggactgct    2100
gtctagcttc ggcgagctgc agtattgtct gtccgagaag ccaaagctgc tgcccctgga    2160
gctggagaag accgccatcc agaactacac cgtgacagag ttccagcccc tgtactatgt    2220
ggccgagtct tttaacgatg ccaaggagaa ggtgagaaat ttcgccgcca caatccctag    2280
```

```
gcccttcagc gtgcggtacg acccttatac ccagaggatc gaggtgctgg ataatacaca    2340
gcagctgaag atcctggctg actcaatcaa tagcgaaatc ggaatcctgt gctccgccct    2400
gcagaaaatc aaatgaggta ccgatccaga catgataaga tacattgatg agtttggaca    2460
aaccacaact agaatgcagt gaaaaaaatg ctttatttgt gaaatttgtg atgctattgc    2520
tttatttgta accattataa gctgcaataa acaagttaac aacaacaatt gcattcattt    2580
tatgtttcag gttcagggggg aggtgtggga ggttttttaa ggatccctgg gatgggatgt    2640
ggaatccttc tagatttctt ttgtaatatt tataaagtgc tctcagcaag gtatcaaaat    2700
ggcaaaattg tgagtaacta tcctcctttc attttgggaa gaagatgagg catgaagaga    2760
attcagacag aaacttactc agaccagggg aggcagaaac taagcagaga ggaaaatgac    2820
caagagttag ccctgggcat ggaatgtgaa agaaccctaa acgtgacttg gaaataatgc    2880
ccaaggtata ttccattctc cgggatttgt tggcattttc ttgaggtgaa gaattgcaga    2940
atacattctt taatgtgacc tacatattta cccatgggag gaagtctgct cctggactct    3000
tgagattcag tcataaagcc caggccaggg aaataatgta agtctgcagg cccctgtcat    3060
cagtaggatt agggagaaga gttctcagta gaaaacaggg aggctggaga gaaaagaatg    3120
gttaatgtta acgttaatat aactagaaag actgcagaac ttaggactga tttttatttg    3180
aatccttaaa aaaaaaaatt tcttatgaaa atagtacatg gctcttagga gacagaactt    3240
attgtacaga ggaacagcgt gagagtcaga gtgatcccag aacaggtcct ggctccatcc    3300
tgcacatagt tttggtgctg ctggcaatac ggtccccaca actgtgggaa ggggttaggg    3360
gcagggatct catcaggaaa gcatagggt ttaaagttct ttatagagca cttagaagat    3420
tgagaatcca caattatat taataacaaa caaagtagtg tcgtgttata tagtaaatgt    3480
gaatttgcag acacatttag ggaaaagtta taattaaaaa aataggctgt atatata       3537

<210> SEQ ID NO 47
<211> LENGTH: 3537
<212> TYPE: DNA
<213> ORGANISM: Artificial Sequence
<220> FEATURE:
<223> OTHER INFORMATION: 32.2 vector correction genome

<400> SEQUENCE: 47
gcttcaggag cagttgtgcg aatagctgga gaacaccagg ctggatttaa acccagatcg     60
ctcttacatt tgctctttac ctgctgtgct cagcgttcac gtgccctcta gctgtagttt    120
tctgaagtca gcgcacagca aggcagtgtg cttagaggtt aacagaaggg aaaacaacaa    180
caacaaaaat ctaaatgaga atcctgactg tttcagctgg gggtaagggg ggcggattat    240
tcatataatt gttataccag acggtcgcag gcttagtcca attgcagaga actcgcttcc    300
caggcttctg agagtcccgg aagtgcctaa acctgtctaa tcgacggggc ttgggtggcc    360
cgtcgctccc tggcttcttc cctttaccca gggcgggcag cgaagtggtg cctcctgcgt    420
cccccacacc ctccctcagc ccctcccctc cggcccgtcc tgggcaggtg acctggagca    480
tccggcaggc tgccctggcc tcctgcgtca ggacaacgcc cacgagggc gttactgtgc    540 ggagatgcac cacgcaagag acacccttg taactctctt ctcctcccta gtgcgaggtt    600
aaaaccttca gccccacgtg ctgtttgcaa acctgctgt acctgaggcc ctaaaaagcc    660
agagacctca ctcccgggga gccaccatgg cggcggcggt cctggaaaac ccaggcttgg    720
gcaggaaact ctctgacttt ggacaggtga gccacgcag cctgagctgc tcagttaggg    780
gaatttgggc ctccagagaa agagatccga agactgctgg tgcttcctgg tttcataagc    840
```

```
tcagtaagaa gtctgaattc gttggaagct gatgagaata tccaggaagt caacagacaa    900
atgtcctcaa caattgtttc taagtaggag aacatctgtc ctcggtggct ttcacaggaa    960
aagcttctga cctcttctct tcctcccaca gggcagcgga gctactaact tcagcctgct   1020
gaagcaggct ggagacgtgg aggagaaccc tggacctatg tccaccgctg tgctggagaa   1080
ccctgggctg gggaggaaac tgtcagactt cgggcaggag acttcataca ttgaggataa   1140
ctgtaaccag aatggcgcca tctctctgat cttcagcctg aaggaggaag tgggcgccct   1200
ggcaaaggtg ctgcgcctgt ttgaggagaa cgacgtgaat ctgacccaca tcgagtcccg   1260
gccttctaga ctgaagaagg acgagtacga gttctttacc cacctggata gcggtccct   1320 gccagccctg acaaacatca tcaagatcct gaggcacgac atcggagcaa ccgtgcacga   1380
gctgtctcgg gacaagaaga aggataccgt gccctggttc cctcggacaa tccaggagct   1440
ggatagattt gccaaccaga tcctgtctta cggagcagag ctggacgcag atcaccctgg   1500
cttcaaggac ccagtgtatc gggcccggag aaagcagttt gccgatatcg cctacaatta   1560
taggcacgga cagccaatcc ctcgcgtgga gtatatggag gaggagaaga agacctgggg   1620
cacagtgttc aagaccctga agagcctgta caagacacac gcctgctacg agtataacca   1680
catcttcccc ctgctggaga gtattgtgg cttcacgag gacaatatcc ctcagctgga   1740
ggacgtgagc cagttcctgc agacctgcac aggctttagg ctgaggccag tggcaggact   1800
gctgagctcc cggacttcc tgggaggact ggccttcaga gtgtttcact gcacccagta   1860
catcaggcac ggctccaagc caatgtatac accagagccc gacatctgtc acgagctgct   1920
gggccacgtg cccctgttta gcgatagatc cttcgcccag ttttcccagg agatcggact   1980
ggcatctctg ggagcacctg acgagtacat cgagaagctg gccaccatct attggttcac   2040
agtggagttt ggcctgtgca gcagggcga tagcatcaag gcctacggag caggactgct   2100
gtctagcttc ggcgagctgc agtattgtct gtccgagaag ccaaagctgc tgccctgga   2160 gctggagaag accgccatcc agaactacac cgtgacagag ttccagccc tgtactatgt   2220 ggccgagtct tttaacgatg ccaaggagaa ggtgagaaat ttcgccgcca caatccctag   2280
gcccttcagc gtgcggtacg acccttatac ccagaggatc gaggtgctgg ataatacaca   2340
gcagctgaag atcctggctg actcaatcaa tagcgaaatc ggaatcctgt gctccgccct   2400
gcagaaaatc aaatgaggta ccgatccaga catgataaga tacattgatg agtttggaca   2460
aaccacaact agaatgcagt gaaaaaaatg ctttatttgt gaaatttgtg atgctattgc   2520
tttatttgta accattataa gctgcaataa acaagttaac aacaacaatt gcattcattt   2580
tatgtttcag gttcaggggg aggtgtggga ggttttttaa ggatccctgg gatgggatgt   2640
ggaatccttc tagatttctt ttgtaatatt tataaagtgc tctcagcaag gtatcaaaat   2700
ggcaaaattg tgagtaacta tcctcctttc attttgggaa gaagatgagg catgaagaga   2760
attcagacag aaacttactc agaccagggg aggcagaaac taagcagaga ggaaaatgac   2820
caagagttag ccctgggcat ggaatgtgaa agaaccctaa acgtgacttg gaaataatgc   2880
ccaaggtata ttccattctc cgggatttgt tggcattttc ttgaggtgaa gaattgcaga   2940
atacattctt taatgtgacc tacatattta cccatgggag gaagtctgct cctggactct   3000
tgagattcag tcataaagcc caggccaggg aaataatgta agtctgcagg ccctgtcat   3060 cagtaggatt agggagaaga gttctcagta gaaaacaggg aggctggaga gaaaagaatg   3120
gttaatgtta acgttaatat aactagaaag actgcagaac ttaggactga tttttatttg   3180
```

| | |
|---|---|
| aatccttaaa aaaaaaaatt tcttatgaaa atagtacatg gctcttagga gacagaactt | 3240 |
| attgtacaga ggaacagcgt gagagtcaga gtgatcccag aacaggtcct ggctccatcc | 3300 |
| tgcacatagt tttggtgctg ctggcaatac ggtccccaca actgtgggaa ggggttaggg | 3360 |
| gcagggatct catcaggaaa gcatagqggt ttaaagttct ttatagagca cttagaagat | 3420 |
| tgagaatcca caattatat taataacaaa caaagtagtg tcgtgttata tagtaaatgt | 3480 |
| gaatttgcag acacatttag ggaaaagtta taattaaaaa aataggctgt atatata | 3537 |

<210> SEQ ID NO 48
<211> LENGTH: 3537
<212> TYPE: DNA
<213> ORGANISM: Artificial Sequence
<220> FEATURE:
<223> OTHER INFORMATION: 32.3 vector correction genome

<400> SEQUENCE: 48

| | |
|---|---|
| gcttcaggag cagttgtgcg aatagctgga gaacaccagg ctggatttaa acccagatcg | 60 |
| ctcttacatt tgctctttac ctgctgtgct cagcgttcac gtgccctcta gctgtagttt | 120 |
| tctgaagtca gcgcacagca aggcagtgtg cttagaggtt aacagaaggg aaaacaacaa | 180 |
| caacaaaaat ctaaatgaga atcctgactg tttcagctga gagtaagggg gcggattat | 240 |
| tcatataatt gttataccag acggtcgcag gcttagtcca attgcagaga actcgcttcc | 300 |
| caggcttctg agagtcccgg aagtgcctaa acctgtctaa tcgacggggc ttgggtggcc | 360 |
| cgtcgctccc tggcttcttc cctttaccca gggcgggcag cgaagtggtg cctcctgcgt | 420 |
| cccccacacc ctccctcagc ccctcccctc cggcccgtcc tgggcaggtg acctggagca | 480 |
| tccggcaggc tgccctggcc tctgcgtcca ggacaacgcc cacgagggc gttactgtgc | 540 |
| ggagatgcac cacgcaagag acacccttg taactctctt ctcctcccta gtgcgaggtt | 600 |
| aaaaccttca gccccacgtg ctgtttgcaa acctgcctgt acctgaggcc ctaaaaagcc | 660 |
| agagacctca ctcccgggga gccagcatgt ccactgcgt cctggaaaac ccaggcttgg | 720 |
| gcaggaaact ctctgacttt ggacaggtga gccacggcag cctgagctgc tcagttaggg | 780 |
| gaatttgggc ctccagagaa agagatccga agactgctgg tgcttcctgg tttcataagc | 840 |
| tcagtaagaa gtctgaattc gttggaagct gatgagaata tccaggaagt caacagacaa | 900 |
| atgtcctcaa caattgtttc taagtaggag aacatctgtc ctcggtggct ttcacaggaa | 960 |
| aagcttctga cctcttctct tcctcccaca gggcagcgga gctactaact tcagcctgct | 1020 |
| gaagcaggct ggagacgtgg aggagaaccc tggacctatg tccaccgctg tgctggagaa | 1080 |
| ccctgggctg gggaggaaac tgtcagactt cgggcaggag acttcataca ttgaggataa | 1140 |
| ctgtaaccag aatggcgcca tctctctgat cttcagcctg aaggaggaag tgggcgccct | 1200 |
| ggcaaaggtg ctgcgcctgt tgaggagaa cgacgtgaat ctgacccaca tcgagtcccg | 1260 |
| gccttctaga ctgaagaagg acgagtacga gttctttacc cacctggata gcggtccct | 1320 |
| gccagccctg acaaacatca tcaagatcct gaggcacgca atcggagcaa ccgtgcacga | 1380 |
| gctgtctcgg gacaagaaga aggataccgt gccctggttc cctcggacaa tccaggagct | 1440 |
| ggatagattt gccaaccaga tcctgtctta cggagcagag ctgacgcag atcccctgg | 1500 |
| cttcaaggac ccagtgtatc gggcccggag aaagcagttt gccgatatcg cctacaatta | 1560 |
| taggcacgga cagccaatcc ctcgcgtgga gtatatggag gaggagaaga agacctgggg | 1620 |
| cacagtgttc aagaccctga agagcctgta caagacacac gcctgctacg agtataacca | 1680 |
| catcttcccc ctgctggaga agtattgtgg ctttcacgag gacaatatcc ctcagctgga | 1740 |

```
ggacgtgagc cagttcctgc agacctgcac aggctttagg ctgaggccag tggcaggact    1800
gctgagctcc cgggacttcc tgggaggact ggccttcaga gtgtttcact gcacccagta    1860
catcaggcac ggctccaagc caatgtatac accagagccc gacatctgtc acgagctgct    1920
gggccacgtg cccctgttta gcgatagatc cttcgcccag ttttcccagg agatcggact    1980
ggcatctctg ggagcacctg acgagtacat cgagaagctg ccaccatct attggttcac     2040 agtggagttt ggcctgtgca agcagggcga tagcatcaag gcctacgag caggactgct     2100 gtctagcttc ggcgagctgc agtattgtct gtccgagaag ccaaagctgc tgcccctgga    2160
gctggagaag accgccatcc agaactacac cgtgacagag ttccagcccc tgtactatgt    2220
ggccgagtct tttaacgatg ccaaggagaa ggtgagaaat ttcgccgcca caatccctag    2280
gcccttcagc gtgcggtacg acccttatac ccagaggatc gaggtgctgg ataatacaca    2340
gcagctgaag atcctggctg actcaatcaa tagcgaaatc ggaatcctgt gctccgccct    2400
gcagaaaatc aaatgaggta ccgatccaga catgataaga tacattgatg agtttggaca    2460
aaccacaact agaatgcagt gaaaaaaatg ctttatttgt gaaatttgtg atgctattgc    2520
tttatttgta accattataa gctgcaataa acaagttaac aacaacaatt gcattcattt    2580
tatgtttcag gttcaggggg aggtgtggga ggtttttaa ggatccctgg gatgggatgt     2640
ggaatccttc tagatttctt ttgtaatatt tataaagtgc tctcagcaag gtatcaaaat    2700
ggcaaaattg tgagtaacta tcctcctttc attttgggaa gaagatgagg catgaagaga    2760
attcagacag aaacttactc agaccagggg aggcagaaac taagcagaga ggaaaatgac    2820
caagagttag ccctgggcat ggaatgtgaa agaaccctaa acgtgacttg gaaataatgc    2880
ccaaggtata ttccattctc cgggatttgt tggcattttc ttgaggtgaa gaattgcaga    2940
atacattctt taatgtgacc tacatattta cccatgggag gaagtctgct cctggactct    3000
tgagattcag tcataaagcc caggccaggg aaataatgta agtctgcagg cccctgtcat    3060
cagtaggatt agggagaaga gttctcagta gaaaacaggg aggctggaga gaaaagaatg    3120
gttaatgtta acgttaatat aactagaaag actgcagaac ttaggactga ttttatttg     3180 aatccttaaa aaaaaaatt tcttatgaaa atagtacatg gctcttagga gacagaactt     3240
attgtacaga ggaacagcgt gagagtcaga gtgatcccag aacaggtcct ggctccatcc    3300
tgcacatagt tttggtgctg ctggcaatac ggtccccaca actgtgggaa ggggttaggg    3360
gcagggatct catcaggaaa gcatagggt ttaaagttct ttatagagca cttagaagat     3420
tgagaatcca caaattatat taataacaaa caaagtagtc tcgtgttata tagtaaatgt    3480
gaatttgcag acacatttag ggaaaagtta taattaaaaa aataggctgt atatata       3537
```

<210> SEQ ID NO 49
<211> LENGTH: 3537
<212> TYPE: DNA
<213> ORGANISM: Artificial Sequence
<220> FEATURE:
<223> OTHER INFORMATION: 32.4 vector correction genome

<400> SEQUENCE: 49

```
gcttcaggag cagttgtgcg aatagctgga gaacaccagg ctggatttaa acccagatcg      60
ctcttacatt tgctctttac ctgctgtgct cagcgttcac gtgccctcta gctgtagttt     120
tctgaagtca gcgcacagca aggcagtgtg cttagaggtt aacagaaggg aaaacaacaa     180
caacaaaaat ctaaatgaga atcctgactg tttcagctgg gggtaagggg ggcggattat     240
```

```
tcatataatt gttataccag acggtcgcag gcttagtcca attgcagaga actcgcttcc    300
caggcttctg agagtcccgg aagtgcctaa acctgtctaa tcgacggggc ttgggtggcc    360
cgtcgctccc tggcttcttc cctttaccca gggcgggcag cgaagtggtg cctcctgcgt    420
cccccacacc ctccctcagc ccctcccctc cggcccgtcc tgggcaggtg acctggagca    480
tccggcaggc tgccctggcc tcctgagtca ggacaacgcc cacgaggggc gttactgtgc    540
ggagatgcac cacgcaagag acacccttg taactctctt ctcctcccta gtgcgaggtt    600
aaaaccttca gccccacgtg ctgtttgcaa acctgcctgt acctgaggcc ctaaaaagcc    660
agagacctca ctcccgggga gccagcatgt ccactgcggt cctggaaaac ccaggcttgg    720
gcaggaaact ctctgacttt ggacaggtga gccacggcag cctgagctgc tcagttaggg    780
gaatttgggc ctccagagaa agagatccga agactgctgg tgcttcctgg tttcataagc    840
tcagtaagaa gtctgaattc gttggaagct gatgagaata tccaggaagt caacagacaa    900
atgtcctcaa caattgtttc taagtaggag aacatctgtc ctcggtggct ttcacaggaa    960
aagcttctga cctcttctct tcctcccaca gggcagcgga gctactaact tcagcctgct   1020
gaagcaggct ggagacgtgg aggagaaccc tggacctatg tccaccgctg tgctggagaa   1080
ccctgggctg gggaggaaac tgtcagactt cgggcaggaa acttcataca ttgaggataa   1140
ctgtaaccag aatggcgcca tctctctgat cttcagcctg aaggaggaag tgggcgccct   1200
ggcaaaggtg ctgcgcctgt ttgaggagaa cgacgtgaat ctgacccaca tcgagtcccg   1260
gccttctaga ctgaagaagg acgagtacga gttctttacc cacctggata gcggtccct    1320 gccagccctg acaaacatca tcaagatcct gaggcacgac atcggagcaa ccgtgcacga   1380
gctgtctcgg gacaagaaga aggataccgt gccctggttc cctcggacaa tccaggagct   1440
ggatagattt gccaaccaga tcctgtctta cggagcagag ctggacgcag atcaccctgg   1500
cttcaaggac ccagtgtatc gggcccggag aaagcagttt gccgatatcg cctacaatta   1560
taggcacgga cagccaatcc ctcgcgtgga gtatatggag gaggagaaga gacctgggg    1620 cacagtgttc aagaccctga gagcctgta caagacacac gcctgctacg agtataacca   1680
catcttcccc ctgctggaga agtattgtgg ctttcacgag acaatatcc ctcagctgga    1740 ggacgtgagc cagttcctgc agacctgcac aggctttagg ctgaggccag tggcaggact   1800
gctgagctcc cgggacttcc tgggaggact ggccttcaga gtgtttcact gcacccagta   1860
catcaggcac ggctccaagc caatgtatac accagagccc gacatctgtc acgagctgct   1920
gggccacgtg cccctgtta gcgatagatc cttcgcccag ttttcccagg atcggact     1980 ggcatctctg ggagcacctg acgagtacat cgagaagctg gccaccatct attggttcac   2040
agtggagttt ggcctgtgca gcagggcga tagcatcaag gcctacgag caggactgct    2100 gtctagcttc ggcgagctgc agtattgtct gtccgagaag ccaaagctgc tgcccctgga   2160
gctggagaag accgccatcc agaactacac cgtgacagag ttccagcccc tgtactatgt   2220
ggccgagtct tttaacgatg ccaaggagaa ggtgagaaat ttcgccgcca caatccctag   2280
gcccttcagc gtgcggtacg acccttatac ccagaggatc gaggtgctgg ataatacaca   2340
gcagctgaag atcctggctg actcaatcaa tagcgaaatc ggaatcctgt gctccgccct   2400
gcagaaaatc aaatgaggta ccgatccaga catgataaga tacattgatg agtttggaca   2460
aaccacaact agaatgcagt gaaaaaaatg ctttatttgt gaaatttgtg atgctattgc   2520
tttatttgta accattataa gctgcaataa acaagttaac aacaacaatt gcattcattt   2580
tatgtttcag gttcagggg aggtgtggga ggttttttaa ggatccctgg gatgggatgt    2640
```

```
ggaatccttc tagatttctt ttgtaatatt tataaagtgc tctcagcaag gtatcaaaat    2700
ggcaaaattg tgagtaacta tcctcctttc attttgggaa gaagatgagg catgaagaga    2760
attcagacag aaacttactc agaccagggg aggcagaaac taagcagaga ggaaaatgac    2820
caagagttag ccctgggcat ggaatgtgaa agaaccctaa acgtgacttg gaaataatgc    2880
ccaaggtata ttccattctc cgggatttgt tggcattttc ttgaggtgaa gaattgcaga    2940
atacattctt taatgtgacc tacatattta cccatgggag gaagtctgct cctggactct    3000
tgagattcag tcataaagcc caggccaggg aaataatgta agtctgcagg ccctgtcat    3060 cagtaggatt agggagaaga gttctcagta gaaaacaggg aggctggaga gaaaagaatg    3120
gttaatgtta acgttaatat aactagaaag actgcagaac ttaggactga tttttatttg    3180
aatccttaaa aaaaaaaatt tcttatgaaa atagtacatg gctcttagga gacagaactt    3240
attgtacaga ggaacagcgt gagagtcaga gtgatcccag aacaggtcct ggctccatcc    3300
tgcacatagt tttggtgctg ctggcaatac ggtccccaca actgtgggaa ggggttaggg    3360
gcagggatct catcaggaaa gcataggggt ttaaagttct ttatagagca cttagaagat    3420
tgagaatcca caaattatat taataacaaa caaagtagtg tcgtgttata tagtaaatgt    3480
gaatttgcag acacatttag ggaaaagtta taattaaaaa aataggctgt atatata       3537
```

<210> SEQ ID NO 50
<211> LENGTH: 3537
<212> TYPE: DNA
<213> ORGANISM: Artificial Sequence
<220> FEATURE:
<223> OTHER INFORMATION: 32.5 vector correction genome

<400> SEQUENCE: 50

```
gcttcaggag cagttgtgcg aatagctgga gaacaccagg ctggatttaa acccagatcg      60
ctcttacatt tgctctttac ctgctgtgct cagcgttcac gtgccctcta gctgtagttt     120
tctgaagtca gcgcacagca aggcagtgtg cttagaggtt aacagaaggg aaaacaacaa     180
caacaaaaat ctaaatgaga atcctgactg tttcagctgg gggtaagggg ggcggattat     240
tcatataatt gttataccag acggtcgcag gcttagtcca attgcagaga actcgcttcc     300
caggcttctg agagtcccgg aagtgcctaa acctgtctaa tcgacggggc ttgggtggcc     360
cgtcgctccc tggcttcttc cctttaccca gggcgggcag cgaagtggtg cctcctgcgt     420
cccccacacc ctccctcagc ccctcccctc cggcccgtcc tgggcaggtg acgtcaagca     480
tccggcaggc tgccctggcc tcctgagtca ggacaacgcc cacgaggggc gttactgtgc     540
ggagatgcac cacgcaagag acacccttg taactctctt ctcctcccta gtgcgaggtt      600
aaaaccttca gccccacgtg ctgtttgcaa acctgcctgt acctgaggcc ctaaaaagcc     660
agagacctca ctcccgggga gccagcatgt ccactgcggt cctggaaaac ccaggcttgg     720
gcaggaaact ctctgacttt ggacaggtga gccacggcag cctgagctgc tcagttaggg     780
gaatttgggc ctccagagaa agagatccga agactgctgg tgcttcctgg tttcataagc     840
tcagtaagaa gtctgaattc gttggaagct gatgagaata tccaggaagt caacagacaa     900
atgtcctcaa caattgtttc taagtaggag aacatctgtc ctcggtggct ttcacaggaa     960
aagcttctga cctcttctct tcctcccaca gggcagcgga gctactaact tcagcctgct    1020
gaagcaggct ggagacgtgg aggagaaccc tggacctatg tccaccgctg tgctggagaa    1080
ccctgggctg gggaggaaac tgtcagactt cgggcaggag acttcataca ttgaggataa    1140
```

-continued

```
ctgtaaccag aatggcgcca tctctctgat cttcagcctg aaggaggaag tgggcgccct    1200
ggcaaaggtg ctgcgcctgt ttgaggagaa cgacgtgaat ctgacccaca tcgagtcccg    1260
gccttctaga ctgaagaagg acgagtacga gttctttacc cacctggata agcggtccct    1320
gccagccctg acaaacatca tcaagatcct gaggcacgac atcggagcaa ccgtgcacga    1380
gctgtctcgg gacaagaaga aggataccgt gccctggttc cctcggacaa tccaggagct    1440
ggatagattt gccaaccaga tcctgtctta cggagcagag ctggacgcag atcaccctgg    1500
cttcaaggac ccagtgtatc gggcccggag aaagcagttt gccgatatcg cctacaatta    1560
taggcacgga cagccaatcc ctcgcgtgga gtatatggag gaggagaaga agacctgggg    1620
cacagtgttc aagaccctga gagcctgta caagacacac gcctgctacg agtataacca    1680
catcttcccc ctgctggaga agtattgtgg cttttcacgag acaatatccc ctcagctgga    1740
ggacgtgagc cagttcctgc agacctgcac aggctttagg ctgaggccag tggcaggact    1800
gctgagctcc cgggacttcc tgggaggact ggccttcaga gtgtttcact gcacccagta    1860
catcaggcac ggctccaagc caatgtatac accagagccc gacatctgtc acgagctgct    1920
gggccacgtg cccctgttta gcgatagatc cttcgcccag ttttcccagg agatcggact    1980
ggcatctctg ggagcacctg acgagtacat cgagaagctg gccaccatct attggttcac    2040
agtggagttt ggcctgtgca gcagggcga tagcatcaag gcctacggag caggactgct    2100
gtctagcttc ggcgagctgc agtattgtct gtccgagaag ccaaagctgc tgccctgga    2160 gctggagaag accgccatcc agaactacac cgtgacagag ttccagccc tgtactatgt    2220 ggccgagtct tttaacgatg ccaaggagaa ggtgagaat tcgccgcca caatccctag    2280 gcccttcagc gtgcggtacg acccttatac ccagaggatc gaggtgctgg ataatacaca    2340
gcagctgaag atcctggctg actcaatcaa tagcgaaatc ggaatcctgt gctccgccct    2400
gcagaaaatc aaatgaggta ccgatccaga catgataaga tacattgatg agtttggaca    2460
aaccacaact agaatgcagt gaaaaaaatg ctttatttgt gaaatttgtg atgctattgc    2520
tttatttgta accattataa gctgcaataa acaagttaac aacaacaatt gcattcattt    2580
tatgtttcag gttcagggg aggtgtggga ggttttttaa ggatccctgg gatgggatgt    2640
ggaatccttc tagatttctt ttgtaatatt tataaagtgc tctcagcaag gtatcaaaat    2700
ggcaaaattg tgagtaacta tcctcctttc attttgggaa gaagatgagg catgaagaga    2760
attcagacag aaacttactc agaccagggg aggcagaaac taagcagaga ggaaaatgac    2820
caagagttag ccctgggcat ggaatgtgaa agaaccctaa acgtgacttg aaataatgc    2880 ccaaggtata ttccattctc cgggatttgt tggcattttc ttgaggtgaa gaattgcaga    2940
atacattctt taatgtgacc tacatattta cccatgggag gaagtctgct cctggactct    3000
tgagattcag tcataaagcc caggccaggg aaataatgta agtctgcagg cccctgtcat    3060
cagtaggatt agggagaaga gttctcagta gaaacagggg aggctggaga gaaaagaatg    3120
gttaatgtta acgttaatat aactagaaag actgcagaac ttaggactga tttttatttg    3180
aatccttaaa aaaaaaaatt tcttatgaaa atagtacatg gctcttagga gacagaactt    3240
attgtacaga ggaacagcgt gagagtcaga gtgatcccag aacaggtcct ggctccatcc    3300
tgcacatagt tttggtgctg ctggcaatac ggtccccaca actgtgggaa ggggttaggg    3360
gcagggatct catcaggaaa gcatagggt ttaaagttct ttatagagca cttagaagat    3420
tgagaatcca caaattatat taataacaaa caaagtagtg tcgtgttata tagtaaatgt    3480
gaatttgcag acacatttag ggaaaagtta taattaaaaa aataggctgt atatata       3537
```

<210> SEQ ID NO 51
<211> LENGTH: 3537
<212> TYPE: DNA
<213> ORGANISM: Artificial Sequence
<220> FEATURE:
<223> OTHER INFORMATION: 32.6 vector correction genome

<400> SEQUENCE: 51

```
gcttcaggag cagttgtgcg aatagctgga gaacaccagg ctggatttaa acccagatcg       60
ctcttacatt tgctctttac ctgctgtgct cagcgttcac gtgccctcta gctgtagttt      120
tctgaagtca gcgcacagca aggcagtgtg cttagaggtt aacagaaggg aaaacaacaa      180
caacaaaaat ctaaatgaga atcctgactg tttcagctgg gggtaagggg ggcggattat      240
tcatataatt gttataccag acggtcgcag gcttagtcca attgcagaga actcgcttcc      300
caggcttctg agagtcccgg aagtgcctaa acctgtctaa tcgacggggc ttgggtggcc      360
cgtcgctccc tggcttcttc cctttaccca gggcgggcag cgaagtggtg cctcctgcgt      420
cccccacacc ctccctcagc cctcccctc cggcccgtcc tgggcaggtg acctggagca      480
tccggcaggc tgccctggcc tcctgcgtca ggacaacgcc cacgagggc gttactgtgc       540 ggagatgcac cacgcaagag acacccttttg taactctctt ctcctcccta gtgcgaggtt    600
aaaaccttca gccccacgtg ctgtttgcaa acctgcctgt acctgaggcc ctaaaaagcc      660
agagacctca ctcccgggga gccagcatgt ccactgcggt cctggaaaac ccaggcttgg      720
gcaggaaact ctctgacttt ggacaggtga gccacggcag cctgagctgc tcagttaggg      780
gaatttgggc ctccagagaa agagatccga agactgctgg tgcttcctgg tttcataagc      840
tcagtaagaa gtctgaattc gttggaagct gatgagaatg tccaggaagt caacagacaa      900
atgtcctcaa caattgtttc taagtaggag aacatctgtc ctcggtggct ttcacaggaa      960
aagcttctga cctcttctct tcctcccaca gggcagcgga gctactaact tcagcctgct     1020
gaagcaggct ggagacgtgg aggagaaccc tggacctatg tccaccgctg tgctggagaa     1080
ccctgggctg gggaggaaac tgtcagactt cgggcaggag acttcataca ttgaggataa     1140
ctgtaaccag aatggcgcca tctctctgat cttcagcctg aaggaggaag tgggcgccct     1200
ggcaaaggtg ctgcgcctgt ttgaggagaa cgacgtgaat ctgacccaca tcgagtcccg     1260
gccttctaga ctgaagaagg acgagtacga gttctttacc cacctggata gcggtccct     1320 gccagccctg acaaacatca tcaagatcct gaggcacgac atcggagcaa ccgtgcacga     1380
gctgtctcgg gacaagaaga aggataccgt gccctggttc cctcggacaa tccaggagct     1440
ggatagattt gccaaccaga tcctgtctta cggagcagag ctggacgcag atcaccctgg     1500
cttcaaggac ccagtgtatc gggcccggag aaagcagttt gccgatatcg cctacaatta     1560
taggcacgga cagccaatcc ctcgcgtgga gtatatggag gaggagaaga gacctgggg     1620 cacagtgttc aagaccctga gagcctgta caagacacac gcctgctacg agtataacca     1680
catcttcccc ctgctggaga gtattgtgg cttttcacgag gacaatatcc ctcagctgga     1740
ggacgtgagc cagttcctgc agacctgcac aggctttagg ctgaggccag tggcaggact     1800
gctgagctcc cgggacttcc tgggaggact ggccttcaga gtgtttcact gcacccagta     1860
catcaggcac ggctccaagc caatgtatac accagagccc gacatctgtc acgagctgct     1920
gggccacgtg cccctgttta gcgatagatc cttcgcccag ttttcccagg agatcggact     1980
ggcatctctg ggagcacctg acgagtacat cgagaagctg gccaccatct attggttcac     2040
```

| | |
|---|---:|
| agtggagttt ggcctgtgca agcagggcga tagcatcaag gcctacggag caggactgct | 2100 |
| gtctagcttc ggcgagctgc agtattgtct gtccgagaag ccaaagctgc tgcccctgga | 2160 |
| gctggagaag accgccatcc agaactacac cgtgacagag ttccagcccc tgtactatgt | 2220 |
| ggccgagtct tttaacgatg ccaaggagaa ggtgagaaat ttcgccgcca caatccctag | 2280 |
| gcccttcagc gtgcggtacg acccttatac ccagaggatc gaggtgctgg ataatacaca | 2340 |
| gcagctgaag atcctggctg actcaatcaa tagcgaaatc ggaatcctgt gctccgccct | 2400 |
| gcagaaaatc aaatgaggta ccgatccaga catgataaga tacattgatg agtttggaca | 2460 |
| aaccacaact agaatgcagt gaaaaaaatg ctttatttgt gaaatttgtg atgctattgc | 2520 |
| tttatttgta accattataa gctgcaataa acaagttaac aacaacaatt gcattcattt | 2580 |
| tatgtttcag gttcaggggg aggtgtggga ggttttttaa ggatccctgg gatgggatgt | 2640 |
| ggaatccttc tagatttctt ttgtaatatt tataaagtgc tctcagcaag gtatcaaaat | 2700 |
| ggcaaaattg tgagtaacta tcctcctttc attttgggaa gaagatgagg catgaagaga | 2760 |
| attcagacag aaacttactc agaccagggg aggcagaaac taagcagaga ggaaaatgac | 2820 |
| caagagttag ccctgggcat ggaatgtgaa agaaccctaa acgtgacttg gaaataatgc | 2880 |
| ccaaggtata ttccattctc cgggatttgt tggcattttc ttgaggtgaa gaattgcaga | 2940 |
| atacattctt taatgtgacc tacatattta cccatgggag gaagtctgct cctggactct | 3000 |
| tgagattcag tcataaagcc caggccaggg aaataatgta agtctgcagg cccctgtcat | 3060 |
| cagtaggatt agggagaaga gttctcagta gaaaacaggg aggctggaga gaaaagaatg | 3120 |
| gttaatgtta acgttaatat aactagaaag actgcagaac ttaggactga ttttttatttg | 3180 |
| aatccttaaa aaaaaaaatt tcttatgaaa atagtacatg gctcttagga gacagaactt | 3240 |
| attgtacaga ggaacagcgt gagagtcaga gtgatcccag aacaggtcct ggctccatcc | 3300 |
| tgcacatagt tttggtgctg ctggcaatac ggtccccaca actgtgggaa ggggttaggg | 3360 |
| gcagggatct catcaggaaa gcatagggggt ttaaagttct ttatagagca cttagaagat | 3420 |
| tgagaatcca caaattatat taataacaaa caaagtagtg tcgtgttata tagtaaatgt | 3480 |
| gaatttgcag acacatttag ggaaaagtta taattaaaaa aataggctgt atatata | 3537 |

```
<210> SEQ ID NO 52
<211> LENGTH: 3537
<212> TYPE: DNA
<213> ORGANISM: Artificial Sequence
<220> FEATURE:
<223> OTHER INFORMATION: 32.7 vector correction genome

<400> SEQUENCE: 52
```

| | |
|---|---:|
| gcttcaggag cagttgtgcg aatagctgga gaacaccagg ctggatttaa acccagatcg | 60 |
| ctcttacatt tgctctttac ctgctgtgct cagcgttcac gtgccctcta gctgtagttt | 120 |
| tctgaagtca gcgcacagca aggcagtgtg cttagaggtt aacagaaggg aaaacaacaa | 180 |
| caacaaaaat ctaaatgaga atcctgactg tttcagctgg gggtaagggg ggcggattat | 240 |
| tcatataatt gttccaccag acggtcgcag gcttagtcca attgcagaga actcgcttcc | 300 |
| caggcttctg agagtcccgg aagtgcctaa acctgtctaa tcgacggggc ttgggtggcc | 360 |
| cgtcgctccc tggcttcttc cctttaccca gggcgggcag cgaagtggtg cctcctgcgt | 420 |
| cccccacacc ctccctcagc ccctcccctc cggcccgtcc tggcaggtg acctggagca | 480 |
| tccggcaggc tgcctggcc tctgcgtca ggacaacgcc cacgagggc gttactgtgc | 540 |
| ggagatgcac cacgcaagag acacccttg taactctctt ctcctcccta gtgcgaggtt | 600 |

```
aaaaccttca gccccacgtg ctgtttgcaa acctgcctgt acctgaggcc ctaaaaagcc      660
agagacctca ctcccgggga gccagcatgt ccactgcgt cctggaaaac ccaggcttgg       720
gcaggaaact ctctgacttt ggacaggtga gccacggcag cctgagctgc tcagttaggg      780
gaatttgggc ctccagagaa agagatccga agactgctgg tgcttcctgg tttcataagc      840
tcagtaagaa gtctgaattc gttggaagct gatgagaata ccaggaagt caacagacaa       900 atgtcctcaa caattgtttc taagtaggag aacatctgtc ctcggtggct ttcacaggaa      960
aagcttctga cctcttctct tcctcccaca gggcagcgga gctactaact tcagcctgct     1020
gaagcaggct ggagacgtgg aggagaaccc tggacctatg tccaccgctg tgctggagaa     1080
ccctgggctg gggaggaaac tgtcagactt cgggcaggag acttcataca ttgaggataa     1140
ctgtaaccag aatggcgcca tctctctgat cttcagcctg aaggaggaag tgggcgccct     1200
ggcaaaggtg ctgcgcctgt ttgaggagaa cgacgtgaat ctgacccaca tcgagtcccg     1260
gccttctaga ctgaagaagg acgagtacga gttctttacc cacctggata agcggtccct     1320
gccagccctg acaaacatca tcaagatcct gaggcacgac atcggagcaa ccgtgcacga     1380
gctgtctcgg gacaagaaga aggataccgt gccctggttc cctcgacaa tccaggagct      1440 ggatagattt gccaaccaga tcctgtctta cggagcagag ctggacgcag atcaccctgg     1500
cttcaaggac ccagtgtatc gggcccggag aaagcagttt gccgatatcg cctacaatta     1560
taggcacgga cagccaatcc ctcgcgtgga gtatatggag gaggagaaga agacctgggg     1620
cacagtgttc aagaccctga agagcctgta caagacacac gcctgctacg agtataacca     1680
catcttcccc ctgctggaga agtattgtgg ctttcacgag gacaatatcc ctcagctgga     1740
ggacgtgagc cagttcctgc agacctgcac aggctttagg ctgaggccag tggcaggact     1800
gctgagctcc cgggacttcc tgggaggact ggccttcaga gtgtttcact gcacccagta     1860
catcaggcac ggctccaagc caatgtatac accagagccc gacatctgtc acagagctgct    1920 gggccacgtg cccctgttta gcgatagatc cttcgcccag tttccccagg atcggact      1980 ggcatctctg ggagcacctg acgagtacat cgagaagctg gccaccatct attggttcac     2040
agtggagttt ggcctgtgca agcagggcga tagcatcaag gcctacgag caggactgct      2100 gtctagcttc ggcgagctgc agtattgtct gtccgagaag ccaaagctgc tgccctgga    2160 gctggagaag accgccatcc agaactacac cgtgacagag ttccagcccc tgtactatgt    2220
ggccgagtct tttaacgatg ccaaggagaa ggtgagaaat ttcgccgcca caatccctag    2280
gcccttcagc gtgcggtacg acccttatac ccagaggatc gaggtgctgg ataatacaca    2340
gcagctgaag atcctggctg actcaatcaa tagcgaaatc ggaatcctgt gctccgccct    2400
gcagaaaatc aaatgaggta ccgatccaga catgataaga tacattgatg agtttggaca    2460
aaccacaact agaatgcagt gaaaaaaatg ctttatttgt gaaatttgtg atgctattgc     2520
tttatttgta accattataa gctgcaataa acaagttaac aacaacaatt gcattcattt     2580
tatgtttcag gttcaggggg aggtgtggga ggttttttaa ggatccctgg gatgggatgt     2640
ggaatccttc tagatttctt ttgtaatatt tataaagtgc tctcagcaag gtatcaaaat     2700
ggcaaaattg tgagtaacta tcctcctttc attttgggaa gaagatgagg catgaagaga     2760
attcagacag aaacttactc agaccagggg aggcagaaac taagcagaga ggaaaatgac     2820
caagagttag ccctgggcat ggaatgtgaa agaaccctaa acgtgacttg gaaataatgc     2880
ccaaggtata ttccattctc cgggatttgt tggcattttc ttgaggtgaa gaattgcaga     2940
```

| | |
|---|---:|
| atacattctt taatgtgacc tacatattta cccatgggag gaagtctgct cctggactct | 3000 |
| tgagattcag tcataaagcc caggccaggg aaataatgta agtctgcagg cccctgtcat | 3060 |
| cagtaggatt agggagaaga gttctcagta gaaaacaggg aggctggaga gaaaagaatg | 3120 |
| gttaatgtta acgttaatat aactagaaag actgcagaac ttaggactga tttttatttg | 3180 |
| aatccttaaa aaaaaaaatt tcttatgaaa atagtacatg gctcttagga gacagaactt | 3240 |
| attgtacaga ggaacagcgt gagagtcaga gtgatcccag aacaggtcct ggctccatcc | 3300 |
| tgcacatagt tttggtgctg ctggcaatac ggtccccaca actgtgggaa ggggttaggg | 3360 |
| gcagggatct catcaggaaa gcataggggt ttaaagttct ttatagagca cttagaagat | 3420 |
| tgagaatcca caattatat taataacaaa caaagtagtg tcgtgttata tagtaaatgt | 3480 |
| gaatttgcag acacatttag ggaaaagtta taattaaaaa aataggctgt atatata | 3537 |

<210> SEQ ID NO 53
<211> LENGTH: 3545
<212> TYPE: DNA
<213> ORGANISM: Artificial Sequence
<220> FEATURE:
<223> OTHER INFORMATION: 32.8 vector correction genome

<400> SEQUENCE: 53

| | |
|---|---:|
| gcttcaggag cagttgtgcg aatagctgga gaacaccagg ctggatttaa acccagatcg | 60 |
| ctcttacatt tgctctttac ctgctgtgct cagcgttcac gtgccctcta gctgtagttt | 120 |
| tctgaagtca gcgcacagca aggcagtgtg cttagaggtt aacagaaggg aaaacaacaa | 180 |
| caacaaaaat ctaaatgaga atcctgactg tttcagctgg gggtaagggg ggcggattat | 240 |
| tcatataatt gttccaccag acggtcgcag gcttagtcca attgcagaga acacgctgtt | 300 |
| cttcgcccca ggcttctgag agtcccgaa gtgcctaaac ctgtctaatc gacgggctt | 360 |
| gggtggcccg tcgctccctg gcttcttccc tttacccagg gcgggcagcg aagtggtgcc | 420 |
| tcctgcgtcc cccacaccct ccctcagccc ctcccctccg gcccgtcctg ggcaggtgac | 480 |
| ctggagcatc cggcaggctg ccctggcctc ctgcgtcagg acaacgccca cgaggggcgt | 540 |
| tactgtgcgg agatgcacca cgcaagagac acctttgta actctcttct cctcccctagt | 600 |
| gcgaggttaa accttcagc cccacgtgct gtttgcaaac ctgcctgtac ctgaggccct | 660 |
| aaaaagccag agacctcact cccgggggagc cagcatgtcc actgcggtcc tggaaaaccc | 720 |
| aggcttgggc aggaaactct ctgactttgg acaggtgagc cacggcagcc tgagctgctc | 780 |
| agttagggga atttgggcct ccagagaaag agatccgaag actgctggtg cttcctggtt | 840 |
| tcataagctc agtaagaagt ctgaattcgt tggaagctga tgagaatatc caggaagtca | 900 |
| acagacaaat gtcctcaaca attgtttcta agtaggagaa catctgtcct cggtggcttt | 960 |
| cacaggaaaa gcttctgacc tcttctcttc ctcccacagg gcagcggagc tactaacttc | 1020 |
| agcctgctga agcaggctgg agacgtggag gagaaccctg gacctatgtc caccgctgtg | 1080 |
| ctggagaacc ctgggctggg gaggaaactg tcagacttcg gcaggagac ttcatacatt | 1140 |
| gaggataact gtaaccagaa tggcgccatc tctctgatct tcagcctgaa ggaggaagtg | 1200 |
| ggcgccctgg caaggtgct gcgcctgttt gaggagaacg acgtgaatct gacccacatc | 1260 |
| gagtcccggc cttctagact gaagaaggac gagtacgagt tctttaccca cctggataag | 1320 |
| cggtccctgc cagccctgac aaacatcatc aagatcctga ggcacgacat cggagcaacc | 1380 |
| gtgcacgagc tgtctcggga caagaagaag gataccgtgc cctggttccc tcggacaatc | 1440 |
| caggagctgg atagatttgc caaccagatc ctgtcttacg agcagagct ggacgcagat | 1500 |

```
caccctggct tcaaggaccc agtgtatcgg gcccggagaa agcagtttgc cgatatcgcc  1560
tacaattata ggcacggaca gccaatccct cgcgtggagt atatggagga ggagaagaag  1620
acctggggca cagtgttcaa gaccctgaag agcctgtaca agacacacgc ctgctacgag  1680
tataaccaca tcttccccct gctggagaag tattgtggct tcacgagga caatatccct  1740 cagctggagg acgtgagcca gttcctgcag acctgcacag gctttaggct gaggccagtg  1800
gcaggactgc tgagctcccg ggacttcctg gaggactgg ccttcagagt gtttcactgc  1860
acccagtaca tcaggcacgg ctccaagcca atgtatacac cagagcccga catctgtcac  1920
gagctgctgg ccacgtgcc cctgtttagc gatagatcct tcgcccagtt ttcccaggag  1980
atcggactgg catctctggg agcacctgac gagtacatcg agaagctggc caccatctat  2040
tggttcacag tggagtttgg cctgtgcaag cagggcgata gcatcaaggc ctacggagca  2100
ggactgctgt ctagcttcgg cgagctgcag tattgtctgt ccgagaagcc aaagctgctg  2160
cccctggagc tggagaagac cgccatccag aactacaccg tgacagagtt ccagcccctg  2220
tactatgtgg ccgagtcttt taacgatgcc aaggagaagg tgagaaattt cgccgccaca  2280
atccctaggc ccttcagcgt gcggtacgac ccttataccc agaggatcga ggtgctggat  2340
aatacacagc agctgaagat cctggctgac tcaatcaata gcgaaatcgg aatcctgtgc  2400
tccgccctgc agaaaatcaa atgaggtacc gatccagaca tgataagata cattgatgag  2460
tttggacaaa ccacaactag aatgcagtga aaaaaatgct ttatttgtga aatttgtgat  2520
gctattgctt tatttgtaac cattataagc tgcaataaac aagttaacaa caacaattgc  2580
attcatttta tgtttcaggt tcaggggggag gtgtgggagg ttttttaagg atccctggga  2640
tgggatgtgg aatccttcta gatttctttt gtaatattta taaagtgctc tcagcaaggt  2700
atcaaaatgg caaaattgtg agtaactatc ctcctttcat tttgggaaga agatgaggca  2760
tgaagagaat tcagacagaa acttactcag accaggggag gcagaaacta agcagagagg  2820
aaaatgacca agagttagcc ctgggcatgg aatgtgaaag aaccctaaac gtgacttgga  2880
aataatgccc aagtatatt ccattctccg ggatttgttg gcattttctt gaggtgaaga  2940
attgcagaat acattcttta atgtgaccta catatttacc catgggagga agtctgctcc  3000
tggactcttg agattcagtc ataaagccca ggccagggaa ataatgtaag tctgcaggcc  3060
cctgtcatca gtaggattag ggagaagagt tctcagtaga aaacaggggag gctggagaga  3120 aaagaatggt taatgttaac gttaatataa ctagaaagac tgcagaactt aggactgatt  3180
tttatttgaa tccttaaaaa aaaaaattc ttatgaaaat agtacatggc tcttaggaga  3240
cagaacttat tgtacagagg aacagcgtga gagtcagagt gatcccagaa caggtcctgg  3300
ctccatcctg cacatagttt tggtgctgct ggcaatacgg tccccacaac tgtgggaagg  3360
ggttaggggc agggatctca tcaggaaagc atagggggtt aaagttcttt atagagcact  3420
tagaagattg agaatccaca aattatatta ataacaaaca aagtagtgtc gtgttatata  3480
gtaaatgtga atttgcagac acatttaggg aaaagttata attaaaaaaa taggctgtat  3540
atata                                                               3545
```

<210> SEQ ID NO 54
<211> LENGTH: 3537
<212> TYPE: DNA
<213> ORGANISM: Artificial Sequence
<220> FEATURE:
<223> OTHER INFORMATION: 32.9 vector correction genome

<400> SEQUENCE: 54

```
gcttcaggag cagttgtgcg aatagctgga gaacaccagg ctggatttaa acccagatcg      60
ctcttacatt tgctctttac ctgctgtgct cagcgttcac gtgccctcta gctgtagttt     120
tctgaagtca gcgcacagca aggcagtgtg cttagaggtt aacagaaggg aaaacaacaa     180
caacaaaaat ctaaatgaga atcctgactg tttcagctga gagtaagggg ggcggattat     240
tcatataatt gttataccag acggtcgcag gcttagtcca attgcagaga actcgcttcc     300
caggcttctg agagtcccgg aagtgcctaa acctgtctaa tcgacagagc ttgggtggcc     360
cgtcgctccc tggcttcttc cctttaccca gggcgggcag cgaagtggtg cctcctgcgt     420
cccccacacc ctccctcagc ccctcccctc cggcccgtcc taggcaggtg acctgaagca     480
tccagcaggc tgccctggcc tcctgcgtca ggacaacgcc cacgaggggc gttactgtgc     540
ggagatgcac cacgcaagag acacccttg taactctctt ctcctcccta gtgcgaggtt     600
aaaaccttca gccccacgtg ctgtttgcaa acctgcctgt acctgaggcc ctaaaaagcc     660
agagacctca ctcccgggga gccagcatgt ccactgcggt cctggaaaac ccaggcttgg     720
gcaggaaact ctctgacttt ggacaggtga gccacggcag cctgagctgc tcagttaggg     780
gaatttgggc ctccagagaa agagatccga agactgctgg tgcttcctgg tttcataagc     840
tcagtaagaa gtctgaattc gttggaagct gatgagaata ccaggaagt caacagacaa     900
atgtcctcaa caattgtttc taagtaggag aacatctgtc ctcggtggct ttcacaggaa     960
aagcttctga cctcttctct tcctcccaca gggcagcgga gctactaact tcagcctgct    1020
gaagcaggct ggagacgtgg aggagaaccc tggacctatg tccaccgctg tgctggagaa    1080
ccctgggctg gggaggaaac tgtcagactt cgggcaggag acttcataca ttgaggataa    1140
ctgtaaccag aatggcgcca tctctctgat cttcagcctg aaggaggaag tgggcgccct    1200
ggcaaaggtg ctgcgcctgt ttgaggagaa cgacgtgaat ctgacccaca tcgagtcccg    1260
gccttctaga ctgaagaagg acgagtacga gttctttacc cacctggata gcgtgtccct    1320
gccagccctg acaaacatca tcaagatcct gaggcacgac atcggagcaa ccgtgcacga    1380
gctgtctcgg gacaagaaga aggataccgt gccctggttc cctcgacaa tccaggagct    1440
ggatagattt gccaaccaga tcctgtctta cggagcagag ctggacgcag atcaccctgg    1500
cttcaaggac ccagtgtatc gggcccggag aaagcagttt gccgatatcg cctacaatta    1560
taggcacgga cagccaatcc ctcgcgtgga gtatatggag gaggagaaga agacctgggg    1620
cacagtgttc aagaccctga agagcctgta caagacacac gcctgctacg agtataacca    1680
catcttcccc ctgctggaga gtattgtgg ctttcacgag acaatatcc ctcagctgga    1740
ggacgtgagc cagttcctgc agacctgcac aggcttagg ctgaggccag tggcaggact    1800
gctgagctcc cggacttcc tgggaggact ggccttcaga gtgtttcact gcacccagta    1860
catcaggcac ggctccaagc caatgtatac accagagccc gacatctgtc acgagctgct    1920
gggccacgtg cccctgtta gcgatagatc cttcgcccag ttttcccagg atcggact    1980
ggcatctctg ggagcacctg acgagtacat cgagaagctg ccaccatct attggttcac    2040
agtggagttt ggcctgtgca agcagggcga tagcatcaag gcctacgag caggactgct    2100
gtctagcttc ggcgagctgc agtattgtct gtccgagaag ccaaagctgc tgcccctgga    2160
gctggagaag accgccatcc agaactacac cgtgacagag ttccagcccc tgtactatgt    2220
ggccgagtct tttaacgatg ccaaggagaa ggtgagaaat ttcgccgcca caatccctag    2280
gcccttcagc gtgcggtacg accccttatac ccagaggatc gaggtgctgg ataatacaca    2340
```

```
gcagctgaag atcctggctg actcaatcaa tagcgaaatc ggaatcctgt gctccgccct    2400
gcagaaaatc aaatgaggta ccgatccaga catgataaga tacattgatg agtttggaca    2460
aaccacaact agaatgcagt gaaaaaaatg ctttatttgt gaaatttgtg atgctattgc    2520
tttatttgta accattataa gctgcaataa acaagttaac aacaacaatt gcattcattt    2580
tatgtttcag gttcaggggg aggtgtggga ggttttttaa ggatccctgg gatgggatgt    2640
ggaatccttc tagatttctt ttgtaatatt tataaagtgc tctcagcaag gtatcaaaat    2700
ggcaaaattg tgagtaacta tcctcctttc attttgggaa gaagatgagg catgaagaga    2760
attcagacag aaacttactc agaccagggg aggcagaaac taagcagaga ggaaaatgac    2820
caagagttag ccctgggcat ggaatgtgaa agaaccctaa acgtgacttg gaaataatgc    2880
ccaaggtata ttccattctc cgggatttgt tggcattttc ttgaggtgaa gaattgcaga    2940
atacattctt taatgtgacc tacatattta cccatgggag gaagtctgct cctggactct    3000
tgagattcag tcataaagcc caggccaggg aaataatgta agtctgcagg cccctgtcat    3060
cagtaggatt agggagaaga gttctcagta gaaaacaggg aggctggaga gaaaagaatg    3120
gttaatgtta acgttaatat aactagaaag actgcagaac ttaggactga ttttttatttg    3180 aatccttaaa aaaaaaaatt tcttatgaaa atagtacatg gctcttagga gacagaactt    3240
attgtacaga ggaacagcgt gagagtcaga gtgatcccag aacaggtcct ggctccatcc    3300
tgcacatagt tttggtgctg ctggcaatac ggtccccaca actgtgggaa ggggttaggg    3360
gcagggatct catcaggaaa gcataggggt ttaaagttct ttatagagca cttagaagat    3420
tgagaatcca caaattatat taataacaaa caaagtagtg tcgtgttata tagtaaatgt    3480
gaatttgcag acacatttag ggaaaagtta taattaaaaa aataggctgt atatata      3537
```

<210> SEQ ID NO 55
<211> LENGTH: 3943
<212> TYPE: DNA
<213> ORGANISM: Artificial Sequence
<220> FEATURE:
<223> OTHER INFORMATION: 32.1 vector correction genome (+ ITRs)

<400> SEQUENCE: 55

```
ttggccactc cctctctgcg cgctcgctcg ctcactgagg ccgggcgacc aaaggtcgcc     60
cgacgcccgg gctttgcccg ggcggcctca gtgagcgagc gagcgcgcag agagggagtg    120
gccaactcca tcactagggg ttcctggagg ggtggagtcg tgacgtgaat tacgtcatag    180
ggttagggag gtcctgcata tgcggccgct tcaggagcag ttgtgcgaat agctggagaa    240
caccaggctg gatttaaacc cagatcgctc ttacatttgc tctttacctg ctgtgctcag    300
cgttcacgtg ccctctagct gtagtttttct gaagtcagcg cacagcaagg cagtgtgctt    360
agaggttaac agaagggaaa acaacaacaa caaaaatcta aatgagaatc ctgactgttt    420
cagctggggg taaggggggc ggattattca tataattgtt ataccagacg gtcgcaggct    480
tagtccaatt gcagagaact cgcttcccag gcttctgaga gtcccggaag tgcctaaacc    540
tgtctaatcg acggggcttg ggtggcccgt cgctccctgg cttcttccct ttacccaggg    600
cgggcagcga agtggtgcct cctgcgtccc ccacaccctc cctcagcccc tcccctccgg    660
cccgtcctgg gcaggtgacc tggagcatcc ggcaggctgc cctggcctcc tgcgtcagga    720
caacgcccac gagggggcgtt actgtgcgga gatgcaccac gcaagagaca ccctttgtaa    780
ctctcttctc ctccctagtg cgaggttaaa accttcagcc ccacgtgctg tttgcaaacc    840
```

```
tgcctgtacc tgaggccta aaaagccaga gacctcactc ccggggagcc agcatgtcca    900
ctgcggtcct ggaaaaccca ggcttgggca ggaaactctc tgactttgga caggtgagcc    960
acggcagcct gagctgctca gttaggggaa tttgggcctc cagagaaaga gatccgaaga   1020
ctgctggtgc ttcctggttt cataagctca gtaagaagtc tgaattcgtt ggaagctgat   1080
gagaatatcc aggaagtcaa cagacaaatg tcctcaacaa ttgtttctaa gtaggagaac   1140
atctgtcctc ggtggctttc acaggaaaag cttctgacct cttctcttcc tcccacaggg   1200
cagcggagct actaacttca gcctgctgaa gcaggctgga gacgtggagg agaaccctgg   1260
acctatgtcc accgctgtgc tggagaaccc tgggctgggg aggaaactgt cagacttcgg   1320
gcaggagact tcatacattg aggataactg taaccagaat ggcgccatct ctctgatctt   1380
cagcctgaag gaggaagtgg gcgccctggc aaaggtgctg cgcctgtttg aggagaacga   1440
cgtgaatctg acccacatcg agtcccggcc ttctagactg aagaaggacg agtacgagtt   1500
ctttacccac ctggataagc ggtccctgcc agccctgaca acatcatca  agatcctgag   1560
gcacgacatc ggagcaaccg tgcacagctg tgtctcggga caagaagaagg ataccgtgcc   1620
ctggttccct cggacaatcc aggagctgga tagatttgcc aaccagatcc tgtcttacgg   1680
agcagagctg gacgcagatc accctggctt caaggaccca gtgtatcggg cccggagaaa   1740
gcagtttgcc gatatcgcct acaattatag gcacggacag ccaatccctc gcgtggagta   1800
tatggaggag gagaagaaga cctggggcac agtgttcaag accctgaaga gcctgtacaa   1860
gacacacgcc tgctacgagt ataaccacat cttccccctg ctggagaagt attgtggctt   1920
tcacgaggac aatatccctc agctggagga cgtgagccaa ttcctgcaga cctgcacagg   1980
ctttaggctg aggccagtgg caggactgct gagctcccgg gacttcctgg gaggactggc   2040
cttcagagtg tttcactgca cccagtacat caggcacggc tccaagccaa tgtatacacc   2100
agagcccgac atctgtcacg agctgctggg ccacgtgccc ctgtttagcg atagatcctt   2160
cgcccagttt tcccaggaga tcggactggc atctctggga gcacctgacg agtacatcga   2220
gaagctggcc accatctatt ggttcacagt ggagtttggc ctgtgcaagc agggcgatag   2280
catcaaggcc tacggagcag gactgctgtc tagcttcggc gagctgcagt attgtctgtc   2340
cgagaagcca aagctgctgc cctggagct ggagaagacc gccatccaga actacaccgt   2400
gacagagttc cagcccctgt actatgtggc cgagtctttt aacgatgcca aggagaaggt   2460
gagaaatttc gccgccacaa tccctaggcc cttcagcgtg cggtacgacc cttatcccca   2520
gaggatcgag gtgctggata atacacagca gctgaagatc ctggctgact caatcaatag   2580
cgaaatcgga atcctgtgct ccgccctgca gaaaatcaaa tgaggtaccg atccagacat   2640
gataagatac attgatgagt ttggacaaac cacaactaga atgcagtgaa aaaaatgctt   2700
tatttgtgaa atttgtgatg ctattgcttt atttgtaacc attataagct gcaataaaca   2760
agttaacaac aacaattgca ttcattttat gtttcaggtt caggggagg tgtgggaggt   2820
tttttaagga tccctgggat gggatgtgga atccttctag atttcttttg taatatttat   2880
aaagtgctct cagcaaggta tcaaaatggc aaaattgtga gtaactatcc tcctttcatt   2940
ttgggaagaa gatgaggcat gaagagaatt cagacagaaa cttactcaga ccaggggagg   3000
cagaaactaa gcagagagga aaatgaccaa gagttagccc tgggcatgga atgtgaaaga   3060
accctaaacg tgacttggaa ataatgccca aggtatattc cattctccgg gatttgttgg   3120
cattttcttg aggtgaagaa ttgcagaata cattctttaa tgtgacctac atatttaccc   3180
atgggaggaa gtctgctcct ggactcttga gattcagtca taaagcccag gccagggaaa   3240
```

```
taatgtaagt ctgcaggccc ctgtcatcag taggattagg gagaagagtt ctcagtagaa    3300
aacagggagg ctggagagaa aagaatggtt aatgttaacg ttaatataac tagaaagact    3360
gcagaactta ggactgattt ttatttgaat ccttaaaaaa aaaaatttct tatgaaaata    3420
gtacatggct cttaggagac agaacttatt gtacagagga acagcgtgag agtcagagtg    3480
atcccagaac aggtcctggc tccatcctgc acatagtttt ggtgctgctg caatacggt     3540 ccccacaact gtgggaaggg gttaggggca gggatctcat caggaaagca taggggttta    3600
aagttcttta tagagcactt agaagattga gaatccacaa attatattaa taacaaacaa    3660
agtagtgtcg tgttatatag taaatgtgaa tttgcagaca catttaggga aaagttataa    3720
ttaaaaaaat aggctgtata tatacctgca ggtctagata cgtagataag tagcatggcg    3780
ggttaatcat taactacaag gaacccctag tgatggagtt ggccactccc tctctgcgcg    3840
ctcgctcgct cactgaggcc gggcgaccaa aggtcgcccg acgcccgggc tttgcccggg    3900
cggcctcagt gagcgagcga gcgcgcagag agggagtggc caa                     3943

<210> SEQ ID NO 56
<211> LENGTH: 3943
<212> TYPE: DNA
<213> ORGANISM: Artificial Sequence
<220> FEATURE:
<223> OTHER INFORMATION: 32.2 vector correction genome (+ ITRs)

<400> SEQUENCE: 56
ttggccactc cctctctgcg cgctcgctcg ctcactgagg ccgggcgacc aaaggtcgcc      60
cgacgcccgg gctttgcccg gcggcctca gtgagcgagc gagcgcgcag agagggagtg     120
gccaactcca tcactagggg ttcctggagg ggtggagtcg tgacgtgaat tacgtcatag    180
ggttagggag gtcctgcata tgcggccgct tcaggagcag ttgtgcgaat agctggagaa    240
caccaggctg gatttaaacc cagatcgctc ttacatttgc tctttacctg ctgtgctcag    300
cgttcacgtg ccctctagct gtagttttct gaagtcagcg cacagcaagg cagtgtgctt    360
agaggttaac agaagggaaa acaacaacaa caaaaatcta aatgagaatc ctgactgttt    420
cagctggggg taaggggggc ggattattca tataattgtt ataccagacg gtcgcaggct    480
tagtccaatt gcagagaact cgcttcccag gcttctgaga gtcccggaag tgcctaaacc    540
tgtctaatcg acggggcttg ggtggcccgt cgctccctgg cttcttccct ttacccaggg    600
cgggcagcga agtggtgcct cctgcgtccc ccacaccctc cctcagcccc tcccctccgg    660
cccgtcctgg gcaggtgacc tggagcatcc ggcaggctgc cctggcctcc tgcgtcagga    720
caacgcccac gagggcgtt actgtgcgga gatgcaccac gcaagagaca cccttttgtaa   780 ctctcttctc ctcccctagtg cgaggttaaa accttcagcc ccacgtgctg tttgcaaacc    840
tgcctgtacc tgaggcccta aaaagccaga gacctcactc ccggggagcc accatggcgg    900
cggcggtcct ggaaaaccca ggcttgggca ggaaactctc tgactttgga caggtgagcc    960
acggcagcct gagctgctca gttaggggaa tttgggcctc cagagaaaga gatccgaaga   1020
ctgctggtgc ttcctggttt cataagctca gtaagaagtc tgaattcgtt ggaagctgat   1080
gagaatatcc aggaagtcaa cagacaaatg tcctcaacaa ttgtttctaa gtaggagaac   1140
atctgtcctc ggtggctttc acaggaaaag cttctgacct cttctcttcc tcccacaggg   1200
cagcggagct actaacttca gcctgctgaa gcaggctgga gacgtggagg agaaccctgg   1260
acctatgtcc accgctgtgc tggagaaccc tgggctgggg aggaaactgt cagacttcgg   1320
```

```
gcaggagact tcatacattg aggataactg taaccagaat ggcgccatct ctctgatctt    1380
cagcctgaag gaggaagtgg gcgccctggc aaaggtgctg cgcctgtttg aggagaacga    1440
cgtgaatctg acccacatcg agtcccggcc ttctagactg aagaaggacg agtacgagtt    1500
ctttacccac ctggataagc ggtccctgcc agccctgaca acatcatca agatcctgag    1560 gcacgacatc ggagcaaccg tgcacgagct gtctcgggac aagaagaagg ataccgtgcc    1620
ctggttccct cggacaatcc aggagctgga tagatttgcc aaccagatcc tgtcttacgg    1680
agcagagctg gacgcagatc accctggctt caaggaccca gtgtatcggg cccggagaaa    1740
gcagtttgcc gatatcgcct acaattatag gcacggacag ccaatccctc gcgtggagta    1800
tatggaggag gagaagaaga cctggggcac agtgttcaag accctgaaga gcctgtacaa    1860
gacacacgcc tgctacgagt ataaccacat cttcccctg ctggagaagt attgtggctt    1920
tcacgaggac aatatccctc agctggagga cgtgagccag ttcctgcaga cctgcacagg    1980
ctttaggctg aggccagtgg caggactgct gagctcccgg gacttcctgg aggactggc    2040 cttcagagtg tttcactgca cccagtacat caggcacggc tccaagccaa tgtatacacc    2100
agagcccgac atctgtcacg agctgctggg ccacgtgccc ctgtttagcg atagatcctt    2160
cgcccagttt tcccaggaga tcggactggc atctctggga gcacctgacg agtacatcga    2220
gaagctggcc accatctatt ggttcacagt ggagtttggc ctgtgcaagc agggcgatag    2280
catcaaggcc tacggagcag gactgctgtc tagcttcggc gagctgcagt attgtctgtc    2340
cgagaagcca aagctgctgc cctggagct ggagaagacc gccatccaga actacaccgt    2400
gacagagttc cagcccctgt actatgtggc cgagtcttt aacgatgcca aggagaaggt    2460
gagaaatttc gccgccacaa tccctaggcc cttcagcgtg cggtacgacc cttatcccca    2520
gaggatcgag gtgctggata atacacagca gctgaagatc ctggctgact caatcaatag    2580
cgaaatcgga atcctgtgct ccgccctgca gaaaatcaaa tgaggtaccg atccagacat    2640
gataagatac attgatgagt ttggacaaac cacaactaga atgcagtgaa aaaaatgctt    2700
tatttgtgaa atttgtgatg ctattgcttt atttgtaacc attataagct gcaataaaca    2760
agttaacaac aacaattgca ttcattttat gtttcaggtt caggggagg tgtgggaggt    2820 tttttaagga tccctgggat gggatgtgga atccttctag atttctttg taatatttat    2880 aaagtgctct cagcaaggta tcaaaatggc aaaattgtga gtaactatcc tcctttcatt    2940
ttgggaagaa gatgaggcat gaagagaatt cagacagaaa cttactcaga ccaggggagg    3000
cagaaactaa gcagagagga aaatgaccaa gagttagccc tgggcatgga atgtgaaga    3060 accctaaacg tgacttggaa ataatgccca aggtatattc cattctccgg gatttgttgg    3120
cattttcttg aggtgaagaa ttgcagaata cattctttaa tgtgacctac atatttaccc    3180
atgggaggaa gtctgctcct ggactcttga gattcagtca taaagcccag gccagggaaa    3240
taatgtaagt ctgcaggccc ctgtcatcag taggattagg gagaagagtt ctcagtagaa    3300
aacagggagg ctggagagaa aagaatggtt aatgttaacg ttaatataac tagaaagact    3360
gcagaactta ggactgattt ttatttgaat ccttaaaaaa aaaatttct tatgaaaata    3420 gtacatggct cttaggagac agaacttatt gtacagagga acagcgtgag agtcagagtg    3480
atcccagaac aggtcctggc tccatcctgc acatagtttt ggtgctgctg gcaatacggt    3540
ccccacaact gtgggaaggg gttaggggca gggatctcat caggaaagca taggggttta    3600
aagttcttta tagagcactt agaagattga gaatccacaa attatattaa taacaaacaa    3660
agtagtgtcg tgttatatag taaatgtgaa tttgcagaca catttaggga aaagttataa    3720
```

```
ttaaaaaaat aggctgtata tatacctgca ggtctagata cgtagataag tagcatggcg    3780
ggttaatcat taactacaag gaacccctag tgatggagtt ggccactccc tctctgcgcg    3840
ctcgctcgct cactgaggcc gggcgaccaa aggtcgcccg acgcccgggc tttgcccggg    3900
cggcctcagt gagcgagcga gcgcgcagag agggagtggc caa                     3943

<210> SEQ ID NO 57
<211> LENGTH: 3943
<212> TYPE: DNA
<213> ORGANISM: Artificial Sequence
<220> FEATURE:
<223> OTHER INFORMATION: 32.3 vector correction genome (+ ITRs)

<400> SEQUENCE: 57
ttggccactc cctctctgcg cgctcgctcg ctcactgagg ccgggcgacc aaaggtcgcc      60
cgacgcccgg gctttgcccg gcggcctca gtgagcgagc gagcgcgcag agagggagtg     120
gccaactcca tcactagggg ttcctggagg ggtggagtcg tgacgtgaat tacgtcatag    180
ggttagggag gtcctgcata tgcggccgct tcaggagcag ttgtgcgaat agctggagaa    240
caccaggctg gatttaaacc cagatcgctc ttacatttgc tctttacctg ctgtgctcag    300
cgttcacgtg ccctctagct gtagtttttct gaagtcagcg cacagcaagg cagtgtgctt    360
agaggttaac agaagggaaa acaacaacaa caaaaatcta aatgagaatc ctgactgttt    420
cagctgagag taagggggc ggattattca tataattgtt ataccagacg gtcgcaggct    480
tagtccaatt gcagagaact cgcttccag gcttctgaga gtcccggaag tgcctaaacc    540
tgtctaatcg acgggcttg ggtggcccgt cgctccctgg cttcttccct ttacccaggg    600
cgggcagcga agtggtgcct cctgcgtccc ccacaccctc cctcagcccc tccctccgg    660 cccgtcctgg gcaggtgacc tggagcatcc ggcaggctgc cctggcctcc tgcgtcagga    720
caacgcccac gagggcgtt actgtgcgga gatgcaccac gcaagagaca ccctttgtaa    780
ctctcttctc ctccctagtg cgaggttaaa accttcagcc ccacgtgctg tttgcaaacc    840
tgcctgtacc tgaggcccta aaaagccaga gacctcactc ccggggagcc agcatgtcca    900
ctgcggtcct ggaaacccca ggcttgggca ggaaactctc tgactttgga caggtgagcc    960
acggcagcct gagctgctca gttagggga tttgggcctc cagagaaaga gatccgaaga    1020
ctgctggtgc ttcctggttt cataagctca gtaagaagtc tgaattcgtt ggaagctgat    1080
gagaatatcc aggaagtcaa cagacaaatg tcctcaacaa ttgtttctaa gtaggagaac    1140
atctgtcctc ggtggctttc acaggaaaag cttctgacct cttctcttcc tcccacaggg    1200
cagcggagct actaacttca gcctgctgaa gcaggctgga gacgtggagg agaaccctgg    1260
acctatgtcc accgctgtgc tggagaaccc tgggctgggg aggaaactgt cagacttcgg    1320
gcaggagact tcatacattg aggataactg taaccagaat ggcgccatct ctctgatctt    1380
cagcctgaag gaggaagtgg gcgccctggc aaaggtgctg cgcctgtttg aggagaacga    1440
cgtgaatctg acccacatcg agtcccggcc ttctagactg aagaaggacg agtacgagtt    1500
ctttacccac ctggataagc ggtccctgcc agcctgaca acatcatca agatcctgag    1560 gcacgacatc ggagcaaccg tgcacgagct gtctcgggac aagaagaagg ataccgtgcc    1620
ctggttccct cggacaatcc aggagctgga tagatttgcc aaccagatcc tgtcttacgg    1680
agcagagctg gacgcagatc accctggctt caaggaccca gtgtatcggg cccgagaaaa    1740
gcagtttgcc gatatcgcct acaattatag gcacggacag ccaatccctc gcgtggagta    1800
```

```
tatggaggag gagaagaaga cctggggcac agtgttcaag accctgaaga gcctgtacaa    1860
gacacacgcc tgctacgagt ataaccacat cttccccctg ctggagaagt attgtggctt    1920
tcacgaggac aatatccctc agctggagga cgtgagccag ttcctgcaga cctgcacagg    1980
ctttaggctg aggccagtgg caggactgct gagctcccgg gacttcctgg gaggactggc    2040
cttcagagtg tttcactgca cccagtacat caggcacggc tccaagccaa tgtatacacc    2100
agagcccgac atctgtcacg agctgctggg ccacgtgccc ctgtttagcg atagatcctt    2160
cgcccagttt tcccaggaga tcggactggc atctctggga gcacctgacg agtacatcga    2220
gaagctggcc accatctatt ggttcacagt ggagtttggc ctgtgcaagc agggcgatag    2280
catcaaggcc tacggagcag gactgctgtc tagcttcggc gagctgcagt attgtctgtc    2340
cgagaagcca agctgctgc ccctggagct ggagaagacc gccatccaga actacaccgt    2400
gacagagttc cagcccctgt actatgtggc cgagtcttt aacgatgcca aggagaaggt    2460
gagaaatttc gccgccacaa tccctaggcc cttcagcgtg cggtacgacc cttatcccca    2520
gaggatcgag gtgctggata atacacagca gctgaagatc ctggctgact caatcaatag    2580
cgaaatcgga atcctgtgct ccgccctgca gaaaatcaaa tgaggtaccg atccagacat    2640
gataagatac attgatgagt ttggacaaac cacaactaga atgcagtgaa aaaatgcttt    2700
tatttgtgaa atttgtgatg ctattgcttt atttgtaacc attataagct gcaataaaca    2760
agttaacaac aacaattgca ttcattttat gtttcaggtt caggggggagg tgtgggaggt    2820 tttttaagga tccctgggat gggatgtgga atccttctag atttcttttg taatatttat    2880
aaagtgctct cagcaaggta tcaaaatggc aaaattgtga gtaactatcc tcctttcatt    2940
ttgggaagaa gatgaggcat gaagagaatt cagacagaaa cttactcaga ccaggggagg    3000
cagaaactaa gcagagagga aaatgaccaa gagttagccc tgggcatgga atgtgaagaa    3060
accctaaacg tgacttggaa ataatgccca aggtatattc cattctccgg gatttgttgg    3120
cattttcttg aggtgaagaa ttgcagaata cattctttaa tgtgacctac atatttaccc    3180
atgggaggaa gtctgctcct ggactcttga gattcagtca taaagcccag gccagggaaa    3240
taatgtaagt ctgcaggccc ctgtcatcag taggattagg gagaagagtt ctcagtagaa    3300
aacagggagg ctggagagaa aagaatggtt aatgttaacg ttaatataac tagaaagact    3360
gcagaactta ggactgattt ttatttgaat ccttaaaaaa aaaatttct tatgaaaata    3420 gtacatggct cttaggagac agaacttatt gtacagagga acagcgtgag agtcagagtg    3480
atcccagaac aggtcctggc tccatcctgc acatagtttt ggtgctgctg caatacggt     3540 ccccacaact gtgggaaggg gttaggggca gggatctcat caggaaagca tagggggttta  3600 aagttcttta tagagcactt agaagattga gaatccacaa attatattaa taacaaacaa   3660
agtagtgtcg tgttatatag taaatgtgaa tttgcagaca catttaggga aaagttataa   3720
ttaaaaaaat aggctgtata tatacctgca ggtctagata cgtagataag tagcatggcg   3780
ggttaatcat taactacaag gaacccctag tgatggagtt ggccactccc tctctgcgcg   3840
ctcgctcgct cactgaggcc gggcgaccaa aggtcgcccg acgcccgggc tttgcccggg   3900
cggcctcagt gagcgagcga gcgcgcagag agggagtggc caa                    3943
```

<210> SEQ ID NO 58
<211> LENGTH: 3943
<212> TYPE: DNA
<213> ORGANISM: Artificial Sequence
<220> FEATURE:
<223> OTHER INFORMATION: 32.4 vector correction genome (+ ITRs)

<400> SEQUENCE: 58

```
ttggccactc cctctctgcg cgctcgctcg ctcactgagg ccgggcgacc aaaggtcgcc      60
cgacgcccgg gctttgcccg ggcggcctca gtgagcgagc gagcgcgcag agagggagtg     120
gccaactcca tcactagggg ttcctggagg ggtggagtcg tgacgtgaat tacgtcatag     180
ggttagggag gtcctgcata tgcggccgct tcaggagcag ttgtgcgaat agctggagaa     240
caccaggctg gatttaaacc cagatcgctc ttacatttgc tctttacctg ctgtgctcag     300
cgttcacgtg ccctctagct gtagttttct gaagtcagcg cacagcaagg cagtgtgctt     360
agaggttaac agaagggaaa acaacaacaa caaaaatcta aatgagaatc ctgactgttt     420
cagctggggg taagggggc ggattattca tataattgtt ataccagacg gtcgcaggct      480
tagtccaatt gcagagaact cgcttcccag gcttctgaga gtcccggaag tgcctaaacc     540
tgtctaatcg acgggcttg ggtggcccgt cgctccctgg cttcttccct ttacccaggg      600
cgggcagcga agtggtgcct cctgcgtccc ccacaccctc cctcagcccc tcccctccgg     660
cccgtcctgg gcaggtgacc tggagcatcc ggcaggctgc cctggcctcc tgagtcagga     720
caacgcccac gagggcgtt actgtgcgga gatgcaccac gcaagagaca ccctttgtaa       780
ctctcttctc ctccctagtg cgaggttaaa accttcagcc ccacgtgctg tttgcaaacc     840
tgcctgtacc tgaggcccta aaaagccaga gacctcactc ccggggagcc agcatgtcca     900
ctgcggtcct ggaaaaccca ggcttgggca ggaaactctc tgactttgga caggtgagcc     960
acggcagcct gagctgctca gttagggaa tttgggcctc cagagaaaga gatccgaaga     1020
ctgctggtgc ttcctggttt cataagctca gtaagaagtc tgaattcgtt ggaagctgat    1080
gagaatatcc aggaagtcaa cagacaaatg tcctcaacaa ttgtttctaa gtaggagaac    1140
atctgtcctc ggtggctttc acaggaaaag cttctgacct cttctcttcc tcccacaggg    1200
cagcggagct actaacttca gcctgctgaa gcaggctgga gacgtggagg agaaccctgg    1260
acctatgtcc accgctgtgc tggagaaccc tgggctgggg aggaaactgt cagacttcgg    1320
gcaggagact tcatacattg aggataactg taaccagaat ggcgccatct ctctgatctt    1380
cagcctgaag gaggaagtgg gcgccctggc aaaggtgctg cgcctgtttg aggagaacga    1440
cgtgaatctg acccacatcg agtcccggcc ttctagactg aagaaggacg agtacgagtt    1500
ctttacccac ctggataagc ggtccctgcc agccctgaca aacatcatca gatcctgag     1560
gcacgacatc ggagcaaccg tgcacgagct gtctcgggac aagaagaagg ataccgtgcc    1620
ctggttccct cggacaatcc aggagctgga tagatttgcc aaccagatcc tgtcttacgg    1680
agcagagctg gacgcagatc accctggctt caaggaccca gtgtatcggg cccggagaaa    1740
gcagtttgcc gatatcgcct acaattatag gcacggacga ccaatccctc gcgtggagta    1800
tatggaggag gagaagaaga cctggggcac agtgttcaag accctgaaga gcctgtacaa    1860
gacacacgcg tgctacgagt ataaccacat cttccccctg ctggagaagt attgtggctt    1920
tcacgaggac aatatccctc agctggagga cgtgagccag ttcctgcaga cctgcacagg    1980
ctttaggctg aggccagtgg caggactgct gagctcccgg gacttcctgg gaggactggc    2040
cttcagagtg tttcactgca cccagtacat caggcacggc tccaagccaa tgtatacacc    2100
agagcccgac atctgtcacg agctgctggg ccacgtgccc ctgtttagcg atagatcctt    2160
cgcccagttt tcccaggaga tcggactggc atctctggga gcacctgacg agtacatcga    2220
gaagctggcc accatctatt ggttcacagt ggagtttggc ctgtgcaagc agggcgatag    2280
```

| | |
|---|---|
| catcaaggcc tacggagcag gactgctgtc tagcttcggc gagctgcagt attgtctgtc | 2340 |
| cgagaagcca aagctgctgc ccctggagct ggagaagacc gccatccaga actacaccgt | 2400 |
| gacagagttc cagcccctgt actatgtggc cgagtctttt aacgatgcca aggagaaggt | 2460 |
| gagaaatttc gccgccacaa tccctaggcc cttcagcgtg cggtacgacc cttataccca | 2520 |
| gaggatcgag gtgctggata atacacagca gctgaagatc ctggctgact caatcaatag | 2580 |
| cgaaatcgga atcctgtgct ccgccctgca gaaaatcaaa tgaggtaccg atccagacat | 2640 |
| gataagatac attgatgagt ttggacaaac cacaactaga atgcagtgaa aaaaatgctt | 2700 |
| tatttgtgaa atttgtgatg ctattgcttt atttgtaacc attataagct gcaataaaca | 2760 |
| agttaacaac aacaattgca ttcattttat gtttcaggtt caggggggagg tgtgggaggt | 2820 |
| tttttaagga tccctgggat gggatgtgga atccttctag atttcttttg taatatttat | 2880 |
| aaagtgctct cagcaaggta tcaaaatggc aaaattgtga gtaactatcc tcctttcatt | 2940 |
| ttgggaagaa gatgaggcat gaagagaatt cagacagaaa cttactcaga ccaggggagg | 3000 |
| cagaaactaa gcagagagga aaatgaccaa gagttagccc tgggcatgga atgtgaaaga | 3060 |
| accctaaacg tgacttggaa ataatgccca aggtatattc cattctccgg gatttgttgg | 3120 |
| cattttcttg aggtgaagaa ttgcagaata cattctttaa tgtgacctac atatttaccc | 3180 |
| atgggaggaa gtctgctcct ggactcttga gattcagtca taaagcccag gccagggaaa | 3240 |
| taatgtaagt ctgcaggccc ctgtcatcag taggattagg gagaagagtt ctcagtagaa | 3300 |
| aacagggagg ctggagagaa aagaatggtt aatgttaacg ttaatataac tagaaagact | 3360 |
| gcagaactta ggactgattt ttatttgaat ccttaaaaaa aaaatttct tatgaaaata | 3420 |
| gtacatggct cttaggagac agaacttatt gtacagagga acagcgtgag agtcagagtg | 3480 |
| atcccagaac aggtcctggc tccatcctgc acatagtttt ggtgctgctg caatacggt | 3540 |
| ccccacaact gtgggaaggg gttaggggca gggatctcat caggaaagca tagggttta | 3600 |
| aagttcttta tagagcactt agaagattga gaatccacaa attatattaa taacaaacaa | 3660 |
| agtagtgtcg tgttatatag taaatgtgaa tttgcagaca catttaggga aaagttataa | 3720 |
| ttaaaaaaat aggctgtata tatacctgca ggtctagata cgtagataag tagcatggcg | 3780 |
| ggttaatcat taactacaag gaacccctag tgatggagtt ggccactccc tctctgcgcg | 3840 |
| ctcgctcgct cactgaggcc gggcgaccaa aggtcgcccg acgcccgggc tttgcccggg | 3900 |
| cggcctcagt gagcgagcga gcgcgcagag agggagtggc caa | 3943 |

<210> SEQ ID NO 59
<211> LENGTH: 3943
<212> TYPE: DNA
<213> ORGANISM: Artificial Sequence
<220> FEATURE:
<223> OTHER INFORMATION: 32.5 vector correction genome (+ ITRs)

<400> SEQUENCE: 59

| | |
|---|---|
| ttggccactc cctctctgcg cgctcgctcg ctcactgagg ccgggcgacc aaaggtcgcc | 60 |
| cgacgcccgg gctttgcccg gcggcctca gtgagcgagc gagcgcgcag agagggagtg | 120 |
| gccaactcca tcactagggg ttcctggagg ggtggagtcg tgacgtgaat tacgtcatag | 180 |
| ggttagggag gtcctgcata tgcggccgct tcaggagcag ttgtgcgaat agctggagaa | 240 |
| caccaggctg gatttaaacc cagatcgctc ttacatttgc tctttacctg ctgtgctcag | 300 |
| cgttcacgtg ccctctagct gtagttttct gaagtcagcg cacagcaagg cagtgtgctt | 360 |
| agaggttaac agaagggaaa acaacaacaa caaaaatcta aatgagaatc ctgactgttt | 420 |

```
cagctgggggg taagggggc ggattattca tataattgtt ataccagacg gtcgcaggct    480
tagtccaatt gcagagaact cgcttcccag gcttctgaga gtcccggaag tgcctaaacc    540
tgtctaatcg acggggcttg ggtggcccgt cgctccctgg cttcttccct ttacccaggg    600
cgggcagcga agtggtgcct cctgcgtccc ccacaccctc cctcagcccc tccctccgg    660
cccgtcctgg gcaggtgacg tcaagcatcc ggcaggctgc cctggcctcc tgagtcagga    720
caacgcccac gaggggcgtt actgtgcgga gatgcaccac gcaagagaca ccctttgtaa    780
ctctcttctc ctccctagtg cgaggttaaa accttcagcc ccacgtgctg tttgcaaacc    840
tgcctgtacc tgaggcccta aaagccaga gacctcactc ccggggagcc agcatgtcca     900
ctgcggtcct ggaaaaccca ggcttgggca ggaaactctc tgactttgga caggtgagcc    960
acggcagcct gagctgctca gttaggggaa tttgggcctc cagagaaaga gatccgaaga   1020
ctgctggtgc ttcctggttt cataagctca gtaagaagtc tgaattcgtt ggaagctgat   1080
gagaatatcc aggaagtcaa cagacaaatg tcctcaacaa ttgtttctaa gtaggagaac   1140
atctgtcctc ggtggctttc acaggaaaag cttctgacct cttctcttcc tcccacaggg   1200
cagcggagct actaacttca gcctgctgaa gcaggctgga gacgtggagg agaaccctgg   1260
acctatgtcc accgctgtgc tggagaaccc tgggctgggg aggaaactgt cagacttcgg   1320
gcaggagact tcatacattg aggataactg taaccagaat ggcgccatct ctctgatctt   1380
cagcctgaag gaggaagtgg gcgccctggc aaaggtgctg cgcctgtttg aggagaacga   1440
cgtgaatctg acccacatcg agtcccggcc ttctagactg aagaaggacg agtacgagtt   1500
ctttacccac ctggataagc ggtccctgcc agccctgaca aacatcatca agatcctgag   1560
gcacgacatc ggagcaaccg tgcacgagct gtctcgggac aagaagaagg ataccgtgcc   1620
ctggttccct cggacaatcc aggagctgga tagatttgcc aaccagatcc tgtcttacgg   1680
agcagagctg gacgcagatc accctggctt caaggaccca gtgtatcggg cccggagaaa   1740
gcagtttgcc gatatcgcct acaattatag gcacggacag ccaatccctc gcgtggagta   1800
tatggaggag gagaagaaga cctggggcac agtgttcaag accctgaaga gcctgtacaa   1860
gacacacgcc tgctacgagt ataaccacat cttcccctg ctggagaagt attgtggctt    1920
tcacgaggac aatatccctc agctggagga cgtgagccag ttcctgcaga cctgcacagg   1980
ctttaggctg aggccagtgg caggactgct gagctcccgg gacttcctgg gaggactggc   2040
cttcagagtg tttcactgca cccagtacat caggcacggc tccaagccaa tgtatacacc   2100
agagcccgac atcgtcacg agctgctggg ccacgtgccc ctgtttagcg atagatcctt   2160
cgcccagttt tcccaggaga tcggactggc atctctggga gcacctgacg agtacatcga   2220
gaagctggcc accatctatt ggttcacagt ggagtttggc ctgtgcaagc agggcgatag   2280
catcaaggcc tacggagcag gactgctgtc tagcttcggc gagctgcagt attgtctgtc   2340
cgagaagcca aagctgctgc ccctggagct ggagaagacc gccatccaga actacaccgt   2400
gacagagttc cagcccctgt actatgtggc cgagtctttt aacgatgcca aggagaaggt   2460
gagaaatttc gccgccacaa tccctaggcc cttcagcgtg cggtacgacc cttatcccca   2520
gaggatcgag gtgctggata atacacagca gctgaagatc ctggctgact caatcaatag   2580
cgaaatcgga atcctgtgct ccgccctgca gaaaatcaaa tgaggtaccg atccagacat   2640
gataagatac attgatgagt ttggacaaac cacaactaga atgcagtgaa aaaatgcttt   2700
tatttgtgaa atttgtgatg ctattgcttt atttgtaacc attataagct gcaataaaca   2760
```

| | |
|---|---|
| agttaacaac aacaattgca ttcattttat gtttcaggtt caggggggagg tgtgggaggt | 2820 |
| tttttaagga tccctgggat gggatgtgga atccttctag atttcttttg taatatttat | 2880 |
| aaagtgctct cagcaaggta tcaaaatggc aaaattgtga gtaactatcc tcctttcatt | 2940 |
| ttgggaagaa gatgaggcat gaagagaatt cagacagaaa cttactcaga ccaggggagg | 3000 |
| cagaaactaa gcagagagga aaatgaccaa gagttagccc tgggcatgga atgtgaaaga | 3060 |
| accctaaacg tgacttggaa ataatgccca aggtatattc cattctccgg gatttgttgg | 3120 |
| cattttcttg aggtgaagaa ttgcagaata cattctttaa tgtgacctac atatttaccc | 3180 |
| atgggaggaa gtctgctcct ggactcttga gattcagtca taaagcccag gccagggaaa | 3240 |
| taatgtaagt ctgcaggccc ctgtcatcag taggattagg gagaagagtt ctcagtagaa | 3300 |
| aacagggagg ctgagagaa aagaatggtt aatgttaacg ttaatataac tagaaagact | 3360 |
| gcagaactta ggactgattt ttatttgaat ccttaaaaaa aaaaatttct tatgaaaata | 3420 |
| gtacatggct cttaggagac agaacttatt gtacagagga acagcgtgag agtcagagtg | 3480 |
| atcccagaac aggtcctggc tccatcctgc acatagtttt ggtgctgctg gcaatacggt | 3540 |
| ccccacaact gtgggaaggg gttaggggca gggatctcat caggaaagca tagggttta | 3600 |
| aagttcttta tagagcactt agaagattga gaatccacaa attatattaa taacaaacaa | 3660 |
| agtagtgtcg tgttatatag taaatgtgaa tttgcagaca catttaggga aaagttataa | 3720 |
| ttaaaaaaat aggctgtata tataacctgca ggtctagata cgtagataag tagcatggcg | 3780 |
| ggttaatcat taactacaag gaaccctag tgatggagtt ggccactccc tctctgcgcg | 3840 |
| ctcgctcgct cactgaggcc gggcgaccaa aggtcgcccg acgcccgggc tttgcccggg | 3900 |
| cggcctcagt gagcgagcga gcgcgcagag agggagtggc caa | 3943 |

<210> SEQ ID NO 60
<211> LENGTH: 3943
<212> TYPE: DNA
<213> ORGANISM: Artificial Sequence
<220> FEATURE:
<223> OTHER INFORMATION: 32.6 vector correction genome (+ ITRs)

<400> SEQUENCE: 60

| | |
|---|---|
| ttggccactc cctctctgcg cgctcgctcg ctcactgagg ccgggcgacc aaaggtcgcc | 60 |
| cgacgcccgg gctttgcccg gcggcctca gtgagcgagc gagcgcgcag agagggagtg | 120 |
| gccaactcca tcactagggg ttcctggagg ggtggagtcg tgacgtgaat tacgtcatag | 180 |
| ggttagggag gtcctgcata tgcggccgct tcaggagcag ttgtgcgaat agctggagaa | 240 |
| caccaggctg gatttaaacc cagatcgctc ttacatttgc tctttacctg ctgtgctcag | 300 |
| cgttcacgtg ccctctagct gtagttttct gaagtcagcg cacagcaagg cagtgtgctt | 360 |
| agaggttaac agaagggaaa acaacaacaa caaaaatcta aatgagaatc ctgactgttt | 420 |
| cagctggggg taaggggggc ggattattca tataattgtt ataccagacg tcgcaggct | 480 |
| tagtccaatt gcagagaact cgcttcccag gcttctgaga gtcccggaag tgcctaaacc | 540 |
| tgtctaatcg acggggcttg ggtggcccgt cgctccctgg cttcttccct ttacccaggg | 600 |
| cgggcagcga agtggtgcct cctgcgtccc ccacaccctc cctcagcccc tcccctccgg | 660 |
| cccgtcctgg gcaggtgacc tggagcatcc ggcaggctgc cctggcctcc tgcgtcagga | 720 |
| caacgcccac gaggggcgtt actgtgcgga gatgcaccac gcaagagaca ccctttgtaa | 780 |
| ctctcttctc ctcccctagtg cgaggttaaa accttcagcc ccacgtgctg tttgcaaacc | 840 |
| tgcctgtacc tgaggcccta aaaagccaga gacctcactc ccggggagcc agcatgtcca | 900 |

-continued

```
ctgcggtcct ggaaaaccca ggcttgggca ggaaactctc tgactttgga caggtgagcc      960
acggcagcct gagctgctca gttaggggaa tttgggcctc cagagaaaga gatccgaaga     1020
ctgctggtgc ttcctggttt cataagctca gtaagaagtc tgaattcgtt ggaagctgat     1080
gagaatgtcc aggaagtcaa cagacaaatg tcctcaacaa ttgtttctaa gtaggagaac     1140
atctgtcctc ggtggctttc acaggaaaag cttctgacct cttctcttcc tcccacaggg     1200
cagcggagct actaacttca gcctgctgaa gcaggctgga gacgtggagg agaaccctgg     1260
acctatgtcc accgctgtgc tggagaaccc tgggctgggg aggaaactgt cagacttcgg     1320
gcaggagact tcatacattg aggataactg taaccagaat ggcgccatct ctctgatctt     1380
cagcctgaag gaggaagtgg gcgccctggc aaaggtgctg cgcctgtttg aggagaacga     1440
cgtgaatctg acccacatcg agtcccggcc ttctagactg aagaaggacg agtacgagtt     1500
ctttacccac ctggataagc ggtccctgcc agccctgaca acatcatca agatcctgag      1560
gcacgacatc ggagcaaccg tgcacgagct gtctcgggac aagaagaagg ataccgtgcc     1620
ctggttccct cggacaatcc aggagctgga tagatttgcc aaccagatcc tgtcttacgg     1680
agcagagctg gacgcagatc accctggctt caaggaccca gtgtatcggg cccggagaaa     1740
gcagtttgcc gatatcgcct acaattatag gcacggacag ccaatccctc gcgtggagta     1800
tatggaggag gagaagaaga cctggggcac agtgttcaag accctgaaga gcctgtacaa     1860
gacacacgcc tgctacgagt ataaccacat cttccccctg ctggagaagt attgtggctt     1920
tcacaggac aatatccctc agctggagga cgtgagccag ttcctgcaga cctgcacagg     1980
ctttaggctg aggccagtgg caggactgct gagctcccgg gacttcctgg aggactggc      2040
cttcagagtg tttcactgca cccagtacat caggcacggc tccaagccaa tgtatacacc     2100
agagcccgac atctgtcacg agctgctggg ccacgtgccc ctgtttagcg atagatcctt     2160
cgcccagttt tcccaggaga tcggactggc atctctggga gcacctgacg agtacatcga     2220
gaagctggcc accatctatt ggttcacagt ggagtttggc ctgtgcaagc agggcgatag     2280
catcaaggcc tacggagcag gactgctgtc tagcttcggc gagctgcagt attgtctgtc     2340
cgagaagcca aagctgctgc ccctggagct ggagaagacc gccatccaga actacaccgt     2400
gacagagttc cagcccctgt actatgtggc cgagtctttt aacgatgcca aggagaaggt     2460
gagaaatttc gccgccacaa tccctaggcc cttcagcgtg cggtacgacc cttataccca     2520
gaggatcgag gtgctggata atacacagca gctgaagatc ctggctgact caatcaatag     2580
cgaaatcgga atcctgtgct ccgccctgca gaaaatcaaa tgaggtaccg atccagacat     2640
gataagatac attgatgagt ttggacaaac cacaactaga atgcagtgaa aaaatgctt      2700
tatttgtgaa atttgtgatg ctattgcttt atttgtaacc attataagct gcaataaaca     2760
agttaacaac aacaattgca ttcattttat gtttcaggtt cagggggagg tgtgggaggt     2820
tttttaagga tccctgggat gggatgtgga atccttctag atttcttttg taatatttat     2880
aaagtgctct cagcaaggta tcaaaatggc aaaattgtga gtaactatcc tcctttcatt     2940
ttgggaagaa gatgaggcat gaagagaatt cagacagaaa cttactcaga ccaggggagg     3000
cagaaactaa gcagagagga aaatgaccaa gagttagccc tgggcatgga atgtgaaaga     3060
accctaaacg tgacttggaa ataatgccca aggtatattc cattctccgg gatttgttgg     3120
catttcttg aggtgaagaa ttgcagaata cattctttaa tgtgacctac atatttaccc      3180
atgggaggaa gtctgctcct ggactcttga gattcagtca taaagcccag gccagggaaa     3240
```

| | |
|---|---:|
| taatgtaagt ctgcaggccc ctgtcatcag taggattagg gagaagagtt ctcagtagaa | 3300 |
| aacagggagg ctggagagaa aagaatggtt aatgttaacg ttaatataac tagaaagact | 3360 |
| gcagaactta ggactgattt ttatttgaat ccttaaaaaa aaaaatttct tatgaaaata | 3420 |
| gtacatggct cttaggagac agaacttatt gtacagagga acagcgtgag agtcagagtg | 3480 |
| atcccagaac aggtcctggc tccatcctgc acatagtttt ggtgctgctg caatacggt | 3540 |
| ccccacaact gtgggaaggg gttaggggca gggatctcat caggaaagca taggggttta | 3600 |
| aagttcttta tagagcactt agaagattga gaatccacaa attatattaa taacaaacaa | 3660 |
| agtagtgtcg tgttatatag taatgtgaa tttgcagaca catttaggga aaagttataa | 3720 |
| ttaaaaaaat aggctgtata tatacctgca ggtctagata cgtagataag tagcatggcg | 3780 |
| ggttaatcat taactacaag gaaccccctag tgatggagtt ggccactccc tctctgcgcg | 3840 |
| ctcgctcgct cactgaggcc gggcgaccaa aggtcgcccg acgcccgggc tttgcccggg | 3900 |
| cggcctcagt gagcgagcga gcgcgcagag agggagtggc caa | 3943 |

<210> SEQ ID NO 61
<211> LENGTH: 3943
<212> TYPE: DNA
<213> ORGANISM: Artificial Sequence
<220> FEATURE:
<223> OTHER INFORMATION: 32.7 vector correction genome (+ ITRs)

<400> SEQUENCE: 61

| | |
|---|---:|
| ttggccactc cctctctgcg cgctcgctcg ctcactgagg ccgggcgacc aaaggtcgcc | 60 |
| cgacgcccgg gctttgcccg gcggcctca gtgagcgagc gagcgcgcag agagggagtg | 120 |
| gccaactcca tcactagggg ttcctggagg ggtggagtcg tgacgtgaat tacgtcatag | 180 |
| ggttagggag gtcctgcata tgcggccgct tcaggagcag ttgtgcgaat agctggagaa | 240 |
| caccaggctg gatttaaacc cagatcgctc ttacatttgc tctttacctg ctgtgctcag | 300 |
| cgttcacgtg ccctctagct gtagttttct gaagtcagcg cacagcaagg cagtgtgctt | 360 |
| agaggttaac agaagggaaa acaacaacaa caaaaatcta atgagaatc ctgactgttt | 420 |
| cagctggggg taaggggggc ggattattca tataattgtt ccaccagacg gtcgcaggct | 480 |
| tagtccaatt gcagagaact cgcttcccag gcttctgaga gtcccggaag tgcctaaacc | 540 |
| tgtctaatcg acggggcttg ggtggcccgt cgctccctgg cttcttccct ttacccaggg | 600 |
| cgggcagcga agtggtgcct cctgcgtccc ccacaccctc cctcagcccc tcccctccgg | 660 |
| cccgtcctgg gcaggtgacc tggagcatcc ggcaggctgc cctggcctcc tgcgtcagga | 720 |
| caacgcccac gaggggcgtt actgtgcgga gatgcaccac gcaagagaca ccctttgtaa | 780 |
| ctctcttctc ctccctagtg cgaggttaaa accttcagcc ccacgtgctg tttgcaaacc | 840 |
| tgcctgtacc tgaggcccta aaaagccaga gacctcactc ccggggagcc agcatgtcca | 900 |
| ctgcggtcct ggaaaaccca ggcttgggca ggaaactctc tgactttgga caggtgagcc | 960 |
| acggcagcct gagctgctca gttaggggaa tttgggcctc cagagaaaga gatccgaaga | 1020 |
| ctgctggtgc ttcctggttt cataagctca gtaagaagtc tgaattcgtt ggaagctgat | 1080 |
| gagaatatcc aggaagtcaa cagacaaatg tcctcaacaa ttgtttctaa gtaggagaac | 1140 |
| atctgtcctc ggtggctttc acaggaaaag cttctgacct cttctcttcc tcccacaggg | 1200 |
| cagcggagct actaacttca gcctgctgaa gcaggctgga gacgtggagg agaaccctgg | 1260 |
| acctatgtcc accgctgtgc tggagaaccc tgggctgggg aggaaactgt cagacttcgg | 1320 |
| gcaggagact tcatacattg aggataactg taaccagaat ggcgccatct ctctgatctt | 1380 |

-continued

```
cagcctgaag gaggaagtgg gcgccctggc aaaggtgctg cgcctgtttg aggagaacga    1440
cgtgaatctg acccacatcg agtcccggcc ttctagactg aagaaggacg agtacgagtt    1500 cttacccac  ctggataagc ggtccctgcc agccctgaca acatcatca  agatcctgag    1560 gcacgacatc ggagcaaccg tgcacgagct gtctcgggac aagaagaagg ataccgtgcc    1620
ctggttccct cggacaatcc aggagctgga tagatttgcc aaccagatcc tgtcttacgg    1680
agcagagctg gacgcagatc accctggctt caaggaccca gtgtatcggg cccggagaaa    1740
gcagtttgcc gatatcgcct acaattatag gcacggacag ccaatccctc gcgtggagta    1800
tatgagggag gagaagaaga cctggggcac agtgttcaag accctgaaga gcctgtacaa    1860
gacacacgcc tgctacgagt ataaccacat cttcccctg  ctggagaagt attgtggctt    1920
tcacggagac aatatccctc agctggagga cgtgagccag ttcctgcaga cctgcacagg    1980
ctttaggctg aggccagtgg caggactgct gagctcccgg gacttcctgg aggactggc    2040 cttcagagtg tttcactgca cccagtacat caggcacggc tccaagccaa tgtatacacc    2100
agagcccgac atctgtcacg agctgctggg ccacgtgccc ctgtttagcg atagatcctt    2160
cgcccagttt tcccaggaga tcggactggc atctctggga gcacctgacg agtacatcga    2220
gaagctggcc accatctatt ggttcacagt ggagtttggc ctgtgcaagc agggcgatag    2280
catcaaggcc tacggagcag gactgctgtc tagcttcggc gagctgcagt attgtctgtc    2340
cgagaagcca aagctgctgc ccctggagct ggagaagacc gccatccaga actacaccgt    2400
gacagagttc cagcccctgt actatgtggc cgagtctttt aacgatgcca aggagaaggt    2460
gagaaatttc gccgccacaa tccctaggcc cttcagcgtg cggtacgacc cttatatccca    2520 gaggatcgag gtgctggata atacacagca gctgaagatc ctggctgact caatcaatag    2580
cgaaatcgga atcctgtgct ccgccctgca gaaaatcaaa tgaggtaccg atccagacat    2640
gataagatac attgatgagt ttggacaaac cacaactaga atgcagtgaa aaaaatgctt    2700
tatttgtgaa atttgtgatg ctattgcttt atttgtaacc attataagct gcaataaaca    2760
agttaacaac aacaattgca ttcattttat gtttcaggtt caggggggagg tgtgggaggt    2820 tttttaagga tccctgggat gggatgtgga atccttctag atttcttttg taatatttat    2880
aaagtgctct cagcaaggta tcaaaatggc aaaattgtga gtaactatcc tcctttcatt    2940
ttgggaagaa gatgaggcat gaagagaatt cagacagaaa cttactcaga ccaggggagg    3000
cagaaactaa gcagagagga aaatgaccaa gagttagccc tgggcatgga atgtgaaaga    3060
accctaaacg tgacttggaa ataatgccca aggtatattc cattctccgg gatttgttgg    3120
cattttcttg aggtgaagaa ttgcagaata cattctttaa tgtgacctac atatttaccc    3180
atgggaggaa gtctgctcct ggactcttga gattcagtca taaagcccag gccagggaaa    3240
taatgtaagt ctgcaggccc ctgtcatcag taggattagg gagaagagtt ctcagtagaa    3300
aacagggagg ctgagagaa  aagaatggtt aatgttaacg ttaatataac tagaaagact    3360
gcagaactta ggactgattt ttatttgaat ccttaaaaaa aaaaatttct tatgaaaata    3420
gtacatggct cttaggagac agaacttatt gtacagagga acagcgtgag agtcagagtg    3480
atcccagaac aggtcctggc tccatcctgc acatagtttt ggtgctgctg caatacggt    3540 ccccacaact gtgggaaggg gttaggggca gggatctcat caggaaagca tagggttta    3600 aagttcttta tagagcactt agaagattga gaatccacaa attatattaa taacaaacaa    3660
agtagtgtcg tgttatatag taaatgtgaa tttgcagaca catttaggga aaagttataa    3720
```

|  |  |
|---|---:|
| ttaaaaaaat aggctgtata tatacctgca ggtctagata cgtagataag tagcatggcg | 3780 |
| ggttaatcat taactacaag gaaccoctag tgatggagtt ggccactccc tctctgcgcg | 3840 |
| ctcgctcgct cactgaggcc gggcgaccaa aggtcgcccg acgcccgggc tttgcccggg | 3900 |
| cggcctcagt gagcgagcga gcgcgcagag agggagtggc caa | 3943 |

```
<210> SEQ ID NO 62
<211> LENGTH: 3951
<212> TYPE: DNA
<213> ORGANISM: Artificial Sequence
<220> FEATURE:
<223> OTHER INFORMATION: 32.8 vector correction genome (+ ITRs)

<400> SEQUENCE: 62
```

|  |  |
|---|---:|
| ttggccactc cctctctgcg cgctcgctcg ctcactgagg ccgggcgacc aaaggtcgcc | 60 |
| cgacgcccgg gctttgcccg gcggcctca gtgagcgagc gagcgcgcag agagggagtg | 120 |
| gccaactcca tcactagggg ttcctggagg ggtggagtcg tgacgtgaat tacgtcatag | 180 |
| ggttagggag gtcctgcata tgcggccgct tcaggagcag ttgtgcgaat agctggagaa | 240 |
| caccaggctg gatttaaacc cagatcgctc ttacatttgc tctttacctg ctgtgctcag | 300 |
| cgttcacgtg ccctctagct gtagtttttct gaagtcagcg cacagcaagg cagtgtgctt | 360 |
| agaggttaac agaagggaaa acaacaacaa caaaaatcta atgagaatc ctgactgttt | 420 |
| cagctggggg taagggggggc ggattattca tataattgtt ccaccagacg gtcgcaggct | 480 |
| tagtccaatt gcagagaaca cgctgttctt cgccccaggc ttctgagagt cccggaagtg | 540 |
| cctaaacctg tctaatcgac ggggcttggg tggcccgtcg ctccctggct tcttcccttt | 600 |
| acccagggcg ggcagcgaag tggtgcctcc tgcgtccccc acaccctccc tcagcccctc | 660 |
| ccctccggcc cgtcctgggc aggtgacctg gagcatccgg caggctgccc tggcctcctg | 720 |
| cgtcaggaca acgcccacga ggggcgttac tgtgcggaga tgcaccacgc aagagacacc | 780 |
| ctttgtaact ctcttctcct ccctagtgcg aggttaaaac cttcagcccc acgtgctgtt | 840 |
| tgcaaacctg cctgtacctg aggccctaaa agccagaga cctcactccc ggggagccag | 900 |
| catgtccact gcggtcctgg aaaacccagg cttgggcagg aaactctctg actttggaca | 960 |
| ggtgagccac ggcagcctga gctgctcagt taggggaatt tgggcctcca gagaaagaga | 1020 |
| tccgaagact gctggtgctt cctggtttca taagctcagt aagaagtctg aattcgttgg | 1080 |
| aagctgatga gaatatccag gaagtcaaca gacaaatgtc ctcaacaatt gtttctaagt | 1140 |
| aggagaacat ctgtcctcgg tggctttcac aggaaaagct tctgacctct tctcttcctc | 1200 |
| ccacagggca gcggagctac taacttcagc ctgctgaagc aggctggaga cgtggaggag | 1260 |
| aaccctggac ctatgtccac cgctgtgctg gagaaccctg gctggggag gaaactgtca | 1320 |
| gacttcgggc aggagacttc atacattgag gataactgta accagaatgg cgccatctct | 1380 |
| ctgatcttca gcctgaagga ggaagtgggc gccctggcaa aggtgctgcg cctgtttgag | 1440 |
| gagaacgacg tgaatctgac ccacatcgag tcccggcctt ctagactgaa gaaggacgag | 1500 |
| tacgagttct ttacccacct ggataagcgg tccctgccag ccctgacaaa catcatcaag | 1560 |
| atcctgaggc acgacatcgg agcaaccgtg cacgagctgt ctcgggacaa gaagaaggat | 1620 |
| accgtgccct ggttccctcg acaatccag gagctggata gatttgccaa ccagatcctg | 1680 |
| tcttacggag cagagctgga cgcagatcac cctggcttca aggacccagt gtatcgggcc | 1740 |
| cggagaaagc agtttgccga tatcgcctac aattataggc acgacagcc aatccctcgc | 1800 |
| gtggagtata tggaggagga gaagaagacc tggggcacag tgttcaagac cctgaagagc | 1860 |

```
ctgtacaaga cacacgcctg ctacgagtat aaccacatct tcccctgct ggagaagtat    1920 tgtggctttc acgaggacaa tatccctcag ctggaggacg tgagccagtt cctgcagacc    1980
tgcacaggct ttaggctgag gccagtggca ggactgctga gctcccggga cttcctggga    2040
ggactggcct tcagagtgtt tcactgcacc cagtacatca ggcacggctc caagccaatg    2100
tatacaccag agcccgacat ctgtcacgag ctgctgggcc acgtgcccct gtttagcgat    2160
agatccttcg cccagttttc ccaggagatc ggactggcat ctctgggagc acctgacgag    2220
tacatcgaga agctggccac catctattgg ttcacagtgg agtttggcct gtgcaagcag    2280
ggcgatagca tcaaggccta cggagcagga ctgctgtcta gcttcggcga gctgcagtat    2340
tgtctgtccg agaagccaaa gctgctgccc ctggagctgg agaagaccgc catccagaac    2400
tacaccgtga cagagttcca gcccctgtac tatgtggccg agtcttttaa cgatgccaag    2460
gagaaggtga gaaatttcgc cgccacaatc cctaggccct cagcgtgcg gtacgaccct    2520 tatacccaga ggatcgaggt gctggataat acacagcagc tgaagatcct ggctgactca    2580
atcaatagcg aaatcggaat cctgtgctcc gccctgcaga aaatcaaatg aggtaccgat    2640
ccagacatga taagatacat tgatgagttt ggacaaacca caactagaat gcagtgaaaa    2700
aaatgcttta tttgtgaaat ttgtgatgct attgctttat ttgtaaccat tataagctgc    2760
aataaacaag ttaacaacaa caattgcatt cattttatgt ttcaggttca ggggaggtg    2820 tgggaggttt tttaaggatc cctgggatgg gatgtggaat ccttctagat ttcttttgta    2880
atatttataa agtgctctca gcaaggtatc aaaatggcaa aattgtgagt aactatcctc    2940
ctttcatttt gggaagaaga tgaggcatga agagaattca gacagaaact tactcagacc    3000
aggggaggca gaaactaagc agagaggaaa atgaccaaga gttagccctg ggcatggaat    3060
gtgaaagaac cctaaacgtg acttggaaat aatgcccaag gtatattcca ttctccggga    3120
tttgttggca ttttcttgag gtgaagaatt gcagaataca ttctttaatg tgacctacat    3180
atttacccat gggaggaagt ctgctcctgg actcttgaga ttcagtcata aagcccaggc    3240
cagggaaata atgtaagtct gcaggcccct gtcatcagta ggattaggga aagagttct    3300 cagtagaaaa cagggaggct ggagagaaaa gaatggttaa tgttaacgtt aatataacta    3360
gaaagactgc agaacttagg actgattttt atttgaatcc ttaaaaaaaa aaatttctta    3420
tgaaaatagt acatggctct taggagacag aacttattgt acagaggaac agcgtgagag    3480
tcagagtgat cccagaacag gtcctggctc catcctgcac atagttttgg tgctgctggc    3540
aatacggtcc ccacaactgt gggaaggggt taggggcagg gatctcatca ggaaagcata    3600
ggggtttaaa gttctcttata gagcacttag aagattgaga atccacaaat tatattaata    3660
acaaacaaag tagtgtcgtg ttatatagta aatgtgaatt tgcagacaca tttagggaaa    3720
agttataatt aaaaaaatag gctgtatata tacctgcagg tctagatacg tagataagta    3780
gcatggcggg ttaatcatta actacaagga accctagtg atggagttgg ccactccctc    3840
tctgcgcgct cgctcgctca ctgaggccgg gcgaccaaag gtcgcccgac gcccgggctt    3900
tgcccgggcg gcctcagtga gcgagcgagc gcgcagagag ggagtggcca a              3951
```

<210> SEQ ID NO 63
<211> LENGTH: 3943
<212> TYPE: DNA
<213> ORGANISM: Artificial Sequence
<220> FEATURE:
<223> OTHER INFORMATION: 32.9 vector correction genome (+ ITRs)

<400> SEQUENCE: 63

```
ttggccactc cctctctgcg cgctcgctcg ctcactgagg ccgggcgacc aaaggtcgcc    60
cgacgcccgg gctttgcccg ggcggcctca gtgagcgagc gagcgcgcag agagggagtg   120
gccaactcca tcactagggg ttcctggagg ggtggagtcg tgacgtgaat tacgtcatag   180
ggttagggag gtcctgcata tgcggccgct tcaggagcag ttgtgcgaat agctggagaa   240
caccaggctg gatttaaacc cagatcgctc ttacatttgc tctttacctg ctgtgctcag   300
cgttcacgtg ccctctagct gtagttttct gaagtcagcg cacagcaagg cagtgtgctt   360
agaggttaac agaagggaaa acaacaacaa caaaaatcta aatgagaatc ctgactgttt   420
cagctgagag taagggggc ggattattca tataattgtt ataccagacg gtcgcaggct   480
tagtccaatt gcagagaact cgcttcccag gcttctgaga gtcccggaag tgcctaaacc   540
tgtctaatcg acagagcttg ggtggcccgt cgctccctgg cttcttccct ttacccaggg   600
cgggcagcga agtggtgcct cctgcgtccc ccacaccctc cctcagcccc tcccctccgg   660
cccgtcctag gcaggtgacc tgaagcatcc agcaggctgc cctggcctcc tgcgtcagga   720
caacgcccac gagggcgtt actgtgcgga gatgcaccac gcaagagaca cccttttgtaa   780
ctctcttctc ctccctagtg cgaggttaaa accttcagcc ccacgtgctg tttgcaaacc   840
tgcctgtacc tgaggcccta aaaagccaga gacctcactc ccggggagcc agcatgtcca   900
ctgcggtcct ggaaaaccca ggcttgggca ggaaactctc tgactttgga caggtgagcc   960
acggcagcct gagctgctca gttagggaa tttgggcctc cagagaaaga gatccgaaga  1020
ctgctggtgc ttcctggttt cataagctca gtaagaagtc tgaattcgtt ggaagctgat  1080
gagaatatcc aggaagtcaa cagacaaatg tcctcaacaa ttgtttctaa gtaggagaac  1140
atctgtcctc ggtggctttc acaggaaaag cttctgacct cttctcttcc tcccacaggg  1200
cagcggagct actaacttca gcctgctgaa gcaggctgga gacgtggagg agaaccctgg  1260
acctatgtcc accgctgtgc tggagaaccc tgggctgggg aggaaactgt cagacttcgg  1320
gcaggagact tcatacattg aggataactg taaccagaat ggcgccatct ctctgatctt  1380
cagcctgaag gaggaagtgg gcgccctggc aaaggtgctg cgcctgtttg aggagaacga  1440
cgtgaatctg acccacatcg agtcccggcc ttctagactg aagaaggacg agtacgagtt  1500
ctttacccac ctggataagc ggtccctgcc agccctgaca aacatcatca agatcctgag  1560
gcacgacatc ggagcaaccg tgcacagct gtctcgggac aagaagaagg ataccgtgcc  1620
ctggttccct cggacaatcc aggagctgga tagatttgcc aaccagatcc tgtcttacgg  1680
agcagagctg gacgcagatc accctggctt caaggaccca gtgtatcggg cccggagaaa  1740
gcagtttgcc gatatcgcct acaattatag gcacggacag ccaatccctc gcgtggagta  1800
tatggaggag gagaagaaga cctggggcac agtgttcaag accctgaaga gcctgtacaa  1860
gacacacgcc tgctacgagt ataaccacat cttcccctg ctggagaagt attgtggctt  1920
tcacgaggac aatatccctc agctggagga cgtgagccga ttcctgcaga cctgcacagg  1980
ctttaggctg aggccagtgg caggactgct gagctcccgg gacttcctgg gaggactggc  2040
cttcagagtg tttcactgca cccagtacat caggcacggc tccaagccaa tgtatacacc  2100
agagcccgac atctgtcacg agctgctggg ccacgtgccc ctgtttagcg atagatcctt  2160
cgcccagttt tcccaggaga tcggactggc atctctggga gcacctgacg agtacatcga  2220
gaagctggcc accatctatt ggttcacagt ggagtttggc ctgtgcaagc agggcgatag  2280
catcaaggcc tacggagcag gactgctgtc tagcttcggc gagctgcagt attgtctgtc  2340
```

-continued

```
cgagaagcca aagctgctgc ccctggagct ggagaagacc gccatccaga actacaccgt    2400
gacagagttc cagcccctgt actatgtggc cgagtctttt aacgatgcca aggagaaggt    2460
gagaaatttc gccgccacaa tccctaggcc cttcagcgtg cggtacgacc cttataccca    2520
gaggatcgag gtgctggata atacacagca gctgaagatc ctggctgact caatcaatag    2580
cgaaatcgga atcctgtgct ccgccctgca gaaaatcaaa tgaggtaccg atccagacat    2640
gataagatac attgatgagt ttggacaaac cacaactaga atgcagtgaa aaaaatgctt    2700
tatttgtgaa atttgtgatg ctattgcttt atttgtaacc attataagct gcaataaaca    2760
agttaacaac aacaattgca ttcattttat gtttcaggtt caggggggagg tgtgggaggt    2820 tttttaagga tccctgggat gggatgtgga atccttctag atttctttg taatatttat     2880 aaagtgctct cagcaaggta tcaaaatggc aaaattgtga gtaactatcc tcctttcatt    2940
ttgggaagaa gatgaggcat gaagagaatt cagacagaaa cttactcaga ccaggggagg    3000
cagaaactaa gcagagagga aaatgaccaa gagttagccc tgggcatgga atgtgaaaga    3060
accctaaacg tgacttggaa ataatgccca aggtatattc cattctccgg gatttgttgg    3120
cattttcttg aggtgaagaa ttgcagaata cattctttaa tgtgacctac atatttaccc    3180
atgggaggaa gtctgctcct ggactcttga gattcagtca taaagcccag gccagggaaa    3240
taatgtaagt ctgcaggccc ctgtcatcag taggattagg gagaagagtt ctcagtagaa    3300
aacagggagg ctgagagaaa aagaatggtt aatgttaacg ttaatataac tagaaagact    3360
gcagaactta ggactgattt ttatttgaat ccttaaaaaa aaaaatttct tatgaaaata    3420
gtacatggct cttaggagac agaacttatt gtacagagga acagcgtgag agtcagagtg    3480
atcccagaac aggtcctggc tccatcctgc acatagtttt ggtgctgctg gcaatacggt    3540
ccccacaact gtgggaaggg gttaggggca gggatctcat caggaaagca tagggggttta   3600 aagttcttta tagagcactt agaagattga gaatccacaa attatattaa taacaaacaa    3660
agtagtgtcg tgttatatag taaatgtgaa tttgcagaca catttaggga aaagttataa    3720
ttaaaaaaat aggctgtata tatacctgca ggtctagata cgtagataag tagcatggcg    3780
ggttaatcat taactacaag gaacccctag tgatggagtt ggccactccc tctctgcgcg    3840
ctcgctcgct cactgaggcc gggcgaccaa aggtcgcccg acgcccgggc tttgcccggg    3900
cggcctcagt gagcgagcga gcgcgcagag agggagtggc caa                      3943
```

<210> SEQ ID NO 64
<211> LENGTH: 912
<212> TYPE: DNA
<213> ORGANISM: Homo sapiens

<400> SEQUENCE: 64

```
atgtccactg cggtcctgga aaacccaggc ttgggcagga aactctctga ctttggacag     60
gaaacaagct atattgaaga caactgcaat caaaatggtg ccatatcact gatcttctca    120
ctcaaagaag aagttggtgc attggccaaa gtattgcgct tatttgagga gaatgatgta    180
aacctgaccc acattgaatc tagaccttct cgtttaaaga agatgagta tgaattttc     240 acccatttgg ataaacgtag cctgcctgct ctgacaaaca tcatcaagat cttgaggcat    300
gacattggtg ccactgtcca tgagctttca cgagataaga agaaagacac agtgccctgg    360
ttcccaagaa ccattcaaga gctggacaga tttgccaatc agattctcag ctatggagcg    420
gaactggatg ctgaccaccc tggttttaaa gatcctgtgt accgtgcaag acggaagcag    480
```

```
tttgctgaca ttgcctacaa ctaccgccat gggcagccca tccctcgagt ggaatacatg    540
gaggaagaaa agaaaacatg gggcacagtg ttcaagactc tgaagtcctt gtataaaacc    600
catgcttgct atgagtacaa tcacattttt ccacttcttg aaaagtactg tggcttccat    660
gaagataaca ttccccagct ggaagacgtt tctcagttcc tgcagacttg cactggtttc    720
cgcctccgac ctgtggctgg cctgctttcc tctcgggatt tcttgggtgg cctggccttc    780
cgagtcttcc actgcacaca gtacatcaga catggatcca agcccatgta taccccgaa    840 cctgacatct gccatgagct gttgggacat gtgcccttgt tttcagatcg cagctttgcc    900
cagttttccc ag                                                        912
```

<210> SEQ ID NO 65
<211> LENGTH: 912
<212> TYPE: DNA
<213> ORGANISM: Artificial Sequence
<220> FEATURE:
<223> OTHER INFORMATION: from start codon to end of exon 8 of silently
altered PAH coding sequence <400> SEQUENCE: 65

```
atgtccaccg ctgtgctgga gaaccctggg ctggggagga aactgtcaga cttcgggcag     60
gagacttcat acattgagga taactgtaac cagaatggcg ccatctctct gatcttcagc    120
ctgaaggagg aagtgggcgc cctggcaaag gtgctgcgcc tgtttgagga gaacgacgtg    180
aatctgaccc acatcgagtc ccggccttct agactgaaga aggacgagta cgagttcttt    240
acccacctgg ataagcggtc cctgccagcc ctgacaaaca tcatcaagat cctgaggcac    300
gacatcggag caaccgtgca cgagctgtct cgggacaaga gaaggatac cgtgccctgg    360 ttccctcgga caatccagga gctggataga tttgccaacc agatcctgtc ttacggagca    420
gagctggacg cagatcaccc tggcttcaag gacccagtgt atcgggccg gagaaagcag    480 tttgccgata tcgcctacaa ttataggcac ggacagccaa tccctcgcgt ggagtatatg    540
gaggaggaga agaagacctg gggcacagtg ttcaagaccc tgaagagcct gtacaagaca    600
cacgcctgct acgagtataa ccacatcttc cccctgctgg agaagtattg tggctttcac    660
gaggacaata tccctcagct ggaggacgtg agccagttcc tgcagacctg cacaggcttt    720
aggctgaggc cagtggcagg actgctgagc tcccgggact tcctgggagg actggccttc    780
agagtgtttc actgcaccca gtacatcagg cacggctcca gcccaatgta taccccagag    840
cccgacatct gtcacgagct gctgggccac gtgcccctgt ttagcgatag atccttcgcc    900
cagttttccc ag                                                        912
```

<210> SEQ ID NO 66
<211> LENGTH: 447
<212> TYPE: DNA
<213> ORGANISM: Homo sapiens
<400> SEQUENCE: 66

```
gaaattggcc ttgcctctct gggtgcacct gatgaataca ttgaaaagct cgccacaatt     60
tactggttta ctgtggagtt tgggctctgc aaacaaggag actccataaa ggcatatggt    120
gctgggctcc tgtcatcctt tggtgaatta cagtactgct atcagagaa gccaaagctt    180 ctcccctgg agctggagaa gacagccatc caaaattaca ctgtcacgga gttccagcc    240 ctctattacg tggcagagag tttttaatgat gccaaggaga agtaaggaa ctttgctgcc    300 acaatacctc ggccccttctc agttcgctac gacccataca cccaaaggat tgaggtcttg    360
```

```
gacaataccc agcagcttaa gattttggct gattccatta acagtgaaat tggaatcctt    420
tgcagtgccc tccagaaaat aaagtaa                                         447
```

<210> SEQ ID NO 67
<211> LENGTH: 447
<212> TYPE: DNA
<213> ORGANISM: Artificial Sequence
<220> FEATURE:
<223> OTHER INFORMATION: from start of exon 9 to stop codon of silently altered PAH coding sequence

<400> SEQUENCE: 67

```
gagatcggac tggcatctct gggagcacct gacgagtaca tcgagaagct ggccaccatc    60
tattggttca cagtggagtt tggcctgtgc aagcagggcg atagcatcaa ggcctacgga    120
gcaggactgc tgtctagctt cggcgagctg cagtattgtc tgtccgagaa gccaaagctg    180 ctgccctgg agctggagaa gaccgccatc agaactaca ccgtgacaga gttccagccc      240
ctgtactatg tggccgagtc ttttaacgat gccaaggaga aggtgagaaa tttcgccgcc    300
acaatcccta ggcccttcag cgtgcggtac gacccttata cccagaggat cgaggtgctg    360
gataatacac agcagctgaa gatcctggct gactcaatca atagcgaaat cggaatcctg    420
tgctccgccc tgcagaaaat caaatga                                         447
```

<210> SEQ ID NO 68
<211> LENGTH: 15
<212> TYPE: DNA
<213> ORGANISM: Artificial Sequence
<220> FEATURE:
<223> OTHER INFORMATION: modification to glucocorticoid binding site

<400> SEQUENCE: 68

```
acgctgttct tcgcc                                                      15
```

<210> SEQ ID NO 69
<211> LENGTH: 800
<212> TYPE: DNA
<213> ORGANISM: Homo sapiens

<400> SEQUENCE: 69

```
tatcttccat ttactgagtg tttatgtgga agaactgtac taaattttaa tgcatttctt    60
tattcctatt cttaaaacct tccagcaagg tggctctacc accctctttt ccagcttca    120 ggagcagttg tgcgaatagc tggagaacac caggctggat ttaaacccag atcgctctta    180
catttgctct ttacctgctg tgctcagcgt tcacgtgccc tctagctgta gttttctgaa    240
gtcagcgcac agcaaggcag tgtgcttaga ggttaacaga agggaaaaca acaacaacaa    300
aaatctaaat gagaatcctg actgtttcag ctggggggtaa ggggggcgga ttattcatat   360
aattgttata ccagacggtc gcaggcttag tccaattgca gagaactcgc ttcccaggct    420
tctgagagtc ccggaagtgc ctaaacctgt ctaatcgacg gggcttgggt ggcccgtcgc    480
tccctggctt cttcccttta cccagggcgg gcagcgaagt ggtgcctcct gcgtccccca    540
caccctccct cagcccctcc cctccggccc gtcctgggca ggtgacctgg agcatccggc    600
aggctgccct ggcctcctgc gtcaggacaa cgccacgag gggcgttact gtgcggagat     660
gcaccacgca agagacaccc tttgtaactc tcttctcctc cctagtgcga ggttaaaacc    720
ttcagcccca cgtgctgttt gcaaacctgc ctgtacctga ggcccctaaaa agccagagac   780 ctcactcccg gggagccagc                                                800
```

<210> SEQ ID NO 70
<211> LENGTH: 800
<212> TYPE: DNA
<213> ORGANISM: Homo sapiens

<400> SEQUENCE: 70

```
tccactgcgg tcctggaaaa cccaggcttg ggcaggaaac tctctgactt tggacaggtg      60
agccacggca gcctgagctg ctcagttagg ggaatttggg cctccagaga aagagatccg     120
aagactgctg gtgcttcctg gtttcataag ctcagtaaga agtctgaatt cgttggaagc     180
tgatgagaat atccaggaag tcaacagaca aatgtcctca acaattgttt ctaagtagga     240
gaacatctgt cctcggtggc tttcacagga atgaatgacc attgctttag ggggttgggg     300
atctggcctc cagaactgcc accaattagc tgtgtgtctt tggacaagtt actgtccctc     360
tctgttgtct gtttactctt ctgtacactg aaggggctgg tccctaatga tctgggatgg     420
gatgtggaat ccttctagat ttcttttgta atatttataa agtgctctca gcaaggtatc     480
aaaatggcaa aattgtgagt aactatcctc ctttcatttt gggaagaaga tgaggcatga     540
agagaattca gacagaaact tactcagacc aggggaggca gaaactaagc agagaggaaa     600
atgaccaaga gttagccctg gcatggaat gtgaaagaac cctaaacgtg acttggaaat     660
aatgcccaag gtatattcca ttctccggga tttgttggca ttttcttgag gtgaagaatt     720
gcagaataca ttctttaatg tgacctacat atttacccat gggaggaagt ctgctcctgg     780
actcttgaga ttcagtcata                                                800
```

<210> SEQ ID NO 71
<211> LENGTH: 16
<212> TYPE: DNA
<213> ORGANISM: Artificial Sequence
<220> FEATURE:
<223> OTHER INFORMATION: targeted integration restriction cassette

<400> SEQUENCE: 71

```
tacgtacgat cgtcga                                                     16
```

<210> SEQ ID NO 72
<211> LENGTH: 800
<212> TYPE: DNA
<213> ORGANISM: Homo sapiens

<400> SEQUENCE: 72

```
aatggttcca aaattttcta tggttaagaa tcacctggga tggttttgaa atggcagatt      60
ctaagacaac ttgattcaac aggtttaggt aaagcccagg gaactgcatt ataagaagga     120
atcacctgta attttggagt caagatccaa ggaacactca ttgagaaaca ctgatttaca     180
aagtgcatgg agagaaatgg agcaagtgaa gggggatcag catggtgaaa tataggctgt     240
taggagtgct attgactaac tgtctggtga ctggaccaga gtaaatcttt tactttgcaa     300
gaaacaggac taaattccca tattatgtcc atagcaaagg gaattatgta gaaaaattga     360
taattaggag cctgagttct tgaccagcct ccactaccta tgtggcctca ggtgagttat     420
tttctccctt tggctctaag ttttccccat ctgtaatgta agggagttta actagatgag     480
cactaaggac aaatcaattt ctgtgagtca attattatga aataccatgt gggcatcaaa     540
tgccaagtgg aaagcataga taagaagtg attgtgcacc tgggctgagg gaacaaaca     600
tttcctaaga gaattgagac ccaaaagagc ctttaaggaa ggtgagatct tggaaaggga     660
aatttggtga atactctaat gaggagctaa aaaggcaaga agaaagcag cttggctgga     720
```

| | | |
|---|---|---|
| aaggaggttc ctgtaggtgg gcctccagag attcggtacc acagaaactg ccaaacatca | 780 | |
| gcaagaagcc atggggatgg | 800 | |

<210> SEQ ID NO 73
<211> LENGTH: 800
<212> TYPE: DNA
<213> ORGANISM: Homo sapiens

<400> SEQUENCE: 73

| | |
|---|---|
| agcgtttgag ggattctaaa tagaaggaca agagtaaaaa tgtcaggctg gatcgatgca | 60 |
| ggccactaag aaatggattc aggtgatggc agtgggaaga aaggacctga tgcccagagg | 120 |
| catttctgga gaagatgaga tcagacttgt gattggctga acacacactg tagtggggtg | 180 |
| gggtttaggg ggtgactcaa cttcaagccc aggtacattc aagtctgaat tgccctagtc | 240 |
| aaaagtggca tctgtggatg tgtatcagaa atatcttact tttcttggaa gccaacagga | 300 |
| gaaaagagtg ctaccaagtg aactagagac aggaatatct tttgtcattt caaggaaact | 360 |
| ggaaagaaga aggctcagta ttctttagta ggaagaagac ttaagtcaga gactcatctg | 420 |
| tacctctctg gcagggttta aaggggggaa gaggaataga ggctgcaaga gattgtgatt | 480 |
| catggacagt atgcagagat caaatgacct gggttcagat cctggctcca ctgctaactg | 540 |
| tgtaactata ggcaagttcc ttaacctctc taagccttaa tcttgtcatc aataaaaggg | 600 |
| ggcacttggt gcctaataaa acctacctct taggttgttg ccaaattaca tgagataatc | 660 |
| caaatcaagt gcttattata atacccagaa attataggct ctaaataaat gtttatatag | 720 |
| gctctaaata aatgaagttt tttagaaaga taacatcatg atcaaaatgg gatatttaac | 780 |
| agtttagtct tccatttcat | 800 |

<210> SEQ ID NO 74
<211> LENGTH: 72
<212> TYPE: DNA
<213> ORGANISM: Artificial Sequence
<220> FEATURE:
<223> OTHER INFORMATION: 2A element

<400> SEQUENCE: 74

| | |
|---|---|
| agatctggca gcggagaggg cagaggaagt cttctaacat gcggtgacgt ggaggagaat | 60 |
| cccggcccta gg | 72 |

<210> SEQ ID NO 75
<211> LENGTH: 8
<212> TYPE: PRT
<213> ORGANISM: Artificial Sequence
<220> FEATURE:
<223> OTHER INFORMATION: Ribosomal skipping peptide consensus sequence
<220> FEATURE:
<221> NAME/KEY: VARIANT
<222> LOCATION: (1)..(1)
<223> OTHER INFORMATION: D or G
<220> FEATURE:
<221> NAME/KEY: VARIANT
<222> LOCATION: (2)..(2)
<223> OTHER INFORMATION: V or I
<220> FEATURE:
<221> NAME/KEY: VARIANT
<222> LOCATION: (4)..(4)
<223> OTHER INFORMATION: any amino acid residue

<400> SEQUENCE: 75

Xaa Xaa Glu Xaa Asn Pro Gly Pro
1               5

<210> SEQ ID NO 76
<211> LENGTH: 18
<212> TYPE: PRT
<213> ORGANISM: Artificial Sequence
<220> FEATURE:
<223> OTHER INFORMATION: T2A peptide

<400> SEQUENCE: 76

Glu Gly Arg Gly Ser Leu Leu Thr Cys Gly Asp Val Glu Glu Asn Pro
1               5                   10                  15

Gly Pro

<210> SEQ ID NO 77
<211> LENGTH: 19
<212> TYPE: PRT
<213> ORGANISM: Artificial Sequence
<220> FEATURE:
<223> OTHER INFORMATION: P2A peptide

<400> SEQUENCE: 77

Ala Thr Asn Phe Ser Leu Leu Lys Gln Ala Gly Asp Val Glu Glu Asn
1               5                   10                  15

Pro Gly Pro

<210> SEQ ID NO 78
<211> LENGTH: 54
<212> TYPE: DNA
<213> ORGANISM: Artificial Sequence
<220> FEATURE:
<223> OTHER INFORMATION: T2A element

<400> SEQUENCE: 78
gagggcagag gaagtcttct aacatgcggt gacgtggagg agaatcccgg ccct         54

<210> SEQ ID NO 79
<211> LENGTH: 57
<212> TYPE: DNA
<213> ORGANISM: Artificial Sequence
<220> FEATURE:
<223> OTHER INFORMATION: P2A element

<400> SEQUENCE: 79
gctactaact tcagcctgct gaagcaggct ggagacgtgg aggagaaccc tggacct      57

<210> SEQ ID NO 80
<211> LENGTH: 1489
<212> TYPE: DNA
<213> ORGANISM: Artificial Sequence
<220> FEATURE:
<223> OTHER INFORMATION: PAH intron-inserted silently altered coding
      sequence (human HBB first intron)

<400> SEQUENCE: 80
atgtccaccg ctgtgctgga gaaccctggg ctggggagga aactgtcaga cttcgggcag    60
gagacttcat acattgagga taactgtaac cagaatggcg ccatctctct gatcttcagc   120
ctgaaggagg aagtgggcgc cctggcaaag gtgctgcgcc tgtttgagga gaacgacgtg   180
aatctgaccc acatcgagtc ccggccttct agactgaaga aggacgagta cgagttcttt   240
acccacctgg ataagcggtc cctgccagcc ctgacaaaca tcatcaagat cctgaggcac   300
gacatcggag caaccgtgca cgagctgtct cgggacaaga gaaggatac cgtgccctgg   360 ttccctcgga caatccagga gctggataga tttgccaacc agatcctgtc ttacggagca   420

```
gagctggacg cagatcaccc tggcttcaag acccagtgt atcgggcccg gagaaagcag      480
tttgccgata tcgcctacaa ttataggcac ggacagccaa tccctcgcgt ggagtatatg     540
gaggaggaga agaagacctg gggcacagtg ttcaagaccc tgaagagcct gtacaagaca     600
cacgcctgct acgagtataa ccacatcttc ccctgctgg agaagtattg tggctttcac      660
gaggacaata tccctcagct ggaggacgtg agccagttcc tgcagacctg cacaggcttt     720
aggctgaggc cagtggcagg actgctgagc tcccgggact tcctgggagg actggccttc     780
agagtgtttc actgcaccca gtacatcagg cacggctcca gccaatgta tacaccagag      840 cccgacatct gtcacgagct gctgggccac gtgcccctgt ttagcgatag atccttcgcc     900
cagttttccc aggttggtat caaggttaca agacaggttt aaggagacca atagaaactg     960
ggcatgtgga gacagagaag actcttgggt ttctgatagg cactgactct ctctgcctat    1020
tggtctattt tcccacccct aggagatcgg actggcatct ctgggagcac ctgacgagta    1080
catcgagaag ctggccacca tctattggtt cacagtggag tttggcctgt gcaagcaggg    1140
cgatagcatc aaggcctacg agcaggact gctgtctagc ttcggcgagc tgcagtattg     1200
tctgtccgag aagccaaagc tgctgcccct ggagctggaa aagaccgcca tccagaacta    1260
caccgtgaca gagttccagc ccctgtacta tgtggccgag tcttttaacg atgccaagga    1320
gaaggtgaga aatttcgccg ccacaatccc taggcccttc agcgtgcggt acgacccta     1380 tacccagagg atcgaggtgc tggataatac acagcagctg aagatcctgg ctgactcaat    1440
caatagcgaa atcggaatcc tgtgctccgc cctgcagaaa atcaaatga                1489
```

<210> SEQ ID NO 81
<211> LENGTH: 1475
<212> TYPE: DNA
<213> ORGANISM: Artificial Sequence
<220> FEATURE:
<223> OTHER INFORMATION: PAH intron-inserted silently altered coding
      sequence (mouse HBB first intron)

<400> SEQUENCE: 81

```
atgtccaccg ctgtgctgga gaaccctggg ctggggagga aactgtcaga cttcgggcag       60
gagacttcat acattgagga taactgtaac cagaatggcg ccatctctct gatcttcagc      120
ctgaaggagg aagtgggcgc cctggcaaag gtgctgcgcc tgtttgagga aacgacgtg       180 aatctgaccc acatcgagtc ccggccttct agactgaaga aggacgagta cgagttcttt      240
acccacctgg ataagcggtc cctgccagcc ctgacaaaca tcatcaagat cctgaggcac      300
gacatcggag caaccgtgca cgagctgtct cgggacaaga agaaggatac cgtgccctgg      360
ttccctcgga caatccagga gctggataga tttgccaacc agatcctgtc ttacggagca      420
gagctggacg cagatcaccc tggcttcaag acccagtgt atcgggcccg gagaaagcag       480
tttgccgata tcgcctacaa ttataggcac ggacagccaa tccctcgcgt ggagtatatg     540
gaggaggaga agaagacctg gggcacagtg ttcaagaccc tgaagagcct gtacaagaca     600
cacgcctgct acgagtataa ccacatcttc ccctgctgg agaagtattg tggctttcac      660
gaggacaata tccctcagct ggaggacgtg agccagttcc tgcagacctg cacaggcttt     720
aggctgaggc cagtggcagg actgctgagc tcccgggact tcctgggagg actggccttc     780
agagtgtttc actgcaccca gtacatcagg cacggctcca gccaatgta tacaccagag      840 cccgacatct gtcacgagct gctgggccac gtgcccctgt ttagcgatag atccttcgcc     900
cagttttccc aggttggtat ccaggttaca aggcagctca caagaagaag ttgggtgctt     960
```

-continued

```
ggagacagag gtctgctttc cagcagacac taactttcag tgtcccctgt ctatgtttcc    1020 cttttagga  gatcggactg gcatctctgg gagcacctga cgagtacatc gagaagctgg    1080
ccaccatcta ttggttcaca gtggagtttg gcctgtgcaa gcagggcgat agcatcaagg    1140
cctacggagc aggactgctg tctagcttcg gcgagctgca gtattgtctg tccgagaagc    1200
caaagctgct gccctggag  ctggagaaga ccgccatcca gaactacacc gtgacagagt    1260
tccagcccct gtactatgtg gccgagtctt taacgatgc  caaggagaag gtgagaaatt    1320
tcgccgccac aatccctagg cccttcagcg tgcggtacga cccttatacc cagaggatcg    1380
aggtgctgga taatacacag cagctgaaga tcctggctga ctcaatcaat agcgaaatcg    1440
gaatcctgtg ctccgccctg cagaaaatca aatga                              1475
```

<210> SEQ ID NO 82
<211> LENGTH: 1451
<212> TYPE: DNA
<213> ORGANISM: Artificial Sequence
<220> FEATURE:
<223> OTHER INFORMATION: PAH intron-inserted silently altered coding
      sequence (MVM intron)

<400> SEQUENCE: 82

```
atgtccaccg ctgtgctgga gaaccctggg ctggggagga aactgtcaga cttcgggcag    60
gagacttcat acattgagga taactgtaac cagaatggcg ccatctctct gatcttcagc    120
ctgaaggagg aagtgggcgc cctggcaaag gtgctgcgcc tgtttgagga gaacgacgtg    180
aatctgaccc acatcgagtc ccggccttct agactgaaga aggacgagta cgagttcttt    240
acccacctgg ataagcggtc cctgccagcc ctgacaaaca tcatcaagat cctgaggcac    300
gacatcggag caaccgtgca cgagctgtct cgggacaaga gaaggatac  cgtgccctgg    360 ttccctcgga caatccagga gctggataga tttgccaacc agatcctgtc ttacggagca    420
gagctggacg cagatcaccc tggcttcaag gacccagtgt atcgggcccg gagaaagcag    480
tttgccgata tcgcctacaa ttataggcac ggacagccaa tccctcgcgt ggagtatatg    540
gaggaggaga agaagacctg gggcacagtg ttcaagaccc tgaagagcct gtacaagaca    600
cacgcctgct acgagtataa ccacatcttc ccctgctgg  agaagtattg tggctttcac    660
gaggacaata tccctcagct ggaggacgtg agccagttcc tgcagacctg cacaggcttt    720
aggctgaggc cagtggcagg actgctgagc tcccgggact tcctgggagg actggccttc    780
agagtgtttc actgcaccca gtacatcagg cacggctcca gccaatgta  tacaccagag    840 cccgacatct gtcacgagct gctgggccac gtgcccctgt ttagcgatag atccttcgcc    900
cagttttccc agaagaggta agggtttaag ggatggttgg ttgtggggt  attaatgttt    960 aattacctgg agcacctgcc tgaaatcact tttttcagg  ttgggagatc ggactggcat    1020
ctctgggagc acctgacgag tacatcgaga agctggccac catctattgg ttcacagtgg    1080
agtttggcct gtgcaagcag gccgatagca tcaaggccta cggagcagga ctgctgtcta    1140
gcttcggcga gctgcagtat tgtctgtccg agaagccaaa gctgctgccc tggagctgg    1200 agaagaccgc catccagaac tacaccgtga cagagttcca gccctgtac  tatgtggccg    1260 agtctttaa  cgatgccaag gagaaggtga gaaatttcgc cgccacaatc cctaggccct    1320
tcagcgtgcg gtacgaccct tatacccaga ggatcgaggt gctggataat acacagcagc    1380
tgaagatcct ggctgactca atcaatagcg aaatcggaat cctgtgctcc gccctgcaga    1440
aaatcaaatg a                                                         1451
```

<210> SEQ ID NO 83
<211> LENGTH: 1607
<212> TYPE: DNA
<213> ORGANISM: Artificial Sequence
<220> FEATURE:
<223> OTHER INFORMATION: pHMI-hPAH-hAC-008 editing element

<400> SEQUENCE: 83

```
atgtccaccg ctgtgctgga gaaccctggg ctggggagga aactgtcaga cttcgggcag      60
gagacttcat acattgagga taactgtaac cagaatggcg ccatctctct gatcttcagc     120
ctgaaggagg aagtgggcgc cctggcaaag gtgctgcgcc tgtttgagga gaacgacgtg     180
aatctgaccc acatcgagtc ccggccttct agactgaaga aggacgagta cgagttcttt     240
acccacctgg ataagcggtc cctgccagcc ctgacaaaca tcatcaagat cctgaggcac     300
gacatcggag caaccgtgca cgagctgtct cgggacaaga agaaggatac cgtgccctgg     360
ttccctcgga caatccagga gctggataga tttgccaacc agatcctgtc ttacggagca     420
gagctggacg cagatcaccc tggcttcaag gacccagtgt atcgggcccg agaaagcag      480
tttgccgata tcgcctacaa ttataggcac ggacagccaa tccctcgcgt ggagtatatg     540
gaggaggaga agaagacctg ggcacagtg ttcaagaccc tgaagagcct gtacaagaca     600
cacgcctgct acgagtataa ccacatcttc cccctgctgg agaagtattg tggctttcac     660
gaggacaata tccctcagct ggaggacgtg agccagttcc tgcagacctg cacaggcttt     720
aggctgaggc cagtggcagg actgctgagc tcccgggact tcctgggagg actggccttc     780
agagtgtttc actgcaccca gtacatcagg cacggctcca agccaatgta tacaccagag     840
cccgacatct gtcacgagct gctgggccac gtgcccctgt ttagcgatag atccttcgcc     900
cagttttccc aggagatcgg actggcatct ctgggagcac ctgacgagta catcgagaag     960
ctggccacca tctattggtt cacagtggag tttggcctgt gcaagcaggg cgatagcatc    1020
aaggcctacg agcaggact gctgtctagc ttcggcgagc tgcagtattg tctgtccgag    1080
aagccaaagc tgctgcccct ggagctggag aagaccgcca tccagaacta caccgtgaca    1140
gagttccagc ccctgtacta tgtggccgag tcttttaacg atgccaagga aaggtgaga    1200
aatttcgccg ccacaatccc tagggccttc agcgtgcggt acgacccta tacccagagg    1260
atcgaggtgc tggataatac acagcagctg aagatcctgg ctgactcaat caatagcgaa    1320
atcggaatcc tgtgctccgc cctgcagaaa atcaaatgag aattcaaggc ctctcgagcc    1380
tctagaacta tagtgagtcg tattacgtag atccagacat gataagatac attgatgagt    1440
ttggacaaac cacaactaga atgcagtgaa aaaatgctt tatttgtgaa atttgtgatg    1500
ctattgcttt atttgtaacc attataagct gcaataaaca agttaacaac aacaattgca    1560
ttcatttat gtttcaggtt cagggggagg tgtgggaggt ttttta              1607
```

<210> SEQ ID NO 84
<211> LENGTH: 1719
<212> TYPE: DNA
<213> ORGANISM: Artificial Sequence
<220> FEATURE:
<223> OTHER INFORMATION: pHMI-hPAH-h1C-007 editing element

<400> SEQUENCE: 84

```
ctgacctctt ctcttcctcc cacagggcgg taccagatct ggcagcggag agggcagagg      60
aagtcttcta acatgcggtg acgtggagga gaatcccggc cctaggggta ccatgtccac     120
```

| | |
|---|---|
| cgctgtgctg gagaaccctg ggctggggag gaaactgtca gacttcgggc aggagacttc | 180 |
| atacattgag gataactgta accagaatgg cgccatctct ctgatcttca gcctgaagga | 240 |
| ggaagtgggc gccctggcaa aggtgctgcg cctgtttgag gagaacgacg tgaatctgac | 300 |
| ccacatcgag tcccggcctt ctagactgaa gaaggacgag tacgagttct ttacccacct | 360 |
| ggataagcgg tccctgccag ccctgacaaa catcatcaag atcctgaggc acgacatcgg | 420 |
| agcaaccgtg cacgagctgt ctcgggacaa gaagaaggat accgtgccct ggttccctcg | 480 |
| gacaatccag gagctggata gatttgccaa ccagatcctg tcttacggag cagagctgga | 540 |
| cgcagatcac cctggcttca aggacccagt gtatcgggcc cggagaaagc agtttgccga | 600 |
| tatcgcctac aattataggc acggacagcc aatccctcgc gtggagtata tggaggagga | 660 |
| gaagaagacc tggggcacag tgttcaagac cctgaagagc ctgtacaaga cacacgcctg | 720 |
| ctacgagtat aaccacatct tcccctgct ggagaagtat tgtggctttc acgaggacaa | 780 |
| tatccctcag ctggaggacg tgagccagtt cctgcagacc tgcacaggct ttaggctgag | 840 |
| gccagtggca ggactgctga gctcccggga cttcctggga ggactggcct tcagagtgtt | 900 |
| tcactgcacc cagtacatca ggcacggctc caagccaatg tatacaccag agcccgacat | 960 |
| ctgtcacgag ctgctgggcc acgtgcccct gtttagcgat agatccttcg cccagttttc | 1020 |
| ccaggagatc ggactggcat ctctgggagc acctgacgag tacatcgaga agctggccac | 1080 |
| catctattgg ttcacagtgg agtttggcct gtgcaagcag ggcgtagca tcaaggccta | 1140 |
| cggagcagga ctgctgtcta gcttcggcga gctgcagtat tgtctgtccg agaagccaaa | 1200 |
| gctgctgccc ctggagctgg agaagaccgc catccagaac tacaccgtga cagagttcca | 1260 |
| gcccctgtac tatgtggccg agtcttttaa cgatgccaag gagaaggtga gaaatttcgc | 1320 |
| cgccacaatc cctaggccct tcagcgtgcg gtacgaccct tatacccaga ggatcgaggt | 1380 |
| gctggataat acacagcagc tgaagatcct ggctgactca atcaatagcg aaatcggaat | 1440 |
| cctgtgctcc gccctgcaga aaatcaaatg agaattcaag gcctctcgag cctctagaac | 1500 |
| tatagtgagt cgtattacgt agatccagac atgataagat acattgatga gtttggacaa | 1560 |
| accacaacta gaatgcagtg aaaaaaatgc tttatttgtg aaatttgtga tgctattgct | 1620 |
| ttatttgtaa ccattataag ctgcaataaa caagttaaca acaacaattg cattcatttt | 1680 |
| atgtttcagg ttcaggggga ggtgtgggag gttttttaa | 1719 |

<210> SEQ ID NO 85
<211> LENGTH: 3227
<212> TYPE: DNA
<213> ORGANISM: Artificial Sequence
<220> FEATURE:
<223> OTHER INFORMATION: pHMI-hPAH-hAC-008 correction genome from 5'
      homology arm to 3' homology arm

<400> SEQUENCE: 85

| | |
|---|---|
| tatcttccat ttactgagtg tttatgtgga agaactgtac taaattttaa tgcatttctt | 60 |
| tattcctatt cttaaaacct tccagcaagg tggctctacc accctctttt ccgagcttca | 120 |
| ggagcagttg tgcgaatagc tggagaacac caggctggat ttaaacccag atcgctctta | 180 |
| catttgctct ttacctgctg tgctcagcgt tcacgtgccc tctagctgta gttttctgaa | 240 |
| gtcagcgcac agcaaggcag tgtgcttaga ggttaacaga agggaaaaca acaacaacaa | 300 |
| aaatctaaat gagaatcctg actgtttcag ctggggtaa gggggcgga ttattcatat | 360 |
| aattgttata ccagacggtc gcaggcttag tccaattgca gagaactcgc ttcccaggct | 420 |

```
tctgagagtc ccggaagtgc ctaaacctgt ctaatcgacg gggcttgggt ggcccgtcgc    480
tccctggctt cttcccttta cccagggcgg gcagcgaagt ggtgcctcct gcgtcccca     540 caccctccct cagcccctcc cctccggccc gtcctgggca ggtgacctgg agcatccggc    600
aggctgccct ggcctcctgc gtcaggacaa cgcccacgag gggcgttact gtgcggagat    660
gcaccacgca agagacaccc tttgtaactc tcttctcctc cctagtgcga ggttaaaacc    720
ttcagcccca cgtgctgttt gcaaacctgc ctgtacctga gccctaaaa agccagagac     780 ctcactcccg gggagccagc atgtccaccg ctgtgctgga gaaccctggg ctggggagga    840
aactgtcaga cttcgggcag gagacttcat acattgagga taactgtaac cagaatggcg    900
ccatctctct gatcttcagc ctgaaggagg aagtgggcgc cctggcaaag gtgctgcgcc    960
tgtttgagga gaacgacgtg aatctgaccc acatcgagtc ccggccttct agactgaaga    1020
aggacgagta cgagttcttt acccacctgg ataagcggtc cctgccagcc ctgacaaaca    1080
tcatcaagat cctgaggcac gacatcggag caaccgtgca cgagctgtct cgggacaaga    1140
agaaggatac cgtgccctgg ttccctcgga caatccagga gctggataga tttgccaacc    1200
agatcctgtc ttacggagca gagctggacg cagatcaccc tggcttcaag gacccagtgt    1260
atcgggcccg gagaaagcag tttgccgata tcgcctacaa ttataggcac ggacagccaa    1320
tccctcgcgt ggagtatatg gaggaggaga agaagacctg ggcacagtg ttcaagaccc     1380 tgaagagcct gtacaagaca cacgcctgct acgagtataa ccacatcttc ccctgctgg    1440 agaagtattg tggctttcac gaggacaata tccctcagct ggaggacgtg agccagttcc    1500
tgcagacctg cacaggcttt aggctgaggc cagtggcagg actgctgagc tcccgggact    1560
tcctgggagg actggccttc agagtgtttc actgcaccca gtacatcagg cacggctcca    1620
agccaatgta taccagagag cccgacatct gtcacgagct gctgggccac gtgcccctgt    1680
ttagcgatag atccttcgcc cagttttccc aggagatcgg actggcatct ctgggagcac    1740
ctgacgagta catcgagaag ctggccacca tctattggtt cacagtggag tttgcctgt    1800 gcaagcaggg cgatagcatc aaggcctacg agcaggact gctgtctagc ttcggcgagc     1860
tgcagtattg tctgtccgag aagccaaagc tgctgcccct ggagctggag aagaccgcca    1920
tccagaacta caccgtgaca gagttccagc ccctgtacta tgtggccgag tcttttaacg    1980
atgccaagga gaaggtgaga aatttcgccg ccacaatccc taggcccttc agcgtgcggt    2040 acgacccta tacccagagg atcgaggtgc tggataatac acagcagctg aagatcctgg    2100
ctgactcaat caatagcgaa atcggaatcc tgtgctccgc cctgcagaaa atcaaatgag    2160
aattcaaggc ctctcgagcc tctagaacta tagtgagtcg tattacgtag atccagacat    2220
gataagatac attgatgagt ttggacaaac cacaactaga atgcagtgaa aaaaatgctt    2280
tatttgtgaa atttgtgatg ctattgcttt atttgtaacc attataagct gcaataaaca    2340
agttaacaac aacaattgca ttcattttat gtttcaggtt cagggggagg tgtgggaggt    2400
tttttaagct ttacgtacga tcgtcgatcc actgcgtgtc tggaaaaccc aggcttgggc    2460
aggaaactct ctgactttgg acaggtgagc cacggcagcc tgagctgctc agttagggga    2520
atttgggcct ccagagaaag agatccgaag actgctggtg cttcctggtt tcataagctc    2580
agtaagaagt ctgaattcgt tggaagctga tgagaatatc caggaagtca acagacaaat    2640
gtcctcaaca attgtttcta gtaggagaa catctgtcct cggtggcttt cacaggaatg    2700
aatgaccatt gctttagggg gttggggatc tggcctccag aactgccacc aattagctgt    2760
gtgtctttgg acaagttact gtccctctct gttgtctgtt tactcttctg tacactgaag    2820
```

| | |
|---|---|
| gggctggtcc ctaatgatct gggatgggat gtggaatcct tctagatttc ttttgtaata | 2880 |
| tttataaagt gctctcagca aggtatcaaa atggcaaaat tgtgagtaac tatcctcctt | 2940 |
| tcattttggg aagaagatga ggcatgaaga gaattcagac agaaacttac tcagaccagg | 3000 |
| ggaggcagaa actaagcaga gaggaaaatg accaagagtt agccctgggc atggaatgtg | 3060 |
| aaagaaccct aaacgtgact tggaaataat gcccaaggta tattccattc tccgggattt | 3120 |
| gttggcattt tcttgaggtg aagaattgca gaatacattc tttaatgtga cctacatatt | 3180 |
| tacccatggg aggaagtctg ctcctggact cttgagattc agtcata | 3227 |

<210> SEQ ID NO 86
<211> LENGTH: 3345
<212> TYPE: DNA
<213> ORGANISM: Artificial Sequence
<220> FEATURE:
<223> OTHER INFORMATION: pHMI-hPAH-h1C-007 correction genome from 5'
    homology arm to 3' homology arm

<400> SEQUENCE: 86

| | |
|---|---|
| aatggttcca aaattttcta tggttaagaa tcacctggga tggttttgaa atggcagatt | 60 |
| ctaagacaac ttgattcaac aggtttaggt aaagcccagg gaactgcatt ataagaagga | 120 |
| atcacctgta attttggagt caagatccaa ggaacactca ttgagaaaca ctgatttaca | 180 |
| aagtgcatgg agagaaatgg agcaagtgaa gggggatcag catggtgaaa tataggctgt | 240 |
| taggagtgct attgactaac tgtctggtga ctggaccaga gtaaatcttt tactttgcaa | 300 |
| gaaacaggac taaattccca tattatgtcc atagcaaagg gaattatgta gaaaaattga | 360 |
| taattaggag cctgagttct tgaccagcct ccactaccta tgtggcctca ggtgagttat | 420 |
| tttctccctt tggctctaag ttttccccat ctgtaatgta agggagttta actagatgag | 480 |
| cactaaggac aaatcaattt ctgtgagtca attattatga aataccatgt gggcatcaaa | 540 |
| tgccaagtgg aaagcataga taagaagtg attgtgcacc tgggctgagg ggaacaaaca | 600 |
| tttcctaaga gaattgagac ccaaaagagc ctttaaggaa ggtgagatct tggaaaggga | 660 |
| aatttggtga atactctaat gaggagctaa aaaggcaaga aagaaagcag cttggctgga | 720 |
| aaggaggttc ctgtaggtgg gcctccagag attcggtacc acagaaactg ccaaacatca | 780 |
| gcaagaagcc atggggatgg aagcttctga cctcttctct tcctcccaca gggcggtacc | 840 |
| agatctggca gcggagaggg cagaggaagt cttctaacat gcggtgacgt ggaggagaat | 900 |
| cccggcccta ggggtaccat gtccaccgct gtgctggaga accctgggct ggggaggaaa | 960 |
| ctgtcagact tcgggcagga gacttcatac attgaggata actgtaacca gaatggcgcc | 1020 |
| atctctctga tcttcagcct gaaggaggaa gtgggcgccc tggcaaaggt gctgcgcctg | 1080 |
| tttgaggaga cgacgtgaa tctgacccac atcgagtccc ggccttctag actgaagaag | 1140 |
| gacgagtacg agttctttac ccacctggat aagcggtccc tgccagccct gacaaacatc | 1200 |
| atcaagatcc tgaggcacga catcggagca accgtgcacg agctgtctcg ggacaagaag | 1260 |
| aaggataccg tgccctggtt ccctcggaca atccaggagc tggatagatt tgccaaccag | 1320 |
| atcctgtctt acggagcaga gctggacgca gatcaccctg gcttcaagga cccagtgtat | 1380 |
| cgggcccgga gaaagcagtt tgccgatatc gcctacaatt ataggcacgg acagccaatc | 1440 |
| cctcgcgtgg agtatatgga ggaggagaag aagacctggg gcacagtgtt caagaccctg | 1500 |
| aagagcctgt acaagacaca cgcctgctac gagtataacc acatcttccc cctgctggag | 1560 |
| aagtattgtg gctttcacga ggacaatatc cctcagctgg aggacgtgag ccagttcctg | 1620 |

```
cagacctgca caggctttag gctgaggcca gtggcaggac tgctgagctc ccgggacttc    1680
ctgggaggac tggccttcag agtgtttcac tgcacccagt acatcaggca cggctccaag    1740
ccaatgtata caccagagcc cgacatctgt cacgagctgc tgggccacgt gcccctgttt    1800
agcgatagat ccttcgccca gttttcccag gagatcggac tggcatctct gggagcacct    1860
gacgagtaca tcgagaagct ggccaccatc tattggttca cagtggagtt tggcctgtgc    1920
aagcagggcg atagcatcaa ggcctacgga gcaggactgc tgtctagctt cggcgagctg    1980
cagtattgtc tgtccgagaa gccaaagctg ctgcccctgg agctggagaa gaccgccatc    2040
cagaactaca ccgtgacaga gttccagccc ctgtactatg tggccgagtc ttttaacgat    2100
gccaaggaga aggtgagaaa tttcgccgcc acaatcccta ggcccttcag cgtgcggtac    2160
gacccttata cccagaggat cgaggtgctg ataatacac agcagctgaa gatcctggct    2220
gactcaatca atagcgaaat cggaatcctg tgctccgccc tgcagaaaat caaatgagaa    2280
ttcaaggcct ctcgagcctc tagaactata gtgagtcgta ttacgtagat ccagacatga    2340
taagatacat tgatgagttt ggacaaacca aactagaat gcagtgaaaa aaatgcttta    2400
tttgtgaaat ttgtgatgct attgctttat ttgtaaccat tataagctgc aataaacaag    2460
ttaacaacaa caattgcatt catttttatgt ttcaggttca gggggaggtg tgggaggttt    2520
tttaagcttt acgtacgatc gtcgaagcgt ttgagggatt ctaaatagaa ggacaagagt    2580
aaaaatgtca ggctggatcg atgcaggcca ctaagaaatg gattcaggtg atggcagtgg    2640
gaagaaagga cctgatgccc agaggcattt ctggagaaga tgagatcaga cttgtgattg    2700
gctgaacaca cactgtagtg gggtggggtt taggggtgtga ctcaacttca agcccaggta    2760
cattcaagtc tgaattgccc tagtcaaaag tggcatctgt ggatgtgtat cagaaatatc    2820 ttactttct tggaagccaa caggagaaaa gagtgctacc aagtgaacta gagacaggaa    2880
tatcttttgt catttcaagg aaactggaaa gaagaaggct cagtattctt tagtaggaag    2940
aagacttaag tcagagactc atctgtacct ctctggcagg gtttaaaagg gggaagagga    3000
atagaggctg caagagattg tgattcatgg acagtatgca gagatcaaat gacctggggtt   3060 cagatcctgg ctccactgct aactgtgtaa ctataggcaa gttccttaac ctctctaagc    3120
cttaatcttg tcatcaataa aaggggggcac ttggtgccta ataaaaccta cctcttaggt    3180
tgttgccaaa ttcatgaga taatccaaat caagtgctta ttataatacc cagaaattat     3240
aggctctaaa taaatgttta tataggctct aaataaatga agttttttag aaagataaca    3300
tcatgatcaa aatgggatat ttaacagttt agtcttccat ttcat                    3345
```

<210> SEQ ID NO 87
<211> LENGTH: 3637
<212> TYPE: DNA
<213> ORGANISM: Artificial Sequence
<220> FEATURE:
<223> OTHER INFORMATION: pHMI-hPAH-hAC-008 correction genome from 5' ITR
      to 3' ITR

<400> SEQUENCE: 87

```
ttggccactc cctctctgcg cgctcgctcg ctcactgagg ccgggcgacc aaaggtcgcc      60
cgacgcccgg gctttgcccg ggcggcctca gtgagcgagc gagcgcgcag agagggagtg     120
gccaactcca tcactagggg ttcctggagg ggtggagtcg tgacgtgaat tacgtcatag     180
ggttagggag gtcctgcata tgcggccgct atcttccatt tactgagtgt ttatgtggaa     240
gaactgtact aaattttaat gcatttcttt attcctattc ttaaaacctt ccagcaaggt     300
```

```
ggctctacca ccctctttc cgagcttcag gagcagttgt gcgaatagct ggagaacacc    360
aggctggatt taaacccaga tcgctcttac atttgctctt tacctgctgt gctcagcgtt    420
cacgtgccct ctagctgtag ttttctgaag tcagcgcaca gcaaggcagt gtgcttagag    480
gttaacagaa gggaaaacaa caacaacaaa atctaaatg agaatcctga ctgtttcagc    540
tgggggtaag ggggcggat tattcatata attgttatac cagacggtcg caggcttagt    600
ccaattgcag agaactcgct tcccaggctt ctgagagtcc cggaagtgcc taaacctgtc    660
taatcgacgg ggcttgggtg ccccgtcgct ccctggcttc ttccctttac ccagggcggg    720
cagcgaagtg gtgcctcctg cgtccccac accctccctc agccctccc ctccggcccg    780
tcctgggcag gtgacctgga gcatccggca ggctgccctg gcctcctgcg tcaggacaac    840
gcccacgagg ggcgttactg tgcggagatg caccacgcaa gagacaccct ttgtaactct    900
cttctcctcc ctagtgcgag gttaaaacct tcagccccac gtgctgtttg caaacctgcc    960
tgtacctgag gccctaaaaa gccagagacc tcactcccgg ggagccagca tgtccaccgc   1020
tgtgctggag aaccctgggc tggggaggaa actgtcagac ttcgggcagg agacttcata   1080
cattgaggat aactgtaacc agaatggcgc catctctctg atcttcagcc tgaaggagga   1140
agtgggcgcc ctggcaaagg tgctgcgcct gtttgaggag aacgacgtga atctgaccca   1200
catcgagtcc cggccttcta gactgaagaa ggacgagtac gagttctta cccacctgga   1260
taagcggtcc ctgccagccc tgacaaacat catcaagatc ctgaggcacg acatcggagc   1320
aaccgtgcac gagctgtctc gggacaagaa gaaggatacc gtgccctggt ccctcggac    1380
aatccaggag ctggatagat tgccaaccg atcctgtct tacggagcag agctggacgc    1440
agatcaccct ggcttcaagg acccagtgta tcgggcccgg agaaagcagt ttgccgatat    1500
cgcctacaat tataggcacg acagccaat ccctcgcgtg gagtatatgg aggaggagaa   1560
gaagacctgg ggcacagtgt tcaagaccct gaagagcctg tacaagacac acgcctgcta    1620
cgagtataac cacatcttcc ccctgctgga aagtattgt ggctttcacg aggacaatat    1680
ccctcagctg gaggacgtga ccagttcct gcagacctgc acaggcttta ggctgaggcc    1740
agtggcagga ctgctgagct cccgggactt cctgggagga ctggccttca gagtgttca    1800
ctgcacccag tacatcaggc acggctccaa gccaatgtat acaccagagc ccgacatctg   1860
tcacgagctg ctgggccacg tgcccctgtt tagcgataga tccttcgccc agttttccca   1920
ggagatcgga ctggcatctc tgggagcacc tgacgagtac atcgagaagc tggccaccat   1980
ctattggttc acagtggagt ttggcctgtg caagcagggc gatagcatca aggcctacgg   2040
agcaggactg ctgtctagct tcggcgagct gcagtattgt ctgtccgaga gccaaagct    2100
gctgccctg gagctggaga agaccgccat ccagaactac accgtgacag agttccagcc    2160
cctgtactat gtggccgagt cttttaacga tgccaaggag aaggtgagaa atttcgccgc    2220
cacaatccct aggcccttca gcgtgcggta cgacccttat acccagagga tcgaggtgct    2280
ggataataca cagcagctga agatcctggc tgactcaatc aatagcgaaa tcggaatcct    2340
gtgctccgcc ctgcagaaaa tcaaatgaga attcaaggcc tctcgagcct ctagaactat    2400
agtgagtcgt attacgtaga tccagacatg ataagataca ttgatgagtt tggacaaacc    2460
acaactagaa tgcagtgaaa aaatgctttt atttgtgaaa tttgtgatgc tattgcttta    2520
tttgtaacca tttataagctg caataaacaa gttaacaaca acaattgcat tcatttatg    2580
tttcaggttc agggggaggt gtgggaggtt ttttaagctt tacgtacgat cgtcgatcca    2640
```

-continued

```
ctgcggtcct ggaaaaccca ggcttgggca ggaaactctc tgactttgga caggtgagcc    2700
acggcagcct gagctgctca gttaggggaa tttgggcctc cagagaaaga gatccgaaga    2760
ctgctggtgc ttcctggttt cataagctca gtaagaagtc tgaattcgtt ggaagctgat    2820
gagaatatcc aggaagtcaa cagacaaatg tcctcaacaa ttgtttctaa gtaggagaac    2880
atctgtcctc ggtggctttc acaggaatga atgaccattg ctttaggggg ttgggatct    2940 ggcctccaga actgccacca attagctgtg tgtctttgga caagttactg tccctctctg    3000
ttgtctgttt actcttctgt acactgaagg ggctggtccc taatgatctg ggatgggatg    3060
tggaatcctt ctagatttct tttgtaatat ttataaagtg ctctcagcaa ggtatcaaaa    3120
tggcaaaatt gtgagtaact atcctccttt cattttggga agaagatgag gcatgaagag    3180
aattcagaca gaaacttact cagaccaggg gaggcagaaa ctaagcagag aggaaaatga    3240
ccaagagtta gccctgggca tggaatgtga aagaaccta aacgtgactt ggaaataatg    3300
cccaaggtat attccattct ccgggatttg ttggcatttt cttgaggtga agaattgcag    3360
aatacattct ttaatgtgac ctacatattt acccatggga ggaagtctgc tcctggactc    3420
ttgagattca gtcataaacc tgcaggtcta gatacgtaga taagtagcat ggcgggttaa    3480
tcattaacta caaggaaccc ctagtgatgg agttggccac tccctctctg cgcgctcgct    3540
cgctcactga ggccgggcga ccaaaggtcg cccgacgccc gggctttgcc cgggcggcct    3600
cagtgagcga gcgagcgcgc agagagggag tggccaa                             3637
```

<210> SEQ ID NO 88
<211> LENGTH: 3755
<212> TYPE: DNA
<213> ORGANISM: Artificial Sequence
<220> FEATURE:
<223> OTHER INFORMATION: pHMI-hPAH-h1C-007 correction genome from 5' ITR
      to 3' ITR

<400> SEQUENCE: 88

```
ttggccactc cctctctgcg cgctcgctcg ctcactgagg ccgggcgacc aaaggtcgcc     60
cgacgcccgg gctttgcccg gcggcctca gtgagcgagc gagcgcgcag agagggagtg    120
gccaactcca tcactagggg ttcctggagg ggtggagtcg tgacgtgaat tacgtcatag    180
ggttagggag gtcctgcata tgcggccgca atggttccaa aattttctat ggttaagaat    240
cacctgggat ggttttgaaa tggcagattc taagacaact tgattcaaca ggtttaggta    300
aagcccaggg aactgcatta taagaaggaa tcacctgtaa ttttggagtc aagatccaag    360
gaacactcat tgagaaacac tgatttacaa agtgcatgga gagaaatgga gcaagtgaag    420
ggggatcagc atggtgaaat ataggctgtt aggagtgcta ttgactaact gtctggtgac    480
tggaccagag taaatctttt actttgcaag aaacaggact aaattcccat attatgtcca    540
tagcaaaggg aattatgtag aaaaattgat aattaggagc ctgagttctt gaccagcctc    600
cactacctat gtgcctcag gtgagttatt ttctcccttt ggctctaagt tttccccatc     660
tgtaatgtaa gggagtttaa ctagatgagc actaaggaca aatcaatttc tgtgagtcaa    720
ttattatgaa ataccatgtg ggcatcaaat gccaagtgga aagcatagat aaagaagtga    780
ttgtgcacct gggctgaggg gaacaaacat tcctaagag aattgagacc caaagagcc     840 tttaaggaag gtgagatctt ggaaagggaa atttggtgaa tactctaatg aggagctaaa    900
aaggcaagaa agaaagcagc ttggctgaa aggaggttcc tgtaggtggg cctccagaga   960
ttcggtacca cagaaactgc caaacatcag caagaagcca tggggatgga agcttctgac   1020
```

```
ctcttctctt cctcccacag ggcggtacca gatctggcag cggagagggc agaggaagtc    1080
ttctaacatg cggtgacgtg gaggagaatc ccggccctag gggtaccatg tccaccgctg    1140
tgctggagaa ccctgggctg gggaggaaac tgtcagactt cgggcaggag acttcataca    1200
ttgaggataa ctgtaaccag aatggcgcca tctctctgat cttcagcctg aaggaggaag    1260
tgggcgccct ggcaaaggtg ctgcgcctgt ttgaggagaa cgacgtgaat ctgacccaca    1320
tcgagtcccg gccttctaga ctgaagaagg acgagtacga gttctttacc cacctggata    1380
agcggtccct gccagccctg acaaacatca tcaagatcct gaggcacgac atcggagcaa    1440
ccgtgcacga gctgtctcgg acaagaagaa ggataccgt gccctggttc cctcggacaa    1500
tccaggagct ggatagattt gccaaccaga tcctgtctta cggagcagag ctggacgcag    1560
atcaccctgg cttcaaggac ccagtgtatc gggcccggag aaagcagttt gccgatatcg    1620
cctacaatta taggcacgga cagccaatcc ctcgcgtgga gtatatggag gaggagaaga    1680
agacctgggg cacagtgttc aagaccctga gagcctgta caagacacac gcctgctacg    1740
agtataacca catcttcccc ctgctggaga gtattgtgg ctttcacgag gacaatatcc    1800
ctcagctgga ggacgtgagc cagttcctgc agacctgcac aggctttagg ctgaggccag    1860
tggcaggact gctgagctcc cgggacttcc tgggaggact ggccttcaga gtgtttcact    1920
gcacccagta catcaggcac ggctccaagc caatgtatac accagagccc gacatctgtc    1980
acgagctgct gggccacgtg cccctgttta gcgatagatc cttcgcccag ttttcccagg    2040
agatcggact ggcatctctg ggagcacctg acgagtacat cgagaagctg gccaccatct    2100
attggttcac agtggagttt ggcctgtgca agcaggcga tagcatcaag gcctacggag    2160
caggactgct gtctagcttc ggcgagctgc agtattgtct gtccgagaag ccaaagctgc    2220 tgccctgga gctggagaag accgccatcc agaactacac cgtgacagag ttccagcccc    2280
tgtactatgt ggccgagtct tttaacgatg ccaaggagaa ggtgagaaat ttcgccgcca    2340
caatccctag gcccttcagc gtgcggtacg accttatac ccagaggatc gaggtgctgg    2400
ataatacaca gcagctgaag atcctggctg actcaatcaa tagcgaaatc ggaatcctgt    2460
gctccgccct gcagaaaatc aaatgagaat tcaaggcctc tcgagcctct agaactatag    2520
tgagtcgtat tacgtagatc cagacatgat aagatacatt gatgagtttg gacaaaccac    2580
aactagaatg cagtgaaaaa aatgctttat ttgtgaaatt tgtgatgcta ttgctttatt    2640
tgtaaccatt ataagctgca ataaacaagt taacaacaac aattgcattc attttatgtt    2700
tcaggttcag ggggaggtgt gggaggtttt ttaagcttta cgtacgatcg tcgaagcgtt    2760
tgagggattc taaatagaag gacaagagta aaaatgtcag gctggatcga tgcaggccac    2820
taagaaatgg attcaggtga tggcagtggg aagaaaggac ctgatgccca gaggcatttc    2880
tggagaagat gagatcagac ttgtgattgg ctgaacacac actgtagtgg ggtggggttt    2940 aggggggtgac tcaacttcaa gcccaggtac attcaagtct gaattgccct agtcaaaagt    3000
ggcatctgtg gatgtgtatc agaaatatct tactttctt ggaagccaac aggagaaaag    3060
agtgctacca agtgaactag agacaggaat atcttttgtc atttcaagga aactggaaag    3120
aagaaggctc agtattcttt agtaggaaga agacttaagt cagagactca tctgtacctc    3180
tctggcaggg tttaaaaggg ggaagaggaa tagaggctgc aagagattgt gattcatgga    3240
cagtatgcag agatcaaatg acctgggttc agatcctggc tccactgcta actgtgtaac    3300
tataggcaag ttccttaacc tctctaagcc ttaatcttgt catcaataaa agggggcact    3360
tggtgcctaa taaaacctac ctcttaggtt gttgccaaat tacatgagat aatccaaatc    3420
```

-continued

```
aagtgcttat tataataccc agaaattata ggctctaaat aaatgtttat ataggctcta    3480
aataaatgaa gtttttttaga aagataacat catgatcaaa atgggatatt taacagttta    3540
gtcttccatt tcataacctg caggtctaga tacgtagata agtagcatgg cgggttaatc    3600
attaactaca aggaacccct agtgatggag ttggccactc cctctctgcg cgctcgctcg    3660
ctcactgagg ccgggcgacc aaaggtcgcc cgacgcccgg gctttgcccg ggcggcctca    3720
gtgagcgagc gagcgcgcag agagggagtg gccaa                               3755
```

<210> SEQ ID NO 89
<211> LENGTH: 20
<212> TYPE: DNA
<213> ORGANISM: Homo sapiens

<400> SEQUENCE: 89
ccaaatccca ccagctcact                                                20

<210> SEQ ID NO 90
<211> LENGTH: 21
<212> TYPE: DNA
<213> ORGANISM: Homo sapiens

<400> SEQUENCE: 90
tcccatgaaa ctgaggtgtg a                                              21

<210> SEQ ID NO 91
<211> LENGTH: 20
<212> TYPE: DNA
<213> ORGANISM: Artificial Sequence
<220> FEATURE:
<223> OTHER INFORMATION: PAH_Genomic Set 1, primer F

<400> SEQUENCE: 91
gctccatcct gcacatagtt                                                20

<210> SEQ ID NO 92
<211> LENGTH: 23
<212> TYPE: DNA
<213> ORGANISM: Artificial Sequence
<220> FEATURE:
<223> OTHER INFORMATION: PAH_Genomic Set 1, primer R

<400> SEQUENCE: 92
cctatgcttt cctgatgaga tcc                                            23

<210> SEQ ID NO 93
<211> LENGTH: 23
<212> TYPE: DNA
<213> ORGANISM: Artificial Sequence
<220> FEATURE:
<223> OTHER INFORMATION: PAH_Genomic Set 1, probe

<400> SEQUENCE: 93
ttggtgctgc tggcaatacg gtc                                            23

<210> SEQ ID NO 94
<211> LENGTH: 22
<212> TYPE: DNA
<213> ORGANISM: Artificial Sequence
<220> FEATURE:
<223> OTHER INFORMATION: SV40_FAM Set 1, primer F

<400> SEQUENCE: 94

```
gcaatagcat cacaaatttc ac                                              22

<210> SEQ ID NO 95
<211> LENGTH: 25
<212> TYPE: DNA
<213> ORGANISM: Artificial Sequence
<220> FEATURE:
<223> OTHER INFORMATION: SV40_FAM Set 1, primer R

<400> SEQUENCE: 95
gatccagaca tgataagata cattg                                           25

<210> SEQ ID NO 96
<211> LENGTH: 28
<212> TYPE: DNA
<213> ORGANISM: Artificial Sequence
<220> FEATURE:
<223> OTHER INFORMATION: SV40_FAM Set 1, probe

<400> SEQUENCE: 96
tcactgcatt ctagttgtgg tttgtcca                                        28

<210> SEQ ID NO 97
<211> LENGTH: 21
<212> TYPE: DNA
<213> ORGANISM: Artificial Sequence
<220> FEATURE:
<223> OTHER INFORMATION: PAH_HA Set 1, primer F

<400> SEQUENCE: 97
tccagtcacc agacagttag t                                               21

<210> SEQ ID NO 98
<211> LENGTH: 22
<212> TYPE: DNA
<213> ORGANISM: Artificial Sequence
<220> FEATURE:
<223> OTHER INFORMATION: PAH_HA Set 1, primer R

<400> SEQUENCE: 98
ggagagaaat ggagcaagtg aa                                              22

<210> SEQ ID NO 99
<211> LENGTH: 28
<212> TYPE: DNA
<213> ORGANISM: Artificial Sequence
<220> FEATURE:
<223> OTHER INFORMATION: PAH_HA Set 1, probe

<400> SEQUENCE: 99
acagcctata tttcaccatg ctgatccc                                        28

<210> SEQ ID NO 100
<211> LENGTH: 800
<212> TYPE: DNA
<213> ORGANISM: Mus musculus

<400> SEQUENCE: 100
agcattagct tccatttatg cagtgtaaat ggtgagaaca gccccgactg aatacccaga     60
gcatcatctc gtctgtgtca ttcatgcaca taacatatct cagcgaggtg gcccttctgt    120
cctctttgca gagacccagc caccatacta gtacctagag aactggctgg atttcagccc    180
cgatacctcc gggcttttgc tcatgttcgc tcataggg t catctgggtg gttgcctaag    240
gaaaagtatg tcatggagac taacttgctt ggcattgaat aaaaggtgag ttgagagtgg    300
```

```
agcgtgttta aattgcaatc ctgcctctat ttctgtgctt gcagggaaca gtcatcctta    360
attgctatcc tccatcatca tcatgattat ttctggtttt tctctggttg cggagaatcc    420
atactccagg tattccaatg tctcagcatt gccaggcctg tctgagcgtc aggatgtagg    480
tagtctgggc tctctgcctt ctattcttgt ccaggatact ctgccaaaag aatcatgttg    540
tggctgccac ccctcccaca aagcctcccg cttgggtcag tccaggactg gagttgggta    600
tggactgttc atgtctatcc actgctacgt cagggcaaca cccactgaga gtgaccttgt    660
agactgcagt gggagacacc cttcaaaacc tcctctcc tgtcctgaga gccaggttaa    720
aaccatcagc cccgcatcct gagtgcaaac ttttcctaac cctgctgcta agctagacac    780
ctcacttact gagagccagc                                                800
```

<210> SEQ ID NO 101
<211> LENGTH: 800
<212> TYPE: DNA
<213> ORGANISM: Mus musculus

<400> SEQUENCE: 101

```
gcagctgttg tcctggagaa cggagtcctg agcagaaaac tctcagactt tgggcaggta     60
agcctgttgg gcttccactg ctaggagaga attggttccc cacatgtgaa agcagtctgg    120
gaaatgctgg tatttccagt ctcctaaggc tactaagaaa tatgacttta tttagaggcg    180
aggaaaatgc ccaggaagtc aactgatgag actagtctta acaagttgag gatacagaaa    240 gttgggggatc tgagctgcta ccaacatctg tgtgtctttg ggtggctcat tggtatcctc    300
tgcctattgg ctttatcttc tgtacactga aggaaatgg ctggtcctta gtcacctggg    360
gtgggagtcc ctatctctcc aggatactt attcaatcct ttcttctggg tatcaaaatg    420
acaagcttgt aagaaactgt cctctttcgg ctttcaggag gtgatgtcgc atgaagagaa    480 tttgggggggg gggacttact cagaaccaag gaggagaaa ttaaacagag agggaaatga    540
acaggagtta gcccggagcc tgaagcacct tggggattat gctgggggtg gaggggaatcc    600 attgtcctcc ctagggaggg cttgcagaac atgttctttt ctgtgatatt tgtactttcc    660
ccagattgca aatcatggtt tgtacactga gattcagtct ctggaggtaa tatgcctttt    720
ctagcttttc cttggacagg actaaggggt tgagggttgc ctggagtcag agaaatttgt    780
gttaaagaag gttgatatga                                                800
```

<210> SEQ ID NO 102
<211> LENGTH: 22
<212> TYPE: DNA
<213> ORGANISM: Artificial Sequence
<220> FEATURE:
<223> OTHER INFORMATION: mPAH_ATG_gDNA_FAM Set 1, primer F

<400> SEQUENCE: 102

```
cagcatcaga agcagaacat tt                                              22
```

<210> SEQ ID NO 103
<211> LENGTH: 21
<212> TYPE: DNA
<213> ORGANISM: Artificial Sequence
<220> FEATURE:
<223> OTHER INFORMATION: mPAH_ATG_gDNA_FAM Set 1, primer R

<400> SEQUENCE: 103

```
aaagcacatc agcagtttca a                                               21
```

<210> SEQ ID NO 104
<211> LENGTH: 29
<212> TYPE: DNA
<213> ORGANISM: Artificial Sequence
<220> FEATURE:
<223> OTHER INFORMATION: mPAH_ATG_gDNA_FAM Set 1, probe

<400> SEQUENCE: 104
agatgaaagc aactgaacat cgactacga                              29

<210> SEQ ID NO 105
<211> LENGTH: 22
<212> TYPE: DNA
<213> ORGANISM: Artificial Sequence
<220> FEATURE:
<223> OTHER INFORMATION: SV40_FAM Set 1, primer F

<400> SEQUENCE: 105
gcaatagcat cacaaatttc ac                                     22

<210> SEQ ID NO 106
<211> LENGTH: 25
<212> TYPE: DNA
<213> ORGANISM: Artificial Sequence
<220> FEATURE:
<223> OTHER INFORMATION: SV40_FAM Set 1, primer R

<400> SEQUENCE: 106
gatccagaca tgataagata cattg                                  25

<210> SEQ ID NO 107
<211> LENGTH: 28
<212> TYPE: DNA
<213> ORGANISM: Artificial Sequence
<220> FEATURE:
<223> OTHER INFORMATION: SV40_FAM Set 1, probe

<400> SEQUENCE: 107
tcactgcatt ctagttgtgg tttgtcca                               28

<210> SEQ ID NO 108
<211> LENGTH: 21
<212> TYPE: DNA
<213> ORGANISM: Artificial Sequence
<220> FEATURE:
<223> OTHER INFORMATION: mPah_1C_LHA_FAM Set 3, primer F

<400> SEQUENCE: 108
gcaagctcca gatcaccaat a                                      21

<210> SEQ ID NO 109
<211> LENGTH: 23
<212> TYPE: DNA
<213> ORGANISM: Artificial Sequence
<220> FEATURE:
<223> OTHER INFORMATION: mPah_1C_LHA_FAM Set 3, primer R

<400> SEQUENCE: 109
ctgagcaatg cattcagcaa taa                                    23

<210> SEQ ID NO 110
<211> LENGTH: 24
<212> TYPE: DNA
<213> ORGANISM: Artificial Sequence
<220> FEATURE:
<223> OTHER INFORMATION: mPah_1C_LHA_FAM Set 3, probe

<400> SEQUENCE: 110
ccctgaacat cccttgacag agca                                  24

<210> SEQ ID NO 111
<211> LENGTH: 800
<212> TYPE: DNA
<213> ORGANISM: Mus musculus

<400> SEQUENCE: 111
agcattagct tccatttatg cagtgtaaat ggtgagaaca gccccgactg aatacccaga     60
gcatcatctc gtctgtgtca ttcatgcaca taacatatct cagcgaggtg gcccttctgt    120
cctctttgca gagacccagc caccatacta gtacctagag aactggctgg atttcagccc    180
cgatacctcc gggcttttgc tcatgttcgc ctcatagggt catctgggtg gttgcctaag    240
gaaaagtatg tcatggagac taacttgctt ggcattgaat aaaaggtgag ttgagagtgg    300
agcgtgttta aattgcaatc ctgcctctat ttctgtgctt gcagggaaca gtcatcctta    360
attgctatcc tccatcatca tcatgattat ttctggtttt tctctggttg cggagaatcc    420
atactccagg tattccaatg tctcagcatt gccaggcctg tctgagcgtc aggatgtagg    480
tagtctgggc tctctgcctt ctattcttgt ccaggatact ctgccaaaag aatcatgttg    540
tggctgccac ccctcccaca aagcctcccg cttgggtcag tccaggactg agttgggta    600 tggactgttc atgtctatcc actgctacgt cagggcaaca cccactgaga gtgaccttgt    660
agactgcagt gggagacacc cttcaaaacc tctcctctcc tgtcctgaga gccaggttaa    720
aaccatcagc cccgcatcct gagtgcaaac ttttcctaac cctgctgcta agctagacac    780
ctcacttact gagagccagc                                              800

<210> SEQ ID NO 112
<211> LENGTH: 800
<212> TYPE: DNA
<213> ORGANISM: Mus musculus

<400> SEQUENCE: 112
gcagctgttg tcctggagaa cggagtcctg agcagaaaac tctcagactt tgggcaggta     60
agcctgttgg gcttccactg ctaggagaga attggttccc cacatgtgaa agcagtctgg    120
gaaatgctgg tatttccagt ctcctaaggc tactaagaaa tatgacttta tttagaggcg    180
aggaaaatgc ccaggaagtc aactgatgag actagtctta acaagttgag gatacagaaa    240 gttgggatc tgagctgcta ccaacatctg tgtgtctttg ggtggctcat ggtatcctc    300 tgcctattgg ctttatcttc tgtacactga aggaaatgg ctggtcctta gtcacctggg    360
gtgggagtcc ctatctctcc agggatactt attcaatcct ttcttctggg tatcaaaatg    420
acaagcttgt aagaaactgt cctctttcgg cttcaggag gtgatgtcgc atgaagagaa    480 tttgggggg gggacttact cagaaccaag gaggagaaa ttaaacagag agggaaatga    540
acaggagtta gcccggagcc tgaagcacct tggggattat gctgggggtg gagggaatcc    600
attgtcctcc ctagggaggg cttgcagaac atgttctttt ctgtgatatt tgtactttcc    660
ccagattgca aatcatggtt tgtacactga gattcagtct ctggaggtaa tatgcctttt    720
ctagcttttc cttggacagg actaaggggt tgagggttgc ctggagtcag agaaatttgt    780
gttaaagaag gttgatatga                                              800

<210> SEQ ID NO 113

<211> LENGTH: 3227
<212> TYPE: DNA
<213> ORGANISM: Artificial Sequence
<220> FEATURE:
<223> OTHER INFORMATION: 006 vector correction genome

<400> SEQUENCE: 113

| | |
|---|---:|
| agcattagct tccatttatg cagtgtaaat ggtgagaaca gccccgactg aatacccaga | 60 |
| gcatcatctc gtctgtgtca ttcatgcaca taacatatct cagcgaggtg gcccttctgt | 120 |
| cctctttgca gagacccagc caccatacta gtacctagag aactggctgg atttcagccc | 180 |
| cgatacctcc gggcttttgc tcatgttcgc tcatagggt catctgggtg gttgcctaag | 240 |
| gaaaagtatg tcatggagac taacttgctt ggcattgaat aaaaggtgag ttgagagtgg | 300 |
| agcgtgttta aattgcaatc ctgcctctat ttctgtgctt gcagggaaca gtcatcctta | 360 |
| attgctatcc tccatcatca tcatgattat ttctggtttt tctctggttg cggagaatcc | 420 |
| atactccagg tattccaatg tctcagcatt gccaggcctg tctgagcgtc aggatgtagg | 480 |
| tagtctgggc tctctgcctt ctattcttgt ccaggatact ctgccaaaag aatcatgttg | 540 |
| tggctgccac ccctcccaca aagcctcccg cttgggtcag tccaggactg gagttgggta | 600 |
| tggactgttc atgtctatcc actgctacgt cagggcaaca cccactgaga gtgaccttgt | 660 |
| agactgcagt gggagacacc cttcaaaacc tctcctctcc tgtcctgaga gccaggttaa | 720 |
| aaccatcagc cccgcatcct gagtgcaaac ttttcctaac cctgctgcta agctagacac | 780 |
| ctcacttact gagagccagc atgtccaccg ctgtgctgga aaccctggg ctggggagga | 840 |
| aactgtcaga cttcgggcag gagacttcat acattgagga taactgtaac cagaatggcg | 900 |
| ccatctctct gatcttcagc ctgaaggagg aagtgggcgc cctggcaaag gtgctgcgcc | 960 |
| tgtttgagga gaacgacgtg aatctgaccc acatcgagtc ccggccttct agactgaaga | 1020 |
| aggacgagta cgagttcttt acccacctgg ataagcggtc cctgccagcc ctgacaaaca | 1080 |
| tcatcaagat cctgaggcac gacatcggag caaccgtgca cgagctgtct cgggacaaga | 1140 |
| agaaggatac cgtgccctgg ttccctcgga caatccagga gctggataga tttgccaacc | 1200 |
| agatcctgtc ttacggagca gagctggacg cagatcaccc tggcttcaag acccagtgt | 1260 |
| atcgggcccg gagaaagcag tttgccgata tcgcctacaa ttataggcac ggacagccaa | 1320 |
| tccctcgcgt ggagtatatg gaggaggaga agaagacctg gggcacagtg ttcaagaccc | 1380 |
| tgaagagcct gtacaagaca cacgcctgct acgagtataa ccacatcttc ccctgctgg | 1440 |
| agaagtattg tggctttcac gaggacaata ccctcagct ggaggacgtg agccagttcc | 1500 |
| tgcagacctg cacaggcttt aggctgaggc cagtggcagg actgctgagc tcccgggact | 1560 |
| tcctgggagg actggccttc agagtgtttc actgcaccca gtacatcagg cacgctcca | 1620 |
| agccaatgta tacaccagag cccgacatct gtcacgagct gctggccac gtgcccctgt | 1680 |
| ttagcgatag atccttcgcc cagttttccc aggagatcgg actggcatct ctgggagcac | 1740 |
| ctgacgagta catcgagaag ctggccacca tctattggtt cacagtggag tttggcctgt | 1800 |
| gcaagcaggg cgatagcatc aaggcctacg agcaggact gctgtctagc ttcggcgagc | 1860 |
| tgcagtattg tctgtccgag aagccaaagc tgctgccct ggagctggag aagaccgcca | 1920 |
| tccagaacta caccgtgaca gagttccagc ccctgtacta tgtggccgag tcttttaacg | 1980 |
| atgccaagga gaaggtgaga aatttcgccg ccacaatccc taggcccttc agcgtgcggt | 2040 |
| acgacccta tacccagagg atcgaggtgc tggataatac acagcagctg aagatcctgg | 2100 |
| ctgactcaat caatagcgaa atcggaatcc tgtgctccgc cctgcagaaa atcaaatgag | 2160 |

```
aattcaaggc ctctcgagcc tctagaacta tagtgagtcg tattacgtag atccagacat      2220
gataagatac attgatgagt ttggacaaac cacaactaga atgcagtgaa aaaaatgctt      2280
tatttgtgaa atttgtgatg ctattgcttt atttgtaacc attataagct gcaataaaca      2340
agttaacaac aacaattgca ttcattttat gtttcaggtt caggggggagg tgtgggaggt      2400 tttttaagct ttacgtacga tcgtcgagca gctgttgtcc tggagaacgg agtcctgagc      2460
agaaaactct cagactttgg gcaggtaagc ctgttgggct tccactgcta ggagagaatt      2520
ggttccccac atgtgaaagc agtctgggaa atgctggtat ttccagtctc ctaaggctac      2580
taagaaatat gactttattt agaggcgagg aaaatgccca ggaagtcaac tgatgagact      2640
agtcttaaca agttgaggat acagaaagtt ggggatctga gctgctacca acatctgtgt      2700
gtctttgggt ggctcattgg tatcctctgc ctattggctt tatcttctgt acactgaaag      2760
gaaatggctg gtccttagtc acctggggtg ggagtcccta tctctccagg gatacttatt      2820 caatccttc ttctgggtat caaaatgaca agcttgtaag aaactgtcct ctttcggctt      2880
tcaggaggtg atgtcgcatg aagagaattt gggggggggg acttactcag aaccaaggag      2940
ggagaaatta aacagagagg gaaatgaaca ggagttagcc cggagcctga agcaccttgg      3000
ggattatgct gggggtggag ggaatccatt gtcctcccta ggagggcttt gcagaacatg      3060
ttcttttctg tgatatttgt actttcccca gattgcaaat catggtttgt acactgagat      3120
tcagtctctg gaggtaatat gccttttcta gcttttcctt ggacaggact aagggggttga     3180 gggttgcctg gagtcagaga aatttgtgtt aaagaaggtt gatatga                   3227
```

<210> SEQ ID NO 114
<211> LENGTH: 3635
<212> TYPE: DNA
<213> ORGANISM: Artificial Sequence
<220> FEATURE:
<223> OTHER INFORMATION: 006 vector correction genome (+ ITRs)

<400> SEQUENCE: 114

```
ttggccactc cctctctgcg cgctcgctcg ctcactgagg ccgggcgacc aaaggtcgcc       60
cgacgcccgg gctttgcccg gcggcctca gtgagcgagc gagcgcgcag agagggagtg      120
gccaactcca tcactagggg ttcctggagg ggtggagtcg tgacgtgaat tacgtcatag      180
ggttagggag gtcctgcata tgcggccgca gcattagctt ccatttatgc agtgtaaatg      240
gtgagaacag ccccgactga atacccagag catcatctcg tctgtgtcat tcatgcacat      300
aacatatctc agcgaggtgg ccctttctgtc ctctttgcag agacccagcc accatactag      360
tacctagaga actggctgga tttcagcccc gatacctccg ggcttttgct catgttcgcc      420
tcatagggtc atctgggtgg ttgcctaagg aaaagtatgt catggagact aacttgcttg      480
gcattgaata aaaggtgagt tgagagtgga gcgtgtttaa attgcaatcc tgcctctatt      540
tctgtgcttg cagggaacag tcatccttaa ttgctatcct ccatcatcat catgattatt      600
tctggttttt ctctggttgc ggagaatcca tactccaggt attccaatgt ctcagcattg      660
ccaggcctgt ctgagcgtca ggatgtaggt agtctgggct ctctgccttc tattcttgtc      720
caggatactc tgccaaaaga atcatgttgt ggctgccacc cctcccacaa agcctcccgc      780
ttgggtcagt ccaggactgg agttgggtat ggactgttca tgtctatcca ctgctacgtc      840
agggcaacac ccactgagag tgaccttgta gactgcagtg ggagacaccc ttcaaaacct      900
ctcctctcct gtcctgagag ccaggttaaa accatcagcc ccgcatcctg agtgcaaact      960
```

```
tttcctaacc ctgctgctaa gctagacacc tcacttactg agagccagca tgtccaccgc    1020
tgtgctggag aaccctgggc tggggaggaa actgtcagac ttcgggcagg agacttcata    1080
cattgaggat aactgtaacc agaatggcgc catctctctg atcttcagcc tgaaggagga    1140
agtgggcgcc ctggcaaagg tgctgcgcct gtttgaggag aacgacgtga atctgaccca    1200
catcgagtcc cggccttcta gactgaagaa ggacgagtac gagttcttta cccacctgga    1260
taagcggtcc ctgccagccc tgacaaacat catcaagatc ctgaggcacg acatcggagc    1320
aaccgtgcac gagctgtctc gggacaagaa gaaggatacc gtgccctggt tccctcggac    1380
aatccaggag ctggatagat tgccaaccca gatcctgtct tacggagcag agctggacgc    1440
agatcaccct ggcttcaagg acccagtgta tcgggcccgg agaaagcagt tgccgatat    1500 cgcctacaat tataggcacg acagccaat ccctcgcgtg gagtatatgg aggaggagaa    1560
gaagacctgg ggcacagtgt tcaagaccct gaagagcctg tacaagacac acgcctgcta    1620
cgagtataac cacatcttcc ccctgctgga aagtattgt ggctttcacg aggacaatat    1680
ccctcagctg gaggacgtga gccagttcct gcagacctgc acaggcttta ggctgaggcc    1740
agtggcagga ctgctgagct cccgggactt cctgggagga ctggccttca gagtgtttca    1800
ctgcacccag tacatcaggc acggctccaa gccaatgtat acaccagagc ccgacatctg    1860
tcacgagctg ctgggccacg tgcccctgtt tagcgataga ccttcgccc agttttccca    1920 ggagatcgga ctggcatctc tgggagcacc tgacgtac atcgagaagc tggccaccat    1980
ctattggttc acagtggagt ttggcctgtg caagcaggc gatagcatca aggcctacgg    2040
agcaggactg ctgtctagct tcggcgagct gcagtattgt ctgtccgaga agccaaagct    2100 gctgccctg gagctggaga agaccgccat ccagaactac accgtgacag agttccagcc    2160
cctgtactat gtggccgagt cttttaacga tgccaaggag aaggtgagaa attcgccgc    2220 cacaatccct aggccttca gcgtgcggta cgacccttat acccagagga tcgaggtgct    2280
ggataataca cagcagctga agatcctggc tgactcaatc aatagcgaaa tcggaatcct    2340
gtgctccgcc ctgcagaaaa tcaaatgaga attcaaggcc tctcgagcct ctagaactat    2400
agtgagtcgt attacgtaga tccagacatg ataagataca ttgatgagtt tggacaaacc    2460
acaactagaa tgcagtgaaa aaaatgcttt atttgtgaaa tttgtgatgc tattgcttta    2520
tttgtaacca ttataagctg caataaacaa gttaacaaca caattgcat tcattttatg    2580 tttcaggttc agggggaggt gtgggaggtt ttttaagctt tacgtacgat cgtcgagcag    2640
ctgttgtcct ggagaacgga gtcctgagca gaaaactctc agactttggg caggtaagcc    2700
tgttgggctt ccactgctag agagaattg gttccccaca tgtgaaagca gtctgggaaa    2760
tgctggtatt tccagtctcc taaggctact aagaaatatg actttattta gaggcgagga    2820
aaatgcccag gaagtcaact gatgagacta gtcttaacaa gttgaggata cagaaagttg    2880
gggatctgag ctgctaccaa catctgtgtg tctttgggtg gctcattggt atcctctgcc    2940
tattggcttt atcttctgta cactgaaagg aaatggctgg tccttagtca cctggggtgg    3000
gagtccctat ctctccaggg atacttattc aatcctttct tctgggtatc aaaatgacaa    3060
gcttgtaaga aactgtcctc tttcggcttt caggaggtga tgtcgcatga agagaatttg    3120
ggggggggga cttactcaga accaaggagg agaaattaa acagagaggg aaatgaacag    3180
gagttagccc ggagcctgaa gcaccttggg gattatgctg ggggtggagg gaatccattg    3240
tcctccctag ggagggcttg cagaacatgt tctttctgt gatatttgta ctttccccag    3300
attgcaaatc atggtttgta cactgagatt cagtctctgg aggtaatatg ccttttctag    3360
```

```
cttttccttg  acaggacta  aggggttgag  ggttgcctgg  agtcagagaa  atttgtgtta    3420
aagaaggttg  atatgacctg  caggtctaga  tacgtagata  agtagcatgg  cgggttaatc    3480
attaactaca  aggaacccct  agtgatggag  ttggccactc  cctctctgcg  cgctcgctcg    3540
ctcactgagg  ccgggcgacc  aaaggtcgcc  cgacgcccgg  gctttgcccg  ggcggcctca    3600
gtgagcgagc  gagcgcgcag  agagggagtg  gccaa                                 3635
```

<210> SEQ ID NO 115
<211> LENGTH: 960
<212> TYPE: DNA
<213> ORGANISM: Homo sapiens

<400> SEQUENCE: 115

```
gcttcaggag  cagttgtgcg  aatagctgga  gaacaccagg  ctggatttaa  acccagatcg      60
ctcttacatt  tgctctttac  ctgctgtgct  cagcgttcac  gtgccctcta  gctgtagttt     120
tctgaagtca  gcgcacagca  aggcagtgtg  cttagaggtt  aacagaaggg  aaaacaacaa     180
caacaaaaat  ctaaatgaga  atcctgactg  tttcagctgg  gggtaagggg  ggcggattat     240
tcatataatt  gttataccag  acggtcgcag  gcttagtcca  attgcagaga  actcgcttcc     300
caggcttctg  agagtcccgg  aagtgcctaa  acctgtctaa  tcgacggggc  ttgggtggcc     360
cgtcgctccc  tggcttcttc  cctttaccca  gggcgggcag  cgaagtggtg  cctcctgcgt     420
cccccacacc  ctccctcagc  ccctcccctc  cggcccgtcc  tgggcaggtg  acctggagca     480
tccggcaggc  tgccctggcc  tcctgcgtca  ggacaacgcc  cacgaggggc  gttactgtgc     540
ggagatgcac  cacgcaagag  acacccttg   taactctctt  ctcctcccta  gtgcgaggtt     600
aaaaccttca  gccccacgtg  ctgtttgcaa  acctgcctgt  acctgaggcc  ctaaaaagcc     660
agagacctca  ctcccgggga  gccagcatgt  ccactgcggt  cctggaaaac  ccaggcttgg     720
gcaggaaact  ctctgacttt  ggacaggtga  gccacggcag  cctgagctgc  tcagttaggg     780
gaatttgggc  ctccagagaa  agagatctga  agactgctgg  tgcttcctgg  tttcataagc     840
tcagtaagaa  gtctgaattc  gttggaagct  gatgagaata  tccaggaagt  caacagacaa     900
atgtcctcaa  caattgtttc  taagtaggag  aacatctgtc  ctcggtggct  ttcacaggaa     960
```

<210> SEQ ID NO 116
<211> LENGTH: 1353
<212> TYPE: DNA
<213> ORGANISM: Artificial Sequence
<220> FEATURE:
<223> OTHER INFORMATION: Silently altered PAH coding sequence

<400> SEQUENCE: 116

```
tccaccgctg  tgctggagaa  ccctgggctg  gggaggaaac  tgtcagactt  cgggcaggag      60
acttcataca  ttgaggataa  ctgtaaccag  aatggcgcca  tctctctgat  cttcagcctg     120
aaggaggaag  tgggcgccct  ggcaaaggtg  ctgcgcctgt  ttgaggagaa  cgacgtgaat     180
ctgacccaca  tcgagtcccg  gccttctaga  ctgaagaagg  acgagtacga  gttctttacc     240
cacctggata  gcggtccct   gccagccctg  acaaacatca  tcaagatcct  gaggcacgac     300
atcggagcaa  ccgtgcacga  gctgtctcgg  gacaagaaga  aggataccgt  gcctggttc      360
cctcggacaa  tccaggagct  ggatagattt  gccaaccaga  tcctgtctta  cggagcagag     420
ctggacgcag  atcaccctgg  cttcaaggac  ccagtgtatc  gggcccggag  aaagcagttt     480
gccgatatcg  cctacaatta  taggcacgga  cagccaatcc  ctcgcgtgga  gtatatggag     540
```

```
gaggagaaga agacctgggg cacagtgttc aagaccctga agagcctgta caagacacac    600
gcctgctacg agtataacca catcttcccc ctgctggaga agtattgtgg ctttcacgag    660
gacaatatcc ctcagctgga ggacgtgagc cagttcctgc agacctgcac aggctttagg    720
ctgaggccag tggcaggact gctgagctcc cgggacttcc tgggaggact ggccttcaga    780
gtgtttcact gcacccagta catcaggcac ggctccaagc caatgtatac accagagccc    840
gacatctgtc acgagctgct gggccacgtg cccctgttta gcgatagatc cttcgcccag    900
ttttcccagg agatcggact ggcatctctg ggagcacctg acgagtacat cgagaagctg    960
gccaccatct attggttcac agtggagttt ggcctgtgca agcagggcga tagcatcaag   1020
gcctacggag caggactgct gtctagcttc ggcgagctgc agtattgtct gtccgagaag   1080
ccaaagctgc tgccccctgga gctggagaag accgccatcc agaactacac cgtgacagag   1140
ttccagcccc tgtactatgt ggccgagtct tttaacgatg ccaaggagaa ggtgagaaat   1200
ttcgccgcca caatccctag gcccttcagc gtgcggtacg accttatac ccagaggatc    1260
gaggtgctgg ataatacaca gcagctgaag atcctggctg actcaatcaa tagcgaaatc   1320
ggaatcctgt gctccgccct gcagaaaatc aaa                                1353

<210> SEQ ID NO 117
<211> LENGTH: 910
<212> TYPE: DNA
<213> ORGANISM: Homo sapiens

<400> SEQUENCE: 117
ctgggatggg atgtggaatc cttctagatt tcttttgtaa tatttataaa gtgctctcag     60
caaggtatca aaatggcaaa attgtgagta actatcctcc tttcattttg ggaagaagat    120
gaggcatgaa gagaattcag acagaaactt actcagacca ggggaggcag aaactaagca    180
gagaggaaaa tgaccaagag ttagccctgg gcatggaatg tgaagaacc ctaaacgtga     240
cttgaaaata atgcccaagg tatattccat tctccgggat tgttggcat tttcttgagg     300
tgaagaattg cagaatacat tctttaatgt gacctacata tttacccatg ggaggaagtc    360
tgctcctgga ctcttgagat tcagtcataa agcccaggcc agggaaataa tgtaagtctg    420
caggcccctg tcatcagtag gattagggag aagagttctc agtagaaaac agggaggctg    480
gagagaaaag aatggttaat gttaacgtta atataactag aaagactgca gaacttagga    540
ctgattttta tttgaatcct taaaaaaaaa atttcttatg aaaatagtac atggctctta    600
ggagacagaa cttattgtac agaggaacag cgtgagagtc agagtgatcc cagaacaggt    660
cctggctcca tcctgcacat agttttggtg ctgctggcaa tacggtcccc acaactgtgg    720
gaaggggtta ggggcaggga tctcatcagg aaagcatagg ggtttaaagt tctttataga    780
gcacttagaa gattgagaat ccacaaatta tattaataac aaacaaagta gtgtcgtgtt    840
atatagtaaa tgtgaatttg cagacacatt tagggaaaag ttataattaa aaaaataggc    900
tgtatatata                                                           910

<210> SEQ ID NO 118
<211> LENGTH: 3713
<212> TYPE: DNA
<213> ORGANISM: Artificial Sequence
<220> FEATURE:
<223> OTHER INFORMATION: 032 correction vector genome

<400> SEQUENCE: 118
gcttcaggag cagttgtgcg aatagctgga gaacaccagg ctggatttaa acccagatcg     60
```

```
ctcttacatt tgctctttac ctgctgtgct cagcgttcac gtgccctcta gctgtagttt     120
tctgaagtca gcgcacagca aggcagtgtg cttagaggtt aacagaaggg aaaacaacaa     180
caacaaaaat ctaaatgaga atcctgactg tttcagctgg gggtaagggg ggcggattat     240
tcatataatt gttataccag acggtcgcag gcttagtcca attgcagaga actcgcttcc     300
caggcttctg agagtcccgg aagtgcctaa acctgtctaa tcgacggggc ttgggtggcc     360
cgtcgctccc tggcttcttc cctttaccca gggcgggcag cgaagtggtg cctcctgcgt     420
cccccacacc ctccctcagc ccctcccctc cggcccgtcc tgggcaggtg acctggagca     480
tccggcaggc tgccctggcc tcctgcgtca ggacaacgcc cacgagggggc gttactgtgc    540 ggagatgcac cacgcaagag acaccctttg taactctctt ctcctcccta gtgcgaggtt     600
aaaaccttca gccccacgtg ctgtttgcaa acctgcctgt acctgaggcc ctaaaaagcc     660
agagacctca ctcccgggga gccagcatgt ccactgcggt cctggaaaac ccaggcttgg     720
gcaggaaact ctctgacttt ggacaggtga gccacggcag cctgagctgc tcagttaggg     780
gaatttgggc ctccagagaa agagatctga agactgctgg tgcttcctgg tttcataagc     840
tcagtaagaa gtctgaattc gttggaagct gatgagaata tccaggaagt caacagacaa     900
atgtcctcaa caattgtttc taagtaggag aacatctgtc ctcggtggct ttcacaggaa     960
aagcttctga cctcttctct tcctcccaca gggcggtacc agatctggca gcggagaggg    1020
cagaggaagt cttctaacat gcggtgacgt ggaggagaat cccggcccta ggggtacctc    1080
caccgctgtg ctggagaacc ctgggctggg gaggaaactg tcagacttcg ggcaggagac    1140
ttcatacatt gaggataact gtaaccagaa tggcgccatc tctctgatct tcagcctgaa    1200
ggaggaagtg ggcgccctgg caaaggtgct gcgcctgttt gaggagaacg acgtgaatct    1260
gacccacatc gagtcccggc cttctagact gaagaaggac gagtacgagt tctttacccca    1320 cctggataag cggtccctgc cagccctgac aaacatcatc aagatcctga ggcacgacat    1380
cggagcaacc gtgcacgagc tgtctcggga caagaagaag gataccgtgc cctggttccc    1440
tcggacaatc caggagctgg atagatttgc caaccagatc ctgtcttacg gagcagagct    1500
ggacgcagat caccctggct tcaaggaccc agtgtatcgg gcccggagaa agcagtttgc    1560
cgatatcgcc tacaattata ggcacggaca gccaatccct cgcgtggagt atatggagga    1620
ggagaagaag acctgggggca cagtgttcaa gaccctgaag agcctgtaca agacacacgc    1680
ctgctacgag tataaccaca tcttccccct gctggagaag tattgtggct tcacgagga     1740 caatatccct cagctggagg acgtgagcca gttcctgcag acctgcacag ctttaggct     1800 gaggccagtg gcaggactgc tgagctcccg ggacttcctg ggaggactgg ccttcagagt    1860
gtttcactgc acccagtaca tcaggcacgg ctccaagcca atgtatacac cagagcccga    1920
catctgtcac gagctgctgg gccacgtgcc cctgtttagc gatagatcct cgcccagtt     1980 ttcccaggag atcggactgg catctctggg agcacctgac gagtacatcg agaagctggc    2040
caccatctat tggttcacag tggagtttgg cctgtgcaag cagggcgata gcatcaaggc    2100
ctacggagca ggactgctgt ctagcttcgg cgagctgcag tattgtctgt ccgaaagcc    2160 aaagctgctg cccctggagc tggagaagac cgccatccag aactacaccg tgacagagtt    2220
ccagcccctg tactatgtgg ccgagtcttt taacgatgcc aaggagaagg tgagaaattt    2280
cgccgccaca atccctaggc ccttcagcgt gcggtacgac cctatatccc agaggatcga    2340
ggtgctggat aatacacagc agctgaagat cctggctgac tcaatcaata gcgaaatcgg    2400
```

```
aatcctgtgc tccgccctgc agaaaatcaa aggtaagcct atccctaacc ctctcctcgg    2460
tctcgattct acgtgatctt gtggaaagga cgaaacaccg gggaattcaa ggcctctcga    2520
gcctctagaa tccccgagac gtttcgtctc gggatcacta tagtgagtcg tattacgtac    2580
acagtgcagg ggaaagaata gtagagatcc agacatgata agatacattg atgagtttgg    2640
acaaaccaca actagaatgc agtgaaaaaa atgctttatt tgtgaaattt gtgatgctat    2700
tgctttattt gtaaccatta taagctgcaa taaacaagtt aacaacaaca attgcattca    2760
ttttatgttt caggttcagg gggaggtgtg ggaggttttt taactgggat gggatgtgga    2820
atccttctag atttcttttg taatatttat aaagtgctct cagcaaggta tcaaaatggc    2880
aaaattgtga gtaactatcc tcctttcatt ttgggaagaa gatgaggcat gaagagaatt    2940
cagacagaaa cttactcaga ccaggggagg cagaaactaa gcagagagga aaatgaccaa    3000
gagttagccc tgggcatgga atgtgaaaga accctaaacg tgacttggaa ataatgccca    3060
aggtatattc cattctccgg gatttgttgg cattttcttg aggtgaagaa ttgcagaata    3120
cattctttaa tgtgacctac atatttaccc atgggaggaa gtctgctcct ggactcttga    3180
gattcagtca taaagcccag gccagggaaa taatgtaagt ctgcaggccc ctgtcatcag    3240
taggattagg gagaagagtt ctcagtagaa acaggggagg ctggagagaa aagaatggtt    3300
aatgttaacg ttaatataac tagaaagact gcagaactta ggactgatttt ttatttgaat   3360 ccttaaaaaa aaaatttctt atgaaaatag tacatggctc ttaggagaca gaacttattg    3420
tacagaggaa cagcgtgaga gtcagagtga tcccagaaca ggtcctggct ccatcctgca    3480
catagttttg gtgctgctgg caatacggtc cccacaactg tgggaagggg ttaggggcag    3540
ggatctcatc aggaaagcat aggggtttaa agttctttat agagcactta gaagattgag    3600
aatccacaaa ttatattaat aacaaacaaa gtagtgtcgt gttatatagt aaatgtgaat    3660
ttgcagacac atttagggaa aagttataat taaaaaaata ggctgtatat ata           3713
```

<210> SEQ ID NO 119
<211> LENGTH: 4139
<212> TYPE: DNA
<213> ORGANISM: Artificial Sequence
<220> FEATURE:
<223> OTHER INFORMATION: 032 vector correction genome (+ ITRs)

<400> SEQUENCE: 119

```
ttggccactc cctctctgcg cgctcgctcg ctcactgagg ccgggcgacc aaaggtcgcc     60
cgacgcccgg gctttgcccg gcggcctca gtgagcgagc gagcgcgcag agagggagtg    120
gccaactcca tcactagggg ttcctggagg ggtggagtcg tgacgtgaat tacgtcatag    180
ggttagggag gtcctgcata tgcggccgct tcaggagcag ttgtgcgaat agctggagaa    240
caccaggctg gatttaaacc cagatcgctc ttacatttgc tctttacctg ctgtgctcag    300
cgttcacgtg ccctctagct gtagttttct gaagtcagcg cacagcaagg cagtgtgctt    360
agaggttaac agaagggaaa acaacaacaa caaaaatcta aatgagaatc ctgactgttt    420
cagctggggg taagggggc ggattattca tataattgtt ataccagacg gtcgcaggct     480
tagtccaatt gcagagaact cgcttcccag gcttctgaga gtcccggaag tgcctaaacc    540
tgtctaatcg acggggcttg ggtggcccgt cgctccctgg cttcttccct ttacccaggg    600
cgggcagcga agtggtgcct cctcgtcccc ccacaccctc cctcagcccc tcccctccgg    660
cccgtcctgg gcaggtgacc tggagcatcc ggcaggctgc cctggcctcc tgcgtcagga    720
caacgcccac gagggggcgtt actgtgcgga gatgcaccac gcaagagaca cccttttgtaa   780
```

```
ctctcttctc ctccctagtg cgaggttaaa accttcagcc ccacgtgctg tttgcaaacc      840
tgcctgtacc tgaggcccta aaaagccaga gacctcactc ccggggagcc agcatgtcca      900
ctgcggtcct ggaaaaccca ggcttgggca ggaaactctc tgactttgga caggtgagcc      960
acggcagcct gagctgctca gttagggaa tttgggcctc cagagaaaga gatctgaaga     1020
ctgctggtgc ttcctggttt cataagctca gtaagaagtc tgaattcgtt ggaagctgat     1080
gagaatatcc aggaagtcaa cagacaaatg tcctcaacaa ttgtttctaa gtaggagaac     1140
atctgtcctc ggtggctttc acaggaaaag cttctgacct cttctcttcc tcccacaggg     1200
cggtaccaga tctggcagcg agagggcag aggaagtctt ctaacatgcg gtgacgtgga     1260
ggagaatccc ggccctaggg gtacctccac cgctgtgctg gagaaccctg gctggggag     1320
gaaactgtca gacttcgggc aggagacttc atacattgag gataactgta accagaatgg     1380
cgccatctct ctgatcttca gcctgaagga ggaagtgggc gccctggcaa aggtgctgcg     1440
cctgtttgag gagaacgacg tgaatctgac ccacatcgag tcccggcctt ctagactgaa     1500
gaaggacgag tacgagttct ttacccacct ggataagcgg tccctgccag ccctgacaaa     1560
catcatcaag atcctgaggc acgacatcgg agcaaccgtg cacgagctgt ctcgggacaa     1620
gaagaaggat accgtgccct ggttccctcg acaatccag gagctggata gatttgccaa     1680
ccagatcctg tcttacgag cagagctgga cgcagatcac cctggcttca aggacccagt     1740
gtatcgggcc cggagaaagc agtttgccga tatcgcctac aattataggc acggacagcc     1800
aatccctcgc gtggagtata tggaggagga agaagagacc tggggcacag tgttcaagac     1860
cctgaagagc ctgtacaaga cacgcctg ctacgagtat aaccacatct tccccctgct     1920
ggagaagtat tgtggctttc acgaggacaa tatccctcag ctggaggacg tgagccagtt     1980
cctgcagacc tgcacaggct taggctgag gccagtggca ggactgctga gctcccggga     2040
cttcctggga ggactggcct tcagagtgtt tcactgcacc cagtacatca ggcacggctc     2100
caagccaatg tatacaccag agcccgacat ctgtcacgag ctgctgggcc acgtgcccct     2160
gtttagcgat agatccttcg cccagttttc ccaggagatc ggactggcat ctctgggagc     2220
acctgacgag tacatcgaga agctggccac catctattgg ttcacagtgg agtttggcct     2280
gtgcaagcag ggcgatagca tcaaggccta cggagcagga ctgctgtcta gcttcggcga     2340
gctgcagtat tgtctgtccg agaagccaaa gctgctgccc ctggagctgg agaagaccgc     2400
catccagaac tacaccgtga cagagttcca gccctgtac tatgtggccg agtctttaa     2460
cgatgccaag gagaaggtga aaatttcgc cgccacaatc cctaggccct tcagcgtgcg     2520
gtacgaccct tatcccaga ggatcgaggt gctggataat acacagcagc tgaagatcct     2580
ggctgactca atcaatagcg aaatcggaat cctgtgctcc gccctgcaga aaatcaaagg     2640
taagcctatc cctaacctc tcctcggtct cgattctacg tgatcttgtg gaaaggacga     2700
aacaccgggg aattcaaggc ctctcgagcc tctagaatcc ccgagacgtt tcgtctcggg     2760
atcactatag tgagtcgtat tacgtacaca gtgcagggga aagaatagta gagatccaga     2820
catgataaga tacattgatg agtttggaca aaccacaact agaatgcagt gaaaaaaatg     2880
ctttatttgt gaaatttgtg atgctattgc tttatttgta accattataa gctgcaataa     2940
acaagttaac aacaacaatt gcattcattt tatgtttcag gttcaggggg aggtgtggga     3000
ggttttttaa ctgggatggg atgtggaatc cttctagatt tcttttgtaa tatttataaa     3060
gtgctctcag caaggtatca aaatggcaaa attgtgagta actatcctcc tttcattttg     3120
```

```
ggaagaagat gaggcatgaa gagaattcag acagaaactt actcagacca ggggaggcag    3180
aaactaagca gagaggaaaa tgaccaagag ttagccctgg gcatggaatg tgaaagaacc    3240
ctaaacgtga cttggaaata atgcccaagg tatattccat tctccgggat ttgttggcat    3300
tttcttgagg tgaagaattg cagaatacat tctttaatgt gacctacata tttacccatg    3360
ggaggaagtc tgctcctgga ctcttgagat tcagtcataa agcccaggcc agggaaataa    3420
tgtaagtctg caggcccctg tcatcagtag gattagggag aagagttctc agtagaaaac    3480
agggaggctg gagagaaaag aatggttaat gttaacgtta atataactag aaagactgca    3540
gaacttagga ctgattttta tttgaatcct taaaaaaaaa atttcttatg aaaatagtac    3600
atggctctta ggagacagaa cttattgtac agaggaacag cgtgagagtc agagtgatcc    3660
cagaacaggt cctggctcca tcctgcacat agttttggtg ctgctggcaa tacggtcccc    3720
acaactgtgg aaggggtta ggggcaggga tctcatcagg aaagcatagg ggtttaaagt    3780
tctttataga gcacttagaa gattgagaat ccacaaatta tattaataac aaacaaagta    3840
gtgtcgtgtt atatagtaaa tgtgaatttg cagacacatt tagggaaaag ttataattaa    3900
aaaaataggc tgtatatata ctagatacgt agataagtag cctgcaggtc tagatacgta    3960
gataagtagc atggcgggtt aatcattaac tacaaggaac ccctagtgat ggagttggcc    4020
actccctctc tgcgcgctcg ctcgctcact gaggccgggc gaccaaaggt cgcccgacgc    4080
ccgggctttg cccgggcggc ctcagtgagc gagcgagcgc gcagagaggg agtggccaa     4139
```

<210> SEQ ID NO 120
<211> LENGTH: 97
<212> TYPE: DNA
<213> ORGANISM: Artificial Sequence
<220> FEATURE:
<223> OTHER INFORMATION: Chymeric MVM intron (ChiMVM)

<400> SEQUENCE: 120

```
gtaagggttt aagggatggt tggttggtgg ggtattaatg tttaattacc tggagcacct    60
gcctgaaatc acctgacctc ttctcttcct cccacag                             97
```

<210> SEQ ID NO 121
<211> LENGTH: 97
<212> TYPE: DNA
<213> ORGANISM: Artificial Sequence
<220> FEATURE:
<223> OTHER INFORMATION: SV40 intron

<400> SEQUENCE: 121

```
gtaagtttag tcttttgtc ttttatttca ggtcccggat ccggtggtgg tgcaaatcaa    60
agaactgctc ctcagtggat gttgccttta cttctag                             97
```

<210> SEQ ID NO 122
<211> LENGTH: 521
<212> TYPE: DNA
<213> ORGANISM: Artificial Sequence
<220> FEATURE:
<223> OTHER INFORMATION: Adenovirus tripartite leader intron (AdTPL)

<400> SEQUENCE: 122

```
gtcctcactc tcttccgcat cgctgtctgc gagggccagc tgttgggctc gcggttgagg    60
acaaactctt cgcggtcttt ccagtactct tggatcggaa accgtcggc ctccgaacgg    120 tactccgcca ccgagggacc tgagcgagtc cgcatcgacc ggatcggaaa acctctcgag    180
aaaggcgtct aaccagtcac agtcgcaagg taggctgagc accgtggcgg gcggcagcgg    240
```

```
gtggcggtcg gggttgtttc tggcggaggt gctgctgatg atgtaattaa agtaggcggt    300
cttgagacgg cggatggtcg aggtgaggtg tggcaggctt gagatccagc tgttggggtg    360
agtactccct ctcaaaagcg ggcattactt ctgcgctaag attgtcagtt tccaaaaacg    420
aggaggattt gatattcacc tggcccgatc tggccataca cttgagtgac aatgacatcc    480
actttgcctt tctctccaca ggtgtccact cccaggtcca g                        521
```

```
<210> SEQ ID NO 123
<211> LENGTH: 124
<212> TYPE: DNA
<213> ORGANISM: Homo sapiens

<400> SEQUENCE: 123
gtaagtatca aggttacaag acaggtttaa ggagaccaat agaaactggg catgtggaga     60
cagagaagac tcttgggttt ctgataggca ctgactctct tcctttgtcc tgttcccatt   120
tcag                                                                124

<210> SEQ ID NO 124
<211> LENGTH: 230
<212> TYPE: DNA
<213> ORGANISM: Artificial Sequence
<220> FEATURE:
<223> OTHER INFORMATION: AdV/Ig chimeric intron (AdVIgG)

<400> SEQUENCE: 124
gtgagtactc cctctcaaaa gcgggcatga cttctgcgct aagattgtca gtttccaaaa     60
acgaggagga tttgatattc acctggcccg cggtgatgcc tttgagggtg gccgcgtcca   120
tctggtcaga aaagacaatc ttttgttgt caagcttgag gtgtggcagg cttgagatct    180
ggccatacac ttgagtgaca atgacatcca ctttgccttt ctctccacag              230

<210> SEQ ID NO 125
<211> LENGTH: 133
<212> TYPE: DNA
<213> ORGANISM: Artificial Sequence
<220> FEATURE:
<223> OTHER INFORMATION: Beta globin Ig heavy chain intron (beta-
      globinIg)

<400> SEQUENCE: 125
gtaagtatca aggttacaag acaggtttaa ggagaccaat agaaactggg cttgtcgaga     60
cagagaagac tcttgcgttt ctgataggca cctattggtc ttactgacat ccactttgcc   120
tttctctcca cag                                                      133

<210> SEQ ID NO 126
<211> LENGTH: 82
<212> TYPE: DNA
<213> ORGANISM: Artificial Sequence
<220> FEATURE:
<223> OTHER INFORMATION: MVM intron

<400> SEQUENCE: 126
gtaagggttt aagggatggt tggttggtgg ggtattaatg tttaattacc tggagcacct     60
gcctgaaatc acttttttc ag                                              82

<210> SEQ ID NO 127
<211> LENGTH: 618
<212> TYPE: DNA
<213> ORGANISM: Artificial Sequence
```

<220> FEATURE:
<223> OTHER INFORMATION: HCR1 element (OptHCR)

<400> SEQUENCE: 127

```
gtaagtttta tggaatgtga atcataattc aatttttcaa catgcgttag gagggacatt      60
tcaaactctt ttttacccta gactttccta ccatcaccca gagtatccag ccaggagggg     120
aggggctaga gacaccagaa gtttagcagg gaggagggcg tagggattcg gggaatgaag     180
ggatgggatt cagactaggg ccaggaccca gggatgagaa aagagatg agagtggttt      240
gggggcttgg tgacttagag aacagagctg caggctcaga ggcacacagg agtttctggg     300
ctggcccggc cccttccaa cccctcatta tggaatccag cagctgtttg tgtgctgcct     360
ctgaagtcca cactgaacaa acttcagcct actcatgtcc catataaggg aaattatgga    420
atcagcaaac agcaaacaca cagccctccc tgcctgctga ccttggacct ggggcagagg    480
tcagagacct ccttggctct atgccacctc caacatccac tcgaccccctt ggaatttcgg   540
tggagaggag cagaggttgt cctggcgtgg tttaggtagt gtgagagggc tgaccatgcc    600
ttcttctttt tcctacag                                                  618
```

<210> SEQ ID NO 128
<211> LENGTH: 476
<212> TYPE: DNA
<213> ORGANISM: Homo sapiens

<400> SEQUENCE: 128

```
gtgagtctat gggacccttg atgttttctt tcccctttctt ttctatggtt aagttcatgt    60
cataggaagg ggagaagtaa cagggtacac atattgacca aatcagggta attttgcatt    120
tgtaatttta aaaatgcttt tcttctttta atatacttttt ttgtttatct tatttctaat   180
actttcccta atctctttct ttcagggcaa taatgataca atgtatcatg cctctttgca    240
ccattctaaa gaataacagt gataattttct gggttaaggc aatagcaata tttctgcata   300
taaatatttc tgcatataaa ttgtaactga tgtaagaggt ttcatattgc taatagcagc    360
tacaatccag ctaccattct gcttttattt tatggttggg ataaggctgg attattctga    420
gtccaagcta ggcccttttg ctaatcatgt tcatacctct tatcttcctc ccacag        476
```

<210> SEQ ID NO 129
<211> LENGTH: 299
<212> TYPE: DNA
<213> ORGANISM: Artificial Sequence
<220> FEATURE:
<223> OTHER INFORMATION: tFIX intron (FIX intron)

<400> SEQUENCE: 129

```
gtaagtttcc tttttaaaa tacattgagt atgcttgcct tttagatata gaaatatctg     60
atgctgtctt cttcactaaa ttttgattac atgatttgac agcaatattg aagagtctaa   120
cagccagcac gcaggttggc aactactgtg gaaacatcac agattttggc tccatgccct   180
aaagagaaat tggctttcag attatttgga ttaaaaacaa agactttctt aagagatgta   240
aaattttcat gatgttttct tttttgctaa aactaaagaa ttattctttt acatttcag    299
```

<210> SEQ ID NO 130
<211> LENGTH: 900
<212> TYPE: DNA
<213> ORGANISM: Artificial Sequence
<220> FEATURE:
<223> OTHER INFORMATION: ch2BLood intron (BloodEnh)

<400> SEQUENCE: 130

```
gtaagtagtc tacactgggg ctaagtaaac atttactgag tgaaagaata aatacgtgca      60
gaacccagcc aacagagagc atccccggag gtggggccat gccctcaggc actcagagga     120
ggcaggcctc tggcagtagc taagcagatt cccgtctcag atgtcagccc tgcccaccct     180
tctgtgcccc cccgcccccc tggttggtgt ttgtgggaca gtttccactg tgttgcctgg     240
gaaacgaggc atcctgccac caccactccc cacctccggg ctgccaacac ctaccacgcc     300
cggcttgggg gttttggctg gtttcccttg tgtcctagtc agcttgagaa accctcggat     360
gcactcgcca cttttacagt gtggctttgc tcatctgggt gggaggtact gcctggggtg     420
agctcatcac ctctggttcc tcagtgcaag gcactaaagt ctcttggcac tgagttctta     480
caacttgttc cagggatat ttggtggttg atggtcacca cccatgtgtc atggtccctg      540
agcatccccc gccacccac tgctccctat tttggcagtt actgtcaccc tctagggatg      600
cagggatgca gtttacctat ctagagtgcg gtgatcaggt ggggaagtac aaatggcaat     660
tgacagctag agagcttgaa accctccac ttggctctgc tcaccctgga ctctgggaga      720
cctcagctgc ccagcagtgg aggctggggc agcagagggg ccagacctgg gagcccagaa     780
gcctggatct gagtctgact cactgctgac ctttgacccc tggaggcttg ggcaagctga     840
ggaacttctc tggtcttaat cctgtgggtg actgaccatg ccttcttctt tttcctacag     900
```

<210> SEQ ID NO 131
<211> LENGTH: 1977
<212> TYPE: DNA
<213> ORGANISM: Artificial Sequence
<220> FEATURE:
<223> OTHER INFORMATION: 006-HCR vector PAH coding sequence

<400> SEQUENCE: 131

```
atgtccaccg ctgtgctgga gaaccctggg ctggggagga aactgtcaga cttcgggcag     60
gtaagtttta tggaatgtga atcataattc aattttcaa catgcgttag gagggacatt     120
tcaaactctt ttttaccccta gactttccta ccatcaccca gagtatccag ccaggagggg     180
aggggctaga gacaccagaa gtttagcagg gaggagggcg tagggattcg gggaatgaag     240
gatgggatt cagactaggg ccaggaccca gggatggaga gaaagagatg agagtggttt      300
gggggcttgg tgacttagag aacagagctg caggctcaga ggcacacagg agtttctggg     360
ctggcccggc ccccttccaa cccctcatta tggaatccag cagctgtttg tgtgctgcct     420
ctgaagtcca cactgaacaa acttcagcct actcatgtcc catataaggg aaattatgga     480
atcagcaaac agcaaacaca cagccctccc tgcctgctga ccttggacct ggggcagagg     540
tcagagacct ccttggctct atgccacctc caacatccac tcgacccctt ggaatttcgg     600
tggagaggag cagaggttgt cctggcgtgg tttaggtagt gtgagagggc tgaccatgcc     660
ttcttctttt tcctacagga aacttcatac attgaggata actgtaacca gaatggcgcc     720
atctctctga tcttcagcct gaaggaggaa gtgggcgccc tggcaaaggt gctgcgcctg     780
tttgaggaga cgacgtgaa tctgacccac atcgagtccc ggccttctag actgaagaag     840
gacgagtacg agttctttac ccacctggat aagcggtccc tgccagccct gacaaacatc     900
atcaagatcc tgaggcacga catcggagca accgtgcacg agctgtctcg ggacaagaag     960
aaggataccg tgccctggtt ccctcggaca atccaggagc tggatagatt tgccaaccag    1020
atcctgtctt acggagcaga gctgacgca gatcaccctg gcttcaagga cccagtgtat    1080
cgggcccgga gaaagcagtt tgccgatatc gcctacaatt ataggcacga acagccaatc    1140
```

```
cctcgcgtgg agtatatgga ggaggagaag aagacctggg gcacagtgtt caagaccctg    1200
aagagcctgt acaagacaca cgcctgctac gagtataacc acatcttccc cctgctggag    1260
aagtattgtg ctttcacga ggacaatatc cctcagctgg aggacgtgag ccagttcctg    1320
cagacctgca caggctttag gctgaggcca gtggcaggac tgctgagctc ccgggacttc    1380
ctgggaggac tggccttcag agtgtttcac tgcacccagt acatcaggca cggctccaag    1440
ccaatgtata caccagagcc cgacatctgt cacgagctgc tgggccacgt gcccctgttt    1500
agcgatagat ccttcgccca gttttcccag gagatcggac tggcatctct gggagcacct    1560
gacgagtaca tcgagaagct ggccaccatc tattggttca cagtggagtt tggcctgtgc    1620
aagcagggcg atagcatcaa ggcctacgga gcaggactgc tgtctagctt cggcgagctg    1680
cagtattgtc tgtccgagaa gccaaagctg ctgcccctgg agctggagaa gaccgccatc    1740
cagaactaca ccgtgacaga gttccagccc ctgtactatg tggccgagtc tttttaacgat    1800 gccaaggaga aggtgagaaa tttcgccgcc acaatcccta ggcccttcag cgtgcggtac    1860 gaccccttata cccagaggat cgaggtgctg ataatacac agcagctgaa gatcctggct    1920
gactcaatca atagcgaaat cggaatcctg tgctccgccc tgcagaaaat caaatga       1977
```

<210> SEQ ID NO 132
<211> LENGTH: 1971
<212> TYPE: DNA
<213> ORGANISM: Artificial Sequence
<220> FEATURE:
<223> OTHER INFORMATION: 032-HCR vector PAH coding sequence

<400> SEQUENCE: 132

```
tccaccgctg tgctggagaa ccctgggctg gggaggaaac tgtcagactt cgggcaggta     60
agttttatgg aatgtgaatc ataattcaat ttttcaacat gcgttaggag ggacatttca    120
aactcttttt taccctagac tttcctacca tcacccagag tatccagcca ggaggggagg    180
ggctagagac accagaagtt tagcagggag gagggcgtag ggattcgggg aatgaaggga    240
tgggattcag actagggcca ggacccaggg atggagagaa agagatgaga gtggtttggg    300
ggcttggtga cttagagaac agagctgcag gctcagaggc acacaggagt ttctgggctg    360
gcccggcccc cttccaaccc ctcattatgg aatccagcag ctgtttgtgt gctgcctctg    420
aagtccacac tgaacaaact tcagcctact catgtcccat ataagggaaa ttatggaatc    480
agcaaacagc aaacacacag ccctcccctgc ctgctgacct tggacctggg gcagaggtca    540
gagacctcct tggctctatg ccacctccaa catccactcg accccttgga atttcggtgg    600
agaggagcag aggttgtcct ggcgtggttt aggtagtgtg agagggctga ccatgccttc    660 ttcttttttcc tacaggaaac ttcatacatt gaggataact gtaaccagaa tggcgccatc    720
tctctgatct tcagcctgaa ggaggaagtg ggcgccctgg caaaggtgct gcgcctgttt    780
gaggagaacg acgtgaatct gacccacatc gagtcccggc cttctagact gaagaaggac    840
gagtacgagt tctttaccca cctggataag cggtccctgc cagcccctga caacatcatc    900
aagatcctga ggcacgacat cggagcaacc gtgcacgagc tgtctcggga caagaagaag    960
gataccgtgc cctggttccc tcggacaatc caggagctga tagatttgc caaccagatc    1020 ctgtcttacg gagcagagct ggacgcagat cacccctggct tcaaggaccc agtgtatcgg    1080
gcccggagaa agcagtttgc cgatatcgcc tacaattata ggcacggaca gccaatccct    1140
cgcgtggagt atatggagga ggagaagaag acctggggca cagtgttcaa gaccctgaag    1200
```

| | | |
|---|---|---|
| agcctgtaca agacacacgc ctgctacgag tataaccaca tcttcccccct gctggagaag | 1260 | |
| tattgtggct ttcacgagga caatatccct cagctggagg acgtgagcca gttcctgcag | 1320 | |
| acctgcacag gctttaggct gaggccagtg gcaggactgc tgagctcccg ggacttcctg | 1380 | |
| ggaggactgg ccttcagagt gtttcactgc acccagtaca tcaggcacgg ctccaagcca | 1440 | |
| atgtatacac cagagcccga catctgtcac gagctgctgg gccacgtgcc cctgtttagc | 1500 | |
| gatagatcct tcgcccagtt ttcccaggag atcggactgg catctctggg agcacctgac | 1560 | |
| gagtacatcg agaagctggc caccatctat tggttcacag tggagtttgg cctgtgcaag | 1620 | |
| cagggcgata gcatcaaggc ctacggagca ggactgctgt ctagcttcgg cgagctgcag | 1680 | |
| tattgtctgt ccgagaagcc aaagctgctg cccctggagc tggagaagac cgccatccag | 1740 | |
| aactacaccg tgacagagtt ccagcccctg tactatgtgg ccgagtcttt taacgatgcc | 1800 | |
| aaggagaagg tgagaaattt cgccgccaca atccctaggc ccttcagcgt gcggtacgac | 1860 | |
| ccttatcccc agaggatcga ggtgctggat aatacacagc agctgaagat cctggctgac | 1920 | |
| tcaatcaata gcgaaatcgg aatcctgtgc tccgccctgc agaaaatcaa a | 1971 | |

<210> SEQ ID NO 133
<211> LENGTH: 174
<212> TYPE: DNA
<213> ORGANISM: Artificial Sequence
<220> FEATURE:
<223> OTHER INFORMATION: ID cassette

<400> SEQUENCE: 133

| | | |
|---|---|---|
| ggtaagccta tccctaaccc tctcctcggt ctcgattcta cgtgatcttg tggaaaggac | 60 | |
| gaaacaccgg ggaattcaag gcctctcgag cctctagaat ccccgagacg tttcgtctcg | 120 | |
| ggatcactat agtgagtcgt attacgtaca cagtgcaggg gaaagaatag taga | 174 | |

<210> SEQ ID NO 134
<211> LENGTH: 800
<212> TYPE: DNA
<213> ORGANISM: Artificial Sequence
<220> FEATURE:
<223> OTHER INFORMATION: 006-HCR vector correction genome

<400> SEQUENCE: 134

| | | |
|---|---|---|
| gcagctgttg tcctggagaa cggagtcctg agcagaaaac tctcagactt tgggcaggta | 60 | |
| agcctgttgg gcttccactg ctaggagaga attggttccc cacatgtgaa agcagtctgg | 120 | |
| gaaatgctgg tatttccagt ctcctaaggc tactaagaaa tatgacttta tttagaggcg | 180 | |
| aggaaaatgc ccaggaagtc aactgatgag actagtctta acaagttgag gatacagaaa | 240 | |
| gttggggatc tgagctgcta ccaacatctg tgtgtctttg ggtggctcat ggtatcctc | 300 | |
| tgcctattgg ctttatcttc tgtacactga aaggaaatgg ctggtcctta gtcacctggg | 360 | |
| gtgggagtcc ctatctctcc agggatactt attcaatcct ttcttctggg tatcaaaatg | 420 | |
| acaagcttgt aagaaactgt cctctttcgg ctttcaggag gtgatgtcgc atgaagagaa | 480 | |
| tttggggggg gggacttact cagaaccaag gagggagaaa ttaaacagag agggaaatga | 540 | |
| acaggagtta gcccggagcc tgaagcacct tggggattat gctgggggtg gagggaatcc | 600 | |
| attgtcctcc ctagggaggg cttgcagaac atgttctttt ctgtgatatt tgtactttcc | 660 | |
| ccagattgca aatcatggtt tgtacactga gattcagtct ctggaggtaa tatgcctttt | 720 | |
| ctagcttttc cttggacagg actaagggg tgagggttgc ctggagtcag agaaatttgt | 780 | |
| gttaaagaag gttgatatga | 800 | |

<210> SEQ ID NO 135
<211> LENGTH: 4253
<212> TYPE: DNA
<213> ORGANISM: Artificial Sequence
<220> FEATURE:
<223> OTHER INFORMATION: 006-HCR vector correction genome (+ITRs)

<400> SEQUENCE: 135

```
ttggccactc cctctctgcg cgctcgctcg ctcactgagg ccgggcgacc aaaggtcgcc      60
cgacgcccgg gctttgcccg ggcggcctca gtgagcgagc gagcgcgcag agagggagtg     120
gccaactcca tcactagggg ttcctggagg ggtggagtcg tgacgtgaat tacgtcatag     180
ggttagggag gtcctgcata tgcggccgca gcattagctt ccatttatgc agtgtaaatg     240
gtgagaacag ccccgactga atacccagag catcatctcg tctgtgtcat tcatgcacat     300
aacatatctc agcgaggtgg cccttctgtc ctctttgcag agacccagcc accatactag     360
tacctagaga actggctgga tttcagcccc gatacctccg ggcttttgct catgttcgcc     420
tcatagggtc atctgggtgg ttgcctaagg aaaagtatgt catggagact aacttgcttg     480
gcattgaata aaaggtgagt tgagagtgga gcgtgtttaa attgcaatcc tgcctctatt     540
tctgtgcttg cagggaacag tcatccttaa ttgctatcct ccatcatcat catgattatt     600
tctggttttt tctctggttgc ggagaatcca tactccaggt attccaatgt ctcagcattg     660
ccaggcctgt ctgagcgtca ggatgtaggt agtctgggct ctctgccttc tattcttgtc     720
caggatactc tgccaaaaga atcatgttgt ggctgccacc cctcccacaa agcctcccgc     780
ttgggtcagt ccaggactgg agttgggtat ggactgttca tgtctatcca ctgctacgtc     840
agggcaacac ccactgagag tgaccttgta gactgcagtg ggagacaccc ttcaaaacct     900
ctcctctcct gtcctgagag ccaggttaaa accatcagcc ccgcatcctg agtgcaaact     960
tttcctaacc ctgctgctaa gctagacacc tcacttactg agagccagca tgtccaccgc    1020
tgtgctggag aaccctgggc tggggaggaa actgtcagac ttcgggcagg taagttttat    1080
ggaatgtgaa tcataattca attttttcaac atgcgttagg agggacattt caaactcttt    1140
tttaccctag actttcctac catcacccag agtatccagc caggaggggga ggggctagag    1200
acaccagaag tttagcaggg aggagggcgt agggattcgg ggaatgaagg gatgggattc    1260
agactagggc caggacccag ggatggagag aaagagatga gagtggtttg ggggcttggt    1320
gacttagaga acagagctgc aggctcagag gcacacagga gtttctgggc tggcccggcc    1380
cccttccaac ccctcattat ggaatccagc agctgtttgt gtgctgcctc tgaagtccac    1440
actgaacaaa cttcagccta ctcatgtccc atataaggga aattatggaa tcagcaaaca    1500
gcaaacacac agccctccct gcctgctgac cttggacctg gggcagaggt cagagacctc    1560
cttggctcta tgccacctcc aacatccact cgacccttg gaatttcggt ggagaggagc    1620
agaggttgtc ctggcgtggt ttaggtagtg tgagagggct gaccatgcct tcttcttttt    1680
cctacaggaa acttcataca ttgaggataa ctgtaaccag aatggcgcca tctctctgat    1740
cttcagcctg aaggaggaag tgggcgcccct ggcaaaggtg ctgcgcctgt ttgaggagaa    1800
cgacgtgaat ctgacccaca tcgagtcccg gccttctaga ctgaagaagg acgagtacga    1860
gttctttacc cacctggata gcggtccct gccagccctg acaaacatca tcaagatcct    1920
gaggcacgac atcggagcaa ccgtgcacga gctgtctcgg acaagaaga aggataccgt    1980
gccctggttc cctcggacaa tccaggagct ggatagattt gccaaccaga tcctgtctta    2040
```

```
cggagcagag ctggacgcag atcaccctgg cttcaaggac ccagtgtatc gggcccggag    2100
aaagcagttt gccgatatcg cctacaatta taggcacgaa cagccaatcc ctcgcgtgga    2160
gtatatggag gaggagaaga agacctgggg cacagtgttc aagaccctga gagcctgta     2220 caagacacac gcctgctacg agtataacca catcttcccc ctgctggaga agtattgtgg    2280 cttttcacgag gacaatatcc ctcagctgga ggacgtgagc cagttcctgc agacctgcac   2340
aggctttagg ctgaggccag tggcaggact gctgagctcc cgggacttcc tgggaggact    2400
ggccttcaga gtgtttcact gcacccagta catcaggcac ggctccaagc caatgtatac    2460
accagagccc gacatctgtc acgagctgct gggccacgtg ccctgtttta gcgatagatc    2520
cttcgcccag ttttcccagg agatcggact ggcatctctg gagcacctg acgagtacat     2580 cgagaagctg gccaccatct attggttcac agtggagttt ggcctgtgca agcagggcga    2640
tagcatcaag gcctacggag caggactgct gtctagcttc ggcgagctgc agtattgtct    2700
gtccgagaag ccaaagctgc tgcccctgga gctggagaag accgccatcc agaactacac    2760
cgtgacagag ttccagcccc tgtactatgt ggccgagtct tttaacgatg ccaaggagaa    2820
ggtgagaaat ttcgccgcca caatccctag gcccttcagc gtgcggtacg acccttatac    2880
ccagaggatc gaggtgctgg ataatacaca gcagctgaag atcctggctg actcaatcaa    2940
tagcgaaatc ggaatcctgt gctccgccct gcagaaaatc aaatgagaat tcaaggcctc    3000
tcgagcctct agaactatag tgagtcgtat tacgtagatc cagacatgat aagatacatt    3060
gatgagtttg gacaaaccac aactagaatg cagtgaaaaa aatgctttat ttgtgaaatt    3120
tgtgatgcta ttgctttatt tgtaaccatt ataagctgca ataaacaagt taacaacaac    3180
aattgcattc attttatgtt tcaggttcag ggggaggtgt gggaggtttt ttaagcttta    3240
cgtacgatcg tcgagcagct gttgtcctgg agaacggagt cctgagcaga aaactctcag    3300
actttgggca ggtaagcctg ttgggcttcc actgctagga gagaattggt tccccacatg    3360
tgaaagcagt ctgggaaatg ctggtatttc cagtctccta aggctactaa gaaatatgac    3420
tttatttaga ggcgaggaaa atgcccagga agtcaactga tgagactagt cttaacaagt    3480
tgaggataca gaaagttggg gatctgagct gctaccaaca tctgtgtgtc tttgggtggc    3540
tcattggtat cctctgccta ttggctttat cttctgtaca ctgaaaggaa atggctggtc    3600
cttagtcacc tggggtggga gtccctatct ctccagggat acttattcaa tcctttcttc    3660
tgggtatcaa aatgacaagc ttgtaagaaa ctgtcctctt tcggctttca ggaggtgatg    3720
tcgcatgaag agaatttggg gggggggact tactcagaac caaggaggga gaaattaaac    3780
agagagggaa atgaacagga gttagcccgg agcctgaagc accttgggga ttatgctggg    3840
ggtggaggga atccattgtc ctccctaggg agggcttgca gaacatgttc ttttctgtga    3900
tatttgtact ttccccagat tgcaaatcat ggtttgtaca ctgagattca gtctctggag    3960
gtaatatgcc ttttctagct tttccttgga caggactaag gggttgaggg ttgcctggag    4020
tcagagaaat ttgtgttaaa gaaggttgat atgacctgca ggtctagata cgtagataag    4080
tagcatggcg ggttaatcat taactacaag gaacccctag tgatggagtt ggccactccc    4140
tctctgcgcg ctcgctcgct cactgaggcc gggcgaccaa aggtcgcccg acgcccgggc    4200
tttgcccggg cggcctcagt gagcgagcga gcgcgcagag agggagtggc caa           4253
```

<210> SEQ ID NO 136
<211> LENGTH: 4331
<212> TYPE: DNA
<213> ORGANISM: Artificial Sequence
<220> FEATURE:
<223> OTHER INFORMATION: 032-HCR vector correction genome

<400> SEQUENCE: 136

```
gcttcaggag cagttgtgcg aatagctgga gaacaccagg ctggatttaa acccagatcg      60
ctcttacatt tgctctttac ctgctgtgct cagcgttcac gtgccctcta gctgtagttt     120
tctgaagtca gcgcacagca aggcagtgtg cttagaggtt aacagaaggg aaaacaacaa     180
caacaaaaat ctaaatgaga atcctgactg tttcagctgg gggtaagggg ggcggattat     240
tcatataatt gttataccag acggtcgcag gcttagtcca attgcagaga actcgcttcc     300
caggcttctg agagtcccgg aagtgcctaa acctgtctaa tcgacggggc ttgggtggcc     360
cgtcgctccc tggcttcttc cctttaccca gggcgggcag cgaagtggtg cctcctgcgt     420
cccccacacc ctccctcagc ccctcccctc cggcccgtcc tgggcaggtg acctggagca     480
tccggcaggc tgccctggcc tcctgcgtca ggacaacgcc cacgaggggc gttactgtgc     540
ggagatgcac cacgcaagag acacccttg taactctctt ctcctcccta gtgcgaggtt     600
aaaaccttca gccccacgtg ctgtttgcaa acctgcctgt acctgaggcc ctaaaaagcc     660
agagacctca ctcccgggga gccagcatgt ccactgcgt cctggaaaac ccaggcttgg     720
gcaggaaact ctctgacttt ggacaggtga gccacggcag cctgagctgc tcagttaggg     780
gaatttgggc ctcagagaa agagatctga agactgctgg tgcttcctgg tttcataagc     840
tcagtaagaa gtctgaattc gttggaagct gatgagaata tccaggaagt caacagacaa     900
atgtcctcaa caattgtttc taagtaggag aacatctgtc ctcggtggct ttcacaggaa     960
aagcttctga cctcttctct tcctcccaca gggcggtacc agatctggca gcggagaggg    1020
cagaggaagt cttctaacat gcggtgacgt ggaggagaat cccggcccta ggggtacctc    1080
caccgctgtg ctggagaacc ctgggctggg gaggaaactg tcagacttcg ggcaggtaag    1140
ttttatggaa tgtgaatcat aattcaattt ttcaacatgc gttaggaggg acatttcaaa    1200
ctcttttta ccctagactt tcctaccatc acccagagta tccagccagg aggggagggg    1260
ctagagacac cagaagttta gcagggagga gggcgtaggg attcggggaa tgaagggatg    1320
ggattcagac tagggccagg acccagggat ggagagaaaa agatgagagt ggtttggggg    1380
cttggtgact tagagaacag agctgcaggc tcagaggcac acaggagttt ctgggctggc    1440
ccggcccct tccaacccct cattatggaa tccagcagct gtttgtgtgc tgcctctgaa    1500
gtccacactg aacaaacttc agcctactca tgtcccatat aagggaaatt atggaatcag    1560
caaacagcaa acacacagcc ctccctgcct gctgaccttg gacctggggc agaggtcaga    1620
gacctccttg gctctatgcc acctccaaca tccactcgac cccttggaat ttcggtggag    1680
aggagcagag gttgtcctgg cgtggtttag gtagtgtgag agggctgacc atgccttctt    1740
ctttttccta caggaaactt catacattga ggataactgt aaccagaatg gcgccatctc    1800
tctgatcttc agcctgaagg aggaagtggg cgccctggca aaggtgctgc gcctgtttga    1860
ggagaacgac gtgaatctga cccacatcga gtcccggcct tctagactga agaaggacga    1920
gtacgagttc tttacccacc tggataagcg gtccctgcca gccctgacaa acatcatcaa    1980
gatcctgagg cacgacatcg gagcaaccgt gcacagctg tctcgggaca agaagaagga    2040
taccgtgccc tggttccctc ggacaatcca ggagctggat agatttgcca accagatcct    2100
gtcttacgga gcagagctgg acgcagatca ccctggcttc aaggaccag tgtatcgggc    2160
ccggagaaag cagtttgccg atatcgccta caattatagg cacggacagc caatccctcg    2220
```

```
cgtggagtat atggaggagg agaagaagac ctggggcaca gtgttcaaga ccctgaagag    2280
cctgtacaag acacacgcct gctacgagta taaccacatc ttccccctgc tggagaagta    2340
ttgtggcttt cacgaggaca atatccctca gctggaggac gtgagccagt tcctgcagac    2400
ctgcacaggc tttaggctga ggccagtggc aggactgctg agctcccggg acttcctggg    2460
aggactggcc ttcagagtgt tcactgcac ccagtacatc aggcacggct ccaagccaat     2520
gtatacacca gagcccgaca tctgtcacga gctgctgggc cacgtgcccc tgtttagcga    2580
tagatccttc gcccagtttt cccaggagat cggactggca tctctgggag cacctgacga    2640
gtacatcgag aagctggcca ccatctattg gttcacagtg gagtttggcc tgtgcaagca    2700
gggcgatagc atcaaggcct acggagcagg actgctgtct agcttcggcg agctgcagta    2760
ttgtctgtcc gagaagccaa agctgctgcc cctggagctg gagaagaccg ccatccagaa    2820
ctacaccgtg acagagttcc agcccctgta ctatgtggcc gagtctttta acgatgccaa    2880
ggagaaggtg agaaatttcg ccgccacaat ccctaggccc ttcagcgtgc ggtacgaccc    2940
ttatacccag aggatcgagg tgctggataa tacacagcag ctgaagatcc tggctgactc    3000
aatcaatagc gaaatcggaa tcctgtgctc cgccctgcag aaaatcaaag gtaagcctat    3060
ccctaacccct ctcctcggtc tcgattctac gtgatcttgt ggaaaggacg aaacaccggg   3120
gaattcaagg cctctcgagc ctctagaatc cccgagacgt ttcgtctcgg gatcactata    3180
gtgagtcgta ttacgtacac agtgcagggg aaagaatagt agagatccag acatgataag    3240
atacattgat gagtttggac aaaccacaac tagaatgcag tgaaaaaat gctttatttg     3300
tgaaatttgt gatgctattg ctttatttgt aaccattata agctgcaata acaagttaa     3360
caacaacaat tgcattcatt ttatgtttca ggttcagggg gaggtgtggg aggttttta     3420
actgggatgg gatgtggaat ccttctagat ttcttttgta atatttataa agtgctctca    3480
gcaaggtatc aaaatggcaa aattgtgagt aactatcctc ctttcatttt gggaagaaga    3540
tgaggcatga agagaattca gacagaaact tactcagacc aggggaggca gaaactaagc    3600
agagaggaaa atgaccaaga gttagccctg ggcatggaat gtgaaagaac cctaaacgtg    3660
acttggaaat aatgcccaag gtatattcca ttctccggga tttgttggca ttttcttgag    3720
gtgaagaatt gcagaataca ttctttaatg tgacctacat atttacccat gggaggaagt    3780
ctgctcctgg actcttgaga ttcagtcata agcccaggc cagggaaata atgtaagtct      3840
gcaggcccct gtcatcagta ggattaggga gaagagttct cagtagaaaa cagggaggct    3900
ggagagaaaa gaatggttaa tgttaacgtt aatataacta gaaagactgc agaacttagg    3960
actgattttt atttgaatcc ttaaaaaaaa aatttcttat gaaaatagta catggctctt    4020
aggagacaga acttattgta cagaggaaca gcgtgagagt cagagtgatc ccagaacagg    4080
tcctggctcc atcctgcaca tagttttggt gctgctggca atacggtccc cacaactgtg    4140
ggaaggggtt aggggcaggg atctcatcag gaaagcatag gggtttaaag ttctttatag    4200
agcacttaga agattgagaa tccacaaatt atattaataa caaacaaagt agtgtcgtgt    4260
tatatagtaa atgtgaattt gcagacacat ttagggaaaa gttataatta aaaaaatagg    4320
ctgtatatat a                                                         4331
```

<210> SEQ ID NO 137
<211> LENGTH: 4737
<212> TYPE: DNA
<213> ORGANISM: Artificial Sequence
<220> FEATURE:
<223> OTHER INFORMATION: 032-HCR vector correction genome (+ ITRs)

<400> SEQUENCE: 137

```
ttggccactc cctctctgcg cgctcgctcg ctcactgagg ccgggcgacc aaaggtcgcc      60
cgacgcccgg gctttgcccg ggcggcctca gtgagcgagc gagcgcgcag agagggagtg     120
gccaactcca tcactagggg ttcctggagg ggtggagtcg tgacgtgaat tacgtcatag     180
ggttagggag gtcctgcata tgcggccgct tcaggagcag ttgtgcgaat agctggagaa     240
caccaggctg gatttaaacc cagatcgctc ttacatttgc tctttacctg ctgtgctcag     300
cgttcacgtg ccctctagct gtagttttct gaagtcagcg cacagcaagg cagtgtgctt     360
agaggttaac agaagggaaa acaacaacaa caaaaatcta aatgagaatc ctgactgttt     420
cagctggggg taagggggc ggattattca tataattgtt ataccagacg gtcgcaggct     480
tagtccaatt gcagagaact cgcttcccag gcttctgaga gtcccggaag tgcctaaacc     540
tgtctaatcg acgggcttg ggtggcccgt cgctccctgg cttcttccct ttacccaggg     600
cgggcagcga agtggtgcct cctgcgtccc ccacaccctc cctcagcccc tccctccgg     660
cccgtcctgg gcaggtgacc tggagcatcc ggcaggctgc cctggcctcc tgcgtcagga     720
caacgcccac gagggggcgtt actgtgcgga gatgcaccac gcaagagaca ccctttgtaa     780
ctctcttctc ctccctagtg cgaggttaaa accttcagcc ccacgtgctg tttgcaaacc     840
tgcctgtacc tgaggcccta aaaagccaga gacctcactc ccgggagcc agcatgtcca     900
ctgcggtcct ggaaaaccca ggcttgggca ggaaactctc tgactttgga caggtgagcc     960
acggcagcct gagctgctca gttaggggaa tttgggcctc cagagaaaga gatctgaaga    1020
ctgctggtgc ttcctggttt cataagctca gtaagaagtc tgaattcgtt ggaagctgat    1080
gagaatatcc aggaagtcaa cagacaaatg tcctcaacaa ttgtttctaa gtaggagaac    1140
atctgtcctc ggtggctttc acaggaaaag cttctgacct cttctcttcc tcccacaggg    1200
cggtaccaga tctggcagcg gagagggcag aggaagtctt ctaacatgcg gtgacgtgga    1260
ggagaatccc ggccctaggg gtacctccac cgctgtgctg gagaaccctg ggctggggag    1320
gaaactgtca gacttcgggc aggtaagttt tatggaatgt gaatcataat tcaatttttc    1380
aacatgcgtt aggagggaca tttcaaactc tttttttaccc tagactttcc taccatcacc    1440
cagagtatcc agccaggagg ggaggggcta gagacaccag aagtttagca gggaggaggg    1500
cgtagggatt cggggaatga agggatggga ttcagactag ggccaggacc cagggatgga    1560
gagaaagaga tgagagtggt ttgggggctt ggtgacttag agaacagagc tgcaggctca    1620
gaggcacaca ggagtttctg ggctggcccg gccccttcc aaccccctcat tatggaatcc    1680
agcagctgtt tgtgtgctgc ctctgaagtc cacactgaac aaacttcagc ctactcatgt    1740
cccatataag ggaaattatg gaatcagcaa acagcaaaca cacagccctc cctgcctgct    1800
gaccttggac ctggggcaga ggtcagagac ctccttggct ctatgccacc tccaacatcc    1860
actcgacccc ttggaatttc ggtggagagg agcagaggtt gtcctggcgt ggtttaggta    1920
gtgtgagagg gctgaccatg ccttcttctt tttcctacag gaaacttcat acattgagga    1980
taactgtaac cagaatggcg ccatctctct gatcttcagc ctgaaggagg aagtgggcgc    2040
cctggcaaag gtgctgcgcc tgtttgagga gaacgacgtg aatctgaccc acatcgagtc    2100
ccggccttct agactgaaga aggacgagta cgagttcttt acccacctgg ataagcggtc    2160
cctgccagcc ctgacaaaca tcatcaagat cctgaggcac gacatcggag caaccgtgca    2220
cgagctgtct cgggacaaga gaaggatac cgtgccctgg ttccctcgga caatccagga    2280
```

```
gctggataga tttgccaacc agatcctgtc ttacggagca gagctggacg cagatcaccc    2340
tggcttcaag gacccagtgt atcgggcccg gagaaagcag tttgccgata tcgcctacaa    2400
ttataggcac ggacagccaa tccctcgcgt ggagtatatg gaggaggaga agaagacctg    2460
gggcacagtg ttcaagaccc tgaagagcct gtacaagaca cacgcctgct acagtataa     2520 ccacatcttc ccctgctgg agaagtattg tggcttttcac gaggacaata tccctcagct    2580
ggaggacgtg agccagttcc tgcagacctg cacaggcttt aggctgaggc agtggcagg    2640 actgctgagc tcccgggact tcctgggagg actggccttc agagtgtttc actgcaccca    2700
gtacatcagg cacggctcca agccaatgta tacaccagag cccgacatct gtcacgagct    2760
gctgggccac gtgcccctgt ttagcgatag atccttcgcc cagttttccc aggagatcgg    2820
actggcatct ctgggagcac ctgacgagta catcgagaag ctggccacca tctattggtt    2880
cacagtggag tttggcctgt gcaagcaggg cgatagcatc aaggcctacg gagcaggact    2940
gctgtctagc ttcggcgagc tgcagtattg tctgtccgag aagccaaagc tgctgcccct    3000
ggagctggag aagaccgcca tccagaacta caccgtgaca gagttccagc ccctgtacta    3060
tgtggccgag tcttttaacg atgccaagga gaaggtgaga aatttcgccg ccacaatccc    3120
taggcccttc agcgtgcggt acgacccctta tacccagaga tcgaggtgc tggataatac    3180 acagcagctg aagatcctgg ctgactcaat caatagcgaa atcggaatcc tgtgctccgc    3240
cctgcagaaa atcaaaggta agcctatccc taaccctctc ctcggtctcg attctacgtg    3300
atcttgtgga aggacgaaa caccggggaa ttcaaggcct ctcgagcctc tagaatcccc    3360
gagacgtttc gtctcgggat cactatagtg agtcgtatta cgtacacagt gcaggggaaa    3420
gaatagtaga gatccagaca tgataagata cattgatgag tttggacaaa ccacaactag    3480
aatgcagtga aaaaaatgct ttatttgtga aatttgtgat gctattgctt tatttgtaac    3540
cattataagc tgcaataaac aagttaacaa caacaattgc attcatttta tgtttcaggt    3600 tcaggggggag gtgtgggagg ttttttaact gggatgggat gtggaatcct tctagatttc    3660
ttttgtaata tttataaagt gctctcagca aggtatcaaa atggcaaaat tgtgagtaac    3720
tatcctcctt tcatttggg aagaagatga ggcatgaaga gaattcagac agaaacttac    3780
tcagaccagg ggaggcagaa actaagcaga gaggaaaatg accaagagtt agccctgggc    3840
atggaatgtg aaagaaccct aaacgtgact tggaaataat gcccaaggta tattccattc    3900
tccgggattt gttggcattt tcttgaggtg aagaattgca gaatacattc tttaatgtga    3960
cctacatatt tacccatggg aggaagtctg ctcctggact cttgagattc agtcataaag    4020
cccaggccag ggaaataatg taagtctgca ggcccctgtc atcagtagga ttagggagaa    4080
gagttctcag tagaaaacag ggaggctgga gagaaaagaa tggttaatgt taacgttaat    4140
ataactagaa agactgcaga acttaggact gattttatt tgaatcctta aaaaaaaat     4200 ttcttatgaa aatagtacat ggctcttagg agacagaact tattgtacag aggaacagcg    4260
tgagagtcag agtgatccca gaacaggtcc tggctccatc ctgcacatag ttttggtgct    4320
gctggcaata cggtccccac aactgtggga aggggttagg ggcagggatc tcatcaggaa    4380
agcatagggg tttaaagttc tttatagagc acttagaaga ttgagaatcc acaaattata    4440
ttaataacaa acaaagtagt gtcgtgttat atagtaaatg tgaatttgca gacacattta    4500
gggaaaagtt ataattaaaa aaataggctg tatatatacc tgcaggtcta gatacgtaga    4560
taagtagcat ggcgggttaa tcattaacta caaggaaccc ctagtgatgg agttggccac    4620
tccctctctg cgcgctcgct cgctcactga ggccgggcga ccaaaggtcg cccgacgccc    4680
```

```
gggctttgcc cgggcggcct cagtgagcga gcgagcgcgc agagagggag tggccaa     4737
```

<210> SEQ ID NO 138
<211> LENGTH: 1359
<212> TYPE: DNA
<213> ORGANISM: Artificial Sequence
<220> FEATURE:
<223> OTHER INFORMATION: 006-SD.3 vector PAH coding sequence

<400> SEQUENCE: 138

```
atgtccaccg ctgtgctgga gaaccctggg ctggggagga aactgtcaga cttcgggcag     60
gagacttcat acattgagga taactgtaac cagaatggcg ccatctctct gatcttcagc    120
ctgaaggagg aagtgggcgc cctggcaaag gtgctgcgcc tgtttgagga acgacgtg     180
aatctgaccc acatcgagtc ccggccttct agactgaaga aggacgagta cgagttcttt    240
acccacctgg ataagcggtc cctgccagcc ctgacaaaca tcatcaagat cctgaggcac    300
gacatcggag caaccgtgca cgagctgtct cgggacaaga gaaggatac cgtgccctgg    360
ttccctcgga caatccagga gctggataga tttgccaacc agatcctgtc ttacggagca    420
gagctggacg cagatcaccc tggcttcaag gacccagtgt atcgggcccg agaaaagcag    480
tttgccgata tcgcctacaa ttataggcac ggacagccaa tccctcgcgt ggagtatatg    540
gaggaggaga gaagacctg ggcacagtg ttcaagaccc tgaagagcct gtacaagaca    600
cacgcctgct acgagtataa ccacatcttc ccctgctgg agaagtattg tggctttcac    660
gaggacaata tcctcagct ggaggacgtg agccagttcc tgcagacctg cacaggcttt    720
aggctgaggc cagtggcagg actgctgagc tcccgggact tcctgggagg actggccttc    780
agagtgtttc actgcaccca gtacatcagg cacggctcca agccaatgta tacaccagag    840
cccgacatct gtcacgagct gctgggccac gtgcccctgt ttagcgatag atccttcgcc    900
cagttttccc aggagatcgg actggcatct ctgggagcac tgacgagta catcgagaag    960
ctggccacca tctattggtt cacagtggag tttggcctgt gcaagcaggg cgatagcatc   1020
aaggcctacg agcaggact gctgtctagc ttcggcgagc tgcagtattg tctgtccgag   1080
aagccaaagc tgctgcccct ggagctggag aagaccgcca tccagaacta caccgtgaca   1140
gagttccagc cctgtacta tgtggccgag tcttttaacg atgccaagga aaggtgaga    1200
aatttcgccg ccacaatccc taggcccttc agtgtgcgtt acgaccctta tcccagagg    1260
atcgaggtgc tggataatac acagcagctg aagatcctgg ctgactcaat caatagcgaa   1320
atcggaatcc tgtgctccgc cctgcagaaa atcaaatga                           1359
```

<210> SEQ ID NO 139
<211> LENGTH: 1353
<212> TYPE: DNA
<213> ORGANISM: Artificial Sequence
<220> FEATURE:
<223> OTHER INFORMATION: 032-SD.3 vector PAH coding sequence

<400> SEQUENCE: 139

```
tccaccgctg tgctggagaa ccctgggctg ggaggaaac tgtcagactt cgggcaggag     60
acttcataca ttgaggataa ctgtaaccag aatggcgcca tctctctgat cttcagcctg    120
aaggaggaag tgggcgccct ggcaaaggtg ctgcgcctgt ttgaggagaa cgacgtgaat    180
ctgacccaca tcgagtcccg gccttctaga ctgaagaagg acgagtacga gttctttacc    240
cacctggata agcggtccct gccagccctg acaaacatca tcaagatcct gaggcacgac    300
```

```
atcggagcaa ccgtgcacga gctgtctcgg gacaagaaga aggataccgt gccctggttc    360
cctcggacaa tccaggagct ggatagattt gccaaccaga tcctgtctta cggagcagag    420
ctggacgcag atcaccctgg cttcaaggac ccagtgtatc gggcccggag aaagcagttt    480
gccgatatcg cctacaatta taggcacgga cagccaatcc ctcgcgtgga gtatatggag    540
gaggagaaga agacctgggg cacagtgttc aagaccctga gagcctgta caagacacac     600 gcctgctacg agtataacca catcttcccc ctgctggaga agtattgtgg ctttcacgag    660
gacaatatcc ctcagctgga ggacgtgagc cagttcctgc agacctgcac aggctttagg    720
ctgaggccag tggcaggact gctgagctcc cgggacttcc tgggaggact ggccttcaga    780
gtgtttcact gcacccagta catcaggcac ggctccaagc caatgtatac accagagccc    840
gacatctgtc acgagctgct gggccacgtg cccctgttta gcgatagatc cttcgcccag    900
ttttcccagg agatcggact ggcatctctg ggagcacctg acgagtacat cgagaagctg    960
gccaccatct attggttcac agtggagttt ggcctgtgca agcagggcga tagcatcaag   1020
gcctacggag caggactgct gtctagcttc ggcgagctgc agtattgtct gtccgagaag   1080
ccaaagctgc tgccccctgga gctggagaag accgccatcc agaactacac cgtgacagag   1140
ttccagcccc tgtactatgt ggccgagtct tttaacgatg ccaaggagaa ggtgagaaat   1200
ttcgccgcca caatccctag gcccttcagt gtgcgttacg accttatac ccagaggatc    1260 gaggtgctgg ataatacaca gcagctgaag atcctggctg actcaatcaa tagcgaaatc   1320
ggaatcctgt gctccgccct gcagaaaatc aaa                                 1353

<210> SEQ ID NO 140
<211> LENGTH: 37
<212> TYPE: DNA
<213> ORGANISM: Artificial Sequence
<220> FEATURE:
<223> OTHER INFORMATION: 37 bp additional 3' ITR sequence from wtAAV2

<400> SEQUENCE: 140
gtagataagt agcatggcgg gttaatcatt aactaca                              37

<210> SEQ ID NO 141
<211> LENGTH: 180
<212> TYPE: DNA
<213> ORGANISM: Artificial Sequence
<220> FEATURE:
<223> OTHER INFORMATION: 3' ITR with additional 37 bp sequence

<400> SEQUENCE: 141
gtagataagt agcatggcgg gttaatcatt aactacaagg aaccccctagt gatggagttg    60 gccactccct ctctgcgcgc tcgctcgctc actgaggccg ggcgaccaaa ggtcgcccga    120
cgcccgggct ttgcccgggc ggcctcagtg agcgagcgag cgcgcagaga gggagtggcc   180

<210> SEQ ID NO 142
<211> LENGTH: 800
<212> TYPE: DNA
<213> ORGANISM: Mus musculus

<400> SEQUENCE: 142
agcattagct tccatttatg cagtgtaaat ggtgagaaca gccccgactg aatacccaga     60
gcatcatctc gtctgtgtca ttcatgcaca taacatatct cagcgaggtg gcccttctgt    120
cctctttgca gagacccagc caccatacta gtacctagag aactggctgg atttcagccc    180
cgatacctcc gggcttttgc tcatgttcgc ctcataggt catctgggtg gttgcctaag    240
```

```
gaaaagtatg tcatggagac taacttgctt ggcattgaat aaaaggtgag ttgagagtgg      300
agcgtgttta aattgcaatc ctgcctctat ttctgtgctt gcagggaaca gtcatcctta      360
attgctatcc tccatcatca tcatgattat ttctggtttt tctctggttg cggagaatcc      420
atactccagg tattccaatg tctcagcatt gccaggcctg tctgagcgtc aggatgtagg      480
tagtctgggc tctctgcctt ctattcttgt ccaggatact ctgccaaaag aatcatgttg      540
tggctgccac cctcccaca aagcctcccg cttgggtcag tccaggactg gagttgggta      600
tggactgttc atgtctatcc actgctacgt cagggcaaca cccactgaga gtgaccttgt      660
agactgcagt gggagacacc cttcaaaacc tctcatctcc tgtcctgaga gccaggttaa      720
aaccatcagc cccgcatcct gagtgcaaac ttttcctaac cctgctgcta agctagacac      780
ctcacttact gagagccagc                                                  800
```

<210> SEQ ID NO 143
<211> LENGTH: 1475
<212> TYPE: DNA
<213> ORGANISM: Artificial Sequence
<220> FEATURE:
<223> OTHER INFORMATION: 006-HBB1 vector PAH coding sequence

<400> SEQUENCE: 143

```
atgtccaccg ctgtgctgga gaaccctggg ctggggagga aactgtcaga cttcgggcag       60
gagacttcat acattgagga taactgtaac cagaatggcg ccatctctct gatcttcagc      120
ctgaaggagg aagtgggcgc cctggcaaag gtgctgcgcc tgtttgagga gaacgacgtg      180
aatctgaccc acatcgagtc ccggccttct agactgaaga aggacgagta cgagttcttt      240
acccacctgg ataagcggtc cctgccagcc ctgacaaaca tcatcaagat cctgaggcac      300
gacatcggag caaccgtgca cgagctgtct cgggacaaga gaaggatac cgtgccctgg      360 ttccctcgga caatccagga gctggataga tttgccaacc agatcctgtc ttacggagca      420
gagctggacg cagatcaccc tggcttcaag gacccagtgt atcgggcccg agaaaagcag      480
tttgccgata tcgcctacaa ttataggcac ggacagccaa tccctcgcgt ggagtatatg      540
gaggaggaga agaagacctg ggcacagtg ttcaagaccc tgaagagcct gtacaagaca      600
cacgcctgct acgagtataa ccacatcttc cccctgctgg agaagtattg tggctttcac      660
gaggacaata tccctcagct ggaggacgtg agccagttcc tgcagacctg cacaggcttt      720
aggctgaggc cagtggcagg actgctgagc tcccgggact tcctgggagg actggccttc      780
agagtgtttc actgcaccca gtacatcagg cacggctcca gccaatgta tacaccagag      840 cccgacatct gtcacgagct gctgggccac gtgcccctgt ttagcgatag atccttcgcc      900 cagtttccc aggttggtat ccaggttaca aggcagctca aagaagaag ttgggtgctt      960 ggagacagag gtctgctttc cagcagacac taactttcag tgtcccctgt ctatgtttcc     1020 cttttttagga gatcggactg gcatctctgg agcacctga cgagtacatc gagaagctgg     1080
ccaccatcta ttggttcaca gtggagtttg gcctgtgcaa gcagggcgat agcatcaagg     1140 cctacgagc aggactgctg tctagcttcg gcgagctgca gtattgtctg tccgagaagc     1200
caaagctgct gcccctggag ctggagaaga ccgccatcca gaactacacc gtgacagagt     1260
tccagcccct gtactatgtg gccgagtctt taacgatgc aaggagaag gtgagaaatt     1320 tcgccgccac aatccctagg cccttcagcg tgcggtacga cccttatacc cagaggatcg     1380
aggtgctgga taatacacag cagctgaaga tcctggctga ctcaatcaat agcgaaatcg     1440
```

| | |
|---|---:|
| gaatcctgtg ctccgccctg cagaaaatca aatga | 1475 |

<210> SEQ ID NO 144
<211> LENGTH: 800
<212> TYPE: DNA
<213> ORGANISM: Mus musculus

<400> SEQUENCE: 144

| | |
|---|---:|
| gcagctgttg tcctggagaa cggagtcctg agcagaaaac tctcagactt tgggcaggta | 60 |
| agcctgttgg gcttccactg ctaggagaga attggttccc cacatgtgaa agcagtctgg | 120 |
| gaaatgctgg tatttccagt ctcctaaggc tactaagaaa tatgacttta tttagaggcg | 180 |
| agaaaaatgc ccaggaagtc aactgatgag actagtctta acaagttgag gatacagaaa | 240 |
| gttggggatc tgagctgcta ccaacatctg tgtgtctttg ggtggctcat ggtatcctc | 300 |
| tgcctattgg ctttatcttc tgtacactga aggaaatgg ctggtcctta gtcacctggg | 360 |
| gtgggagtcc ctatctctcc aggatactt attcaatcct ttcttctggg tatcaaaatg | 420 |
| acaagcttgt aagaaactgt cctctttcgg ctttcaggag gtgatgtcgc atgaagagaa | 480 |
| tttgggggg gggacttact cagaaccaag gagggagaaa ttaaacagag agggaaatga | 540 |
| acaggagtta gcccggagcc tgaagcacct tggggattat gctgggggtg gagggaatcc | 600 |
| attgtcctcc ctaggagggg cttgcagaac atgttctttt ctgtgatatt tgtactttcc | 660 |
| ccagattgca aatcatggtt tgtacactga gattcagtct ctgaggtaa tatgcctttt | 720 |
| ctagcttttc cttggacagg actaaggggt tgagggttgc ctggagtcag agaaatttgt | 780 |
| gttaaagaag gttgatatga | 800 |

<210> SEQ ID NO 145
<211> LENGTH: 3343
<212> TYPE: DNA
<213> ORGANISM: Artificial Sequence
<220> FEATURE:
<223> OTHER INFORMATION: 006-HBB1 vector correction genome

<400> SEQUENCE: 145

| | |
|---|---:|
| agcattagct tccatttatg cagtgtaaat ggtgagaaca gccccgactg aatacccaga | 60 |
| gcatcatctc gtctgtgtca ttcatgcaca taacatatct cagcgaggtg gcccttctgt | 120 |
| cctctttgca gagacccagc caccatacta gtacctagag aactggctgg atttcagccc | 180 |
| cgatacctcc gggcttttgc tcatgttcgc ctcatagggt catctgggtg gttgcctaag | 240 |
| gaaaagtatg tcatggagac taacttgctt ggcattgaat aaaaggtgag ttgagagtgg | 300 |
| agcgtgttta aattgcaatc ctgcctctat ttctgtgctt gcagggaaca gtcatcctta | 360 |
| attgctatcc tccatcatca tcatgattat ttctggtttt tctctggttg cggagaatcc | 420 |
| atactccagg tattccaatg tctcagcatt gccaggcctg tctgagcgtc aggatgtagg | 480 |
| tagtctgggc tctctgcctt ctattcttgt ccaggatact ctgccaaaag aatcatgttg | 540 |
| tggctgccac ccctcccaca aagcctcccg cttgggtcag tccaggactg gagttgggta | 600 |
| tggactgttc atgtctatcc actgctacgt caggcaaca cccactgaga gtgaccttgt | 660 |
| agactgcagt gggagacacc cttcaaaacc tctcatctcc tgtcctgaga gccaggttaa | 720 |
| aaccatcagc cccgcatcct gagtgcaaac ttttcctaac cctgctgcta agctagacac | 780 |
| ctcacttact gagagccagc atgtccaccg ctgtgctgga gaaccctggg ctggggagga | 840 |
| aactgtcaga cttcgggcag gagacttcat acattgagga taactgtaac cagaatggcg | 900 |
| ccatctctct gatcttcagc ctgaaggagg aagtgggcgc cctggcaaag gtgctgcgcc | 960 |

```
tgtttgagga gaacgacgtg aatctgaccc acatcgagtc ccggccttct agactgaaga   1020
aggacgagta cgagttcttt acccacctgg ataagcggtc cctgccagcc ctgacaaaca   1080
tcatcaagat cctgaggcac gacatcggag caaccgtgca cgagctgtct cgggacaaga   1140
agaaggatac cgtgccctgg ttccctcgga caatccagga gctggataga tttgccaacc   1200
agatcctgtc ttacggagca gagctggacg cagatcaccc tggcttcaag acccagtgt   1260 atcgggcccg gagaaagcag tttgccgata tcgcctacaa ttataggcac ggacagccaa   1320
tccctcgcgt ggagtatatg gaggaggaga agaagacctg ggcacagtg ttcaagaccc    1380 tgaagagcct gtacaagaca cacgcctgct acgagtataa ccacatcttc ccctgctgg    1440 agaagtattg tggcttcac gaggacaata tccctcagct ggaggacgtg agccagttcc    1500
tgcagacctg cacaggcttt aggctgaggc cagtggcagg actgctgagc tcccgggact   1560
tcctgggagg actggccttc agagtgttc actgcaccca gtacatcagg cacggctcca   1620
agccaatgta taccagagag cccgacatct gtcacgagct gctgggccac gtgcccctgt   1680
ttagcgatag atccttcgcc cagttttccc aggttggtat ccaggttaca aggcagctca   1740
caagaagaag ttgggtgctt ggagacagag gtctgctttc cagcagacac taactttcag   1800
tgtcccctgt ctatgtttcc ctttttagga gatcggactg gcatctctgg gagcacctga   1860
cgagtacatc gagaagctgg ccaccatcta ttggttcaca gtggagtttg gcctgtgcaa   1920
gcagggcgat agcatcaagg cctacggagc aggactgctg tctagcttcg gcgagctgca   1980
gtattgtctg tccagaaagc caaagctgct gcccctggag ctggagaaga ccgccatcca   2040
gaactacacc gtgacagagt ccagccccct gtactatgtg gccgagtctt ttaacgatgc   2100
caaggagaag gtgagaaatt cgccgccac aatccctagg cccttcagcg tgcggtacga    2160
cccttatacc cagaggatcg aggtgctgga taatacacag cagctgaaga tcctggctga   2220
ctcaatcaat agcgaaatcg aatcctgtgt ctccgccctg cagaaaatca atgagaatt    2280 caaggcctct cgagcctcta gaactatagt gagtcgtatt acgtagatcc agacatgata   2340
agatacattg atgagtttgg acaaaccaca actagaatgc agtgaaaaaa atgctttatt   2400
tgtgaaattt gtgatgctat tgctttattt gtaaccatta taagctgcaa taaacaagtt   2460
aacaacaaca attgcattca ttttatgttt caggttcagg ggaggtgtg ggaggttttt    2520 taagctttac gtacgatcgt cgagcagctg ttgtcctgga aacggagtc ctgagcagaa    2580 aactctcaga cttggggcag gtaagcctgt tgggcttcca ctgctaggag agaattggtt   2640
ccccacatgt gaaagcagtc tgggaaatgc tggtatttcc agtctcctaa ggctactaag   2700
aaatatgact ttatttagag gcgagaaaaa tgcccaggaa gtcaactgat gagactagtc   2760
ttaacaagtt gaggatacag aaagttgggg atctgagctg ctaccaacat ctgtgtgtct   2820
ttgggtggct cattggtatc ctctgcctat tggctttatc ttctgtacac tgaaaggaaa   2880
tggctggtcc ttagtcacct gggtgggag tccctatctc tccagggata cttattcaat   2940
cctttcttct gggtatcaaa atgacaagct tgtaagaaac tgtcctcttt cggctttcag   3000
gaggtgatgt cgcatgaaga gaatttgggg gggggactt actcagaacc aaggagggag    3060
aaattaaaca gagagggaaa tgaacaggag ttagcccgga gcctgaagca ccttggggat   3120
tatgctgggg gtggagggaa tccattgtcc tccctaggga gggcttgcag aacatgttct   3180
tttctgtgat atttgtactt tccccagatt gcaaatcatg gtttgtacac tgagattcag   3240
tctctggagg taatatgcct tttctagctt ttccttggac aggactaagg ggttgagggt   3300
```

| | |
|---|---|
| tgcctggagt cagagaaatt tgtgttaaag aaggttgata tga | 3343 |

<210> SEQ ID NO 146
<211> LENGTH: 3751
<212> TYPE: DNA
<213> ORGANISM: Artificial Sequence
<220> FEATURE:
<223> OTHER INFORMATION: 006-HBB1 vector correction genome (+ ITRs)

<400> SEQUENCE: 146

| | |
|---|---|
| ttggccactc cctctctgcg cgctcgctcg ctcactgagg ccgggcgacc aaaggtcgcc | 60 |
| cgacgcccgg gctttgcccg ggcggcctca gtgagcgagc gagcgcgcag agagggagtg | 120 |
| gccaactcca tcactagggg ttcctggagg ggtggagtcg tgacgtgaat tacgtcatag | 180 |
| ggttagggag gtcctgcata tgcggccgca gcattagctt ccatttatgc agtgtaaatg | 240 |
| gtgagaacag ccccgactga atacccagag catcatctcg tctgtgtcat tcatgcacat | 300 |
| aacatatctc agcgaggtgg cccttctgtc ctctttgcag agacccagcc accatactag | 360 |
| tacctagaga actggctgga tttcagcccc gatacctccg ggcttttgct catgttcgcc | 420 |
| tcatagggtc atctgggtgg ttgcctaagg aaaagtatgt catggagact aacttgcttg | 480 |
| gcattgaata aaaggtgagt tgagagtgga gcgtgtttaa attgcaatcc tgcctctatt | 540 |
| tctgtgcttg cagggaacag tcatccttaa ttgctatcct ccatcatcat catgattatt | 600 |
| tctgtttttt ctctggttgc ggagaatcca tactccaggt attccaatgt ctcagcattg | 660 |
| ccaggcctgt ctgagcgtca ggatgtaggt agtctgggct ctctgccttc tattcttgtc | 720 |
| caggatactc tgccaaaaga atcatgttgt ggctgccacc cctcccacaa agcctcccgc | 780 |
| ttgggtcagt ccaggactgg agttgggtat ggactgttca tgtctatcca ctgctacgtc | 840 |
| agggcaacac ccactgagag tgaccttgta gactgcagtg ggagacaccc ttcaaaacct | 900 |
| ctcatctcct gtcctgagag ccaggttaaa accatcagcc ccgcatcctg agtgcaaact | 960 |
| tttcctaacc ctgctgctaa gctagacacc tcacttactg agagccagca tgtccaccgc | 1020 |
| tgtgctggag aaccctgggc tggggaggaa actgtcagac ttcgggcagg agacttcata | 1080 |
| cattgaggat aactgtaacc agaatggcgc catctctctg atcttcagcc tgaaggagga | 1140 |
| agtgggcgcc ctggcaaagg tgctgcgcct gtttgaggag aacgacgtga atctgaccca | 1200 |
| catcgagtcc cggccttcta gactgaagaa ggacgagtac gagttctttt cccacctgga | 1260 |
| taagcggtcc ctgccagccc tgacaaacat catcaagatc ctgaggcacg acatcggagc | 1320 |
| aaccgtgcac gagctgtctc gggacaagaa gaaggatacc gtgccctggt tccctcggac | 1380 |
| aatccaggag ctggatagat tgccaaccca gatcctgtct tacggagcag agctggacgc | 1440 |
| agatcaccct ggcttcaagg acccagtgta tcgggcccgg agaaagcagt ttgccgatat | 1500 |
| cgcctacaat tataggcacg acagccaatc cctcgcgtg gagtatatgg aggaggagaa | 1560 |
| gaagacctgg ggcacagtgt tcaagaccct gaagagcctg tacaagacac acgcctgcta | 1620 |
| cgagtataac cacatcttcc ccctgctgga gaagtattgt ggctttcacg aggacaatat | 1680 |
| ccctcagctg gaggacgtga gccagttcct gcagacctgc acaggcttta ggctgaggcc | 1740 |
| agtggcagga ctgctgagct cccgggactt cctgggagga ctggccttca gagtgtttca | 1800 |
| ctgcacccag tacatcaggc acggctccaa gccaatgtat acaccagagc cgacatctg | 1860 |
| tcacgagctg ctgggccacg tgccctgtt tagcgataga tccttcgccc agttttccca | 1920 |
| ggttggtatc caggttacaa ggcagctcac aagaagaagt tgggtgcttg agacagagg | 1980 |
| tctgcttttcc agcagacact aactttcagt gtccctgtc tatgttccc ttttaggag | 2040 |

| | |
|---|---|
| atcggactgg catctctggg agcacctgac gagtacatcg agaagctggc caccatctat | 2100 |
| tggttcacag tggagtttgg cctgtgcaag cagggcgata gcatcaaggc ctacggagca | 2160 |
| ggactgctgt ctagcttcgg cgagctgcag tattgtctgt ccgagaagcc aaagctgctg | 2220 |
| cccctggagc tggagaagac cgccatccag aactaccg tgacagagtt ccagcccctg | 2280 |
| tactatgtgg ccgagtcttt taacgatgcc aaggagaagg tgagaaattt cgccgccaca | 2340 |
| atccctaggc ccttcagcgt gcggtacgac ccttatccc agaggatcga ggtgctggat | 2400 |
| aatacacagc agctgaagat cctggctgac tcaatcaata gcgaaatcgg aatcctgtgc | 2460 |
| tccgccctgc agaaaatcaa atgagaattc aaggcctctc gagcctctag aactatagtg | 2520 |
| agtcgtatta cgtagatcca gacatgataa gatacattga tgagtttgga caaaccacaa | 2580 |
| ctagaatgca gtgaaaaaaa tgctttattt gtgaaatttg tgatgctatt gctttatttg | 2640 |
| taaccattat aagctgcaat aaacaagtta acaacaacaa ttgcattcat tttatgtttc | 2700 |
| aggttcaggg ggaggtgtgg gaggtttttt aagctttacg tacgatcgtc gagcagctgt | 2760 |
| tgtcctggag aacggagtcc tgagcagaaa actctcagac tttgggcagg taagcctgtt | 2820 |
| gggcttccac tgctaggaga gaattggttc cccacatgtg aaagcagtct gggaaatgct | 2880 |
| ggtatttcca gtctcctaag gctactaaga aatatgactt tatttagagg cgagaaaaat | 2940 |
| gcccaggaag tcaactgatg agactagtct taacaagttg aggatacaga agttggggga | 3000 |
| tctgagctgc taccaacatc tgtgtgtctt tgggtggctc attggtatcc tctgcctatt | 3060 |
| ggctttatct tctgtacact gaaaggaaat ggctggtcct tagtcacctg gggtgggagt | 3120 |
| ccctatctct ccagggatac ttattcaatc ctttcttctg ggtatcaaaa tgacaagctt | 3180 |
| gtaagaaact gtcctctttc ggctttcagg aggtgatgtc gcatgaagag aatttggggg | 3240 |
| gggggactta ctcagaacca aggagggaga aattaaacag agagggaaat gaacaggagt | 3300 |
| tagcccggag cctgaagcac cttgggatt atgctggggg tggagggaat ccattgtcct | 3360 |
| ccctagggag ggcttgcaga acatgttctt ttctgtgata tttgtacttt ccccagattg | 3420 |
| caaatcatgg tttgtacact gagattcagt ctctggaggt aatatgcctt ttctagcttt | 3480 |
| tccttggaca ggactaaggg gttgagggtt gcctggagtc agagaaattt gtgttaaaga | 3540 |
| aggttgatat gacctgcagg tctagatacg tagataagta gcatggcggg ttaatcatta | 3600 |
| actacaagga accctagtg atggagttgg ccactccctc tctgcgcgct cgctcgctca | 3660 |
| ctgaggccgg gcgaccaaag gtcgcccgac gcccgggctt gcccgggcg gcctcagtga | 3720 |
| gcgagcgagc gcgcagagag ggagtggcca a | 3751 |

<210> SEQ ID NO 147
<211> LENGTH: 1607
<212> TYPE: DNA
<213> ORGANISM: Artificial Sequence
<220> FEATURE:
<223> OTHER INFORMATION: 006 vector editing element

<400> SEQUENCE: 147

| | |
|---|---|
| atgtccaccg ctgtgctgga gaaccctggg ctggggagga aactgtcaga cttcgggcag | 60 |
| gagacttcat acattgagga taactgtaac cagaatggcg ccatctctct gatcttcagc | 120 |
| ctgaaggagg aagtgggcgc cctggcaaag gtgctgcgcc tgtttgagga gaacgacgtg | 180 |
| aatctgaccc acatcgagtc ccggccttct agactgaaga aggacgagta cgagttcttt | 240 |
| acccacctgg ataagcggtc cctgccagcc ctgacaaaca tcatcaagat cctgaggcac | 300 |

```
gacatcggag caaccgtgca cgagctgtct cgggacaaga agaaggatac cgtgccctgg    360
ttccctcgga caatccagga gctggataga tttgccaacc agatcctgtc ttacggagca    420
gagctggacg cagatcaccc tggcttcaag acccagtgt atcgggcccg agaaagcag     480 tttgccgata tcgcctacaa ttataggcac ggacagccaa tccctcgcgt ggagtatatg    540
gaggaggaga agaagacctg ggcacagtg ttcaagaccc tgaagagcct gtacaagaca    600
cacgcctgct acgagtataa ccacatcttc cccctgctgg agaagtattg tggctttcac    660
gaggacaata tccctcagct ggaggacgtg agccagttcc tgcagacctg cacaggcttt    720
aggctgaggc cagtggcagg actgctgagc tcccgggact tcctgggagg actggccttc    780
agagtgtttc actgcaccca gtacatcagg cacggctcca agccaatgta tacaccagag    840
cccgacatct gtcacgagct gctgggccac gtgcccctgt ttagcgatag atccttcgcc    900
cagttttccc aggagatcgg actggcatct ctgggagcac ctgacgagta catcgagaag    960
ctggccacca tctattggtt cacagtggag tttggcctgt gcaagcaggg cgatagcatc   1020
aaggcctacg gagcaggact gctgtctagc ttcgcgagc tgcagtattg tctgtccgag   1080
aagccaaagc tgctgcccct ggagctggaa aagaccgcca tccagaacta caccgtgaca   1140
gagttccagc ccctgtacta tgtggccgag tcttttaacg atgccaagga aaggtgaga   1200 aatttcgccg ccacaatccc taggcccttc agcgtgcggt acgacccta tacccagagg   1260 atcgaggtgc tggataatac acagcagctg aagatcctgg ctgactcaat caatagcgaa   1320
atcggaatcc tgtgctccgc cctgcagaaa tcaaatgag aattcaaggc ctctcgagcc   1380
tctagaacta tagtgagtcg tattacgtag atccagacat gataagatac attgatgagt   1440
ttggacaaac cacaactaga atgcagtgaa aaaaatgctt tatttgtgaa atttgtgatg   1500
ctattgcttt atttgtaacc attataagct gcaataaaca agttaacaac aacaattgca   1560
ttcattttat gtttcaggtt cagggggagg tgtgggaggt ttttttaa              1607
```

<210> SEQ ID NO 148
<211> LENGTH: 1837
<212> TYPE: DNA
<213> ORGANISM: Artificial Sequence
<220> FEATURE:
<223> OTHER INFORMATION: 032 vector editing element

<400> SEQUENCE: 148

```
ctgacctctt ctcttcctcc cacagggcgg taccagatct ggcagcggag agggcagagg     60
aagtcttcta acatgcggtg acgtggagga gaatcccggc cctagggta cctccaccgc    120 tgtgctggag aaccctgggc tggggaggaa actgtcagac ttcgggcagg agacttcata   180
cattgaggat aactgtaacc agaatggcgc catctctctg atcttcagcc tgaaggagga   240
agtgggcgcc ctggcaaagg tgctgcgcct gtttgaggag aacgacgtga atctgaccca   300
catcgagtcc cggccttcta gactgaagaa ggacgagtac gagttctta cccacctgga   360 taagcggtcc ctgccagccc tgacaaacat catcaagatc ctgaggcacg acatcggagc   420
aaccgtgcac gagctgtctc gggacaagaa gaaggatacc gtgccctggt tccctcggac   480
aatccaggag ctggatagat ttgccaacca gatcctgtct tacggagcag agctggacgc   540
agatcaccct ggcttcaagg acccagtgta tcgggcccgg agaaagcagt tgccgatat   600 cgcctacaat tataggcacg gacagccaat ccctcgcgtg gagtatatgg aggaggagaa   660
gaagacctgg ggcacagtgt tcaagaccct gaagagcct tacaagacac acgcctgcta   720
cgagtataac cacatcttcc ccctgctgga gaagtattgt ggctttcacg aggacaatat   780
```

```
ccctcagctg gaggacgtga gccagttcct gcagacctgc acaggcttta ggctgaggcc      840
agtggcagga ctgctgagct cccgggactt cctgggagga ctggccttca gagtgtttca      900
ctgcacccag tacatcaggc acggctccaa gccaatgtat acaccagagc ccgacatctg      960
tcacgagctg ctgggccacg tgcccctgtt tagcgataga tccttcgccc agttttccca     1020
ggagatcgga ctggcatctc tgggagcacc tgacgagtac atcgagaagc tggccaccat     1080
ctattggttc acagtggagt ttggcctgtg caagcagggc gatagcatca aggcctacgg     1140
agcaggactg ctgtctagct tcggcgagct gcagtattgt ctgtccgaga gccaaagct      1200 gctgccctg gagctggaga agaccgccat ccagaactac accgtgacag agttccagcc     1260
cctgtactat gtggccgagt cttttaacga tgccaaggag aaggtgagaa atttcgccgc     1320
cacaatccct aggcccttca gcgtgcggta cgacccttat acccagagga tcgaggtgct     1380
ggataataca cagcagctga agatcctggc tgactcaatc aatagcgaaa tcggaatcct     1440
gtgctccgcc ctgcagaaaa tcaaaggtaa gcctatccct aaccctctcc tcggtctcga     1500
ttctacgtga tcttgtggaa aggacgaaac accgggaat tcaaggcctc tcgagcctct     1560
agaatccccg agacgtttcg tctcgggatc actatagtga gtcgtattac gtacacagtg     1620
caggggaaag aatagtagag atccagacat gataagatac attgatgagt ttggacaaac     1680
cacaactaga atgcagtgaa aaaaatgctt tatttgtgaa atttgtgatg ctattgcttt     1740
atttgtaacc attataagct gcaataaaca agttaacaac aacaattgca ttcattttat     1800
gtttcaggtt cagggggagg tgtgggaggt ttttttaa                             1837
```

<210> SEQ ID NO 149
<211> LENGTH: 2225
<212> TYPE: DNA
<213> ORGANISM: Artificial Sequence
<220> FEATURE:
<223> OTHER INFORMATION: 006-HCR vector editing element

<400> SEQUENCE: 149

```
atgtccaccg ctgtgctgga gaaccctggg ctggggagga aactgtcaga cttcgggcag       60 gtaagttta tggaatgtga atcataattc aattttcaa catgcgttag gagggacatt       120
tcaaactctt ttttacccta gactttccta ccatcaccca gagtatccag ccaggagggg      180 agggctaga gacaccagaa gtttagcagg gaggagggcg tagggattcg gggaatgaag      240
ggatgggatt cagactaggg ccaggaccca gggatggaga gaaagagatg agagtggttt     300
gggggcttgg tgacttagag aacagagctg caggctcaga ggcacacagg agtttctggg     360
ctggcccggc cccttccaa cccctcatta tggaatccag cagctgtttg tgtgctgcct       420
ctgaagtcca cactgaacaa acttcagcct actcatgtcc catataaggg aaattatgga     480
atcagcaaac agcaaacaca cagccctccc tgcctgctga ccttggacct ggggcagagg     540
tcagagacct ccttggctct atgccacctc aacatccac tcgacccctt ggaatttcgg     600
tggagaggag cagaggttgt cctggcgtgg tttaggtagt gtgagagggc tgaccatgcc     660
ttcttctttt tcctacagga aacttcatac attgaggata actgtaacca gaatggcgcc     720
atctctctga tcttcagcct gaaggaggaa gtgggcgccc tggcaaaggt gctgcgcctg     780
tttgaggaga cgacgtgaa tctgacccac atcgagtccc ggccttctag actgaagaag     840
gacgagtacg agttctttac ccacctggat aagcggcccc tgccagccct gacaaacatc     900
atcaagatcc tgaggcacga catcggagca accgtgcacg agctgtctcg ggacaagaag     960
```

| aaggataccg tgccctggtt ccctcggaca atccaggagc tggatagatt tgccaaccag | 1020 |
| atcctgtctt acggagcaga gctggacgca gatcaccctg gcttcaagga cccagtgtat | 1080 |
| cgggcccgga gaaagcagtt tgccgatatc gcctacaatt ataggcacga acagccaatc | 1140 |
| cctcgcgtgg agtatatgga ggaggagaag aagacctggg gcacagtgtt caagaccctg | 1200 |
| aagagcctgt acaagacaca cgcctgctac gagtataacc acatcttccc cctgctggag | 1260 |
| aagtattgtg gctttcacga ggacaatatc cctcagctgg aggacgtgag ccagttcctg | 1320 |
| cagacctgca caggctttag gctgaggcca gtggcaggac tgctgagctc ccgggacttc | 1380 |
| ctggggaggac tggccttcag agtgtttcac tgcacccagt acatcaggca cggctccaag | 1440 |
| ccaatgtata caccagagcc cgacatctgt cacgagctgc tgggccacgt gcccctgttt | 1500 |
| agcgatagat ccttcgccca gttttcccag gagatcggac tggcatctct gggagcacct | 1560 |
| gacgagtaca tcgagaagct ggccaccatc tattggttca cagtggagtt tggcctgtgc | 1620 |
| aagcagggcg atagcatcaa ggcctacgga gcaggactgc tgtctagctt cggcgagctg | 1680 |
| cagtattgtc tgtccgagaa gccaaagctg ctgcccctgg agctggagaa gaccgccatc | 1740 |
| cagaactaca ccgtgacaga gttccagccc ctgtactatg tggccgagtc tttttaacgat | 1800 |
| gccaaggaga aggtgagaaa tttcgccgcc acaatcccta ggcccttcag cgtgcggtac | 1860 |
| gaccccttata cccagaggat cgaggtgctg gataatacac agcagctgaa gatcctggct | 1920 |
| gactcaatca atagcgaaat cggaatcctg tgctccgccc tgcagaaaat caatgagaa | 1980 |
| ttcaaggcct ctcgagcctc tagaactata gtgagtcgta ttacgtagat ccagacatga | 2040 |
| taagatacat tgatgagttt ggacaaacca aactagaat gcagtgaaaa aaatgcttta | 2100 |
| tttgtgaaat ttgtgatgct attgctttat ttgtaaccat tataagctgc aataaacaag | 2160 |
| ttaacaacaa caattgcatt cattttatgt ttcaggttca gggggaggtg tgggaggttt | 2220 |
| tttaa | 2225 |

<210> SEQ ID NO 150
<211> LENGTH: 2455
<212> TYPE: DNA
<213> ORGANISM: Artificial Sequence
<220> FEATURE:
<223> OTHER INFORMATION: 032-HCR vector editing element

<400> SEQUENCE: 150

| ctgacctctt ctcttcctcc cacagggcgg taccagatct ggcagcggag agggcagagg | 60 |
| aagtcttcta acatgcggtg acgtggagga gaatcccggc cctagggta cctccaccgc | 120 |
| tgtgctggag aaccctgggc tggggaggaa actgtcagac ttcgggcagg taagttttat | 180 |
| ggaatgtgaa tcataattca attttttcaac atgcgttagg agggacattt caaactcttt | 240 |
| tttaccctag actttcctac catcacccag agtatccagc caggagggga ggggctagag | 300 |
| acaccagaag tttagcaggg aggagggcgt agggattcgg ggaatgaagg gatgggattc | 360 |
| agactagggc caggacccag ggatggagag aaagagatga gagtggtttg ggggcttggt | 420 |
| gacttagaga acagagctgc aggctcagag gcacacagga gtttctgggc tggcccggcc | 480 |
| cccttccaac ccctcattat ggaatccagc agctgtttgt gtgctgcctc tgaagtccac | 540 |
| actgaacaaa cttcagccta ctcatgtccc atataaggga aattatggaa tcagcaaaca | 600 |
| gcaaacacac agccctccct gcctgctgac cttggacctg gggcagaggt cagagacctc | 660 |
| cttggctcta tgccacctcc aacatccact cgacccttg gaatttcggt ggagaggagc | 720 |
| agaggttgtc ctggcgtggt ttaggtagtg tgagagggct gaccatgcct tcttcttttt | 780 |

```
cctacaggaa acttcataca ttgaggataa ctgtaaccag aatggcgcca tctctctgat      840
cttcagcctg aaggaggaag tgggcgccct ggcaaaggtg ctgcgcctgt ttgaggagaa      900
cgacgtgaat ctgacccaca tcgagtcccg gccttctaga ctgaagaagg acgagtacga     960
gttctttacc cacctggata agcggtccct gccagccctg acaaacatca tcaagatcct    1020
gaggcacgac atcggagcaa ccgtgcacga gctgtctcgg gacaagaaga aggataccgt    1080
gccctggttc cctcggacaa tccaggagct ggatagattt gccaaccaga tcctgtctta    1140
cggagcagag ctggacgcag atcaccctgg cttcaaggac ccagtgtatc gggcccggag    1200
aaagcagttt gccgatatcg cctacaatta taggcacgga cagccaatcc ctcgcgtgga    1260
gtatatggag gaggagaaga agacctgggg cacagtgttc aagaccctga gagcctgta     1320 caagacacac gcctgctacg agtataacca catcttcccc ctgctggaga gtattgtgg     1380 cttttcacgag gacaatatcc ctcagctgga ggacgtgagc cagttcctgc agacctgcac    1440
aggctttagg ctgaggccag tggcaggact gctgagctcc cggacttcc tgggaggact     1500 ggccttcaga gtgtttcact gcacccagta catcaggcac ggctccaagc caatgtatac    1560
accagagccc gacatctgtc acgagctgct gggccacgtg cccctgttta gcgatagatc    1620
cttcgcccag ttttcccagg agatcggact ggcatctctg ggagcacctg acgagtacat    1680
cgagaagctg gccaccatct attggttcac agtggagttt ggcctgtgca agcagggcga    1740
tagcatcaag gcctacggag caggactgct gtctagcttc ggcgagctgc agtattgtct    1800
gtccgagaaa ccaaagctgc tgcccctgga gctggagaag accgccatcc agaactacac    1860
cgtgacagag ttccagcccc tgtactatgt ggccgagtct tttaacgatg ccaaggagaa    1920
ggtgagaaat ttcgccgcca caatccctag gcccttcagc gtgcggtacg acccttatac    1980
ccagaggatc gaggtgctgg ataatacaca gcagctgaag atcctggctg actcaatcaa    2040
tagcgaaatc ggaatcctgt gctccgccct gcagaaaatc aaaggtaagc ctatccctaa    2100
ccctctcctc ggtctcgatt ctacgtgatc ttgtggaaag gacgaaacac cggggaattc    2160
aaggcctctc gagcctctag aatccccgag acgtttcgtc tcgggatcac tatagtgagt    2220
cgtattacgt acacagtgca ggggaaagaa tagtagagat ccagacatga taagatacat    2280
tgatgagttt ggacaaacca caactagaat gcagtgaaaa aaatgcttta tttgtgaaat    2340
ttgtgatgct attgctttat ttgtaaccat tataagctgc aataaacaag ttaacaacaa    2400
caattgcatt cattttatgt ttcaggttca gggggaggtg tgggaggttt tttaa         2455
```

<210> SEQ ID NO 151
<211> LENGTH: 1723
<212> TYPE: DNA
<213> ORGANISM: Artificial Sequence
<220> FEATURE:
<223> OTHER INFORMATION: 006-HBB1 vector editing element

<400> SEQUENCE: 151

```
atgtccaccg ctgtgctgga gaaccctggg ctggggagga aactgtcaga cttcgggcag      60
gagacttcat acattgagga taactgtaac cagaatggcg ccatctctct gatcttcagc     120
ctgaaggagg aagtgggcgc cctggcaaag gtgctgcgcc tgtttgagga gaacgacgtg     180
aatctgaccc acatcgagtc ccggccttct agactgaaga aggacgagta cgagttcttt     240 acccaccctgg ataagcggtc cctgccagcc ctgacaaaca tcatcaagat cctgaggcac     300
gacatcggag caaccgtgca cgagctgtct cgggacaaga gaaggatac cgtgccctgg     360
```

```
ttccctcgga caatccagga gctggataga tttgccaacc agatcctgtc ttacggagca    420
gagctggacg cagatcaccc tggcttcaag gacccagtgt atcgggcccg gagaaagcag    480
tttgccgata tcgcctacaa ttataggcac ggacagccaa tccctcgcgt ggagtatatg    540
gaggaggaga agaagacctg ggcacagtg ttcaagaccc tgaagagcct gtacaagaca    600
cacgcctgct acgagtataa ccacatcttc ccctgctgg agaagtattg tggctttcac    660
gaggacaata tccctcagct ggaggacgtg agccagttcc tgcagacctg cacaggcttt    720
aggctgaggc cagtggcagg actgctgagc tcccgggact tcctgggagg actggccttc    780
agagtgtttc actgcaccca gtacatcagg cacggctcca agccaatgta tacaccagag    840
cccgacatct gtcacgagct gctgggccac gtgcccctgt ttagcgatag atccttcgcc    900
cagttttccc aggttggtat ccaggttaca aggcagctca agaagaag ttgggtgctt    960 ggagacagag gtctgctttc cagcagacac taactttcag tgtccctgt ctatgtttcc    1020 cttttagga gatcggactg gcatctctga gcacctga cgagtacatc gagaagctgg    1080
ccaccatcta ttggttcaca gtggagtttg gcctgtgcaa gcagggcgat agcatcaagg    1140
cctacggagc aggactgctg tctagcttcg gcgagctgca gtattgtctg tccgagaagc    1200
caaagctgct gccccctggag ctggagaaga ccgccatcca gaactacacc gtgacagagt    1260
tccagcccct gtactatgtg gccgagtctt taacgatgc aaggagaag gtgagaaatt    1320 tcgccgccac aatccctagg cccttcagcg tgcggtacga cccttatacc cagaggatcg    1380
aggtgctgga taatacacag cagctgaaga tcctggctga ctcaatcaat agcgaaatcg    1440
gaatcctgtg ctccgccctg cagaaaatca aatgagaatt caaggcctct cgagcctcta    1500
gaactatagt gagtcgtatt acgtagatcc agacatgata agatacattg atgagttttgg    1560 acaaaccaca actagaatgc agtgaaaaaa atgctttatt tgtgaaattt gtgatgctat    1620
tgctttattt gtaaccatta taagctgcaa taaacaagtt aacaacaaca attgcattca    1680
ttttatgttt caggttcagg gggaggtgtg ggaggttttt taa    1723
```

<210> SEQ ID NO 152
<211> LENGTH: 1607
<212> TYPE: DNA
<213> ORGANISM: Artificial Sequence
<220> FEATURE:
<223> OTHER INFORMATION: 006-SD.3 vector editing element

<400> SEQUENCE: 152

```
atgtccaccg ctgtgctgga gaaccctggg ctggggagga aactgtcaga cttcgggcag     60
gagacttcat acattgagga taactgtaac cagaatggcg ccatctctct gatcttcagc    120
ctgaaggagg aagtgggcgc cctggcaaag gtgctgcgcc tgtttgagga gaacgacgtg    180
aatctgaccc acatcgagtc ccggccttct agactgaaga aggacgagta cgagttcttt    240
acccacctgg ataagcggtc cctgccagcc ctgacaaaca tcatcaagat cctgaggcac    300
gacatcggag caaccgtgca cgagctgtct cgggacaaga agaggatac cgtgccctgg    360 ttccctcgga caatccagga gctggataga tttgccaacc agatcctgtc ttacggagca    420
gagctggacg cagatcaccc tggcttcaag gacccagtgt atcgggcccg gagaaagcag    480
tttgccgata tcgcctacaa ttataggcac ggacagccaa tccctcgcgt ggagtatatg    540
gaggaggaga agaagacctg ggcacagtg ttcaagaccc tgaagagcct gtacaagaca    600
cacgcctgct acgagtataa ccacatcttc ccctgctgg agaagtattg tggctttcac    660
gaggacaata tccctcagct ggaggacgtg agccagttcc tgcagacctg cacaggcttt    720
```

```
aggctgaggc cagtggcagg actgctgagc tcccgggact tcctgggagg actggccttc    780
agagtgtttc actgcaccca gtacatcagg cacggctcca agccaatgta tacaccagag    840
cccgacatct gtcacgagct gctgggccac gtgcccctgt ttagcgatag atccttcgcc    900
cagttttccc aggagatcgg actggcatct ctgggagcac ctgacgagta catcgagaag    960
ctggccacca tctattggtt cacagtggag tttggcctgt gcaagcaggg cgatagcatc   1020
aaggcctacg gagcaggact gctgtctagc ttcggcgagc tgcagtattg tctgtccgag   1080
aagccaaagc tgctgcccct ggagctggag aagaccgcca tccagaacta caccgtgaca   1140
gagttccagc ccctgtacta tgtggccgag tcttttaacg atgccaagga gaaggtgaga   1200
aatttcgccg ccacaatccc taggcccttc agtgtgcgtt acgacccttc tacccagagg   1260
atcgaggtgc tggataatac acagcagctg aagatcctgg ctgactcaat caatagcgaa   1320
atcggaatcc tgtgctccgc cctgcagaaa atcaaatgag aattcaaggc ctctcgagcc   1380
tctagaacta tagtgagtcg tattacgtag atccagacat gataagatac attgatgagt   1440
ttggacaaac cacaactaga atgcagtgaa aaaaatgctt tatttgtgaa atttgtgatg   1500
ctattgcttt atttgtaacc attataagct gcaataaaca agttaacaac aacaattgca   1560
ttcattttat gtttcaggtt caggggagg tgtgggaggt tttttaa                  1607

<210> SEQ ID NO 153
<211> LENGTH: 1837
<212> TYPE: DNA
<213> ORGANISM: Artificial Sequence
<220> FEATURE:
<223> OTHER INFORMATION: 032-SD.3 vector editing element

<400> SEQUENCE: 153
ctgacctctt ctcttcctcc cacagggcgg taccagatct ggcagcggag agggcagagg     60
aagtcttcta acatgcggtg acgtggagga gaatcccggc cctagggta cctccaccgc    120 tgtgctggag aaccctgggc tggggaggaa actgtcagac ttcgggcagg agacttcata    180
cattgaggat aactgtaacc agaatggcgc catctctctg atcttcagcc tgaaggagga    240
agtgggcgcc ctggcaaagg tgctgcgcct gtttgaggag aacgacgtga atctgaccca    300
catcgagtcc cggccttcta gactgaagaa ggacgagtac gagttctta cccacctgga    360 taagcggtcc ctgccagccc tgacaaacat catcaagatc ctgaggcacg acatcggagc    420
aaccgtgcac gagctgtctc gggacaagaa gaaggatacc gtgccctggt ccctcggac    480 aatccaggag ctggatagat tgccaaccag atcctgtctt acggagcag agctggacgc    540 agatcaccct ggcttcaagg acccagtgta tcgggcccgg agaaagcagt ttgccgatat    600
cgcctacaat tataggcacg gacagccaat ccctcgcgtg gagtatatgg aggaggagaa    660
gaagacctgg ggcacagtgt tcaagaccct gaagagcctg tacaagacac acgcctgcta    720
cgagtataac cacatcttcc ccctgctgga gaagtattgt ggctttcacg aggacaatat    780
ccctcagctg gaggacgtga gccagttcct gcagacctgc acaggcttta ggctgaggcc    840
agtggcagga ctgctgagct cccgggactt cctgggagga ctggccttca gagtgtttca    900
ctgcacccag tacatcaggc acggctccaa gccaatgtat acaccagagc cgacatctg    960 tcacgagctg ctgggccacg tgcccctgtt tagcgataga tccttcgccc agttttccca   1020
ggagatcgga ctggcatctc tgggagcacc tgacagtac atcgagaagc tggccaccat   1080
ctattggttc acagtggagt ttggcctgtg caagcagggc gatagcatca aggcctacgg   1140
```

-continued

```
agcaggactg ctgtctagct tcggcgagct gcagtattgt ctgtccgaga agccaaagct    1200
gctgcccctg gagctggaga agaccgccat ccagaactac accgtgacag agttccagcc    1260
cctgtactat gtggccgagt cttttaacga tgccaaggag aaggtgagaa atttcgccgc    1320
cacaatccct aggcccttca gtgtgcgtta cgacccttat acccagagga tcgaggtgct    1380
ggataataca cagcagctga agatcctggc tgactcaatc aatagcgaaa tcggaatcct    1440
gtgctccgcc ctgcagaaaa tcaaaggtaa gcctatccct aaccctctcc tcggtctcga    1500
ttctacgtga tcttgtggaa aggacgaaac accggggaat tcaaggcctc tcgagcctct    1560
agaatccccg agacgtttcg tctcgggatc actatagtga gtcgtattac gtacacagtg    1620 cagggaaag  aatagtagag atccagacat gataagatac attgatgagt ttggacaaac    1680
cacaactaga atgcagtgaa aaaaatgctt tatttgtgaa atttgtgatg ctattgcttt    1740
atttgtaacc attataagct gcaataaaca agttaacaac aacaattgca ttcattttat    1800
gtttcaggtt caggggagg tgtgggaggt tttttaa                              1837
```

ADENO-ASSOCIATED VIRUS COMPOSITIONS FOR RESTORING PAH GENE FUNCTION AND METHODS OF USE THEREOF

RELATED APPLICATIONS

This application is a continuation of International Patent Application No. PCT/US2019/016354, which claims priority to U.S. Provisional Patent Application Ser. Nos. 62/625,149, filed Feb. 1, 2018, and 62/672,377, filed May 16, 2018, the entire disclosures of which are hereby incorporated herein by reference.

REFERENCE TO SEQUENCE LISTING SUBMITTED ELECTRONICALLY

The content of the electronically submitted sequence listing in ASCII text file (Name: 711076_HMW-024PCCON_ST25.txt; Size: 367,334 bytes; and Date of Creation: Oct. 19, 2020) is incorporated herein by reference in its entirety.

BACKGROUND

Phenylketonuria (PKU) is an autosomal recessive genetic disorder where the majority of cases are caused by mutations in the phenylalanine hydroxylase (PAH) gene. The PAH gene encodes a hepatic enzyme that catalyzes the hydroxylation of L-phenylalanine (Phe) to L-tyrosine (Tyr) upon multimerization. Reduction or loss of PAH activity leads to phenylalanine accumulation and its conversion into phenylpyruvate (also known as phenylketone). This abnormality in phenylalanine metabolism impairs neuronal maturation and the synthesis of myelin, resulting in mental retardation, seizures and other serious medical problems.

Currently, there is no cure for PKU. The standard of care is diet management by minimizing foods that contain high amounts of phenylalanine. Dietary management from birth with a low phenylalanine formula largely prevents the development of the neurological consequences of the disorder. However, even on a low-protein diet, children still suffer from growth retardation, and adults often have osteoporosis and vitamin deficiencies. Moreover, adherence to life-long dietary treatment is difficult, particularly beyond school age.

New treatment strategies have recently emerged, including large neutral amino acid (LNAA) supplementation, cofactor tetrahydrobiopterin therapy, enzyme replacement therapy, and genetically modified probiotic therapy. However, these strategies suffer from shortcomings. The LNAA supplementation is suitable only for adults not adhering to a low Phe diet. The cofactor tetrahydrobiopterin can only be used in some mild forms of PKU. Enzyme replacement by administration of a substitute for PAH, e.g., phenylalanine ammonia-lyase (PAL), can lead to immune responses that reduce the efficacy and/or cause side effects. As to genetically modified probiotic therapy, the pathogenicity of PAL-expressing E. coli has been a concern.

Gene therapy provides a unique opportunity to cure PKU. Retroviral vectors, including lentiviral vectors, are capable of integrating nucleic acids into host cell genomes. However, these vectors may raise safety concerns due to their non-targeted insertion into the genome. For example, there is a risk of the vector disrupting a tumor suppressor gene or activating an oncogene, thereby causing a malignancy. Indeed, in a clinical trial for treating X-linked severe combined immunodeficiency (SCID) by transducing CD34+ bone marrow precursors with a gammaretroviral vector, four out of ten patients developed leukemia (Hacein-Bey-Abina et al., J Clin Invest. (2008) 118(9):3132-42).

It has also been speculated that nuclease-based gene editing technologies, such as meganucleases, zinc finger nucleases (ZFNs), transcription activator-like effector nucleases (TALENs), and clustered, regularly interspaced, short palindromic repeat (CRISPR) technology, may be used to correct defects in the PAH gene in PKU patients. However, each of these technologies raises safety concerns due to the potential for off-target mutation of sites in the human genome similar in sequence to the intended target site.

Accordingly, there is a need in the art for improved gene therapy compositions and methods that can efficiently and safely restore PAH gene function in PKU patients.

SUMMARY

Provided herein are adeno-associated virus (AAV) compositions that can restore PAH gene function in cells, and methods for using the same to treat diseases associated with reduction of PAH gene function (e.g., PKU). Also provided are packaging systems for making the adeno-associated virus compositions.

Accordingly, in one aspect, the instant disclosure provides a method for correcting a mutation in a phenylalanine hydroxylase (PAH) gene in a cell, the method comprising transducing the cell with a replication-defective adeno-associated virus (AAV) comprising:
(a) an AAV capsid; and
(b) a correction genome comprising: (i) an editing element for editing a target locus in the PAH gene; (ii) a 5' homology arm nucleotide sequence 5' of the editing element having homology to a first genomic region 5' to the target locus; and (iii) a 3' homology arm nucleotide sequence 3' of the editing element having homology to a second genomic region 3' to the target locus,
wherein the cell is transduced without co-transducing or co-administering an exogenous nuclease or a nucleotide sequence that encodes an exogenous nuclease.

In certain embodiments, the cell is a hepatocyte, a renal cell, or a cell in the brain, pituitary gland, adrenal gland, pancreas, urinary bladder, gallbladder, colon, small intestine, or breast. In certain embodiments, the cell is in a mammalian subject and the AAV is administered to the subject in an amount effective to transduce the cell in the subject. In another aspect, the instant disclosure provides a method for treating a subject having a disease or disorder associated with a PAH gene mutation, the method comprising administering to the subject an effective amount of a replication-defective AAV comprising:
(a) an AAV capsid; and
(b) a correction genome comprising: (i) an editing element for editing a target locus in the PAH gene; (ii) a 5' homology arm nucleotide sequence 5' of the editing element having homology to a first genomic region 5' to the target locus; and (iii) a 3' homology arm nucleotide sequence 3' of the editing element having homology to a second genomic region 3' to the target locus, wherein an exogenous nuclease or a nucleotide sequence that encodes an exogenous nuclease is not co-administered to the subject.

In certain embodiments, the disease or disorder is phenylketonuria. In certain embodiments, the subject is a human subject.

In another aspect, the instant disclosure provides a replication-defective adeno-associated virus (AAV) comprising: (a) an AAV capsid; and
(b) a correction genome comprising: (i) an editing element for editing a target locus in the PAH gene; (ii) a 5' homology arm nucleotide sequence 5' of the editing element having homology to a first genomic region 5' to the target locus; and (iii) a 3' homology arm nucleotide sequence 3' of the editing element having homology to a second genomic region 3' to the target locus.

The following embodiments apply to each of the foregoing aspects.

In certain embodiments, the editing element comprises at least a portion of a PAH coding sequence. In certain embodiments, the editing element comprises a PAH coding sequence. In certain embodiments, the PAH coding sequence encodes an amino acid sequence set forth in SEQ ID NO: 23. In certain embodiments, the PAH coding sequence comprises the sequence set forth in SEQ ID NO: 24. In certain embodiments, the PAH coding sequence is silently altered. In certain embodiments, the PAH coding sequence comprises the sequence set forth in SEQ ID NO: 25, 116, 131, 132, 138, 139, or 143.

In certain embodiments, the editing element comprises a PAH intron-inserted coding sequence, optionally wherein the PAH intron-inserted coding sequence comprises a nonnative intron inserted in a PAH coding sequence. In certain embodiments, the nonnative intron is selected from the group consisting of a first intron of a hemoglobin beta gene and a minute virus in mice (MVM) intron. In certain embodiments, the nonnative intron consists of a nucleotide sequence at least 90% identical to any one of SEQ ID NOs: 28-30, and 120-130. In certain embodiments, the nonnative intron consists of a nucleotide sequence set forth in any one of SEQ ID NOs: 28-30, and 120-130.

In certain embodiments, the PAH intron-inserted coding sequence encodes an amino acid sequence set forth in SEQ ID NO: 23. In certain embodiments, the PAH intron-inserted coding sequence comprises from 5' to 3': a first portion of a PAH coding sequence, the intron, and a second portion of a PAH coding sequence, wherein the first portion and the second portion, when spliced together, form a complete PAH coding sequence. In certain embodiments, the PAH coding sequence comprises the sequence set forth in SEQ ID NO: 24. In certain embodiments, the PAH coding sequence is silently altered. In certain embodiments, the PAH coding sequence comprises the sequence set forth in SEQ ID NO: 25 or 116. In certain embodiments, the first portion of the PAH coding sequence comprises the amino acid sequence set forth in SEQ ID NO: 64 or 65, and/or the second portion of the PAH coding sequence comprises the amino acid sequence set forth in SEQ ID NO: 66 or 67. In certain embodiments, the first portion of the PAH coding sequence consist of the amino acid sequence set forth in SEQ ID NO: 64 or 65, and the second portion of the PAH coding sequence consists of the amino acid sequence set forth in SEQ ID NO: 66 or 67.

In certain embodiments, the editing element comprises from 5' to 3': a ribosomal skipping element, and the PAH coding sequence or the PAH intron-inserted coding sequence. In certain embodiments, the editing element further comprises a polyadenylation sequence 3' to the PAH coding sequence or the PAH intron-inserted coding sequence. In certain embodiments, the polyadenylation sequence is an exogenous polyadenylation sequence, optionally wherein the exogenous polyadenylation sequence is an SV40 polyadenylation sequence. In certain embodiments, the SV40 polyadenylation sequence comprises a nucleotide sequence selected from the group consisting of SEQ ID NOs: 31-34, and a sequence complementary thereto.

In certain embodiments, the nucleotide 5' to the target locus is in an exon of the PAH gene. In certain embodiments, the nucleotide 5' to the target locus is in exon 1 of the PAH gene.

In certain embodiments, the editing element further comprises a splice acceptor 5' to the ribosomal skipping element. In certain embodiments, the nucleotide 5' to the target locus is in an intron of the PAH gene. In certain embodiments, the nucleotide 5' to the target locus is in intron 1 of the PAH gene. In certain embodiments, the editing element comprises the nucleotide sequence set forth in SEQ ID NO: 35.

In certain embodiments, the 5' homology arm nucleotide sequence is at least 90%, 95%, 96%, 97%, 98%, or 99% identical to the first genomic region. In certain embodiments, the 3' homology arm nucleotide sequence is at least 90%, 95%, 96%, 97%, 98%, or 99% identical to the second genomic region.

In certain embodiments, the first genomic region is located in a first editing window, and the second genomic region is located in a second editing window. In certain embodiments, the first editing window consists of the nucleotide sequence set forth in SEQ ID NO: 36 or 45. In certain embodiments, the second editing window consists of the nucleotide sequence set forth in SEQ ID NO: 36 or 45. In certain embodiments, the first editing window consists of the nucleotide sequence set forth in SEQ ID NO: 36, and the second editing window consists of the nucleotide sequence set forth in SEQ ID NO: 45.

In certain embodiments, the first genomic region consists of the nucleotide sequence set forth in SEQ ID NO: 36. In certain embodiments, the second genomic region consists of the nucleotide sequence set forth in SEQ ID NO: 45.

In certain embodiments, each of the 5' and 3' homology arm nucleotide sequences independently has a length of about 100 to about 2000 nucleotides.

In certain embodiments, the 5' homology arm comprises: C corresponding to nucleotide-2 of the PAH gene, G corresponding to nucleotide 4 of the PAH gene, G corresponding to nucleotide 6 of the PAH gene, G corresponding to nucleotide 7 of the PAH gene, G corresponding to nucleotide 9 of the PAH gene, A corresponding to nucleotide-467 of the PAH gene, A corresponding to nucleotide-465 of the PAH gene, A corresponding to nucleotide-181 of the PAH gene, G corresponding to nucleotide-214 of the PAH gene, C corresponding to nucleotide-212 of the PAH gene, A corresponding to nucleotide-211 of the PAH gene, G corresponding to nucleotide 194 of the PAH gene, C corresponding to nucleotide-433 of the PAH gene, C corresponding to nucleotide-432 of the PAH gene, ACGCTGTTCTTCGCC (SEQ ID NO: 68) corresponding to nucleotides-394 to-388 of the PAH gene, A corresponding to nucleotide-341 of the PAH gene, A corresponding to nucleotide-339 of the PAH gene, A corresponding to nucleotide-225 of the PAH gene, A corresponding to nucleotide-211 of the PAH gene, and/or A corresponding to nucleotide-203 of the PAH gene. In certain embodiments, the 5' homology arm comprises:
  (a) C corresponding to nucleotide-2 of the PAH gene, G corresponding to nucleotide 4 of the PAH gene, G corresponding to nucleotide 6 of the PAH gene, G corresponding to nucleotide 7 of the PAH gene, and G corresponding to nucleotide 9 of the PAH gene;
  (b) A corresponding to nucleotide-467 of the PAH gene, and A corresponding to nucleotide-465 of the PAH gene;

(c) A corresponding to nucleotide-181 of the PAH gene;
(d) G corresponding to nucleotide-214 of the PAH gene, C corresponding to nucleotide-212 of the PAH gene, and A corresponding to nucleotide-211 of the PAH gene;
(e) G corresponding to nucleotide 194 of the PAH gene;
(f) C corresponding to nucleotide-433 of the PAH gene, and C corresponding to nucleotide-432 of the PAH gene;
(g) ACGCTGTTCTTCGCC (SEQ ID NO: 68) corresponding to nucleotides-394 to-388 of the PAH gene; and/or
(h) A corresponding to nucleotide-341 of the PAH gene, A corresponding to nucleotide-339 of the PAH gene, A corresponding to nucleotide-225 of the PAH gene, A corresponding to nucleotide-211 of the PAH gene, and A corresponding to nucleotide-203 of the PAH gene.

In certain embodiments, the 5' homology arm comprises the modifications of (c) and (d), (0 and (g), and/or (b) and (h).

In certain embodiments, the 5' homology arm consists of a nucleotide sequence set forth in any one of SEQ ID NOs: 36-44, 111, 115, and 142. In certain embodiments, the 3' homology arm consists of the nucleotide sequence set forth in SEQ ID NO: 45, 112, 117, 144.

In certain embodiments, the correction genome comprises the nucleotide sequence set forth in any one of SEQ ID NOs: 46-54, 113, 118, 134, 136, and 145.

In certain embodiments, the correction genome further comprises a 5' inverted terminal repeat (5' ITR) nucleotide sequence 5' of the 5' homology arm nucleotide sequence, and a 3' inverted terminal repeat (3' ITR) nucleotide sequence 3' of the 3' homology arm nucleotide sequence. In certain embodiments, the 5' ITR nucleotide sequence has at least 95% sequence identity to SEQ ID NO: 18, and the 3' ITR nucleotide sequence has at least 95% sequence identity to SEQ ID NO: 19. In certain embodiments, the 5' ITR nucleotide sequence has at least 95% sequence identity to SEQ ID NO: 20, and the 3' ITR nucleotide sequence has at least 95% sequence identity to SEQ ID NO: 21. In certain embodiments, the 5' ITR nucleotide sequence has at least 95% sequence identity to SEQ ID NO: 26, and the 3' ITR nucleotide sequence has at least 95% sequence identity to SEQ ID NO: 27.

In certain embodiments, the correction genome comprises the nucleotide sequence set forth in any one of SEQ ID NOs: 55-63, 114, 119, 135, 137, and 146. In certain embodiments, the correction genome consists of the nucleotide sequence set forth in any one of SEQ ID NOs: 55-63, 114, 119, 135, 137, and 146.

In certain embodiments, the AAV capsid comprises an AAV Clade F capsid protein.

In certain embodiments, the AAV Clade F capsid protein comprises an amino acid sequence having at least 95% sequence identity with the amino acid sequence of amino acids 203-736 of SEQ ID NO: 2, 3, 4, 6, 7, 10, 11, 12, 13, 15, 16, or 17. In certain embodiments, the amino acid in the capsid protein corresponding to amino acid 206 of SEQ ID NO: 2 is C; the amino acid in the capsid protein corresponding to amino acid 296 of SEQ ID NO: 2 is H; the amino acid in the capsid protein corresponding to amino acid 312 of SEQ ID NO: 2 is Q; the amino acid in the capsid protein corresponding to amino acid 346 of SEQ ID NO: 2 is A; the amino acid in the capsid protein corresponding to amino acid 464 of SEQ ID NO: 2 is N; the amino acid in the capsid protein corresponding to amino acid 468 of SEQ ID NO: 2 is S; the amino acid in the capsid protein corresponding to amino acid 501 of SEQ ID NO: 2 is I; the amino acid in the capsid protein corresponding to amino acid 505 of SEQ ID NO: 2 is R; the amino acid in the capsid protein corresponding to amino acid 590 of SEQ ID NO: 2 is R; the amino acid in the capsid protein corresponding to amino acid 626 of SEQ ID NO: 2 is G or Y; the amino acid in the capsid protein corresponding to amino acid 681 of SEQ ID NO: 2 is M; the amino acid in the capsid protein corresponding to amino acid 687 of SEQ ID NO: 2 is R; the amino acid in the capsid protein corresponding to amino acid 690 of SEQ ID NO: 2 is K; the amino acid in the capsid protein corresponding to amino acid 706 of SEQ ID NO: 2 is C; or, the amino acid in the capsid protein corresponding to amino acid 718 of SEQ ID NO: 2 is G. In certain embodiments, (a) the amino acid in the capsid protein corresponding to amino acid 626 of SEQ ID NO: 2 is G, and the amino acid in the capsid protein corresponding to amino acid 718 of SEQ ID NO: 2 is G;
(b) the amino acid in the capsid protein corresponding to amino acid 296 of SEQ ID NO: 2 is H, the amino acid in the capsid protein corresponding to amino acid 464 of SEQ ID NO: 2 is N, the amino acid in the capsid protein corresponding to amino acid 505 of SEQ ID NO: 2 is R, and the amino acid in the capsid protein corresponding to amino acid 681 of SEQ ID NO: 2 is M;
(c) the amino acid in the capsid protein corresponding to amino acid 505 of SEQ ID NO: 2 is R, and the amino acid in the capsid protein corresponding to amino acid 687 of SEQ ID NO: 2 is R;
(d) the amino acid in the capsid protein corresponding to amino acid 346 of SEQ ID NO: 2 is A, and the amino acid in the capsid protein corresponding to amino acid 505 of SEQ ID NO: 2 is R; or
(e) the amino acid in the capsid protein corresponding to amino acid 501 of SEQ ID NO: 2 is I, the amino acid in the capsid protein corresponding to amino acid 505 of SEQ ID NO: 2 is R, and the amino acid in the capsid protein corresponding to amino acid 706 of SEQ ID NO: 2 is C.

In certain embodiments, the capsid protein comprises the amino acid sequence of amino acids 203-736 of SEQ ID NO: 2, 3, 4, 6, 7, 10, 11, 12, 13, 15, 16, or 17.

In certain embodiments, the AAV Clade F capsid protein comprises an amino acid sequence having at least 95% sequence identity with the amino acid sequence of amino acids 138-736 of SEQ ID NO: 2, 3, 4, 5, 6, 7, 9, 10, 11, 12, 13, 15, 16, or 17. In certain embodiments, the amino acid in the capsid protein corresponding to amino acid 151 of SEQ ID NO: 2 is R; the amino acid in the capsid protein corresponding to amino acid 160 of SEQ ID NO: 2 is D; the amino acid in the capsid protein corresponding to amino acid 206 of SEQ ID NO: 2 is C; the amino acid in the capsid protein corresponding to amino acid 296 of SEQ ID NO: 2 is H; the amino acid in the capsid protein corresponding to amino acid 312 of SEQ ID NO: 2 is Q; the amino acid in the capsid protein corresponding to amino acid 346 of SEQ ID NO: 2 is A; the amino acid in the capsid protein corresponding to amino acid 464 of SEQ ID NO: 2 is N; the amino acid in the capsid protein corresponding to amino acid 468 of SEQ ID NO: 2 is S; the amino acid in the capsid protein corresponding to amino acid 501 of SEQ ID NO: 2 is I; the amino acid in the capsid protein corresponding to amino acid 505 of SEQ ID NO: 2 is R; the amino acid in the capsid protein corresponding to amino acid 590 of SEQ ID NO: 2 is R; the amino acid in the capsid protein corresponding to amino acid 626 of SEQ ID NO: 2 is G or Y; the amino acid in the capsid protein corresponding to amino acid 681 of SEQ ID NO: 2 is M; the amino acid in the capsid protein corresponding to amino acid 687 of SEQ ID NO: 2 is R; the amino acid in the capsid protein corresponding to amino acid 690 of SEQ ID NO: 2 is K; the amino acid in the capsid protein corresponding to amino acid 706 of SEQ ID NO: 2 is C; or, the amino acid in the capsid protein corresponding to amino acid 718 of SEQ ID NO: 2 is G. In certain embodiments, (a) the amino acid in the capsid protein corresponding to amino acid 626 of SEQ ID NO: 2 is G, and the amino acid in the capsid protein corresponding to amino acid 718 of SEQ ID NO: 2 is G;

(b) the amino acid in the capsid protein corresponding to amino acid 296 of SEQ ID NO: 2 is H, the amino acid in the capsid protein corresponding to amino acid 464 of SEQ ID NO: 2 is N, the amino acid in the capsid protein corresponding to amino acid 505 of SEQ ID NO: 2 is R, and the amino acid in the capsid protein corresponding to amino acid 681 of SEQ ID NO: 2 is M;

(c) the amino acid in the capsid protein corresponding to amino acid 505 of SEQ ID NO: 2 is R, and the amino acid in the capsid protein corresponding to amino acid 687 of SEQ ID NO: 2 is R;

(d) the amino acid in the capsid protein corresponding to amino acid 346 of SEQ ID NO: 2 is A, and the amino acid in the capsid protein corresponding to amino acid 505 of SEQ ID NO: 2 is R; or (e) the amino acid in the capsid protein corresponding to amino acid 501 of SEQ ID NO: 2 is I, the amino acid in the capsid protein corresponding to amino acid 505 of SEQ ID NO: 2 is R, and the amino acid in the capsid protein corresponding to amino acid 706 of SEQ ID NO: 2 is C.

In certain embodiments, the capsid protein comprises the amino acid sequence of amino acids 138-736 of SEQ ID NO: 2, 3, 4, 5, 6, 7, 9, 10, 11, 12, 13, 15, 16, or 17.

In certain embodiments, the AAV Clade F capsid protein comprises an amino acid sequence having at least 95% sequence identity with the amino acid sequence of amino acids 1-736 of SEQ ID NO: 2, 3, 4, 5, 6, 7, 8, 9, 10, 11, 12, 13, 15, 16, or 17. In certain embodiments, the amino acid in the capsid protein corresponding to amino acid 2 of SEQ ID NO: 2 is T; the amino acid in the capsid protein corresponding to amino acid 65 of SEQ ID NO: 2 is I; the amino acid in the capsid protein corresponding to amino acid 68 of SEQ ID NO: 2 is V; the amino acid in the capsid protein corresponding to amino acid 77 of SEQ ID NO: 2 is R; the amino acid in the capsid protein corresponding to amino acid 119 of SEQ ID NO: 2 is L; the amino acid in the capsid protein corresponding to amino acid 151 of SEQ ID NO: 2 is R; the amino acid in the capsid protein corresponding to amino acid 160 of SEQ ID NO: 2 is D; the amino acid in the capsid protein corresponding to amino acid 206 of SEQ ID NO: 2 is C; the amino acid in the capsid protein corresponding to amino acid 296 of SEQ ID NO: 2 is H; the amino acid in the capsid protein corresponding to amino acid 312 of SEQ ID NO: 2 is Q; the amino acid in the capsid protein corresponding to amino acid 346 of SEQ ID NO: 2 is A; the amino acid in the capsid protein corresponding to amino acid 464 of SEQ ID NO: 2 is N; the amino acid in the capsid protein corresponding to amino acid 468 of SEQ ID NO: 2 is S; the amino acid in the capsid protein corresponding to amino acid 501 of SEQ ID NO: 2 is I; the amino acid in the capsid protein corresponding to amino acid 505 of SEQ ID NO: 2 is R; the amino acid in the capsid protein corresponding to amino acid 590 of SEQ ID NO: 2 is R; the amino acid in the capsid protein corresponding to amino acid 626 of SEQ ID NO: 2 is G or Y; the amino acid in the capsid protein corresponding to amino acid 681 of SEQ ID NO: 2 is M; the amino acid in the capsid protein corresponding to amino acid 687 of SEQ ID NO: 2 is R; the amino acid in the capsid protein corresponding to amino acid 690 of SEQ ID NO: 2 is K; the amino acid in the capsid protein corresponding to amino acid 706 of SEQ ID NO: 2 is C; or, the amino acid in the capsid protein corresponding to amino acid 718 of SEQ ID NO: 2 is G. In certain embodiments, (a) the amino acid in the capsid protein corresponding to amino acid 2 of SEQ ID NO: 2 is T, and the amino acid in the capsid protein corresponding to amino acid 312 of SEQ ID NO: 2 is Q;

(b) the amino acid in the capsid protein corresponding to amino acid 65 of SEQ ID NO: 2 is I, and the amino acid in the capsid protein corresponding to amino acid 626 of SEQ ID NO: 2 is Y;

(c) the amino acid in the capsid protein corresponding to amino acid 77 of SEQ ID NO: 2 is R, and the amino acid in the capsid protein corresponding to amino acid 690 of SEQ ID NO: 2 is K;

(d) the amino acid in the capsid protein corresponding to amino acid 119 of SEQ ID NO: 2 is L, and the amino acid in the capsid protein corresponding to amino acid 468 of SEQ ID NO: 2 is S;

(e) the amino acid in the capsid protein corresponding to amino acid 626 of SEQ ID NO: 2 is G, and the amino acid in the capsid protein corresponding to amino acid 718 of SEQ ID NO: 2 is G;

(f) the amino acid in the capsid protein corresponding to amino acid 296 of SEQ ID NO: 2 is H, the amino acid in the capsid protein corresponding to amino acid 464 of SEQ ID NO: 2 is N, the amino acid in the capsid protein corresponding to amino acid 505 of SEQ ID NO: 2 is R, and the amino acid in the capsid protein corresponding to amino acid 681 of SEQ ID NO: 2 is M;

(g) the amino acid in the capsid protein corresponding to amino acid 505 of SEQ ID NO: 2 is R, and the amino acid in the capsid protein corresponding to amino acid 687 of SEQ ID NO: 2 is R;

(h) the amino acid in the capsid protein corresponding to amino acid 346 of SEQ ID NO: 2 is A, and the amino acid in the capsid protein corresponding to amino acid 505 of SEQ ID NO: 2 is R; or (i) the amino acid in the capsid protein corresponding to amino acid 501 of SEQ ID NO: 2 is I, the amino acid in the capsid protein corresponding to amino acid 505 of SEQ ID NO: 2 is R, and the amino acid in the capsid protein corresponding to amino acid 706 of SEQ ID NO: 2 is C.

In certain embodiments, the capsid protein comprises the amino acid sequence of amino acids 1-736 of SEQ ID NO: 2, 3, 4, 5, 6, 7, 8, 9, 10, 11, 12, 13, 15, 16, or 17.

In certain embodiments, the integration efficiency of the editing element into the target locus is at least 1% when the AAV is administered to a mouse implanted with human hepatocytes in the absence of an exogenous nuclease under standard AAV administration conditions. In certain embodiments, the allelic frequency of integration of the editing element into the target locus is at least 0.5% when the AAV is administered to a mouse implanted with human hepatocytes in the absence of an exogenous nuclease under standard AAV administration conditions.

In another aspect, the instant disclosure provides a pharmaceutical composition comprising an AAV disclosed herein.

In another aspect, the instant disclosure provides a packaging system for recombinant preparation of an AAV, wherein the packaging system comprises:
(a) a Rep nucleotide sequence encoding one or more AAV Rep proteins;
(b) Cap nucleotide sequence encoding one or more AAV Clade F capsid proteins as disclosed herein; and
(c) a correction genome or transfer genome as disclosed herein, wherein the packaging system is operative in a cell for enclosing the correction genome or transfer genome in the capsid to form the AAV.

In certain embodiments, the packaging system comprises a first vector comprising the Rep nucleotide sequence and the Cap nucleotide sequence, and a second vector comprising the correction genome. In certain embodiments, the Rep nucleotide sequence encodes an AAV2 Rep protein. In certain embodiments, the AAV2 Rep protein is 78/68 or Rep 68/52. In certain embodiments, the AAV2 Rep protein comprises an amino acid sequence having a minimum percent sequence identity to the AAV2 Rep amino acid sequence of SEQ ID NO: 22, wherein the minimum percent sequence identity is at least 70% across the length of the amino acid sequence encoding the AAV2 Rep protein.

In certain embodiments, the packaging system further comprises a third vector, wherein the third vector is a helper virus vector. In certain embodiments, the helper virus vector is an independent third vector. In certain embodiments, the helper virus vector is integral with the first vector. In certain embodiments, the helper virus vector is integral with the second vector. In certain embodiments, the third vector comprises genes encoding helper virus proteins.

certain embodiments, the helper virus is selected from the group consisting of adenovirus, herpes virus, vaccinia virus, and cytomegalovirus (CMV). In certain embodiments, the helper virus is adenovirus. In certain embodiments, the adenovirus genome comprises one or more adenovirus RNA genes selected from the group consisting of E1, E4 and VA. In certain embodiments, the helper virus is herpes simplex virus (HSV). In certain embodiments, the HSV genome comprises one or more of HSV genes selected from the group consisting of UL5/8/52, ICPO, ICP4, ICP22 and UL30/UL42.

In certain embodiments, the first vector and the third vector are contained within a first transfecting plasmid. In certain embodiments, the nucleotides of the second vector and the third vector are contained within a second transfecting plasmid. In certain embodiments, the nucleotides of the first vector and the third vector are cloned into a recombinant helper virus. In certain embodiments, the nucleotides of the second vector and the third vector are cloned into a recombinant helper virus.

In another aspect, the instant disclosure provides a method for recombinant preparation of an AAV, the method comprising introducing a packaging system as described herein into a cell under conditions operative for enclosing the correction genome or the transfer genome in the capsid to form the AAV.

BRIEF DESCRIPTION OF THE DRAWINGS

FIG. 1A is a map of the pHMI-hPAH-hAC-008 vector.
FIG. 1B is a map of the pHMI-hPAH-h1C-007 vector.
FIG. 1C is a map of the pHMIA-hPAH-hI1C-032.1 vector.

FIG. 17A, 17B, 17C, 17D, 17E depict vector maps of pKITR-hPAH-mAC-006-HCR, pKITR-hPAH-hI1C-032-

Figure 2:
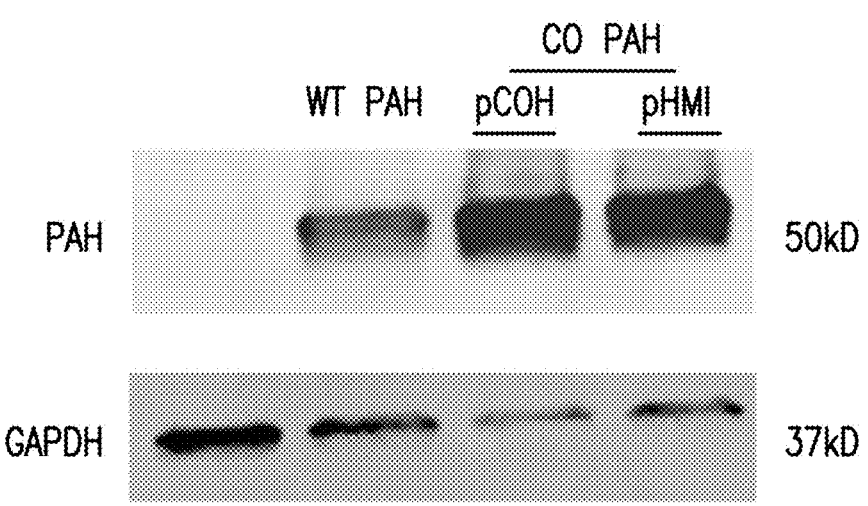
FIG. 2 is an image of Western blot showing the expression of human PAH from the pCOH-WT-PAH ("WT PAH"), pCOH-CO-PAH ("CO PAH pCOH"), and pHMI-CO-PAH ("CO PAH pHMI") vectors. $5 \times 10^5$ HEK 293 cells were transfected with 1 μg of vector. Lysate of the cells was collected 48 hours after transfection. The expression of human PAH was detected by Western blotting with an anti-PAH antibody (Sigma HPA031642). The amount of GAPDH protein as detected by an anti-GAPDH antibody (Millipore MAB 374) was shown as a loading control.

HCR, pKITR-hPAH-mAC-006-SD.3, pHMIA2-hPAH-hI1C-032-SD.3, and pHMIA2-hPAH-mAC-006-HBB1, respectively.

DETAILED DESCRIPTION

The instant disclosure provided adeno-associated virus (AAV) compositions that can restore PAH gene function in a cell. Also provide are packaging systems for making the adeno-associated virus compositions.

I. DEFINITIONS

As used herein, the term "replication-defective adeno-associated virus" refers to an AAV comprising a genome lacking Rep and Cap genes.

As used herein, the term "PAH gene" refers to the phenylalanine hydroxylase (PAH) gene, including but not limited to the coding regions, exons, introns, 5' UTR, 3' UTR, and transcriptional regulatory regions of the PAH gene. The human PAH gene is identified by Entrez Gene ID 5053. An exemplary nucleotide sequence of a PAH mRNA is provided as SEQ ID NO: 24. An exemplary amino acid sequence of a PAH polypeptide is provided as SEQ ID NO: 23.

As used herein, the term "correcting a mutation in a PAH gene" refers to the insertion, deletion, or substitution of one or more nucleotides at a target locus in a mutant PAH gene to create a PAH gene that is capable of expressing a wild-type PAH polypeptide. In certain embodiments, "correcting a mutation in a PAH gene" involves inserting a nucleotide sequence encoding at least a portion of a wild-type PAH polypeptide or a functional equivalent thereof into the mutant PAH gene, such that a wild-type PAH polypeptide or a functional equivalent thereof is expressed from the mutant PAH gene locus (e.g., under the control of an endogenous PAH gene promoter).

As used herein, the term "correction genome" refers to a recombinant AAV genome that is capable of integrating an editing element (e.g., one or more nucleotides or an internucleotide bond) via homologous recombination into a target locus to correct a genetic defect in a PAH gene. In certain embodiments, the target locus is in the human PAH gene. The skilled artisan will appreciate that the portion of a correction genome comprising the 5' homology arm, editing element, and 3' homology arm can be in the sense or antisense orientation relative to the target locus (e.g., the human PAH gene).

As used herein, the term "editing element" refers to the portion of a correction genome that when integrated at a target locus modifies the target locus. An editing element can mediate insertion, deletion, or substitution of one or more nucleotides at the target locus. As used herein, the term "target locus" refers to a region of a chromosome or an internucleotide bond (e.g., a region or an internucleotide bond of the human PAH gene) that is modified by an editing element.

As used herein, the term "homology arm" refers to a portion of a correction genome positioned 5' or 3' of an editing element that is substantially identical to the genome flanking a target locus. In certain embodiments, the target locus is in a human PAH gene, and the homology arm comprises a sequence substantially identical to the genome flanking the target locus.

As used herein, the term "Clade F capsid protein" refers to an AAV VP1, VP2, or VP3 capsid protein that comprises an amino acid sequence having at least 90% identity with the VP1, VP2, or VP3 amino acid sequences set forth, respectively, in amino acids 1-736, 138-736, and 203-736 of SEQ ID NO: 1 herein.

As used herein, the identity between two nucleotide sequences or between two amino acid sequences is determined by the number of identical nucleotides or amino acids in alignment divided by the full length of the longer nucleotide or amino acid sequence.

As used herein, the term "a disease or disorder associated with a PAH gene mutation" refers to any disease or disorder caused by, exacerbated by, or genetically linked with variation of a PAH gene. In certain embodiments, the disease or disorder associated with a PAH gene mutation is phenylketonuria (PKU).

As used herein, the term "silently altered" refers to alteration of a coding sequence or a stuffer-inserted coding sequence of a gene (e.g., by nucleotide substitution) without changing the amino acid sequence of the polypeptide encoded by the coding sequence or stuffer-inserted coding sequence. Codon alteration can be conducted by any method known in the art (e.g., as described in Mauro & Chappell (2014) Trends Mol Med. 20(11):604-13, which is incorporated by reference herein in its entirety). Such silent alteration is advantageous in that it reduces the likelihood of integration of the correction genome into loci of other genes or pseudogenes paralogous to the target gene. Such silent alteration also reduces the homology between the editing element and the target gene, thereby reducing undesired integration mediated by the editing element rather than by a homology arm.

As used herein, the term "coding sequence" refers to the portion of a complementary DNA (cDNA) that encodes a polypeptide, starting at the start codon and ending at the stop codon. A gene may have one or more coding sequences due to alternative splicing and/or alternative translation initiation. A coding sequence may either be wild-type or silently altered. An exemplary wild-type PAH coding sequence is set forth in SEQ ID NO: 24.

As used herein, the term "intron-inserted coding sequence" of a gene refers to a nucleotide sequence comprising one or more introns inserted in a coding sequence of the gene. In certain embodiments, at least one of the introns is a nonnative intron, i.e., having a sequence different from a native intron of the gene. In certain embodiments, all of the introns in the intron-inserted coding sequence are nonnative introns. A nonnative intron can have the sequence of an intron from a different species or the sequence of an intron in a different gene from the same species. Alternatively or additionally, at least a portion of a nonnative intron sequence can be synthetic. A skilled worker will appreciate that nonnative intron sequences can be designed to mediate RNA splicing by introducing any consensus splicing motifs known in the art. Exemplary consensus splicing motifs are provided in Sibley et al., (2016) Nature Reviews Genetics, 17, 407-21, which is incorporated by reference herein in its entirety. Insertion of a nonnative intron may promote the efficiency and robustness of vector packaging, as stuffer sequences allow adjustments of the vector to reach an optimal size (e.g., 4.5-4.8 kb). In certain embodiments, at least one of the introns is a native intron of the gene. In certain embodiments, all of the introns in the intron-inserted coding sequence are native introns of the gene. The nonnative or native introns can be inserted at any internucleotide bonds in the coding sequence. In certain embodiments, one or more nonnative or native introns are inserted at internucleotide bonds predicted to promote efficient splicing (see e.g., Zhang (1998) Human Molecular Genetics, 7(5):919-32, which is incorporated by reference herein in its entirety). In certain embodiments, one or more nonnative or native introns are inserted at internucleotide bonds that link two endogenous exons.

As used herein, the term "ribosomal skipping element" refers to a nucleotide sequence encoding a short peptide sequence capable of causing generation of two peptide chains from translation of one mRNA molecule. In certain embodiments, the ribosomal skipping element encodes a peptide comprising a consensus motif of $X_1X_2EX_3NPGP$, wherein $X_1$ is D or G, $X_2$ is V or I, and $X_3$ is any amino acid (SEQ ID NO: 75). In certain embodiments, the ribosomal skipping element encodes thosea-asigna virus 2A peptide (T2A), porcine teschovirus-1 2A peptide (P2A), foot-and-mouth disease virus 2A peptide (F2A), equine rhinitis A virus 2A peptide (E2A), cytoplasmic polyhedrosis virus 2A peptide (BmCPV 2A), or flacherie virus of *B. mori* 2A peptide (BmIFV 2A). Exemplary amino acid sequences of T2A peptide and P2A peptide are set forth in SEQ ID NOs: 76 and 77, respectively. Exemplary nucleotide sequences of T2A element and P2A element are set forth in SEQ ID NOs: 78 and 79, respectively. In certain embodiments, the ribosomal skipping element encodes a peptide that further comprises a sequence of Gly-Ser-Gly at the N terminus, optionally wherein the sequence of Gly-Ser-Gly is encoded by the nucleotide sequence of GGCAGCGGA. While not wishing to be bound by theory, it is hypothesized that ribosomal skipping elements function by: terminating translation of the first peptide chain and re-initiating translation of the second peptide chain; or by cleavage of a peptide bond in the peptide sequence encoded by the ribosomal skipping element by an intrinsic protease activity of the encoded peptide, or by another protease in the environment (e.g., cytosol).

As used herein, the term "ribosomal skipping peptide" refers to a peptide encoded by a ribosomal skipping element.

As used herein, the term "polyadenylation sequence" refers to a DNA sequence that when transcribed into RNA constitutes a polyadenylation signal sequence. The polyadenylation sequence can be native (e.g., from the PAH gene) or exogenous. The exogenous polyadenylation sequence can be a mammalian or a viral polyadenylation sequence (e.g., an SV40 polyadenylation sequence).

In the instant disclosure, nucleotide positions in a PAH gene are specified relative to the first nucleotide of the start codon. The first nucleotide of a start codon is position 1; the nucleotides 5' to the first nucleotide of the start codon have negative numbers; the nucleotides 3' to the first nucleotide of the start codon have positive numbers. As used herein, nucleotide 1 of the human PAH gene is nucleotide 5,473 of the NCBI Reference Sequence: NG_008690.1, and nucleotide-1 of the human PAH gene is nucleotide 5,472 of the NCBI Reference Sequence: NG_008690.1.

In the instant disclosure, exons and introns in a PAH gene are specified relative to the exon encompassing the first nucleotide of the start codon, which is nucleotide 5473 of the NCBI Reference Sequence: NG_008690.1. The exon encompassing the first nucleotide of the start codon is exon 1. Exons 3' to exon 1 are from 5' to 3': exon 2, exon 3, etc. Introns 3' to exon 1 are from 5' to 3': intron 1, intron 2, etc. Accordingly, the PAH gene comprises from 5' to 3': exon 1, intron 1, exon 2, intron 2, exon 3, etc. As used herein, exon 1 of the human PAH gene is nucleotides 5001-5532 of the NCBI Reference Sequence: NG_008690.1, and intron 1 of the human PAH gene is nucleotides 5533-9704 of the NCBI Reference Sequence: NG_008690.1.

As used herein, the term "integration" refers to introduction of an editing element into a target locus (e.g., of a PAH gene) by homologous recombination between a correction genome and the target locus. Integration of an editing element can result in substitution, insertion and/or deletion of one or more nucleotides in a target locus (e.g., of a PAH gene).

As used herein, the term "integration efficiency of the editing element into the target locus" refers to the percentage of cells in a transduced population in which integration of the editing element into the target locus has occurred.

As used herein, the term "allelic frequency of integration of the editing element into the target locus" refers to the percentage of alleles in a population of transduced cells in which integration of the editing element into the target locus has occurred.

As used herein, the term "standard AAV administration conditions" refers to transduction of human hepatocytes implanted into a mouse following hepatocyte ablation, wherein the AAV is administered intravenously at a dose of $1 \times 10^{13}$ vector genomes per kilogram of body weight, as provided by the method of Example 5, section b.

As used herein, the term "effective amount" in the context of the administration of an AAV to a subject refers to the amount of the AAV that achieves a desired prophylactic or therapeutic effect.

II. ADENO-ASSOCIATED VIRUS COMPOSITIONS

In one aspect, provided herein are novel replication-defective AAV compositions useful for restoring PAH expression in cells with reduced or otherwise defective PAH gene function. Such AAV compositions are highly efficient at correcting mutations in the PAH gene or restoring PAH expression, and do not require cleavage of the genome at the target locus by the action of an exogenous nuclease (e.g., a meganuclease, a zinc finger nuclease, a transcriptional activator-like nuclease (TALEN), or an RNA-guided nuclease such as a Cas9) to facilitate such correction. Accordingly, in certain embodiments, the AAV composition disclosed herein does not comprise an exogenous nuclease or a nucleotide sequence that encodes an exogenous nuclease.

In certain embodiments, the AAV disclosed herein comprise: an AAV capsid; and a correction genome for editing a target locus in a PAH gene. The AAV capsid proteins that can be used in the AAV compositions disclosed herein include without limitation AAV capsid proteins and derivatives thereof of Clade A AAVs, Clade B AAVs, Clade C AAVs, Clade D AAVs, Clade E AAVs, and Clade F AAVs. In certain embodiments, the AAV capsid protein is an AAV capsid protein or a derivative thereof of AAV1, AAV2, AAV3, AAV4, AAV5, AAV6, AAV7, AAV8, AAV9, or AAVrh10. In certain embodiments, the AAV capsid comprises an AAV Clade F capsid protein.

Any AAV Clade F capsid protein or derivative thereof can be used in the AAV compositions disclosed herein. For example, in certain embodiments, the AAV Clade F capsid protein comprises an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the amino acid sequence of amino acids 203-736 of SEQ ID NO: 2, 3, 4, 5, 6, 7, 8, 9, 10, 11, 12, 13, 15, 16, or 17. In certain embodiments, the AAV Clade F capsid protein comprises an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the amino acid sequence of amino acids 203-736 of SEQ ID NO: 2, 3, 4, 5, 6, 7, 8, 9, 10, 11, 12, 13, 15, 16, or 17, wherein: the amino acid in the capsid protein corresponding to amino acid 206 of SEQ ID NO: 2 is C; the amino acid in the capsid protein corresponding to amino acid 296 of SEQ ID NO: 2 is H; the amino acid in the capsid protein corresponding to amino acid 312 of SEQ ID NO: 2 is Q; the amino acid in the capsid protein corresponding to amino acid 346 of SEQ ID NO: 2 is A; the amino acid in the capsid protein corresponding to amino acid 464 of SEQ ID NO: 2 is N; the amino acid in the capsid protein corresponding to amino acid 468 of SEQ ID NO: 2 is S; the amino acid in the capsid protein corresponding to amino acid 501 of SEQ ID NO: 2 is I; the amino acid in the capsid protein corresponding to amino acid 505 of SEQ ID NO: 2 is R; the amino acid in the capsid protein corresponding to amino acid 590 of SEQ ID NO: 2 is R; the amino acid in the capsid protein corresponding to amino acid 626 of SEQ ID NO: 2 is G or Y; the amino acid in the capsid protein corresponding to amino acid 681 of SEQ ID NO: 2 is M; the amino acid in the capsid protein corresponding to amino acid 687 of SEQ ID NO: 2 is R; the amino acid in the capsid protein corresponding to amino acid 690 of SEQ ID NO: 2 is K; the amino acid in the capsid protein corresponding to amino acid 706 of SEQ ID NO: 2 is C; or, the amino acid in the capsid protein corresponding to amino acid 718 of SEQ ID NO: 2 is G. In certain embodiments, the amino acid in the capsid protein corresponding to amino acid 626 of SEQ ID NO: 2 is G, and the amino acid in the capsid protein corresponding to amino acid 718 of SEQ ID NO: 2 is G. In certain embodiments, the amino acid in the capsid protein corresponding to amino acid 296 of SEQ ID NO: 2 is H, the amino acid in the capsid protein corresponding to amino acid 464 of SEQ ID NO: 2 is N, the amino acid in the capsid protein corresponding to amino acid 505 of SEQ ID NO: 2 is R, and the amino acid in the capsid protein corresponding to amino acid 681 of SEQ ID NO: 2 is M. In certain embodiments, the amino acid in the capsid protein corresponding to amino acid 505 of SEQ ID NO: 2 is R, and the amino acid in the capsid protein corresponding to amino acid 687 of SEQ ID NO: 2 is R. In certain embodiments, the amino acid in the capsid protein corresponding to amino acid 346 of SEQ ID NO: 2 is A, and the amino acid in the capsid protein corresponding to amino acid 505 of SEQ ID NO: 2 is R. In certain embodiments, the amino acid in the capsid protein corresponding to amino acid 501 of SEQ ID NO: 2 is I, the amino acid in the capsid protein corresponding to amino acid 505 of SEQ ID NO: 2 is R, and the amino acid in the capsid protein corresponding to amino acid 706 of SEQ ID NO: 2 is C. In certain embodiments, the AAV Clade F capsid protein comprises the amino acid sequence of amino acids 203-736 of SEQ ID NO: 2, 3, 4, 6, 7, 10, 11, 12, 13, 15, 16, or 17.

For example, in certain embodiments, the AAV Clade F capsid protein comprises an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the amino acid sequence of amino acids 138-736 of SEQ ID NO: 2, 3, 4, 5, 6, 7, 8, 9, 10, 11, 12, 13, 15, 16, or 17. In certain embodiments, the AAV Clade F capsid protein comprises an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the amino acid sequence of amino acids 138-736 of SEQ ID NO: 2, 3, 4, 5, 6, 7, 8, 9, 10, 11, 12, 13, 15, 16, or 17, wherein: the amino acid in the capsid protein corresponding to amino acid 151 of SEQ ID NO: 2 is R; the amino acid in the capsid protein corresponding to amino acid 160 of SEQ ID NO: 2 is D; the amino acid in the capsid protein corresponding to amino acid 206 of SEQ ID NO: 2 is C; the amino acid in the capsid protein corresponding to amino acid 296 of SEQ ID NO: 2 is H; the amino acid in the capsid protein corresponding to amino acid 312 of SEQ ID NO: 2 is Q; the amino acid in the capsid protein corresponding to amino acid 346 of SEQ ID NO: 2 is A; the amino acid in the capsid protein corresponding to amino acid 464 of SEQ ID NO: 2 is N; the amino acid in the capsid protein corresponding to amino acid 468 of SEQ ID NO: 2 is S; the amino acid in the capsid protein corresponding to amino acid 501 of SEQ ID NO: 2 is I; the amino acid in the capsid protein corresponding to amino acid 505 of SEQ ID NO: 2 is R; the amino acid in the capsid protein corresponding to amino acid 590 of SEQ ID NO: 2 is R; the amino acid in the capsid protein corresponding to amino acid 626 of SEQ ID NO: 2 is G or Y; the amino acid in the capsid protein corresponding to amino acid 681 of SEQ ID NO: 2 is M; the amino acid in the capsid protein corresponding to amino acid 687 of SEQ ID NO: 2 is R; the amino acid in the capsid protein corresponding to amino acid 690 of SEQ ID NO: 2 is K; the amino acid in the capsid protein corresponding to amino acid 706 of SEQ ID NO: 2 is C; or, the amino acid in the capsid protein corresponding to amino acid 718 of SEQ ID NO: 2 is G. In certain embodiments, the amino acid in the capsid protein corresponding to amino acid 626 of SEQ ID NO: 2 is G, and the amino acid in the capsid protein corresponding to amino acid 718 of SEQ ID NO: 2 is G. In certain embodiments, the amino acid in the capsid protein corresponding to amino acid 296 of SEQ ID NO: 2 is H, the amino acid in the capsid protein corresponding to amino acid 464 of SEQ ID NO: 2 is N, the amino acid in the capsid protein corresponding to amino acid 505 of SEQ ID NO: 2 is R, and the amino acid in the capsid protein corresponding to amino acid 681 of SEQ ID NO: 2 is M. In certain embodiments, the amino acid in the capsid protein corresponding to amino acid 505 of SEQ ID NO: 2 is R, and the amino acid in the capsid protein corresponding to amino acid 687 of SEQ ID NO: 2 is R. In certain embodiments, the amino acid in the capsid protein corresponding to amino acid 346 of SEQ ID NO: 2 is A, and the amino acid in the capsid protein corresponding to amino acid 505 of SEQ ID NO: 2 is R. In certain embodiments, the amino acid in the capsid protein corresponding to amino acid 501 of SEQ ID NO: 2 is I, the amino acid in the capsid protein corresponding to amino acid 505 of SEQ ID NO: 2 is R, and the amino acid in the capsid protein corresponding to amino acid 706 of SEQ ID NO: 2 is C. In certain embodiments, the AAV Clade F capsid protein comprises the amino acid sequence of amino acids 138-736 of SEQ ID NO: 2, 3, 4, 5, 6, 7, 9, 10, 11, 12, 13, 15, 16, or 17.

For example, in certain embodiments, the AAV Clade F capsid protein comprises an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the amino acid sequence of amino acids 1-736 of SEQ ID NO: 2, 3, 4, 5, 6, 7, 8, 9, 10, 11, 12, 13, 15, 16, or 17. In certain embodiments, the AAV Clade F capsid protein comprises an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the amino acid sequence of amino acids 1-736 of SEQ ID NO: 2, 3, 4, 5, 6, 7, 8, 9, 10, 11, 12, 13, 15, 16, or 17, wherein: the amino acid in the capsid protein corresponding to amino acid 2 of SEQ ID NO: 2 is T; the amino acid in the capsid protein corresponding to amino acid 65 of SEQ ID NO: 2 is I; the amino acid in the capsid protein corresponding to amino acid 68 of SEQ ID NO: 2 is V; the amino acid in the capsid protein corresponding to amino acid 77 of SEQ ID NO: 2 is R; the amino acid in the capsid protein corresponding to amino acid 119 of SEQ ID NO: 2 is L; the amino acid in the capsid protein corresponding to amino acid 151 of SEQ ID NO: 2 is R; the amino acid in the capsid protein corresponding to amino acid 160 of SEQ ID NO: 2 is D; the amino acid in the capsid protein corresponding to amino acid 206 of SEQ ID NO: 2 is C; the amino acid in the capsid protein corresponding to amino acid 296 of SEQ ID NO: 2 is H; the amino acid in the capsid protein corresponding to amino acid 312 of SEQ ID NO: 2 is Q; the amino acid in the capsid protein corresponding to amino acid 346 of SEQ ID NO: 2 is A; the amino acid in the capsid protein corresponding to amino acid 464 of SEQ ID NO: 2 is N; the amino acid in the capsid protein corresponding to amino acid 468 of SEQ ID NO: 2 is S; the amino acid in the capsid protein corresponding to amino acid 501 of SEQ ID NO: 2 is I; the amino acid in the capsid protein corresponding to amino acid 505 of SEQ ID NO: 2 is R; the amino acid in the capsid protein corresponding to amino acid 590 of SEQ ID NO: 2 is R; the amino acid in the capsid protein corresponding to amino acid 626 of SEQ ID NO: 2 is G or Y; the amino acid in the capsid protein corresponding to amino acid 681 of SEQ ID NO: 2 is M; the amino acid in the capsid protein corresponding to amino acid 687 of SEQ ID NO: 2 is R; the amino acid in the capsid protein corresponding to amino acid 690 of SEQ ID NO: 2 is K; the amino acid in the capsid protein corresponding to amino acid 706 of SEQ ID NO: 2 is C; or, the amino acid in the capsid protein corresponding to amino acid 718 of SEQ ID NO: 2 is G. In certain embodiments, the amino acid in the capsid protein corresponding to amino acid 2 of SEQ ID NO: 2 is T, and the amino acid in the capsid protein corresponding to amino acid 312 of SEQ ID NO: 2 is Q. In certain embodiments, the amino acid in the capsid protein corresponding to amino acid 65 of SEQ ID NO: 2 is I, and the amino acid in the capsid protein corresponding to amino acid 626 of SEQ ID NO: 2 is Y. In certain embodiments, the amino acid in the capsid protein corresponding to amino acid 77 of SEQ ID NO: 2 is R, and the amino acid in the capsid protein corresponding to amino acid 690 of SEQ ID NO: 2 is K. In certain embodiments, the amino acid in the capsid protein corresponding to amino acid 119 of SEQ ID NO: 2 is L, and the amino acid in the capsid protein corresponding to amino acid 468 of SEQ ID NO: 2 is S. In certain embodiments, the amino acid in the capsid protein corresponding to amino acid 626 of SEQ ID NO: 2 is G, and the amino acid in the capsid protein corresponding to amino acid 718 of SEQ ID NO: 2 is G. In certain embodiments, the amino acid in the capsid protein corresponding to amino acid 296 of SEQ ID NO: 2 is H, the amino acid in the capsid protein corresponding to amino acid 464 of SEQ ID NO: 2 is N, the amino acid in the capsid protein corresponding to amino acid 505 of SEQ ID NO: 2 is R, and the amino acid in the capsid protein corresponding to amino acid 681 of SEQ ID NO: 2 is M. In certain embodiments, the amino acid in the capsid protein corresponding to amino acid 505 of SEQ ID NO: 2 is R, and the amino acid in the capsid protein corresponding to amino acid 687 of SEQ ID NO: 2 is R. In certain embodiments, the amino acid in the capsid protein corresponding to amino acid 346 of SEQ ID NO: 2 is A, and the amino acid in the capsid protein corresponding to amino acid 505 of SEQ ID NO: 2 is R. In certain embodiments, the amino acid in the capsid protein corresponding to amino acid 501 of SEQ ID NO: 2 is I, the amino acid in the capsid protein corresponding to amino acid 505 of SEQ ID NO: 2 is R, and the amino acid in the capsid protein corresponding to amino acid 706 of SEQ ID NO: 2 is C. In certain embodiments, the AAV Clade F capsid protein comprises the amino acid sequence of amino acids 1-736 of SEQ ID NO: 2, 3, 4, 5, 6, 7, 8, 9, 10, 11, 12, 13, 15, 16, or 17.

In certain embodiments, the AAV capsid comprises two or more of: (a) a Clade F capsid protein comprising the amino acid sequence of amino acids 203-736 of SEQ ID NO: 2, 3, 4, 6, 7, 10, 11, 12, 13, 15, 16, or 17; (b) a Clade F capsid protein comprising the amino acid sequence of amino acids 138-736 of SEQ ID NO: 2, 3, 4, 5, 6, 7, 9, 10, 11, 12, 13, 15, 16, or 17; and (c) a Clade F capsid protein comprising the amino acid sequence of amino acids 1-736 of SEQ ID NO: 2, 3, 4, 5, 6, 7, 8, 9, 10, 11, 12, 13, 15, 16, or 17. In certain embodiments, the AAV capsid comprises: (a) a Clade F capsid protein having an amino acid sequence consisting of amino acids 203-736 of SEQ ID NO: 2, 3, 4, 6, 7, 10, 11, 12, 13, 15, 16, or 17; (b) a Clade F capsid protein having an amino acid sequence consisting of amino acids 138-736 of SEQ ID NO: 2, 3, 4, 5, 6, 7, 9, 10, 11, 12, 13, 15, 16, or 17; and (c) a Clade F capsid protein having an amino acid sequence consisting of amino acids 1-736 of SEQ ID NO: 2, 3, 4, 5, 6, 7, 8, 9, 10, 11, 12, 13, 15, 16, or 17.

In certain embodiments, the AAV capsid comprises one or more of: (a) a Clade F capsid protein comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the sequence of amino acids 203-736 of SEQ ID NO: 8; (b) a Clade F capsid protein comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the sequence of amino acids 138-736 of SEQ ID NO: 8; and (c) a Clade F capsid protein comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the sequence of amino acids 1-736 of SEQ ID NO: 8. In certain embodiments, the AAV capsid comprises one or more of: (a) a Clade F capsid protein comprising the amino acid sequence of amino acids 203-736 of SEQ ID NO: 8; (b) a Clade F capsid protein comprising the amino acid sequence of amino acids 138-736 of SEQ ID NO: 8; and (c) a Clade F capsid protein comprising the amino acid sequence of amino acids 1-736 of SEQ ID NO: 8. In certain embodiments, the AAV capsid comprises two or more of: (a) a Clade F capsid protein comprising the amino acid sequence of amino acids 203-736 of SEQ ID NO: 8; (b) a Clade F capsid protein comprising the amino acid sequence of amino acids 138-736 of SEQ ID NO: 8; and (c) a Clade F capsid protein comprising the amino acid sequence of amino acids 1-736 of SEQ ID NO: 8. In certain embodiments, the AAV capsid comprises: (a) a Clade F capsid protein having an amino acid sequence consisting of amino acids 203-736 of SEQ ID NO: 8; (b) a Clade F capsid protein having an amino acid sequence consisting of amino acids 138-736 of SEQ ID NO: 8; and (c) a Clade F capsid protein having an amino acid sequence consisting of amino acids 1-736 of SEQ ID NO: 8.

In certain embodiments, the AAV capsid comprises one or more of: (a) a Clade F capsid protein comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the sequence of amino acids 203-736 of SEQ ID NO: 11; (b) a Clade F capsid protein comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the sequence of amino acids 138-736 of SEQ ID NO: 11; and (c) a Clade F capsid protein comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the sequence of amino acids 1-736 of SEQ ID NO: 11. In certain embodiments, the AAV capsid comprises one or more of: (a) a Clade F capsid protein comprising the amino acid sequence of amino acids 203-736 of SEQ ID NO: 11; (b) a Clade F capsid protein comprising the amino acid sequence of amino acids 138-736 of SEQ ID NO: 11; and (c) a Clade F capsid protein comprising the amino acid sequence of amino acids 1-736 of SEQ ID NO: 11. In certain embodiments, the AAV capsid comprises two or more of: (a) a Clade F capsid protein comprising the amino acid sequence of amino acids 203-736 of SEQ ID NO: 11; (b) a Clade F capsid protein comprising the amino acid sequence of amino acids 138-736 of SEQ ID NO: 11; and (c) a Clade F capsid protein comprising the amino acid sequence of amino acids 1-736 of SEQ ID NO: 11. In certain embodiments, the AAV capsid comprises: (a) a Clade F capsid protein having an amino acid sequence consisting of amino acids 203-736 of SEQ ID NO: 11; (b) a Clade F capsid protein having an amino acid sequence consisting of amino acids 138-736 of SEQ ID NO: 11; and (c) a Clade F capsid protein having an amino acid sequence consisting of amino acids 1-736 of SEQ ID NO: 11.

In certain embodiments, the AAV capsid comprises one or more of: (a) a Clade F capsid protein comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the sequence of amino acids 203-736 of SEQ ID NO: 13; (b) a Clade F capsid protein comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the sequence of amino acids 138-736 of SEQ ID NO: 13; and (c) a Clade F capsid protein comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the sequence of amino acids 1-736 of SEQ ID NO: 13. In certain embodiments, the AAV capsid comprises one or more of: (a) a Clade F capsid protein comprising the amino acid sequence of amino acids 203-736 of SEQ ID NO: 13; (b) a Clade F capsid protein comprising the amino acid sequence of amino acids 138-736 of SEQ ID NO: 13; and (c) a Clade F capsid protein comprising the amino acid sequence of amino acids 1-736 of SEQ ID NO: 13. In certain embodiments, the AAV capsid comprises two or more of: (a) a Clade F capsid protein comprising the amino acid sequence of amino acids 203-736 of SEQ ID NO: 13; (b) a Clade F capsid protein comprising the amino acid sequence of amino acids 138-736 of SEQ ID NO: 13; and (c) a Clade F capsid protein comprising the amino acid sequence of amino acids 1-736 of SEQ ID NO: 13. In certain embodiments, the AAV capsid comprises: (a) a Clade F capsid protein having an amino acid sequence consisting of amino acids 203-736 of SEQ ID NO: 13; (b) a Clade F capsid protein having an amino acid sequence consisting of amino acids 138-736 of SEQ ID NO: 13; and (c) a Clade F capsid protein having an amino acid sequence consisting of amino acids 1-736 of SEQ ID NO: 13.

In certain embodiments, the AAV capsid comprises one or more of: (a) a Clade F capsid protein comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the sequence of amino acids 203-736 of SEQ ID NO: 16; (b) a Clade F capsid protein comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the sequence of amino acids 138-736 of SEQ ID NO: 16; and (c) a Clade F capsid protein comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the sequence of amino acids 1-736 of SEQ ID NO: 16. In certain embodiments, the AAV capsid comprises one or more of: (a) a Clade F capsid protein comprising the amino acid sequence of amino acids 203-736 of SEQ ID NO: 16; (b) a Clade F capsid protein comprising the amino acid sequence of amino acids 138-736 of SEQ ID NO: 16; and (c) a Clade F capsid protein comprising the amino acid sequence of amino acids 1-736 of SEQ ID NO: 16. In certain embodiments, the AAV capsid comprises two or more of: (a) a Clade F capsid protein comprising the amino acid sequence of amino acids 203-736 of SEQ ID NO: 16; (b) a Clade F capsid protein comprising the amino acid sequence of amino acids 138-736 of SEQ ID NO: 16; and (c) a Clade F capsid protein comprising the amino acid sequence of amino acids 1-736 of SEQ ID NO: 16. In certain embodiments, the AAV capsid comprises: (a) a Clade F capsid protein having an amino acid sequence consisting of amino acids 203-736 of SEQ ID NO: 16; (b) a Clade F capsid protein having an amino acid sequence consisting of amino acids 138-736 of SEQ ID NO: 16; and (c) a Clade F capsid protein having an amino acid sequence consisting of amino acids 1-736 of SEQ ID NO: 16.

Correction genomes useful in the AAV compositions disclosed herein generally comprise: (i) an editing element for editing a target locus in an PAH gene, (ii) a 5' homology arm nucleotide sequence 5' of the editing element having homology to a first genomic region 5' to the target locus, and (iii) a 3' homology arm nucleotide sequence 3' of the editing element having homology to a second genomic region 3' to the target locus, wherein the portion of the correction genome comprising the 5' homology arm, editing element, and 3' homology arm can be in the sense or antisense orientation relative to the PAH gene locus. In certain embodiments, the correction genome comprises a 5' inverted terminal repeat (5' ITR) nucleotide sequence 5' of the 5' homology arm nucleotide sequence, and a 3' inverted terminal repeat (3' ITR) nucleotide sequence 3' of the 3' homology arm nucleotide sequence.

Editing elements used in the correction genomes disclosed herein can mediate insertion, deletion or substitution of one or more nucleotides at the target locus.

In certain embodiments, when correctly integrated by homologous recombination at the target locus, the editing element inserts a nucleotide sequence comprising at least a portion of a PAH coding sequence into a mutant PAH gene, such that a wild-type PAH polypeptide or a functional equivalent thereof is expressed from the mutant PAH gene locus. In certain embodiments, the editing element comprises a complete PAH coding sequence (e.g., a wild-type PAH coding sequence or a silently altered PAH coding sequence). In certain embodiments, the editing element comprises nucleotides 4 to 1359 of a PAH coding sequence. In certain embodiments, the editing element comprises a PAH intron-inserted coding sequence (e.g., comprising an intron inserted in a wild-type or silently altered PAH coding sequence).

In certain embodiments, the PAH coding sequence encodes a wild-type PAH polypeptide (e.g., having the amino acid sequence set forth in SEQ ID NO: 23). In certain embodiments, the PAH coding sequence is wild-type (e.g., comprising the nucleotide sequence set forth in SEQ ID NO: 24). In certain embodiments, the PAH coding sequence is silently altered to be less than 100% (e.g., less than 95%, 90%, 85%, 80%, 75%, 70%, 65%, 60%, 55%, or 50%) identical to the corresponding exons of the wild-type PAH gene. In certain embodiments, the PAH coding sequence comprises the nucleotide sequence set forth in SEQ ID NO: 25). In certain embodiments, the PAH coding sequence comprises the nucleotide sequence set forth in SEQ ID NO: 116).

In certain embodiments, the PAH intron-inserted coding sequence encodes a wild-type PAH polypeptide (e.g., having the amino acid sequence set forth in SEQ ID NO: 23). In certain embodiments, the PAH intron-inserted coding sequence comprises at least one (e.g., 1, 2, 3, 4, 5, 6, 7, 8, 9, 10, 11, or 12) intron inserted in a PAH coding sequence. The intron can comprise a native intron sequence of the PAH gene, an intron sequence from a different species or a different gene from the same species, and/or a synthetic intron sequence. In certain embodiments, the nonnative intron is no more than 100, 200, 300, 400, 500, 600, 700, 800, 900, 1000, 1,500, or 2,000 nucleotides in length. While not wishing to be bound by theory, it is hypothesized that introns can increase transgene expression, for example, by reducing transcriptional silencing and enhancing mRNA export from the nucleus to the cytoplasm. A skilled worker will appreciate that synthetic intron sequences can be designed to mediate RNA splicing by introducing any consensus splicing motifs known in the art (e.g., in Sibley et al., (2016) Nature Reviews Genetics, 17, 407-21, which is incorporated by reference herein in its entirety). Exemplary intron sequences are provided in Lu et al. (2013) Molecular Therapy 21(5): 954-63, and Lu et al. (2017) Hum. Gene Ther. 28(1): 125-34, which are incorporated by reference herein in their entirety. In certain embodiments, the editing element comprises a first intron of a hemoglobin beta gene in any species (e.g., human, mouse, or rabbit). In certain embodiments, the editing element comprises a first intron of a human HBB gene (e.g., comprising a nucleotide sequence at least 90%, 91%, 92%, 93%, 94%, 95%, 96%, 97%, 98%, or 99% identical to SEQ ID NO: 28). In certain embodiments, the editing element comprises a first intron of a mouse HBB gene (e.g., comprising a nucleotide sequence at least 90%, 91%, 92%, 93%, 94%, 95%, 96%, 97%, 98%, or 99% identical to SEQ ID NO: 29). In certain embodiments, the editing element comprises a minute virus of mouse (MVM) intron (e.g., comprising a nucleotide sequence at least 90%, 91%, 92%, 93%, 94%, 95%, 96%, 97%, 98%, or 99% identical to SEQ ID NO: 30).

In certain embodiments, the editing element comprises a chimeric MVM intron (also referred to herein as ChiMVM), e.g., comprising or consisting of a nucleotide sequence of at least 90%, 91%, 92%, 93%, 94%, 95%, 96%, 97%, 98%, or 99% identical to SEQ ID NO: 120. In certain embodiments, the editing element comprises an SV40 intron, e.g., comprising or consisting of a nucleotide sequence of at least 90%, 91%, 92%, 93%, 94%, 95%, 96%, 97%, 98%, or 99% identical to SEQ ID NO: 121. In certain embodiments, the editing element comprises an adenovirus tripartite leader intron (also referred to herein as AdTPL), e.g., comprising or consisting of a nucleotide sequence of at least 90%, 91%, 92%, 93%, 94%, 95%, 96%, 97%, 98%, or 99% identical to SEQ ID NO: 122. In certain embodiments, the editing element comprises a mini 0-globin intron (also referred to herein as MiniBGlobin), e.g., comprising or consisting of a nucleotide sequence of at least 90%, 91%, 92%, 93%, 94%, 95%, 96%, 97%, 98%, or 99% identical to SEQ ID NO: 123. In certain embodiments, the editing element comprises an AdV/Ig chimeric intron (also referred to herein as AdVIgG), e.g., comprising or consisting of a nucleotide sequence of at least 90%, 91%, 92%, 93%, 94%, 95%, 96%, 97%, 98%, or 99% identical to SEQ ID NO: 124. In certain embodiments, the editing element comprises a 0-globin Ig heavy chain intron (also referred to herein as BglobinIg), which is a chimeric intron comprising a 0-globin splice donor region and a IgG heavy chain splice acceptor region, e.g., comprising or consisting of a nucleotide sequence of at least 90%, 91%, 92%, 93%, 94%, 95%, 96%, 97%, 98%, or 99% identical to SEQ ID NO: 125. In certain embodiments, the editing element comprises a Wu MVM intron (also referred to herein as Wu MVM), which is a variant of the wild type MVM intron, e.g., comprising or consisting of a nucleotide sequence of at least 90%, 91%, 92%, 93%, 94%, 95%, 96%, 97%, 98%, or 99% identical to SEQ ID NO: 126. In certain embodiments, the editing element comprises an HCR1 element (also referred to herein as OptHCR), e.g., comprising or consisting of a nucleotide sequence of at least 90%, 91%, 92%, 93%, 94%, 95%, 96%, 97%, 98%, or 99% identical to SEQ ID NO: 127. In certain embodiments, the editing element comprises a 0-globin intron (also referred to herein as Bglobin), e.g., comprising or consisting of a nucleotide sequence of at least 90%, 91%, 92%, 93%, 94%, 95%, 96%, 97%, 98%, or 99% identical to SEQ ID NO: 128. In certain embodiments, the editing element comprises a Factor IX intron (also referred to herein as tFIX or FIX intron), e.g., comprising or consisting of a nucleotide sequence of at least 90%, 91%, 92%, 93%, 94%, 95%, 96%, 97%, 98%, or 99% identical to SEQ ID NO: 129. In certain embodiments, the editing element comprises a ch2BLood intron (also referred to herein as BloodEnh), e.g., comprising or consisting of a nucleotide sequence of at least 90%, 91%, 92%, 93%, 94%, 95%, 96%, 97%, 98%, or 99% identical to SEQ ID NO: 130. In certain embodiments, the PAH intron-inserted coding sequence encodes a wild-type PAH polypeptide (e.g., having the amino acid sequence set forth in SEQ ID NO: 23). In certain embodiments, the PAH intron-inserted coding sequence comprises portions of a PAH coding sequence that when spliced together, form a complete PAH coding sequence. In certain embodiments, the PAH coding sequence is wild-type (e.g., comprising the nucleotide sequence set forth in SEQ ID NO: 24). In certain embodiments, the PAH coding sequence is silently altered to be less than 100% (e.g., less than 95%, 90%, 85%, 80%, 75%, 70%, 65%, 60%, 55%, or 50%) identical to the corresponding exons of the wild-type PAH gene. In certain embodiments, the PAH coding sequence comprises the nucleotide sequence set forth in SEQ ID NO: 25). In certain embodiments, the PAH coding sequence comprises or consists of the nucleotide sequence set forth in SEQ ID NO: 116. In certain embodiments, an intron-inserted PAH coding sequence comprises a nucleotide sequence at least 90%, 91%, 92%, 93%, 94%, 95%, 96%, 97%, 98%, or 99% identical to SEQ ID NO: 116. In certain embodiments, the PAH coding sequence consists of the nucleotide sequence set forth in SEQ ID NO: 116. In certain embodiments, an intron-inserted PAH coding sequence comprises the nucleotide sequence set forth in SEQ ID NO: 80, 81, 82, 131, 132, or 143. In certain embodiments, an intron-inserted PAH coding sequence comprises a nucleotide sequence at least 90%, 91%, 92%, 93%, 94%, 95%, 96%, 97%, 98%, or 99% identical to SEQ ID NO: 80, 81, 82, 131, 132, or 143. In certain embodiments, an intron-inserted PAH coding sequence consists of the nucleotide sequence set forth in SEQ ID NO: 80, 81, 82, 131, 132, or 143.

The intron can be inserted at any position in the PAH coding sequence. In certain embodiments, the intron is inserted at a position corresponding to an internucleotide bond that links two native exons. In certain embodiments, the intron is inserted at a position corresponding to an internucleotide bond that links native exon 8 and exon 9. In certain embodiments, the PAH intron-inserted coding sequence comprises from 5' to 3': a first portion of a PAH coding sequence, the intron, and a second portion of a PAH coding sequence, wherein the first portion and the second portion, when spliced together, form a complete PAH coding sequence (e.g., wild-type PAH coding sequence, or silently altered PAH coding sequence). In certain embodiments, the first portion of the PAH coding sequence comprises the amino acid sequence set forth in SEQ ID NO: 64 or 65, and/or the second portion of the PAH coding sequence comprises the amino acid sequence set forth in SEQ ID NO: 66 or 67. In certain embodiments, the first portion of the PAH coding sequence consist of the amino acid sequence set forth in SEQ ID NO: 64 or 65, and the second portion of the PAH coding sequence consists of the amino acid sequence set forth in SEQ ID NO: 66 or 67. In certain embodiments, the first portion of the PAH coding sequence consist of the amino acid sequence set forth in SEQ ID NO: 65, and the second portion of the PAH coding sequence consists of the amino acid sequence set forth in SEQ ID NO: 67. In certain embodiments, the editing element comprises from 3' to 5': a first portion of a PAH coding sequence consist of the nucleotide sequence set forth in SEQ ID NO: 64, or a silently altered variant thereof (e.g., consisting of the nucleotide sequence set forth in SEQ ID NO: 65); an intron (e.g., consisting the nucleotide sequence set forth in SEQ ID NO: 28, 29, or 30); and a second portion of a PAH coding sequence consist of the nucleotide sequence set forth in SEQ ID NO: 66, or a silently altered variant thereof (e.g., consisting of the nucleotide sequence set forth in SEQ ID NO: 66).

In certain embodiments, the PAH coding sequence comprises a modified splice donor site. In certain embodiments, a splice donor site-modified PAH coding sequence comprises the nucleotide sequence set forth in SEQ ID NO: 138 or 139. In certain embodiments, a splice donor site-modified PAH coding sequence comprises a nucleotide sequence at least 90%, 91%, 92%, 93%, 94%, 95%, 96%, 97%, 98%, or 99% identical to SEQ ID NO: 138 or 139. In certain embodiments, a splice donor site-modified PAH coding sequence consists of the nucleotide sequence set forth in SEQ ID NO: 138 or 139.

In certain embodiments, the editing element further comprises a transcription terminator 3' to the PAH coding sequence or the PAH intron-inserted coding sequence. In certain embodiments, the transcription terminator comprises a polyadenylation sequence (e.g., an exogenous polyadenylation sequence). In certain embodiments, the exogenous polyadenylation sequence comprises an SV40 polyadenylation sequence (e.g., comprising a nucleotide sequence selected from the group consisting of SEQ ID NOs: 31-34, or a sequence complementary thereto). In certain embodiments, the SV40 polyadenylation sequence comprises the nucleotide sequence set forth in SEQ ID NO: 31. In certain embodiments, the editing element comprises from 5' to 3': a PAH coding sequence (e.g., comprising the nucleotide sequence set forth in SEQ ID NO: 25) or a PAH intron-inserted coding sequence (e.g., comprising the nucleotide sequence set forth in SEQ ID NO: 80), and an SV40 polyadenylation sequence (e.g., comprising the nucleotide sequence set forth in SEQ ID NO: 31).

In certain embodiments, the editing element may further comprise an ID cassette 5' to an SV40 polyadenylation sequence (e.g., comprising the nucleotide sequence set forth in SEQ ID NO: 31). The ID cassette provides a sequence that can be used for identification purposes when performing next generation sequencing experiments. In certain embodiments, the ID cassette comprises the nucleotide sequence set forth in SEQ ID NO: 33. In certain embodiments, the ID cassette comprises a nucleotide sequence at least 90%, 91%, 92%, 93%, 94%, 95%, 96%, 97%, 98%, or 99% identical to SEQ ID NO: 33. In certain embodiments, the ID cassette consists of the nucleotide sequence set forth in SEQ ID NO: 33. In certain embodiments, the editing element comprises from 5' to 3': a PAH coding sequence or PAH intron-inserted coding sequence, an ID cassette, and an SV40 polyadenylation sequence.

In certain embodiments, the editing element further comprises a ribosomal skipping element 5' to the PAH coding sequence or the PAH intron-inserted coding sequence. In certain embodiments, the editing element comprises from 5' to 3': a ribosomal skipping element; a PAH coding sequence or a PAH intron-inserted coding sequence; and optionally a transcription terminator (e.g., polyadenylation sequence). In certain embodiments, the aforementioned editing elements can be integrated into an exon of the PAH gene (e.g., the nucleotide 5' to the target locus is in an exon of the PAH gene) by homologous recombination to produce a recombinant sequence comprising from 5' to 3': a portion of the PAH gene 5' to the target locus; the ribosomal skipping element; the PAH coding sequence or PAH intron-inserted coding sequence; and the transcription terminator (e.g., polyadenylation sequence), wherein the ribosomal skipping element is positioned such that it is in frame with the portion of the PAH gene 5' to the target locus and the complete PAH coding sequence. Transcription and translation of this recombinant sequence produces a first polypeptide comprising the amino acid sequence encoded by the portion of the PAH gene 5' to the target locus fused to a 5' portion of the encoded ribosomal skipping peptide, and a second polypeptide comprising a 3' portion of the encoded ribosomal skipping peptide fused to the complete amino acid sequence of the PAH polypeptide.

In certain embodiments, the nucleotide 5' to the target locus is in an exon (e.g., exon 1, exon 2, exon 3, exon 4, exon 5, exon 6, exon 7, exon 8, exon 9, exon 10, exon 11, exon 12, or exon 13) of the PAH gene. In certain embodiments, the target locus is an internucleotide bond in an exon (e.g., exon 1, exon 2, exon 3, exon 4, exon 5, exon 6, exon 7, exon 8, exon 9, exon 10, exon 11, exon 12, or exon 13) of the PAH gene. In certain embodiments, the target locus is a sequence in the PAH gene, wherein the 5' end of this sequence is in an exon (e.g., exon 1, exon 2, exon 3, exon 4, exon 5, exon 6, exon 7, exon 8, exon 9, exon 10, exon 11, exon 12, or exon 13) of the PAH gene or in the intergenic region between Achaete-scute homolog 1 (ASCL1) and PAH, and wherein the 3' end of this sequence can be any nucleotide in the PAH gene or in the intergenic region between PAH and insulin-like growth factor 1 (IGF1). In certain embodiments, the nucleotide 5' to the target locus is in exon 1, exon 2, or exon 3 of the PAH gene. In certain embodiments, the target locus is an internucleotide bond in exon 1, exon 2, or exon 3 of the PAH gene. In certain embodiments, the target locus is a sequence in the PAH gene wherein the 5' end of this sequence is in exon 1, exon 2, or exon 3 of the PAH gene, wherein the 3' end of this sequence can be any nucleotide in the PAH gene or in the intergenic region between PAH and IGF1.

In certain embodiments, the editing element comprises a splice acceptor 5' to the ribosomal skipping element. In certain embodiments, the editing element comprises from 5' to 3': a splice acceptor; a ribosomal skipping element; a PAH coding sequence or a PAH intron-inserted coding sequence; and optionally a transcription terminator (e.g., polyadenylation sequence). In certain embodiments, the aforementioned editing element can be integrated into an intron of the PAH gene (e.g., the nucleotide 5' to the target locus is in an intron of the PAH gene) by homologous recombination to produce a recombinant sequence comprising 5' to 3': a portion of the PAH gene 5' to the target locus including the endogenous splice donor site but not the endogenous splice acceptor of the intron; the splice acceptor; the ribosomal skipping element, the PAH coding sequence or PAH intron-inserted coding sequence; and the transcription terminator (e.g., polyadenylation sequence), wherein the ribosomal skipping element is positioned such that it is in frame with the PAH coding sequence or PAH intron-inserted coding sequence, and such that splicing of the splice acceptor to the endogenous splice donor of the intron of PAH places it in frame with the portion of the PAH gene 5' to the target locus. Expression of this recombinant sequence produces a first polypeptide comprising the amino acid sequence encoded by the portion of the PAH gene 5' to the target locus fused to a 5' portion of the encoded ribosomal skipping peptide, and a second polypeptide comprising the complete amino acid sequence of the PAH polypeptide fused to a 3' portion of the encoded ribosomal skipping peptide.

In certain embodiments, the nucleotide 5' to the target locus is in an intron (e.g., intron 1, intron 2, intron 3, intron 4, intron 5, intron 6, intron 7, intron 8, intron 9, intron 10, intron 11, or intron 12) of the PAH gene. In certain embodiments, the target locus is an internucleotide bond in an intron (e.g., intron 1, intron 2, intron 3, intron 4, intron 5, intron 6, intron 7, intron 8, intron 9, intron 10, intron 11, or intron 12) of the PAH gene. In certain embodiments, the target locus is a sequence in the PAH gene wherein the 5' end of this sequence is in an intron (e.g., intron 1, intron 2, intron 3, intron 4, intron 5, intron 6, intron 7, intron 8, intron 9, intron 10, intron 11, or intron 12) of the PAH gene, wherein the 3' end of this sequence can be any nucleotide in the PAH gene or in the intergenic region between PAH and IGF1. In certain embodiments, the nucleotide 5' to the target locus is in intron 1, intron 2, or intron 3 of the PAH gene. In certain embodiments, the target locus is an internucleotide bond in intron 1, intron 2, or intron 3 of the PAH gene. In certain embodiments, the target locus is a sequence in the PAH gene wherein the 5' end of this sequence is in intron 1, intron 2, or intron 3 of the PAH gene, wherein the 3' end of this sequence can be any nucleotide in the PAH gene or in the intergenic region between PAH and IGF1. In certain embodiments, the nucleotide 5' to the target locus is in intron 1 of the PAH gene. In certain embodiments, the target locus is a sequence in the PAH gene wherein the 5' end of this sequence is in intron 1 of the PAH gene, wherein the 3' end of this sequence can be any nucleotide in the PAH gene or in the intergenic region between PAH and IGF1.

Any and all of the editing elements disclosed herein can further comprise a restriction endonuclease site not present in the wild-type PAH gene. Such restriction endonuclease sites allow for identification of cells that have integration of the editing element at the target locus based upon restriction fragment length polymorphism analysis or by nucleic acid sequencing analysis of the target locus and its flanking regions, or a nucleic acid amplified therefrom.

Any and all of the editing elements disclosed herein can comprise one or more nucleotide alterations that cause one or more amino acid mutations in PAH polypeptide when integrated into the target locus. In certain embodiments, the mutant PAH polypeptide is a functional equivalent of the wild-type PAH polypeptide, i.e., can function as a wild-type PAH polypeptide. In certain embodiments, the functionally equivalent PAH polypeptide further comprises at least one characteristic not found in the wild-type PAH polypeptide, e.g., the ability to stabilize PAH protein (e.g., dimer or tetramer), or the ability to resist protein degradation.

In certain embodiments, an editing element as described herein comprises at least 0, 1, 2, 10, 100, 200, 500, 1000, 1500, 2000, 3000, 4000, or 5000 nucleotides. In certain embodiments, the editing element comprises or consists of 1 to 5000, 1 to 4500, 1 to 4000, 1 to 3000, 1 to 2000, 1 to 1000, 1 to 500, 1 to 200, 1 to 100, 1 to 50, or 1 to 10 nucleotides.

In certain embodiments, an editing element as described herein comprises or consists of a PAH coding sequence or a portion thereof (e.g., the complete human PAH coding sequence, or nucleotides 4 to 1359 of the human PAH coding sequence), a 5' untranslated region (UTR), a 3' UTR, a promoter, a splice donor, a splice acceptor, a sequence encoding a non-coding RNA, an insulator, a gene, or a combination thereof.

In certain embodiments, the editing element comprises a nucleotide sequence at least 70%, 75%, 80%, 85%, 90%, 91%, 92%, 93%, 94%, 95%, 96%, 97%, 98%, 99%, or 99.5% identical to the sequence set forth in SEQ ID NO: 35, 83, or 84. In certain embodiments, the editing element comprises the nucleotide sequence set forth in SEQ ID NO: 35, 83, or 84. In certain embodiments, the editing element consists of the nucleotide sequence set forth in SEQ ID NO: 35, 83, or 84. In certain embodiments, the editing element comprises a nucleotide sequence at least 70%, 75%, 80%, 85%, 90%, 91%, 92%, 93%, 94%, 95%, 96%, 97%, 98%, 99%, or 99.5% identical to the sequence set forth in SEQ ID NO: 147, 148, 149, 150, 151, 152, or 153. In certain embodiments, the editing element comprises the nucleotide sequence set forth in SEQ ID NO: 147, 148, 149, 150, 151, 152, or 153. In certain embodiments, the editing element consists of the nucleotide sequence set forth in SEQ ID NO: 147, 148, 149, 150, 151, 152, or 153.

Homology arms used in the correction genomes disclosed herein can be directed to any region of the PAH gene or a gene nearby on the genome. The precise identity and positioning of the homology arms are determined by the identity of the editing element and/or the target locus.

Homology arms employed in the correction genomes disclosed herein are substantially identical to the genome flanking a target locus (e.g., a target locus in a PAH gene). In certain embodiments, the 5' homology arm has at least about 90% (e.g., at least about 91%, 92%, 93%, 94%, 95%, 96%, 97%, 98%, 99%, or 99.5%) nucleotide sequence identity to a first genomic region 5' to the target locus. In certain embodiments, the 5' homology arm has 100% nucleotide sequence identity to the first genomic region. In certain embodiments, the 3' homology arm has at least about 90% (e.g., at least about 91%, 92%, 93%, 94%, 95%, 96%, 97%, 98%, 99%, or 99.5%) nucleotide sequence identity to a second genomic region 3' to the target locus. In certain embodiments, the 3' homology arm has 100% nucleotide sequence identity to the second genomic region. In certain embodiments, the 5' and 3' homology arms are each at least about 90% (e.g., at least about 91%, 92%, 93%, 94%, 95%, 96%, 97%, 98%, 99%, or 99.5%) identical to the first and second genomic regions flanking the target locus (e.g., a target locus in the PAH gene), respectively. In certain embodiments, the 5' and 3' homology arms are each 100% identical to the first and second genomic regions flanking the target locus (e.g., a target locus in the PAH gene), respectively. In certain embodiments, differences in nucleotide sequences of the 5' homology arm and/or the 3' homology arm and the corresponding regions the genome flanking a target locus comprise, consist essentially of or consist of non-coding differences in nucleotide sequences.

The skilled worker will appreciate that homology arms do not need to be 100% identical to the genomic sequence flanking the target locus to be able to mediate integration of an editing element into that target locus by homologous recombination. For example, the homology arms can comprise one or more genetic variations in the human population, and/or one or more modifications (e.g., nucleotide substitutions, insertions, or deletions) designed to improve expression level or specificity. Human genetic variations include both inherited variations and de novo variations that are private to the target genome, and encompass simple nucleotide polymorphisms, insertions, deletions, rearrangements, inversions, duplications, micro-repeats, and combinations thereof. Such variations are known in the art, and can be found, for example, in the databases of dnSNP (see Sherry et al. Nucleic Acids Res. 2001; 29(1):308-11), the Database of Genomic Variants (see Nucleic Acids Res. 2014; 42(Database issue):D986-92), ClinVar (see Nucleic Acids Res. 2014; 42(Database issue): D980-D985), Genbank (see Nucleic Acids Res. 2016; 44(Database issue): D67-D72), ENCODE (genome.ucsc.edu/encode/terms.html), JASPAR (see Nucleic Acids Res. 2018; 46(D1): D260-D266), and PROMO (see Messeguer et al. Bioinformatics 2002; 18(2):333-334; Farre et al. Nucleic Acids Res. 2003; 31(13):3651-3653), each of which is incorporated herein by reference. The skilled worker will further appreciate that in situations where a homology arm is not 100% identical to the genomic sequence flanking the target locus, homologous recombination between the homology arm and the genome may alter the genomic sequence flanking the target locus such that it becomes identical to the sequence of the homology arm used.

In certain embodiments, the first genomic region 5' to the target locus is located in a first editing window, wherein the first editing window consists of the nucleotide sequence set forth in SEQ ID NO: 36. In certain embodiments, the second genomic region 3' to the target locus is located in a second editing window, wherein the second editing window consists of the nucleotide sequence set forth in SEQ ID NO: 45. In certain embodiments, the first genomic region 5' to the target locus is located in a first editing window, wherein the first editing window consists of the nucleotide sequence set forth in SEQ ID NO: 36; and the second genomic region 3' to the target locus is located in a second PAH targeting locus, wherein the second editing window consists of the nucleotide sequence set forth in SEQ ID NO: 45.

In certain embodiments, the first and second editing windows are different. In certain embodiments, the first editing window is located 5' to the second editing window. In certain embodiments, the first genomic region consists of a sequence shorter than the sequence of the first editing window in which the first genomic region is located. In certain embodiments, the first genomic region consists of the sequence of the first editing window in which the first genomic region is located. In certain embodiments, the second genomic region consists of a sequence shorter than the sequence of the second editing window in which the second genomic region is located. In certain embodiments, the second genomic region consists of the sequence of the second editing window in which the second genomic region is located. In certain embodiments, the first genomic region 5' to the target locus has the sequence set forth in SEQ ID NO: 36. In certain embodiments, the second genomic region 3' to the target locus has the sequence set forth in SEQ ID NO: 45. In certain embodiments, the first genomic region 5' to the target locus and the second genomic region 3' to the target locus have the sequences set forth in SEQ ID NOs: 36 and 45, respectively.

In certain embodiments, the first and second editing windows are the same. In certain embodiments, the target locus is an internucleotide bond or a nucleotide sequence in the editing window, wherein the first genomic region consists of a first portion of the editing window 5' to the target locus, and the second genomic region consists of a second portion of the editing window 3' to the target locus. In certain embodiments, the first portion of the editing window consists of the sequence from the 5' end of the editing window to the nucleotide adjacently 5' to the target locus. In certain embodiments, the second portion of the editing window consists of the sequence from the nucleotide adjacently 3' to the target locus to the 3' end of the editing window. In certain embodiments, the first portion of the editing window consists of the sequence from the 5' end of the editing window to the nucleotide adjacently 5' to the target locus, and the second portion of the editing window consists of the sequence from the nucleotide adjacently 3' to the target locus to the 3' end of the editing window. In certain embodiments, the editing window consists of the nucleotide sequence set forth in SEQ ID NO: 36 or 45. In certain embodiments, the first and second portions of the editing windows have substantially equal lengths (e.g., the ratio of the length of the shorter portion to the length of the longer portion is greater than 0.5, 0.55, 0.6, 0.65, 0.7, 0.75, 0.8, 0.85, 0.9, 0.95, 0.96, 0.97, 0.98, or 0.99).

In certain embodiments, the 5' homology arm has a length of about 50 to about 4000 nucleotides (e.g., about 100 to about 3000, about 200 to about 2000, about 500 to about 1000 nucleotides). In certain embodiments, the 5' homology arm has a length of about 800 nucleotides. In certain embodiments, the 5' homology arm has a length of about 100 nucleotides. In certain embodiments, the 3' homology arm has a length of about 50 to about 4000 nucleotides (e.g., about 100 to about 3000, about 200 to about 2000, about 500 to about 1000 nucleotides). In certain embodiments, the 3' homology arm has a length of about 800 nucleotides. In certain embodiments, the 3' homology arm has a length of about 100 nucleotides. In certain embodiments, each of the 5' and 3' homology arms independently has a length of about 50 to about 4000 nucleotides (e.g., about 100 to about 3000, about 200 to about 2000, about 500 to about 1000 nucleotides). In certain embodiments, the 5' and 3' homology arm has a length of about 800 nucleotides.

In certain embodiments, the 5' and 3' homology arms have substantially equal nucleotide lengths. In certain embodiments, the 5' and 3' homology arms have asymmetrical nucleotide lengths. In certain embodiments, the asymmetry in nucleotide length is defined by a difference between the 5' and 3' homology arms of up to 90% in the length, such as up to an 80%, 70%, 60%, 50%, 40%, 30%, 20%, or 10% difference in the length.

In certain embodiments, the 5' homology arm comprises: C corresponding to nucleotide-2 of the PAH gene, G corresponding to nucleotide 4 of the PAH gene, G corresponding to nucleotide 6 of the PAH gene, G corresponding to nucleotide 7 of the PAH gene, G corresponding to nucleotide 9 of the PAH gene, A corresponding to nucleotide-467 of the PAH gene, A corresponding to nucleotide-465 of the PAH gene, A corresponding to nucleotide-181 of the PAH gene, G corresponding to nucleotide-214 of the PAH gene, C corresponding to nucleotide-212 of the PAH gene, A corresponding to nucleotide-211 of the PAH gene, G corresponding to nucleotide 194 of the PAH gene, C corresponding to nucleotide-433 of the PAH gene, C corresponding to nucleotide-432 of the PAH gene, ACGCTGTTCTTCGCC (SEQ ID NO: 68) corresponding to nucleotides-394 to-388 of the PAH gene, A corresponding to nucleotide-341 of the PAH gene, A corresponding to nucleotide-339 of the PAH gene, A corresponding to nucleotide-225 of the PAH gene, A corresponding to nucleotide-211 of the PAH gene, and/or A corresponding to nucleotide-203 of the PAH gene.

In certain embodiments, the 5' homology arm comprises:
(a) C corresponding to nucleotide-2 of the PAH gene, G corresponding to nucleotide 4 of the PAH gene, G corresponding to nucleotide 6 of the PAH gene, G corresponding to nucleotide 7 of the PAH gene, and G corresponding to nucleotide 9 of the PAH gene;
(b) A corresponding to nucleotide-467 of the PAH gene, and A corresponding to nucleotide-465 of the PAH gene;
(c) A corresponding to nucleotide-181 of the PAH gene;
(d) G corresponding to nucleotide-214 of the PAH gene, C corresponding to nucleotide-212 of the PAH gene, and A corresponding to nucleotide-211 of the PAH gene;
(e) G corresponding to nucleotide 194 of the PAH gene;
(f) C corresponding to nucleotide-433 of the PAH gene, and C corresponding to nucleotide-432 of the PAH gene;
(g) ACGCTGTTCTTCGCC (SEQ ID NO: 68) corresponding to nucleotides-394 to-388 of the PAH gene; and/or
(h) A corresponding to nucleotide-341 of the PAH gene, A corresponding to nucleotide-339 of the PAH gene, A corresponding to nucleotide-225 of the PAH gene, A corresponding to nucleotide-211 of the PAH gene, and A corresponding to nucleotide-203 of the PAH gene.

In certain embodiments, the 5' homology arm comprises:
(a) C corresponding to nucleotide-2 of the PAH gene, G corresponding to nucleotide 4 of the PAH gene, G corresponding to nucleotide 6 of the PAH gene, G corresponding to nucleotide 7 of the PAH gene, and G corresponding to nucleotide 9 of the PAH gene;
(b) A corresponding to nucleotide-467 of the PAH gene, and A corresponding to nucleotide-465 of the PAH gene;
(c) A corresponding to nucleotide-181 of the PAH gene;
(d) A corresponding to nucleotide-181 of the PAH gene, G corresponding to nucleotide-214 of the PAH gene, C corresponding to nucleotide-212 of the PAH gene, and A corresponding to nucleotide-211 of the PAH gene;
(e) G corresponding to nucleotide 194 of the PAH gene;
(f) C corresponding to nucleotide-433 of the PAH gene, and C corresponding to nucleotide-432 of the PAH gene;
(g) C corresponding to nucleotide-433 of the PAH gene, C corresponding to nucleotide-432 of the PAH gene, and ACGCTGTTCTTCGCC (SEQ ID NO: 68) corresponding to nucleotides-394 to-388 of the PAH gene; and/or
(h) A corresponding to nucleotide-467 of the PAH gene, A corresponding to nucleotide-465 of the PAH gene, A corresponding to nucleotide-341 of the PAH gene, A corresponding to nucleotide-339 of the PAH gene, A corresponding to nucleotide-225 of the PAH gene, A corresponding to nucleotide-211 of the PAH gene, and A corresponding to nucleotide-203 of the PAH gene.

In certain embodiments, the 5' homology arm has at least about 90% (e.g., at least about 91%, 92%, 93%, 94%, 95%, 96%, 97%, 98%, 99%, or 99.5%) nucleotide sequence identity to the nucleotide sequence set forth in SEQ ID NO: 36, optionally comprising one or more of the nucleotides at the positions set forth above. In certain embodiments, the 5' homology arm further comprises one or more genetic variations in the human population. In certain embodiments, the 5' homology arm comprises the nucleotide sequence set forth in SEQ ID NO: 36, 37, 38, 39, 40, 41, 42, 43, or 44. In certain embodiments, the 5' homology arm consists of the nucleotide sequence set forth in SEQ ID NO: 36, 37, 38, 39, 40, 41, 42, 43, or 44.

In certain embodiments, the 3' homology arm has at least about 90% (e.g., at least about 91%, 92%, 93%, 94%, 95%, 96%, 97%, 98%, 99%, or 99.5%) nucleotide sequence identity to the nucleotide sequence set forth in SEQ ID NO: 45. In certain embodiments, the 3' homology arm further comprises one or more genetic variations in the human population. In certain embodiments, the 3' homology arm comprises the nucleotide sequence set forth in SEQ ID NO: 45. In certain embodiments, the 3' homology arm consists of the nucleotide sequence set forth in SEQ ID NO: 45.

In certain embodiments, the 5' homology arm and the 3' homology arm each have at least about 90% (e.g., at least about 91%, 92%, 93%, 94%, 95%, 96%, 97%, 98%, 99%, or 99.5%) nucleotide sequence identity to the nucleotide sequences set forth in SEQ ID NOs: 36 and 45, respectively, optionally wherein the 5' homology arm comprises one or more of the nucleotides at the positions set forth above. In certain embodiments, the 5' homology arm and the 3' homology arm comprise the nucleotide sequences set forth in SEQ ID NOs: 36 and 45, 37 and 45, 38 and 45, 39 and 45, 40 and 45, 41 and 45, 42 and 45, 43 and 45, or, 44 and 45, respectively. In certain embodiments, the 5' homology arm and the 3' homology arm consist of the nucleotide sequences set forth in SEQ ID NOs: 36 and 45, 37 and 45, 38 and 45, 39 and 45, 40 and 45, 41 and 45, 42 and 45, 43 and 45, or, 44 and 45, respectively.

In certain embodiments, the 5' homology arm comprises the nucleotide sequence set forth in SEQ ID NO: 69 or 72. In certain embodiments, the 5' homology arm consists of the nucleotide sequence set forth in SEQ ID NO: 69 or 72. In certain embodiments, the 3' homology arm comprises the nucleotide sequence set forth in SEQ ID NO: 70 or 73. In certain embodiments, the 3' homology arm consists of the nucleotide sequence set forth in SEQ ID NO: 70 or 73. In certain embodiments, the 5' homology arm and the 3' homology arm comprise the nucleotide sequences set forth in SEQ ID NOs: 69 and 70, or 72 and 73, respectively. In certain embodiments, the 5' homology arm and the 3' homology arm consist of the nucleotide sequences set forth in SEQ ID NOs: 69 and 70, or 72 and 73, respectively.

In certain embodiments, the 5' homology arm comprises the nucleotide sequence set forth in SEQ ID NO: 111, 115, or 142. In certain embodiments, the 5' homology arm consists of the nucleotide sequence set forth in SEQ ID NO: 111, 115, or 142. In certain embodiments, the 3' homology arm comprises the nucleotide sequence set forth in SEQ ID NO: 112, 117, or 144. In certain embodiments, the 3' homology arm consists of the nucleotide sequence set forth in SEQ ID NO: 112, 117, or 144. In certain embodiments, the 5' homology arm and the 3' homology arm comprise the nucleotide sequences set forth in SEQ ID NOs: 111 and 112, 115 and 117, or 142 and 144, respectively. In certain embodiments, the 5' homology arm and the 3' homology arm consist of the nucleotide sequences set forth in SEQ ID NOs: 111 and 112, 115 and 117, or 142 and 144, respectively.

In certain embodiments, the correction genome comprises a nucleotide sequence at least 90% (e.g., at least 91%, 92%, 93%, 94%, 95%, 96%, 97%, 98%, 99%, or 99.5%) identical to SEQ ID NO: 46, 47, 48, 49, 50, 51, 52, 53, 54, 85, 86, 113, 118, 134, 136, or 145. In certain embodiments, the correction genome comprises the nucleotide sequence set forth in SEQ ID NO: 46, 47, 48, 49, 50, 51, 52, 53, 54, 85, 86, 113, 118, 134, 136, or 145. In certain embodiments, the correction genome consists of the nucleotide sequence set forth in SEQ ID NO: 46, 47, 48, 49, 50, 51, 52, 53, 54, 85, 86, 113, 118, 134, 136, or 145

In certain embodiments, the correction genomes disclosed herein further comprise a 5' inverted terminal repeat (5' ITR) nucleotide sequence 5' of the 5' homology arm nucleotide sequence, and a 3' inverted terminal repeat (3' ITR) nucleotide sequence 3' of the 3' homology arm nucleotide sequence. ITR sequences from any AAV serotype or variant thereof can be used in the correction genomes disclosed herein. The 5' and 3' ITR can be from an AAV of the same serotype or from AAVs of different serotypes. Exemplary ITRs for use in the correction genomes disclosed herein are set forth in SEQ ID NO: 18-21 herein. In certain embodiments, the 5' ITR nucleotide sequence and the 3' ITR nucleotide sequence are substantially complementary to each other (e.g., are complementary to each other except for mismatch at 1, 2, 3, 4 or 5 nucleotide positions in the 5' or 3' ITR).

In certain embodiments, the 5' ITR or 3' ITR is from AAV2. In certain embodiments, both the 5' ITR and the 3' ITR are from AAV2. In certain embodiments, the 5' ITR nucleotide sequence has at least 95% (e.g., at least 96%, at least 97%, at least 98%, at least 99%, or 100%) sequence identity to SEQ ID NO: 18, or the 3' ITR nucleotide sequence has at least 95% (e.g., at least 96%, at least 97%, at least 98%, at least 99%, or 100%) sequence identity to SEQ ID NO: 19. In certain embodiments, the 5' ITR nucleotide sequence has at least 95% (e.g., at least 96%, at least 97%, at least 98%, at least 99%, or 100%) sequence identity to SEQ ID NO: 18, and the 3' ITR nucleotide sequence has at least 95% (e.g., at least 96%, at least 97%, at least 98%, at least 99%, or 100%) sequence identity to SEQ ID NO: 19. In certain embodiments, the correction genome comprises an editing element having the nucleotide sequence set forth in SEQ ID NO: 35, a 5' ITR nucleotide sequence having the sequence of SEQ ID NO: 18, and a 3' ITR nucleotide sequence having the sequence of SEQ ID NO: 19. In certain embodiments, the correction genome comprises the nucleotide sequence set forth in any one of SEQ ID NOs: 46-54, a 5' ITR nucleotide sequence having the sequence of SEQ ID NO: 18, and a 3' ITR nucleotide sequence having the sequence of SEQ ID NO: 19. In certain embodiments, the correction genome consists of 5' to 3' a 5' ITR nucleotide sequence having the sequence of SEQ ID NO: 18, the nucleotide sequence set forth in any one of SEQ ID NOs: 46-54, and a 3' ITR nucleotide sequence having the sequence of SEQ ID NO: 19.

In certain embodiments, the 5' ITR or 3' ITR are from AAVS. In certain embodiments, both the 5' ITR and 3' ITR are from AAVS. In certain embodiments, the 5' ITR nucleotide sequence has at least 95% (e.g., at least 96%, at least 97%, at least 98%, at least 99%, or 100%) sequence identity to SEQ ID NO: 20, or the 3' ITR nucleotide sequence has at least 95% sequence identity to SEQ ID NO: 21. In certain embodiments, the 5' ITR nucleotide sequence has at least 95% (e.g., at least 96%, at least 97%, at least 98%, at least 99%, or 100%) sequence identity to SEQ ID NO: 20, and the 3' ITR nucleotide sequence has at least 95% (e.g., at least 96%, at least 97%, at least 98%, at least 99%, or 100%) sequence identity to SEQ ID NO: 21. In certain embodiments, the correction genome comprises an editing element having the nucleotide sequence set forth in SEQ ID NO: 35, a 5' ITR nucleotide sequence having the sequence of SEQ ID NO: 20, and a 3' ITR nucleotide sequence having the sequence of SEQ ID NO: 21. In certain embodiments, the correction genome comprises the nucleotide sequence set forth in any one of SEQ ID NOs: 46-54, a 5' ITR nucleotide sequence having the sequence of SEQ ID NO: 20, and a 3' ITR nucleotide sequence having the sequence of SEQ ID NO: 21. In certain embodiments, the correction genome consists of 5' to 3' a 5' ITR nucleotide sequence having the sequence of SEQ ID NO: 20, the nucleotide sequence set forth in any one of SEQ ID NOs: 46-54, and a 3' ITR nucleotide sequence having the sequence of SEQ ID NO: 21.

In certain embodiments, the 5' ITR nucleotide sequence and the 3' ITR nucleotide sequence are substantially complementary to each other (e.g., are complementary to each other except for mismatch at 1, 2, 3, 4 or 5 nucleotide positions in the 5' or 3' ITR).

In certain embodiments, the 5' ITR or the 3' ITR is modified to reduce or abolish resolution by Rep protein ("non-resolvable ITR"). In certain embodiments, the non-resolvable ITR comprises an insertion, deletion, or substitution in the nucleotide sequence of the terminal resolution site. Such modification allows formation of a self-complementary, double-stranded DNA genome of the AAV after the transfer genome is replicated in an infected cell. Exemplary non-resolvable ITR sequences are known in the art (see e.g., those provided in U.S. Pat. Nos. 7,790,154 and 9,783,824, which are incorporated by reference herein in their entirety). In certain embodiments, the 5' ITR comprises a nucleotide sequence at least 95%, 96%, 97%, 98%, or 99% identical to SEQ ID NO: 26. In certain embodiments, the 5' ITR consists of a nucleotide sequence at least 95%, 96%, 97%, 98%, or 99% identical to SEQ ID NO: 26. In certain embodiments, the 5' ITR consists of the nucleotide sequence set forth in SEQ ID NO: 26. In certain embodiments, the 3' ITR comprises a nucleotide sequence at least 95%, 96%, 97%, 98%, or 99% identical to SEQ ID NO: 27. In certain embodiments, the 5' ITR consists of a nucleotide sequence at least 95%, 96%, 97%, 98%, 3or 99% identical to SEQ ID NO: 27. In certain embodiments, the 3' ITR consists of the nucleotide sequence set forth in SEQ ID NO: 27. In certain embodiments, the 5' ITR consists of the nucleotide sequence set forth in SEQ ID NO: 26, and the 3' ITR consists of the nucleotide sequence set forth in SEQ ID NO: 27. In certain embodiments, the 5' ITR consists of the nucleotide sequence set forth in SEQ ID NO: 26, and the 3' ITR consists of the nucleotide sequence set forth in SEQ ID NO: 19.

In certain embodiments, the 3' ITR is flanked by an additional nucleotide sequence derived from a wild-type AAV2 genomic sequence. In certain embodiments, the 3'

ITR is flanked by an additional 37 bp sequence derived from a wild-type AAV2 sequence that is adjacent to a wild-type AAV2 ITR. See, e.g., Savy et al., Human Gene Therapy Methods (2017) 28(5): 277-289 (which is hereby incorporated by reference herein in its entirety). In certain embodiments, the additional 37 bp sequence is internal to the 3' ITR. In certain embodiments, the 37 bp sequence consists of the sequence set forth in SEQ ID NO: 140. In certain embodiments, the 3' ITR comprises a nucleotide sequence at least 95%, 96%, 97%, 98%, or 99% identical to SEQ ID NO: 141. In certain embodiments, the 3' ITR comprises the nucleotide sequence set forth in SEQ ID NO: 141. In certain embodiments, the nucleotide sequence of the 3' ITR consists of a nucleotide sequence at least 95%, 96%, 97%, 98%, or 99% identical to SEQ ID NO: 141. In certain embodiments, the nucleotide sequence of the 3' ITR consists of the nucleotide sequence set forth in SEQ ID NO: 141.

In certain embodiments, the correction genome disclosed herein has a length of about 0.5 to about 8 kb (e.g., about 1 to about 5, about 2 to about 5, about 3 to about 5, about 4 to about 5, about 4.5 to about 4.8, or about 4.7 kb).

In certain embodiments, the correction genome comprises a nucleotide sequence at least 90% (e.g., at least 91%, 92%, 93%, 94%, 95%, 96%, 97%, 98%, 99%, or 99.5%) identical to SEQ ID NO: 55, 56, 57, 58, 59, 60, 61, 62, 63, 87, 88, 114, 119, 135, 137, or 146. In certain embodiments, the correction genome comprises the nucleotide sequence set forth in SEQ ID NO: 55, 56, 57, 58, 59, 60, 61, 62, 63, 87, 88, 114, 119, 135, 137, or 146. In certain embodiments, the correction genome consists of the nucleotide sequence set forth in SEQ ID NO: 55, 56, 57, 58, 59, 60, 61, 62, 63, 87, 88, 114, 119, 135, 137, or 146.

In certain embodiments, the replication-defective AAV comprises: (a) an AAV capsid protein comprising the amino acid sequence of amino acids 203-736 of SEQ ID NO: 16, and a transfer genome comprising 5' to 3' the following genetic elements: a 5' ITR element (e.g., the 5' ITR of SEQ ID NOs: 18), a 5' homology arm (e.g., the 5' homology arm of SEQ ID NOs: 115), a splice acceptor (e.g., the splice acceptor of SEQ ID NOs: 14), a 2A element (e.g., the 2A element of SEQ ID NOs: 74), a silently altered human PAH coding sequence (e.g., the PAH coding sequence of SEQ ID NOs: 116), an SV40 polyadenylation sequence e.g., the SV40 polyadenylation sequence of SEQ ID NOs: 31), a 3' homology arm (e.g., the 3' homology arm of SEQ ID NOs: 117, and a 3' ITR element (e.g., the 3' ITR of SEQ ID NOs: 19); (b) an AAV capsid protein comprising the amino acid sequence of amino acids 138-736 of SEQ ID NO: 16, and a transfer genome comprising 5' to 3' the following genetic elements: a 5' ITR element (e.g., the 5' ITR of SEQ ID NOs: 18), a 5' homology arm (e.g., the 5' homology arm of SEQ ID NOs: 115), a splice acceptor (e.g., the splice acceptor of SEQ ID NOs: 14), a 2A element (e.g., the 2A element of SEQ ID NOs: 74), a silently altered human PAH coding sequence (e.g., the PAH coding sequence of SEQ ID NOs: 116), an SV40 polyadenylation sequence e.g., the SV40 polyadenylation sequence of SEQ ID NOs: 31), a 3' homology arm (e.g., the 3' homology arm of SEQ ID NOs: 117, and a 3' ITR element (e.g., the 3' ITR of SEQ ID NOs: 19); and/or (c) an AAV capsid protein comprising the amino acid sequence of SEQ ID NO: 16, and a transfer genome comprising 5' to 3' the following genetic elements: a 5' ITR element (e.g., the 5' ITR of SEQ ID NOs: 18), a 5' homology arm (e.g., the 5' homology arm of SEQ ID NOs: 115), a splice acceptor (e.g., the splice acceptor of SEQ ID NOs: 14), a 2A element (e.g., the 2A element of SEQ ID NOs: 74), a silently altered human PAH coding sequence (e.g., the PAH coding sequence of SEQ ID NOs: 116), an SV40 polyadenylation sequence e.g., the SV40 polyadenylation sequence of SEQ ID NOs: 31), a 3' homology arm (e.g., the 3' homology arm of SEQ ID NOs: 117, and a 3' ITR element (e.g., the 3' ITR of SEQ ID NOs: 19).

In certain embodiments, the replication-defective AAV comprises: (a) an AAV capsid protein comprising the amino acid sequence of amino acids 203-736 of SEQ ID NO: 16, and a correction genome comprising the nucleotide sequence set forth in any one of SEQ ID NOs: 25, 46-63, 113, 114, 116, 118, 119, 134-137, 145, and 146; (b) an AAV capsid protein comprising the amino acid sequence of amino acids 138-736 of SEQ ID NO: 16, and a correction genome comprising the nucleotide sequence set forth in any one of SEQ ID NOs: 25, 46-63, 113, 114, 116, 118, 119, 134-137, 145, and 146; and/or (c) an AAV capsid protein comprising the amino acid sequence of SEQ ID NO: 16, and a correction genome comprising the nucleotide sequence set forth in any one of SEQ ID NOs: 25, 46-63, 113, 114, 116, 118, 119, 134-137, 145, and 146.

The AAV compositions disclosed herein are particularly advantageous in that they are capable of correcting a PAH gene in a cell with high efficiency both in vivo and in vitro. In certain embodiments, the integration efficiency of the editing element into the target locus is at least 1% (e.g. at least 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, or 95%) when the AAV is administered to a mouse implanted with human hepatocytes in the absence of an exogenous nuclease under standard AAV administration conditions. In certain embodiments, the allelic frequency of integration of the editing element into the target locus is at least 0.5% (e.g. at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, or 95%) when the AAV is administered to a mouse implanted with human hepatocytes in the absence of an exogenous nuclease under standard AAV administration conditions.

Any methods of determining the efficiency of editing of the PAH gene can be employed. In certain embodiments, individual cells are separated from the population of transduced cells and subject to single-cell PCR using PCR primers that can identify the presence of an editing element correctly integrated into the target locus of the PAH gene. Such method can further comprise single-cell PCR of the same cells using PCR primers that selectively amplify an unmodified target locus. In this way, the genotype of the cells can be determined. For example, if the single cell PCR showed that a cell has both an edited target locus and an unmodified target locus, then the cell would be considered heterozygous for the edited PAH gene.

Additionally or alternatively, in certain embodiments, linear amplification mediated PCR (LAM-PCR), quantitative PCR (qPCR) or digital droplet PCR (ddPCR) can be performed on DNA extracted from the population of transduced cells using primers and probes that only detect edited PAH alleles. Such methods can further comprise an additional qPCR or ddPCR (either in the same reaction or a separate reaction) to determine the number of total genomes in the sample and the number of unedited PAH alleles. These numbers can be used to determine the allelic frequency of integration of the editing element into the target locus.

Additionally or alternatively, in certain embodiments, the PAH locus can be amplified from DNA extracted from the population of transduced cells either by PCR using primers that bind to regions of the PAH gene flanking the target locus, or by LAM-PCR using a primer that binds a region within the correction genome (e.g., a region comprising an exogenous sequence non-native to the locus). The resultant PCR amplicons can be individually sequenced using single molecule next generation sequencing (NGS) techniques to determine the relative number of edited and unedited PAH alleles present in the population of transduced cells. These numbers can be used to determine the allelic frequency of integration of the editing element into the target locus.

In another aspect, the instant disclosure provides pharmaceutical compositions comprising an AAV as disclosed herein together with a pharmaceutically acceptable excipient, adjuvant, diluent, vehicle or carrier, or a combination thereof. A "pharmaceutically acceptable carrier" includes any material which, when combined with an active ingredient of a composition, allows the ingredient to retain biological activity and without causing disruptive physiological reactions, such as an unintended immune reaction. Pharmaceutically acceptable carriers include water, phosphate buffered saline, emulsions such as oil/water emulsion, and wetting agents. Compositions comprising such carriers are formulated by well-known conventional methods such as those set forth in Remington's Pharmaceutical Sciences, current Ed., Mack Publishing Co., Easton Pa. 18042, USA; A.

Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al, 7th ed., Lippincott, Williams, & Wilkins; and Handbook of Pharmaceutical Excipients (2000) A. H. Kibbe et al, 3rd ed. Amer. Pharmaceutical Assoc.

III. METHOD OF USE

In another aspect, the instant disclosure provides methods for correcting a mutation in the PAH gene or expressing a PAH polypeptide in a cell. The methods generally comprise transducing the cell with a replication-defective AAV as disclosed herein. Such methods are highly efficient at correcting mutations in the PAH gene or restoring PAH expression, and do not require cleavage of the genome at the target locus by the action of an exogenous nuclease (e.g., a meganuclease, a zinc finger nuclease, a transcriptional activator-like nuclease (TALEN), or an RNA-guided nuclease such as a Cas9) to facilitate such correction. Accordingly, in certain embodiments, the methods disclosed herein involve transducing the cell with a replication-defective AAV as disclosed herein without co-transducing or co-administering an exogenous nuclease or a nucleotide sequence that encodes an exogenous nuclease.

The methods disclosed herein can be applied to any cell harboring a mutation in the PAH gene. The skilled worker will appreciate that cells that actively express PAH are of particular interest. Accordingly, in certain embodiments, the method is applied to cells in the liver, kidney, brain, pituitary gland, adrenal gland, pancreas, urinary bladder, gallbladder, colon, small intestine, or breast. In certain embodiments, the method is applied to hepatocytes and/or renal cells.

The methods disclosed herein can be performed in vitro for research purposes or can be performed ex vivo or in vivo for therapeutic purposes.

In certain embodiments, the cell to be transduced is in a mammalian subject and the AAV is administered to the subject in an amount effective to transduce the cell in the subject. Accordingly, in certain embodiments, the instant disclosure provides a method for treating a subject having a disease or disorder associated with a PAH gene mutation, the method generally comprising administering to the subject an effective amount of a replication-defective AAV as disclosed herein. The subject can be a human subject or a rodent subject (e.g., a mouse) containing human liver cells. Suitable mouse subjects include without limitation, mice into which human liver cells (e.g., human hepatocytes) have been engrafted. Any disease or disorder associated with a PAH gene mutation can be treated using the methods disclosed herein. Suitable diseases or disorders include, without limitation, phenylketonuria. In certain embodiments, the cell is transduced without co-transducing or co-administering an exogenous nuclease or a nucleotide sequence that encodes an exogenous nuclease.

The methods disclosed herein are particularly advantageous in that they are capable of correcting a PAH gene in a cell with high efficiency both in vivo and in vitro. In certain embodiments, the integration efficiency of the editing element into the target locus is at least 1% (e.g. at least 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, or 95%) when the AAV is administered to a mouse implanted with human hepatocytes in the absence of an exogenous nuclease under standard AAV administration conditions. In certain embodiments, the allelic frequency of integration of the editing element into the target locus is at least 0.5% (e.g. at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, or 95%) when the AAV is administered to a mouse implanted with human hepatocytes in the absence of an exogenous nuclease under standard AAV administration conditions.

In certain embodiments, transduction of a cell with an AAV composition disclosed herein can be performed as provided herein or by any method of transduction known to one of ordinary skill in the art. In certain embodiments, the cell may be contacted with the AAV at a multiplicity of infection (MOI) of 50,000; 100,000; 150,000; 200,000; 250,000; 300,000; 350,000; 400,000; 450,000; or 500,000, or at any MOI that provides for optimal transduction of the cell.

In certain embodiments, the foregoing methods employ a replication-defective AAV comprising: (a) an AAV capsid protein comprising the amino acid sequence of amino acids 203-736 of SEQ ID NO: 16, and a transfer genome comprising 5' to 3' the following genetic elements: a 5' ITR element (e.g., the 5' ITR of SEQ ID NOs: 18), a 5' homology arm (e.g., the 5' homology arm of SEQ ID NOs: 115), a splice acceptor (e.g., the splice acceptor of SEQ ID NOs: 14), a 2A element (e.g., the 2A element of SEQ ID NOs: 74), a silently altered human PAH coding sequence (e.g., the PAH coding sequence of SEQ ID NOs: 116), an SV40 polyadenylation sequence e.g., the SV40 polyadenylation sequence of SEQ ID NOs: 31), a 3' homology arm (e.g., the 3' homology arm of SEQ ID NOs: 117, and a 3' ITR element (e.g., the 3' ITR of SEQ ID NOs: 19); (b) an AAV capsid protein comprising the amino acid sequence of amino acids 138-736 of SEQ ID NO: 16, and a transfer genome comprising 5' to 3' the following genetic elements: a 5' ITR element (e.g., the 5' ITR of SEQ ID NOs: 18), a 5' homology arm (e.g., the 5' homology arm of SEQ ID NOs: 115), a splice acceptor (e.g., the splice acceptor of SEQ ID NOs: 14), a 2A element (e.g., the 2A element of SEQ ID NOs: 74), a silently altered human PAH coding sequence (e.g., the PAH coding sequence of SEQ ID NOs: 116), an SV40 polyadenylation sequence e.g., the SV40 polyadenylation sequence of SEQ ID NOs: 31), a 3' homology arm (e.g., the 3' homology arm of SEQ ID NOs: 117, and a 3' ITR element (e.g., the 3' ITR of SEQ ID NOs: 19); and/or (c) an AAV capsid protein comprising the amino acid sequence of SEQ ID NO: 16, and a transfer genome comprising 5' to 3' the following genetic elements: a 5' ITR element (e.g., the 5' ITR of SEQ ID NOs: 18), a 5' homology arm (e.g., the 5' homology arm of SEQ ID NOs: 115), a splice acceptor (e.g., the splice acceptor of SEQ ID NOs: 14), a 2A element (e.g., the 2A element of SEQ ID NOs: 74), a silently altered human PAH coding sequence (e.g., the PAH coding sequence of SEQ ID NOs: 116), an SV40 polyadenylation sequence e.g., the SV40 polyadenylation sequence of SEQ ID NOs: 31), a 3' homology arm (e.g., the 3' homology arm of SEQ ID NOs: 117, and a 3' ITR element (e.g., the 3' ITR of SEQ ID NOs: 19).

In certain embodiments, the foregoing methods employ a replication-defective AAV comprising: (a) an AAV capsid protein comprising the amino acid sequence of amino acids 203-736 of SEQ ID NO: 16, and a correction genome comprising the nucleotide sequence set forth in any one of SEQ ID NOs: 25, 46-63, 113, 114, 116, 118, 119, 134-137, 145, and 146; (b) an AAV capsid protein comprising the amino acid sequence of amino acids 138-736 of SEQ ID NO: 16, and a correction genome comprising the nucleotide sequence set forth in any one of SEQ ID NOs: 25, 46-63, 113, 114, 116, 118, 119, 134-137, 145, and 146; and/or (c) an AAV capsid protein comprising the amino acid sequence of SEQ ID NO: 16, and a correction genome comprising the nucleotide sequence set forth in any one of SEQ ID NOs: 25, 46-63, 113, 114, 116, 118, 119, 134-137, 145, and 146.

An AAV composition disclosed herein can be administered to a subject by any appropriate route including, without limitation, intravenous, intraperitoneal, subcutaneous, intramuscular, intranasal, topical or intradermal routes. In certain embodiments, the composition is formulated for administration via intravenous injection or subcutaneous injection.

IV. AAV PACKAGING SYSTEMS

In another aspect, the instant disclosure provides packaging systems for recombinant preparation of a replication-defective AAV disclosed herein. Such packaging systems generally comprise: a Rep nucleotide sequence encoding one or more AAV Rep proteins; a Cap nucleotide sequence encoding one or more AAV Clade F capsid proteins as disclosed herein; and a correction genome for correction of the PAH gene or a transfer genome for expression of the PAH gene as disclosed herein, wherein the packaging system is operative in a cell for enclosing the correction genome in the capsid to form the AAV.

In certain embodiments, the packaging system comprises a first vector comprising the Rep nucleotide sequence and the Cap nucleotide sequence, and a second vector comprising the correction genome or transfer genome. As used in the context of a packaging system as described herein, a "vector" refers to a nucleic acid molecule that is a vehicle for introducing nucleic acids into a cell (e.g., a plasmid, a virus, a cosmid, an artificial chromosome, etc.).

Any AAV Rep protein can be employed in the packaging systems disclosed herein. In certain embodiments of the packaging system, the Rep nucleotide sequence encodes an AAV2 Rep protein. Suitable AAV2 Rep proteins include, without limitation, Rep 78/68 or Rep 68/52. In certain embodiments of the packaging system, the nucleotide sequence encoding the AAV2 Rep protein comprises a nucleotide sequence that encodes a protein having a minimum percent sequence identity to the AAV2 Rep amino acid sequence of SEQ ID NO: 22, wherein the minimum percent sequence identity is at least 70% (e.g., at least 75%, at least 80%, at least 85%, at least 90%, at least 95%, at least 98%, at least 99%, or 100%) across the length of the amino acid sequence of the AAV2 Rep protein. In certain embodiments of the packaging system, the AAV2 Rep protein has the amino acid sequence set forth in SEQ ID NO: 22.

In certain embodiments of the packaging system, the packaging system further comprises a third vector, e.g., a helper virus vector. The third vector may be an independent third vector, integral with the first vector, or integral with the second vector. In certain embodiments, the third vector comprises genes encoding helper virus proteins.

In certain embodiments of the packaging system, the helper virus is selected from the group consisting of adenovirus, herpes virus (including herpes simplex virus (HSV)), poxvirus (such as vaccinia virus), cytomegalovirus (CMV), and baculovirus. In certain embodiments of the packaging system, where the helper virus is adenovirus, the adenovirus genome comprises one or more adenovirus RNA genes selected from the group consisting of E1, E2, E4 and VA. In certain embodiments of the packaging system, where the helper virus is HSV, the HSV genome comprises one or more of HSV genes selected from the group consisting of UL5/8/52, ICPO, ICP4, ICP22 and UL30/UL42.

In certain embodiments of the packaging system, the first, second, and/or third vector are contained within one or more transfecting plasmids. In certain embodiments, the first vector and the third vector are contained within a first transfecting plasmid. In certain embodiments the second vector and the third vector are contained within a second transfecting plasmid.

In certain embodiments of the packaging system, the first, second, and/or third vector are contained within one or more recombinant helper viruses. In certain embodiments, the first vector and the third vector are contained within a recombinant helper virus. In certain embodiments, the second vector and the third vector are contained within a recombinant helper virus.

In a further aspect, the disclosure provides a method for recombinant preparation of an AAV as described herein, wherein the method comprises transfecting or transducing a cell with a packaging system as described under conditions operative for enclosing the correction genome in the capsid to form the AAV as described herein. Exemplary methods for recombinant preparation of an AAV include transient transfection (e.g., with one or more transfection plasmids containing a first, and a second, and optionally a third vector as described herein), viral infection (e.g. with one or more recombinant helper viruses, such as a adenovirus, poxvirus (such as vaccinia virus), herpes virus (including HSV, cytomegalovirus, or baculovirus, containing a first, and a second, and optionally a third vector as described herein), and stable producer cell line transfection or infection (e.g., with a stable producer cell, such as a mammalian or insect cell, containing a Rep nucleotide sequence encoding one or more AAV Rep proteins and/or a Cap nucleotide sequence encoding one or more AAV Clade F capsid proteins as described herein, and with a correction genome as described herein being delivered in the form of a transfecting plasmid or a recombinant helper virus).

V. EXAMPLES

The recombinant AAV vectors disclosed herein mediate highly efficient gene editing in vitro and in vivo. The following examples provide correction vectors that can be packaged with an AAV Glade F capsid (e.g., AAVHSC7, AAVHSC15 or AAVHSC17, as disclosed in U.S. Pat. No. 9,623,120, which is incorporated by reference herein in its entirety), and demonstrate the efficient restoration of the expression of the PAH gene which is mutated in certain human diseases, such as phenylketonuria. These examples are offered by way of illustration, and not by way of limitation.

Example 1

PAH correction vector pHMI-hPAH-hAC-008 a) PAH Correction Vector pHMI-hPAH-hAC-008

PAH correction vector pHMI-hPAH-hAC-008, as shown in FIG. 1A, comprises 5' to 3' the following genetic elements: a 5' ITR element, a 5' homology arm, a silently altered human PAH coding sequence, an SV40 polyadenylation sequence, a targeted integration restriction cassette ("TI RE"), a 3' homology arm, and a 3' ITR element. The sequences of these elements are set forth in Table 1. The 5' homology arm comprises a wild-type genomic sequence 800 nucleotides upstream from the human PAH start codon, and thus has the ability to correct mutations in the start codon and/or 5' untranslated region (UTR) that affect PAH expression as observed in some PKU patients. The 3' homology arm comprises the wild-type genomic sequence 800 nucleotides downstream from the start codon. Integration of the PAH correction vector pHMI-hPAH-hAC-008 into the human genome inserts the silently altered human PAH coding sequence, the SV40 polyadenylation sequence, and the targeted integration restriction cassette at the PAH start codon target locus (i.e., replacing nucleotides 1-3 of the PAH gene), thereby restoring the expression of a wild-type PAH protein that has been impaired by mutations in 5' UTR, coding sequence, or 3' UTR of the PAH gene.

TABLE 1

Genetic elements in PAH correction vector pHMI-hPAH-hAC-008

| Genetic Element | SEQ ID NO |
| --- | --- |
| 5' ITR element | 18 |
| 5' homology arm | 69 |
| silently altered human PAH coding sequence | 25 |
| SV40 polyadenylation sequence | 31 |
| targeted integration restriction cassette | 71 |
| 3' homology arm | 70 |
| 3' ITR element | 19 |
| Editing element | 83 |
| Correction genome from 5' homology arm to 3' homology arm | 85 |
| Correction genome from 5' ITR to 3' ITR | 87 | b) PAH Correction Vector pHMI-hPAH-hl C-007

PAH correction vector pHMI-hPAH-h1C-007, as shown in FIG. 1B, comprises 5' to 3' the following genetic elements: a 5' ITR element, a 5' homology arm, a splice acceptor, a 2A element, a silently altered human PAH coding sequence, an SV40 polyadenylation sequence, a targeted integration restriction cassette ("TI RE"), a 3' homology arm, and a 3' ITR element. The sequences of these elements are set forth in Table 2. The 5' homology arm comprises the wild-type genomic sequence of 800 nucleotides upstream from nucleotide 2128 of human PAH, which is located in intron 1. The 3' homology arm comprises the wild-type genomic sequence of 800 nucleotides downstream from nucleotide 2127 of human PAH. Integration of the PAH correction vector pHMI-hPAH-h1C-007 into the human genome allows transcription of the PAH locus into a pre-mRNA comprising 5' to 3' the following elements: exon 1 of endogenous PAH, part of intron 1 from its 5' splice donor to nucleotide 2127, the splice acceptor in the vector pHMI-hPAH-h1C-007, the 2A element, the silently altered human PAH coding sequence, and the SV40 polyadenylation sequence. Splicing of this pre-mRNA generates an mRNA comprising 5' to 3' the following elements: exon 1 of endogenous PAH, the 2A element (in frame with the PAH exon 1), the silently altered human PAH coding sequence (in frame with the 2A element), and the SV40 polyadenylation sequence. The 2A element leads to generation of two polypeptides: a truncated PAH peptide terminated at the end of exon 1 fused with an N-terminal part of the 2A peptide, and a proline from the 2A peptide fused with a full-length PAH polypeptide. Therefore, integration of the vector pHMI-hPAH-hl C-007 can restore the expression of wild-type PAH protein that has been impaired by mutations in the coding sequence or 3' UTR of the PAH gene.

TABLE 2

Genetic elements in PAH correction vector pHMI-hPAH-h1C-007

| Genetic Element | SEQ ID NO |
| --- | --- |
| 5' ITR element | 18 |
| 5' homology arm | 72 |
| Splice acceptor | 14 |
| 2A element | 74 |
| silently altered human PAH coding sequence | 25 |
| SV40 polyadenylation sequence | 31 |
| targeted integration restriction cassette | 71 |
| 3' homology arm | 73 |
| 3' ITR element | 19 |
| Editing element | 84 |
| Correction genome from 5' homology arm to 3' homology arm | 86 |
| Correction genome from 5' ITR to 3' ITR | 88 |

The silent alteration adopted in the two vectors above significantly improved the expression of the PAH protein, as demonstrated by comparison of expression vectors pCOH-WT-PAH, pCOH-CO-PAH, and pHMI-CO-PAH. The pCOH-WT-PAH vector comprises a CBA promoter operably linked to a wild-type PAH coding sequence set forth in SEQ ID NO: 24. The pCOH-CO-PAH and pHMI-CO-PAH vectors each comprise a CBA promoter operably linked to a silently altered human PAH coding sequence as set forth in SEQ ID NO: 25. The pCOH-CO-PAH and pHMI-CO-PAH vectors were highly similar. Each vector was transfected in HEK 293 cells which is naturally deficient in PAH. As shown in FIG. 2, VG-GT-CO-PAH ("CO-hPAH") gave rise to an expression level of human PAH notably higher than VG-GT-PAH ("WT-hPAH").

Example 2

PAH Correction Vector pHMIA-hPAH-hI1C-032.1 and its Variants

In order to identify homology arm sequences that facilitate efficient gene editing, 130 correction vectors were designed, and 70 of them were tested in human hepatocellular carcinoma cells. The pHMIA-hPAH-hI1C-032.1 vector showed the highest editing efficiency in vitro. This example provides the structure of this vector and its variants.

a) PAH Correction Vector pHMIA-hPAH-hI1C-032.1

PAH correction vector pHMIA-hPAH-hI1C-032.1, as shown in FIG. 1C, comprises 5' to 3' the following genetic elements: a 5' ITR element, a 5' homology arm, a splice acceptor, a P2A element, a silently altered human PAH coding sequence, an SV40 polyadenylation sequence, a 3' homology arm, and a 3' ITR element. The sequences of these elements are set forth in Table 3. The 5' homology arm comprises the wild-type genomic sequence of nucleotides-686 to 274 of human PAH, the 3' end of which is located in intron 1. The 3' homology arm comprises the wild-type genomic sequence of nucleotides 415 to 1325 of human PAH. Integration of the PAH correction vector pHMIA-hPAH-hI1C032.1 into the human genome allows transcription of the PAH locus into a pre-mRNA comprising 5' to 3' the following elements: exon 1 of endogenous PAH, part of intron 1 from its 5' splice donor to nucleotide 274, the splice acceptor in the vector pHMIA-hPAH-hI1C-032.1, the P2A element, the silently altered human PAH coding sequence, and the SV40 polyadenylation sequence. Splicing of this pre-mRNA generates an mRNA comprising 5' to 3' the following elements: exon 1 of endogenous PAH, the P2A element (in frame with the PAH exon 1), the silently altered human PAH coding sequence (in frame with the P2A element), and the SV40 polyadenylation sequence. The P2A element leads to generation of two polypeptides: a truncated PAH peptide terminated at the end of exon 1 fused with an N-terminal part of the P2A peptide, and a proline from the P2A peptide fused with a full-length PAH polypeptide. Therefore, integration of the vector pHMIA-hPAH-hI1C-032.1 can restore the expression of wild-type PAH protein that has been impaired by mutations in the coding sequence or 3' UTR of the PAH gene.

TABLE 3

Genetic elements in PAH correction vector pHMIA-hPAH-hI1C-032.1

| Genetic Element | SEQ ID NO |
| --- | --- |
| 5' ITR element | 18 |
| 5' homology arm | 36 |
| Splice acceptor | 14 |
| P2A element | 79 |
| silently altered human PAH coding sequence | 25 |
| SV40 polyadenylation sequence | 31 |
| 3' homology arm | 45 |
| 3' ITR element | 19 |
| Editing element | 35 |
| Correction genome from 5' homology arm to 3' homology arm | 46 |
| Correction genome from 5' ITR to 3' ITR | 55 | b) Variants of PAH Correction Vector pHMIA-hPAH-hI1C-032.1

Eight variants of the pHMIA-hPAH-hI1C-032.1 vector have been designed to improve the expression of the PAH gene locus. These variants, named pHMIA-hPAH-hI1C032.2 to pHMIA-hPAH-hI1C-032. 9, differ from pHMIA-hPAH-hI1C-032.1 only in the 5' homology arm. The sequences of the different elements are set forth in Table 4.

TABLE 4

Variants of the pHMIA-hPAH-hI1C-032.1 vector

| | SEQ ID NO | | |
| --- | --- | --- | --- |
| Vector name | 5' homology arm (HA) | Correction genome from 5' HA to 3' HA | Correction genome from 5' ITR to 3' ITR |
| pHMIA-hPAH-hI1C-032.2 | 37 | 47 | 56 |
| pHMIA-hPAH-hI1C-032.3 | 38 | 48 | 57 |
| pHMIA-hPAH-hI1C-032.4 | 39 | 49 | 58 |
| pHMIA-hPAH-hI1C-032.5 | 40 | 50 | 59 |
| pHMIA-hPAH-hI1C-032.6 | 41 | 51 | 60 |
| pHMIA-hPAH-hI1C-032.7 | 42 | 52 | 61 |
| pHMIA-hPAH-hI1C-032.8 | 43 | 53 | 62 |
| pHMIA-hPAH-hI1C-032.9 | 44 | 54 | 63 |

The pHMIA-hPAH-hI1C-032.2 vector was designed to optimize the Kozak sequence for improved ribosome recruitment to the transcript. It differs from pHMIA-hPAH-hI1C-032.1 in having the nucleotides C, G, G, G, and G at positions-2, 4, 6, 7, and 9, respectively, of the PAH gene.

The pHMIA-hPAH-hI1C-032.3 vector was designed to remove a single quadruplex in 5' UTR of the PAH gene that might suppress expression. It differs from pHMIA-hPAH-hI1C-032.1 in having the nucleotides A and A at positions-467 and-465, respectively, of the PAH gene.

The pHMIA-hPAH-hI1C-032.4 vector was designed to optimize a cyclic AMP response element to increase expression. It differs from pHMIA-hPAH-hI1C-032.1 in having the nucleotide A at position-181 of the PAH gene.

The pHMIA-hPAH-hI1C-032.5 vector was designed to optimize two cyclic AMP response elements to increase expression. It differs from pHMIA-hPAH-hI1C-032.1 in having the nucleotides G, C, A, and A at positions-214,-212,-211, and-181, respectively, of the PAH gene.

The pHMIA-hPAH-hI1C-032.6 vector was designed to incorporate the minor allele of SNP rs1522295, which correlates with altered PAH expression in humans. It differs from pHMIA-hPAH-hI1C032.1 in having the nucleotide G at position 194 of the PAH gene.

The pHMIA-hPAH-hI1C-032.7 vector was designed to optimize a glucocorticoid binding site in the 5' UTR to increase expression. It differs from pHMIA-hPAH-hI1C-032.1 in having the nucleotides C and C at positions-433 and-432, respectively, of the PAH gene.

The pHMIA-hPAH-hI1C-032.8 vector was designed to modify two glucocorticoid binding sites and a single AP2 binding site for improved expression. It differs from pHMIA-hPAH-hI1C-032.1 in having the nucleotides C and C at positions-433 and-432, respectively, of the PAH gene, and having the nucleotide sequence ACGCTGTTCTTCGCC (SEQ ID NO: 68) at positions-394 to-388 of the PAH gene.

The pHMIA-hPAH-hI1C-032.9 vector was designed to disrupt three G-quadruplexes in the 5' UTR that might suppress expression. It differs from pHMIA-hPAH-hI1C-032.1 in having the nucleotide A at each of the nucleotide positions-467,-465,-341,-339,-225,-211, and-203 of the PAH gene.

Example 3

In Vitro Human PAH Gene Editing

This example provides an in vitro method for examining PAH correction vectors, such as those described in the previous examples.

PAH correction vector pHMI-hPAH-hA-002, a variant of pHMI-hPAH-hAC-008 wherein the PAH coding sequence is wild-type (i.e., not silently altered), and PAH correction vector pHMI-hPAH-h1-001, a variant of pHMI-hPAH-h1 C-007 wherein the PAH coding sequence is wild-type (i.e., not silently altered), were examined for assessment of targeted integration. K562 cells were transduced with the pHMI-hPAH-hA-002 vector packaged in AAVHSC17 at an MOI of 150,000. The genomic DNA of the cells was collected after 48 hours. Single biotinylated primers with the sequences ccaaatcccaccagctcact (SEQ ID NO: 89) and tcc-catgaaactgaggtgtga (SEQ ID NO: 90), each located outside the homology arms, were separately used to amplify the DNA samples by linear amplification. Both the edited and unedited alleles were amplified without bias. The amplified DNA samples were pooled and enriched by streptavidin pulldown. The number of alleles with pHMI-hPAH-hA-002 integration was measured by ddPCR using the PAH Genomic Set 1 primer/probe set.

Figure 3A:
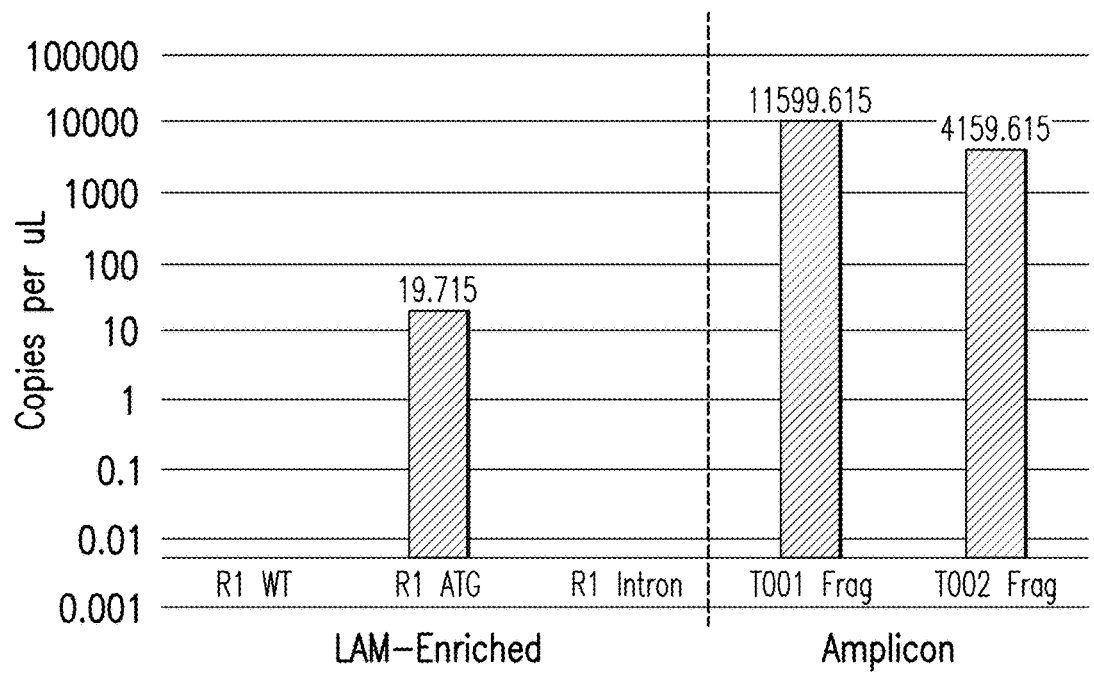
FIG. 3A is a graph showing quantitation of the PAH cDNA cassette following linear amplification ("LAM-Enriched") or PCR amplification ("Amplicon") of the editing target site.

As shown in FIG. 3A, left panel ("LAM-Enriched"), the desired integration was detected in a sample from cells transduced with the pHMI-hPAH-hA-002 vector ("R1 ATG"), but not detected in samples from cells transduced with the pHMI-hPAH-h1-001 vector ("R1 Intron") or untransduced cells ("R1 WT"). In the right panel of FIG. 3A ("Amplicon"), the amount of vector integration was measured by ddPCR using the SV40_FAM Set 1 primer/probe set. Positive signals were detected in samples from both the cells transduced with the pHMI-hPAH-hA-002 vector ("T001 Frag") and the cells transduced with the pHMI-hPAH-h1-001 vector ("T002 Frag"), indicating that both cells underwent vector integration.

To quantify the targeted integration, three sets of primers and probes, as shown in Table 6, were designed for detection the integration by ddPCR. PAH_Genomic Set 1 detected the unedited genome and the edited genome after the targeted integration of pHMI-hPAH-hA-002. SV40_FAM Set 1 detected a sequence in the SV40 polyadenylation sequence, which was present in the edited genome and the unintegrated vectors. PAH_HA Set 1 detected a region in the homology arm, which was present in both edited and unedited genomes, as well as in the unintegrated vectors.

DNA samples were partitioned into oil droplets. The concentration of DNA was optimized to a concentration of 600 pg per 20 μL in order to significantly reduce the probability that one oil droplet randomly contains two DNA molecules (e.g., a vector particle and a genomic DNA particle) (p<0.001). The quantity of DNA identified by PAH_Genomic Set 1 (Quantity_genome) represented the total amount of unedited and edited genomes. The quantity of DNA identified by SV40_FAM Set 1 (Quantity_payload) represented the total amount of edited genomes and unintegrated vectors. The quantity of DNA identified by PAH_HA Set 1 (Quantity_HA) represented the total amount of unedited genomes, edited genomes, and unintegrated vectors. Thus, the quantity of edited genome can be calculated by the follow formula: Quantity_genome+Quantity_payload—Quantity_HA. The fraction of genome having the correct integration can be calculated as the quantity of edited genome divided by Quantity_genome.

TABLE 5

Primers and probes for quantifying integration of human PAH into the human genome

| Primer or Probe | Sequence | SEQ ID NO |
|---|---|---|
| PAH_Genomic Set 1, primer F | GCTCCATCCTGCACATAGTT | 91 |
| PAH_Genomic Set 1, primer R | CCTATGCTTTCCTGATGAGA TCC | 92 |
| PAH_Genomic Set 1, probe | TTGGTGCTGCTGGCAATACG GTC | 93 |
| SV40_FAM Set 1, primer F | GCAATAGCATCACAAATTTC AC | 94 |
| SV40_FAM Set 1, primer R | GATCCAGACATGATAAGATA CATTG | 95 |
| SV40_FAM Set 1, probe | TCACTGCATTCTAGTTGTGG TTTGTCCA | 96 |
| PAH_HA Set 1, primer F | TCCAGTCACCAGACAGTTAG T | 97 |
| PAH_HA Set 1, primer R | GGAGAGAAATGGAGCAAGTG AA | 98 |
| PAH_HA Set 1, probe 1 | ACAGCCTATATTTCACCATG CTGATCCC | 99 |

Figure 3B:
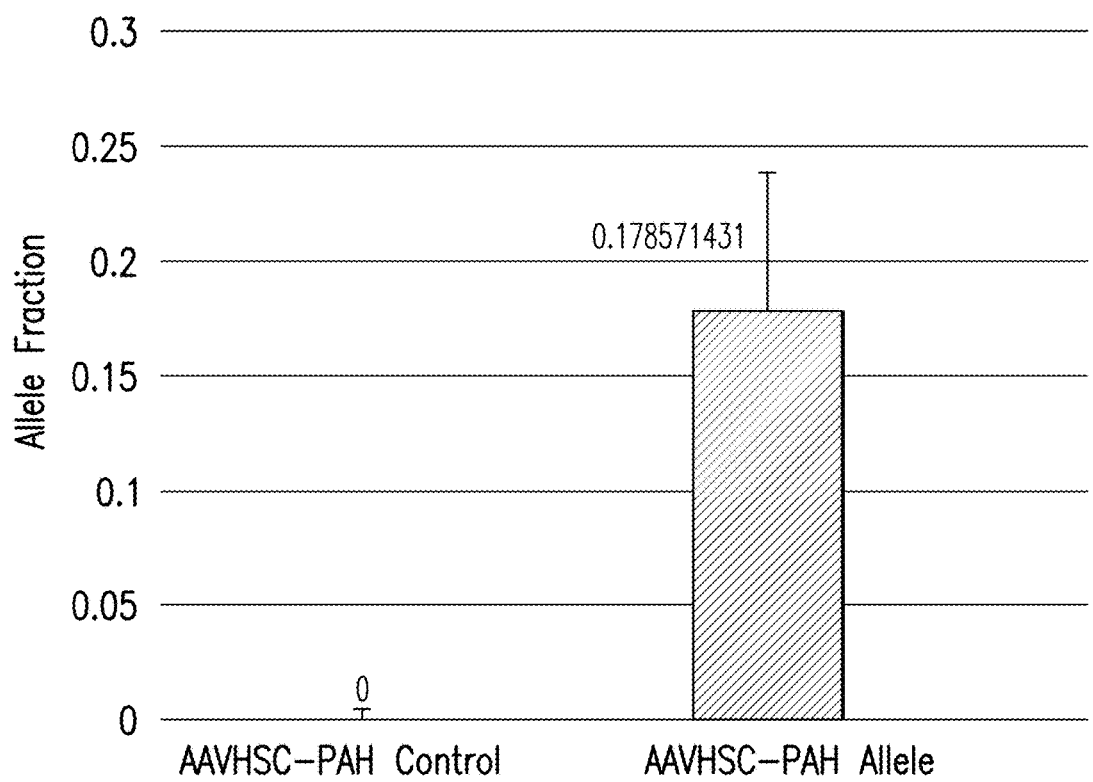
FIG. 3B is a graph showing quantitative analysis of integration of the pHMI-hPAH-hA-002 vector by droplet digital PCR (ddPCR).

As shown in FIG. 3B, the percentage of genome having the correct integration of the pHMI-hPAH-hA-002 vector, as measured by the above primer/probe sets, was 17.86%. No integration was detected in the control cells which were not transduced with the pHMI-hPAH-hA-002 vector.

Example 4

In Vivo PAH Gene Editing in Mouse Liver

Figure 4A:
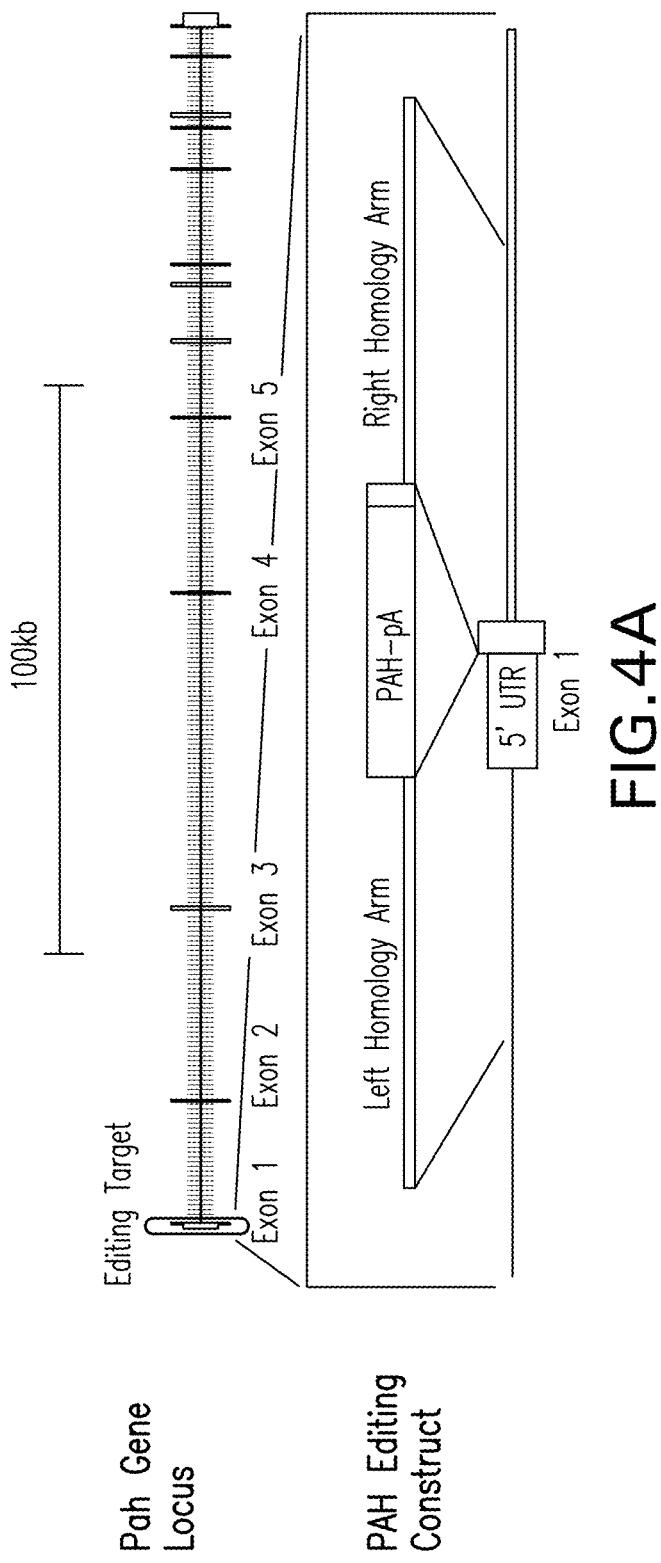
FIG. 4A shows the design of the pHMI-hPAH-mAC-006 vector and its expected integration into a mouse genome.

This example provides animal models for examining PAH correction vectors that are capable of editing mouse PAH gene, and determining their editing efficiency in mouse liver.
a) Editing of the Mouse PAH Gene in Wild-Type Mice In a specific example, provided herein is in vivo editing of the mouse genome using the pHMI-hPAH-mAC-006 vector. The pHMI-hPAH-mAC-006 vector was similar to the pHMI-hPAH-hAC-008 vector, but was capable of editing the mouse PAH gene rather than the human PAH gene (FIG. 4A). Specifically, pHMI-hPAH-mAC-006 comprised 5' to 3' the following genetic elements: a 5' ITR element, a 5' homology arm, a silently altered human PAH coding sequence, an SV40 polyadenylation sequence, a targeted integration restriction cassette ("TI RE"), a 3' homology arm, and a 3' ITR element. The sequences of these elements are set forth in Table 6. The 5' homology arm comprised the wild-type genomic sequence upstream from and including the mouse PAH start codon, and thus had the ability to correct mutations in the start codon and/or 5' untranslated region (UTR) of the mouse PAH gene. The 3' homology arm comprised the wild-type genomic sequence downstream from the start codon of mouse PAH. Integration of the PAH correction vector pHMI-hPAH-mAC-006 into the mouse genome could insert the silently altered human PAH coding sequence, the SV40 polyadenylation sequence, and the targeted integration restriction cassette at the start codon of the mouse PAH gene (i.e., replacing nucleotides 1-3 of the mouse PAH gene), thereby expressing a wild-type human PAH protein in a mouse cell. The vector alone did not include a promoter sequence, and could not drive independent PAH expression without genomic integration.

TABLE 6

Genetic elements in PAH correction vector pHMI-hPAH-mAC-006

| Genetic Element | SEQ ID NO |
|---|---|
| 5' ITR element | 18 |
| 5' homology arm | 100 |
| Silently altered human PAH coding sequence | 25 |
| SV40 polyadenylation sequence | 31 |
| targeted integration restriction cassette | 71 |
| 3' homology arm | 101 |
| 3' ITR element | 19 |

The pHMI-hPAH-mAC-006 vector was packaged in AAVHSC17 capsid and injected to two wild-type neonatal mice intravenously via the tail vein at a dose of $2 \times 10^{13}$ vector genomes per kg of body weight. Two control mice received saline injection via the tail vein. Liver samples were collected after 2 weeks.

Figure 4B:
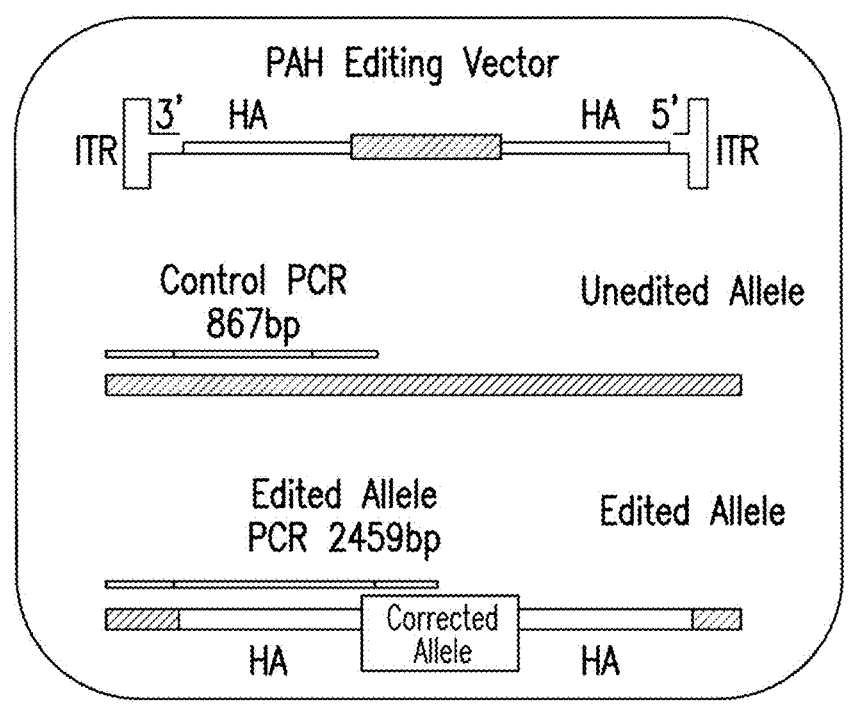
FIG. 4B is a diagram illustrating a method for detecting by PCR an allele edited by the pHMI-hPAH-mAC-006 vector. Two pairs of primers were designed: the first pair could amplify a 867 bp DNA from an unedited allele ("Control PCR"); the second pair could specifically amplify a 2459 bp DNA from an edited allele ("Edited Allele PCR").
Figure 4C:
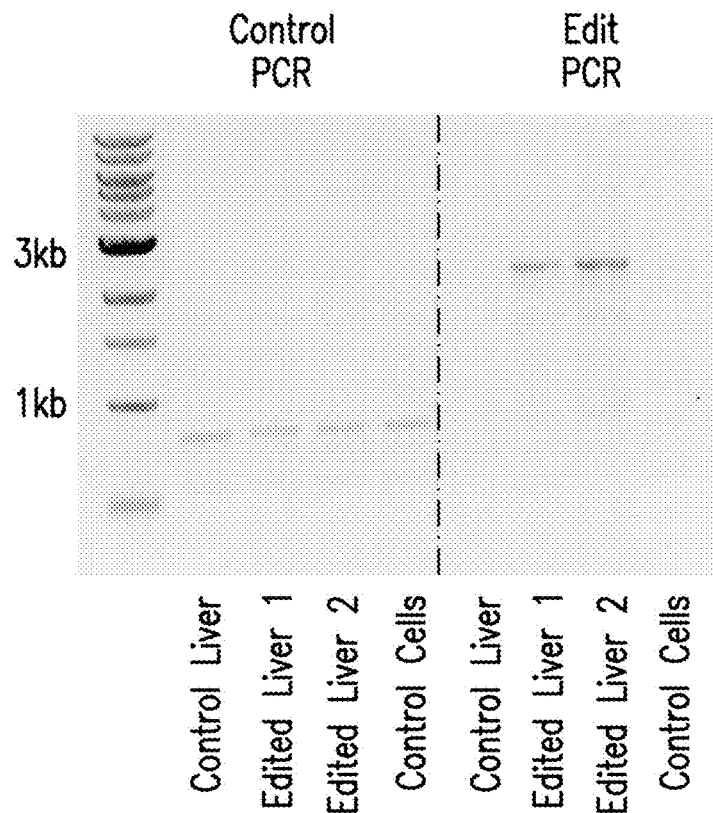
FIG. 4C is an image of DNA electrophoresis showing the PCR product from the Control PCR ("Control PCR") and Edited Allele PCR ("Edit PCR") as illustrated in FIG. 4A. The pHMI-hPAH-mAC-006 vector packaged in an AAVHSC capsid was injected to two wild-type neonatal mice intravenously via the tail vein at a dose of $2 \times 10^{13}$ vector genomes per kg of body weight. Liver samples were collected after 2 weeks. A liver sample from a saline treated mouse and a cell sample of 3T3 mouse fibroblasts were used as negative control for the Edited Allele PCR.

A PCR method was developed to detect the integration of the pHMI-hPAH-mAC-006 vector into the mouse genome. As shown in FIG. 4B, a first pair of primers (SEQ ID NOs: 62 and 63) were designed to amplify an 867 bp DNA from an unedited allele ("Control PCR"); a second pair of primers (SEQ ID NOs: 64 and 65) were designed to specifically amplify a 2459 bp DNA from an edited allele ("Edited Allele PCR"). As shown in FIG. 4C, a liver sample from a saline treated mouse and a cell sample of 3T3 mouse fibroblasts did not generate the PCR product corresponding to the edited allele, whereas the liver samples from the two mice injected with the pHMI-hPAH-mAC-006 vector generated the PCR product corresponding to the edited allele. All four samples generated similar levels of the PCR product corresponding to the unedited allele, suggesting that the samples were comparable in quality.

Figure 5A:
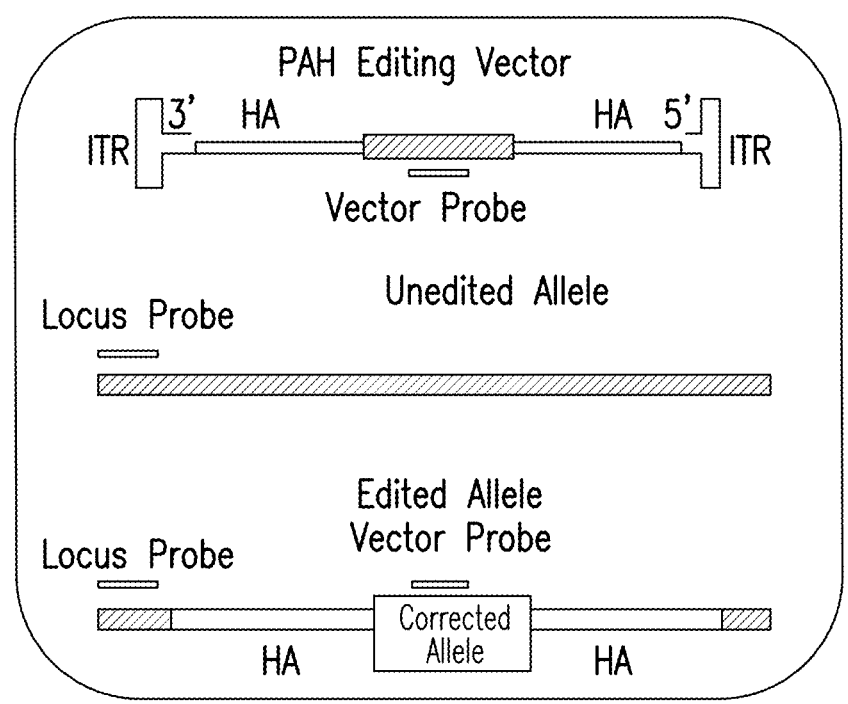
FIG. 5A is a diagram illustrating a method for quantifying an edited allele by ddPCR. A first pair of primers was designed to amplify a first sequence in the pHMI-hPAH-mAC-006 vector, and a first probe ("vector probe") was designed to hybridize to the first sequence. A second pair of primers was designed to amplify a second sequence on the mouse genome near the vector, and a second probe ("locus probe") was designed to hybridize to the second sequence. DNA samples were partitioned into oil droplets. The concentration of DNA was optimized to 600 pg per 20 μL in order to significantly reduce the probability that one oil droplet randomly contains a vector particle and a genomic DNA particle (p<0.001). Upon integration of the vector into the genome, the rate of double positivity of the vector probe and the locus probe in the same droplet increases.

A ddPCR method was developed to quantify the integration of the pHMI-hPAH-mAC-006 vector into the mouse genome. Two sets of primers and probes, as shown in Table 7, were designed for detection the integration by ddPCR. mPAH_ATG_gDNA_FAM Set 1 detected the unedited genome and the edited genome after the targeted integration of pHMI-hPAH-mAC-006. SV40 FAM Set 1 detected a sequence in the SV40 polyadenylation sequence, which was present in the edited genome and the unintegrated vectors (FIG. 5A).

Figure 5B:
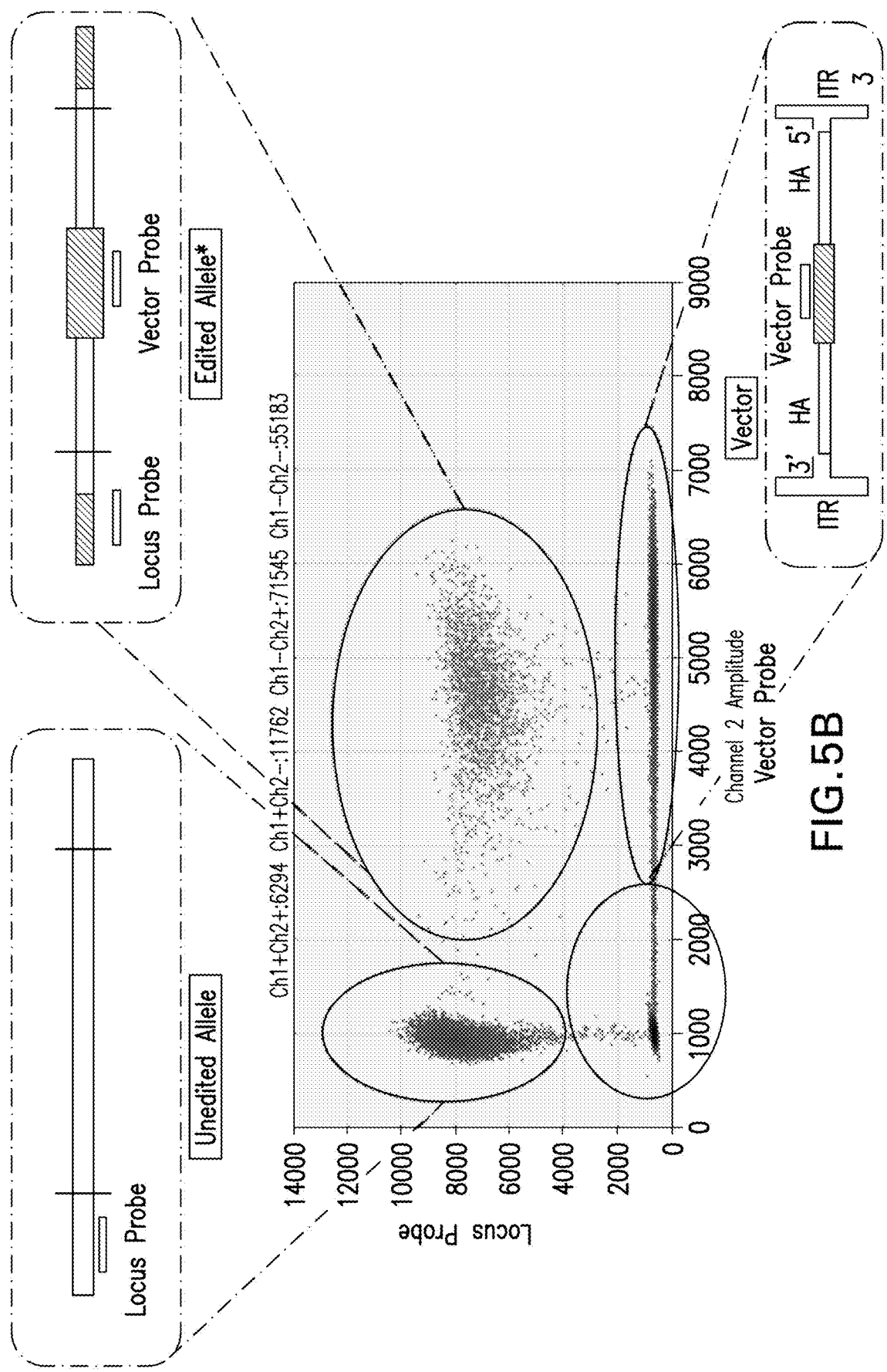
FIG. 5B is a diagram illustrating an expected result using the method described in FIG. 5A. In this diagram, each dot represents a single oil droplet. The dots with negative vector probe signal but positive locus probe signal represent the unedited alleles, whereas the dots with positive vector probe signal but positive locus probe signal represent the edited alleles.
Figure 5C:
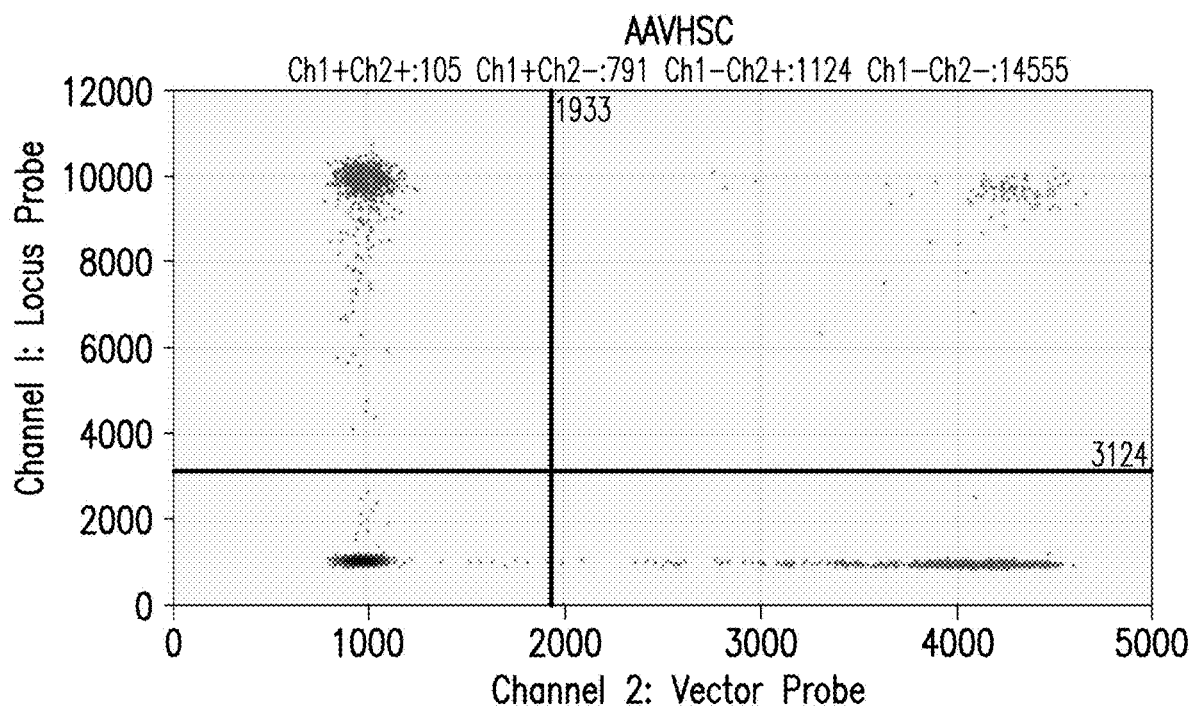
FIG. 5C is a graph showing the data generated from mouse liver using the method described in FIG. 5A. The pHMI-hPAH-mAC-006 vector packaged in an AAVHSC capsid was injected to two wild-type neonatal mice intravenously via the tail vein at a dose of $2 \times 10^{13}$ vector genomes per kg of body weight. Liver samples were collected after 2 weeks. One sample was analyzed using the method described in FIG. 5A. Vector probe and locus probe double positive droplets were detected.
Figure 5D:
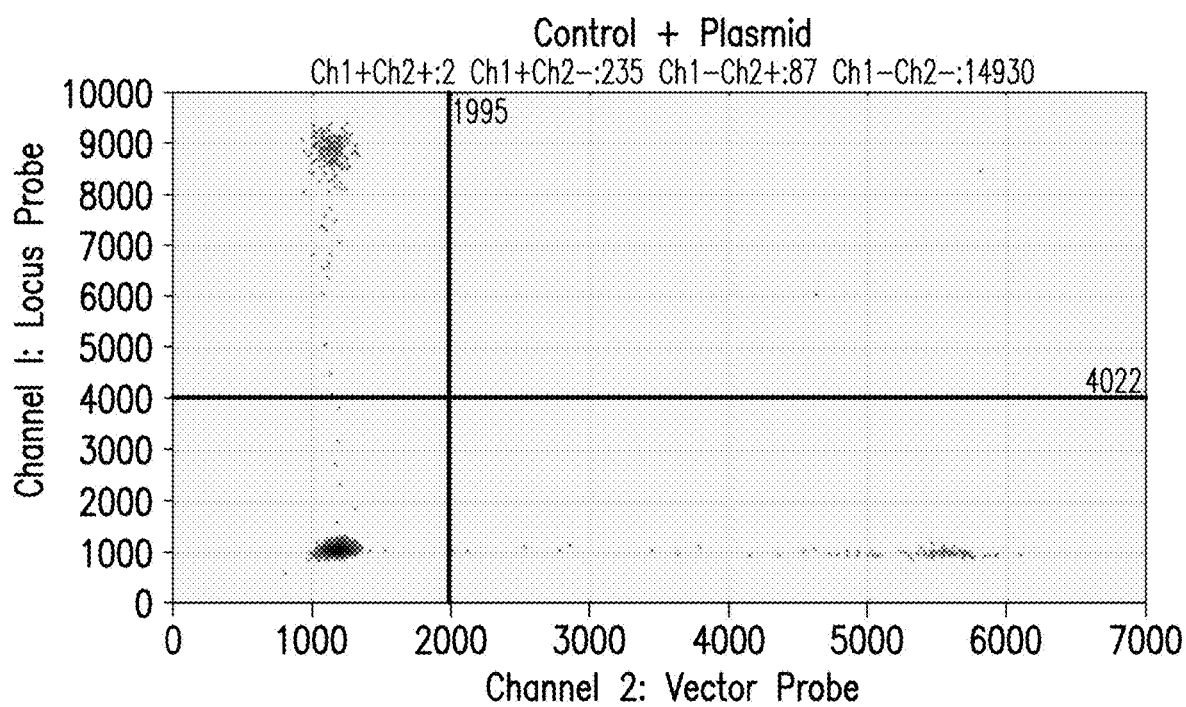
FIG. 5D is a graph showing the data generated from a sample containing liver from a saline treated mouse and the pHMI-hPAH-mAC-006 plasmid. Few probe and locus probe double positive droplets were detected, suggesting that the sample has been sufficiently diluted so that the probability that one oil droplet randomly contains a vector particle and a genomic DNA particle is very low.
Figure 5E:
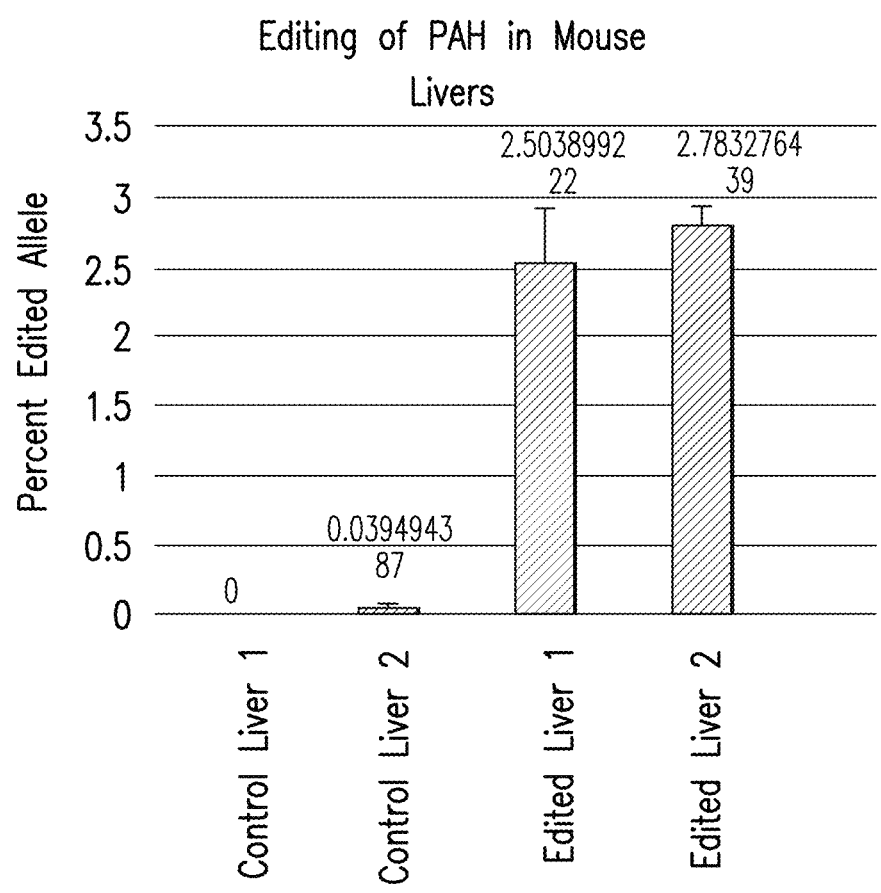
FIG. 5E is a graph showing the quantification of the graph in FIG. 5D and the graphs generated from other samples. The two control mice had 0% and 0.0395% edited alleles in the liver, respectively, and the two mice treated with the pHMI-hPAH-mAC-006 vector had 2.504% and 2.783% edited alleles in the liver, respectively.

DNA samples were partitioned into oil droplets. The concentration of DNA was optimized to 600 pg per 20 μL in order to significantly reduce the probability that one oil droplet randomly contains a vector particle and a genomic DNA particle (p<0.001) (FIG. 5C and 5D). Upon integration of the vector into the genome, the rate of double positivity of the vector probe and the locus probe in the same droplet increases (FIG. 5B). As shown in FIG. 5E, the two control mice had 0% and 0.0395% edited alleles in the liver, respectively, and the two mice treated with the pHMI-hPAH-mAC-006 vector had 2.504% and 2.783% edited alleles in the liver, respectively. Thus, the overall integration efficiency of the pHMI-hPAH-mAC-006 vector in the liver under the given conditions was about 2.6%. The integration efficiency for each individual cell is expected to be higher, because not all cells were transduced with the vector.

TABLE 7

Primers and probes for quantifying integration of human PAH into the mouse genome

| Primer or Probe | Sequence | SEQ ID NO |
|---|---|---|
| mPAH_ATG_gDNA_FAM Set 1, primer F | CAGCATCAGAAGCAG AACATTT | 102 |
| mPAH_ATG_gDNA_FAM Set 1, primer R | AAAGCACATCAGCAG TTTCAA | 103 |
| mPAH_ATG_gDNA_FAM Set 1, probe | AGATGAAAGCAACTG AACATCGACTACGA | 104 |
| SV40_FAM Set 1, primer F | GCAATAGCATCACAA ATTTCAC | 105 |
| SV40_FAM Set 1, primer R | GATCCAGACATGATA AGATACATTG | 106 |
| SV40_FAM Set 1, probe | TCACTGCATTCTAGT TGTGGTTTGTCCA | 107 |
| mPah_1C_LHA_FAM Set 3, primer F | gcaagctccagatca ccaata | 108 |
| mPah_1C_LHA_FAM Set 3, primer R | ctgagcaatgcattc agcaataa | 109 |
| mPah_1C_LHA_FAM Set 3, probe | CCCTGAACATCCCTT GACAGAGCA | 110 |

Figure 6:
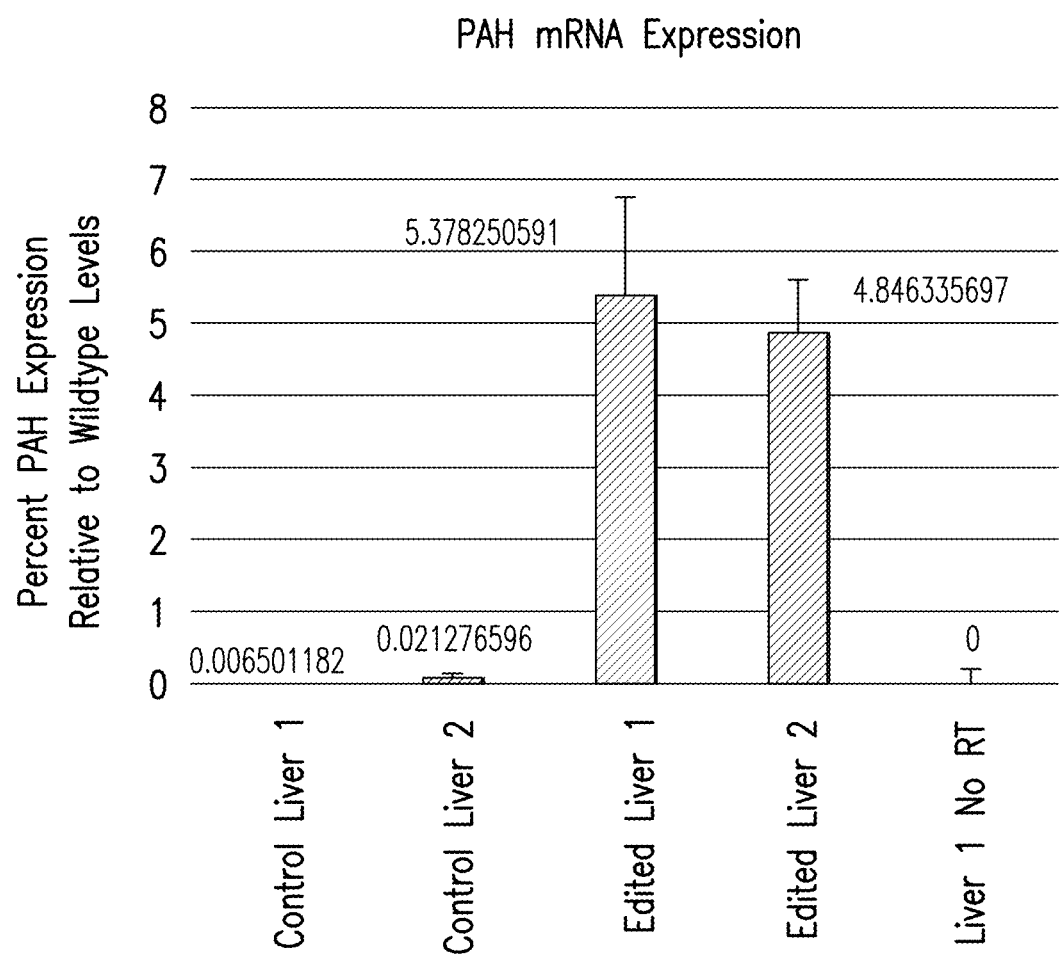
FIG. 6 is a graph showing the mRNA expression of human PAH in the liver after administration of the pHMI-hPAH-mAC-006 vector. RNA was extracted and reverse transcribed. A pair of primers and a probe were designed to specifically detect PAH expression from the edited allele. Each PAH expression level is normalized to the expression level of endogenous Hprt.

The relative quantity of the mRNA expressed from the edited allele was determined by ddPCR. SV40_FAM Set 1 was used to specifically detect human PAH expression from the edited allele. Each PAH expression level was normalized to the expression level of endogenous Hprt. As shown in FIG. 6, control mice showed no expression of human PAH, suggesting that the primers and probe did not cross react with the endogenous mouse PAH. The percent PAH expression relative to wild-type levels was calculated based on the human PAH signal relative to Hprt normalized against the endogenous mouse PAH signal relative to Hprt. The two mice treated with the pHMI-hPAH-mAC-006 vector had 5.378% and 4.846% mRNA levels relative to the endogenous mouse PAH levels, respectively. Thus, the overall mRNA level of the pHMI-hPAH-mAC-006 vector in the liver under the given conditions was about 5%. The mRNA level for each individual cell is expected to be higher, because not all cells were transduced with the vector.

b) Editing of the Mouse PAH Gene in Pah Knockout Mice

In one experiment, the efficacy of the pHMI-hPAH-mAC-006 vector in phenotypic correction was determined using a PAH knock-out mouse model ($PAH^{ENU2}$). Briefly, the hPAH-mAC-006 vector packaged in AAVHSC15 capsids was administered intravenously, in 5 consecutive days, to these mice at a dose of $1.16 \times 10^{14}$ vector genomes per kilogram of body weight. Serum phenylalanine (Phe) was measured weekly for 5 months by mass spectrometry. After 5 months, DNA was extracted from liver samples, and the numbers of vector genomes per cell were analyzed by ddPCR using primer and probe sets to measure the vector and the human PAH genomic locus copy numbers.

Transduction efficiency (measured in number of vector genomes per cell ("VG per Cell")) was the determined by ddPCR using primer and probe sets to measure the vector, and the mouse and human PAH genomic loci copy numbers. Editing frequency was measured by multiplexed ddPCR using primer probe sets to measure the frequency of the editing element DNA from the AAV vector ("payload") integrated into the mouse PAH locus and the human PAH locus. Briefly, single DNA strands were partitioned into oil droplets. Each droplet was tested for the presence of either human or mouse PAH DNA along with the presence or absence of the payload. Editing frequency was calculated based on the detected co-partitioning of a payload and a target DNA in a single droplet in excess of expected probability of co-partitioning of a payload and a target DNA in separate nucleic acid molecules.

The PAH knock-out mice had a phenotype of increased phenylalanine (Phe) levels in the blood. To examine phenotypic changes, the serum levels of Phe after administration of the AAV vectors were measured, the percentage levels were calculated relative to the baseline at time zero, and the percentage levels were compared to the control mice that did not receive the AAV vectors.

Figure 7A:
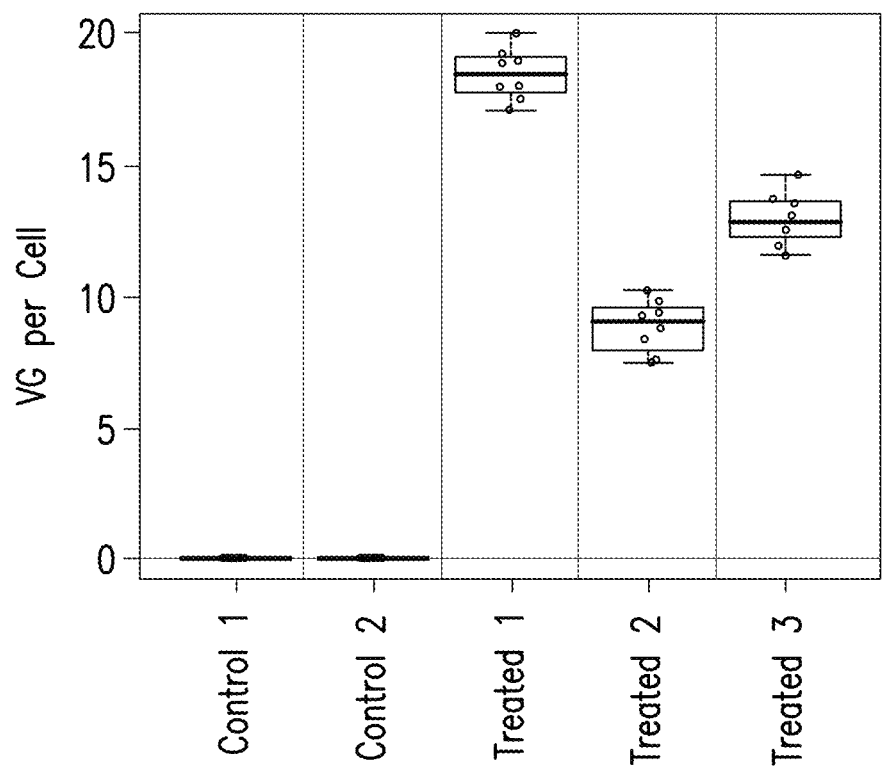
FIG. 7A is a graph showing the transduction efficiency of the pHMI-hPAH-mAC-006 vector packaged in AAVHSC capsids in mouse blood samples, measured by ddPCR using primer and probe sets to measure the vector and the mouse PAH genomic loci copy numbers. The numbers of vector genomes per cell ("VG per Cell") is calculated from the measured ratio of number of vectors versus the copy numbers of the genomic locus of mouse PAH.
Figure 7B:
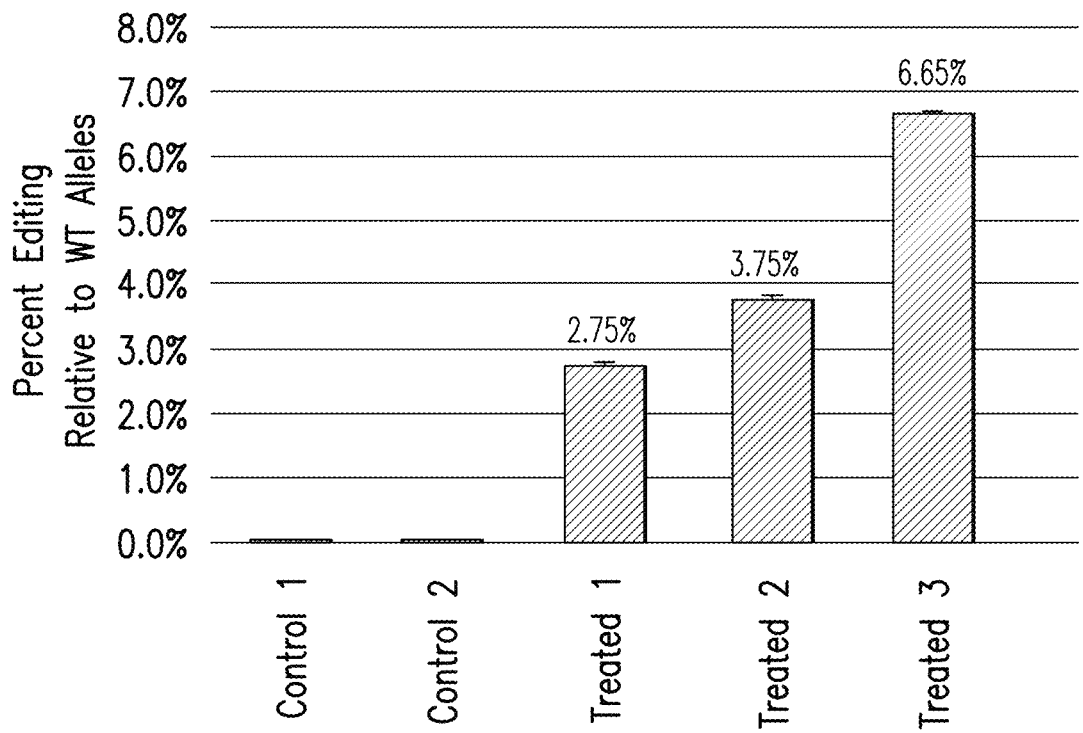
FIG. 7B is a graph showing the percentage editing efficiency in mouse blood samples measured by multiplexed ddPCR using primer probe sets to measure the frequency of the integrated DNA from the AAV vector ("payload") integrating into the mouse PAH locus and the human PAH locus. Editing frequency was calculated based on the detected co-partitioning of a payload and a target DNA in a single droplet in excess of expected probability of co-partitioning of a payload and a target DNA in separate nucleic acid molecules.
Figure 7C:
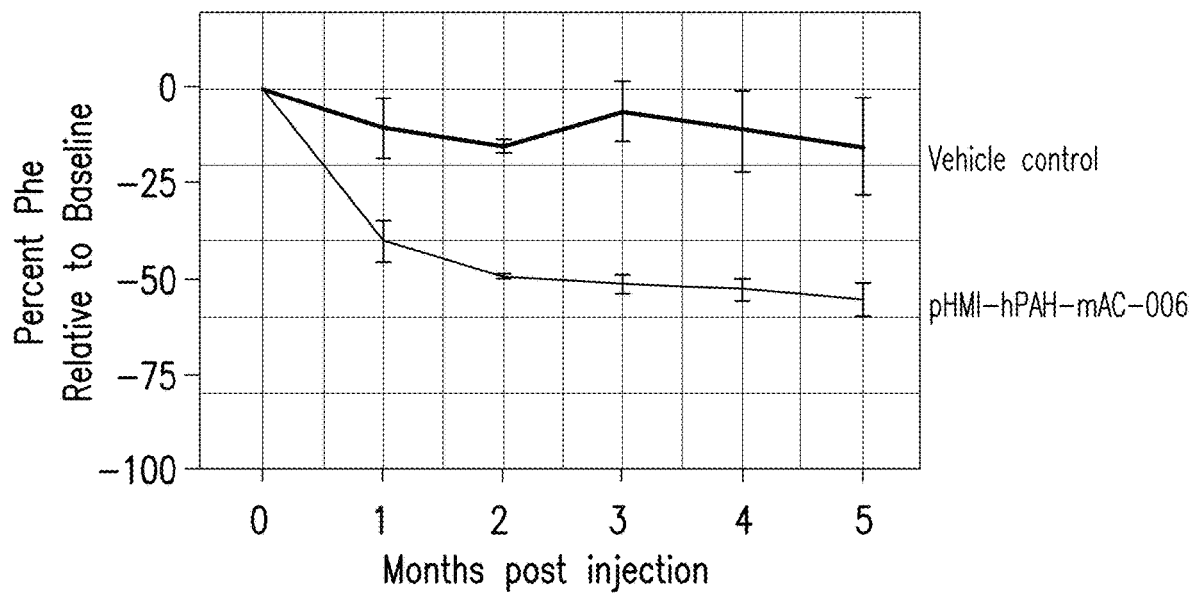
FIG. 7C is a graph showing the percentage levels of serum phenylalanine relative to the baseline in the mice after administration of the pHMI-hPAH-mAC-006 vector packaged in an AAVHSC capsid. The average levels in the treated animals and control animals (mice that did not receive AAV administration) are plotted.
Figure 7D:
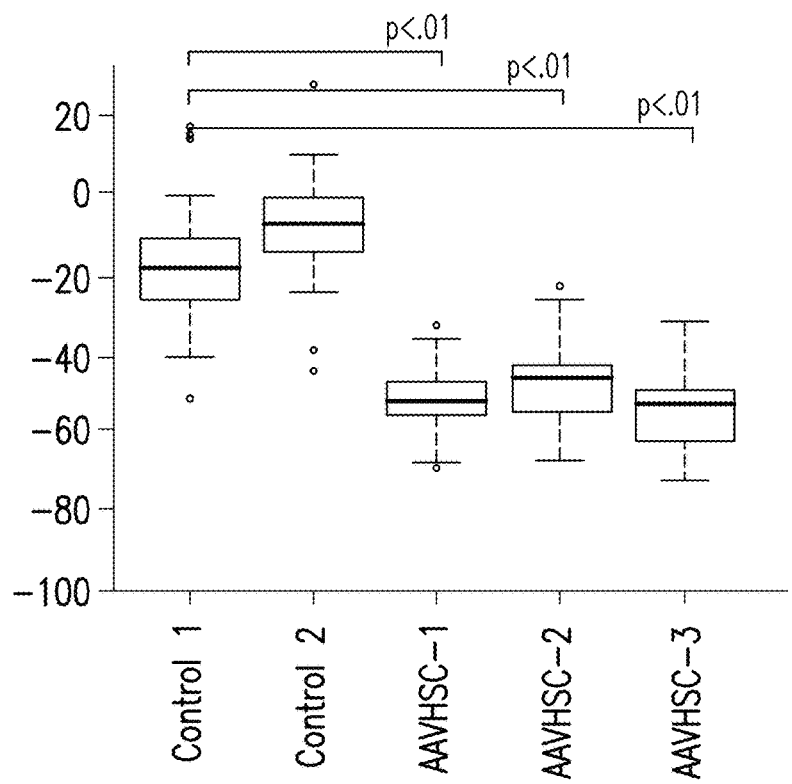
FIG. 7D is a graph showing the percentage levels of serum phenylalanine relative to the baseline in each individual mouse injected with the pHMI-hPAH-mAC-006 vector packaged in an AAVHSC capsid or in each control mice that did not receive AAV administration. The p values were calculated by ANOVA against the control distribution.
Figure 7E:
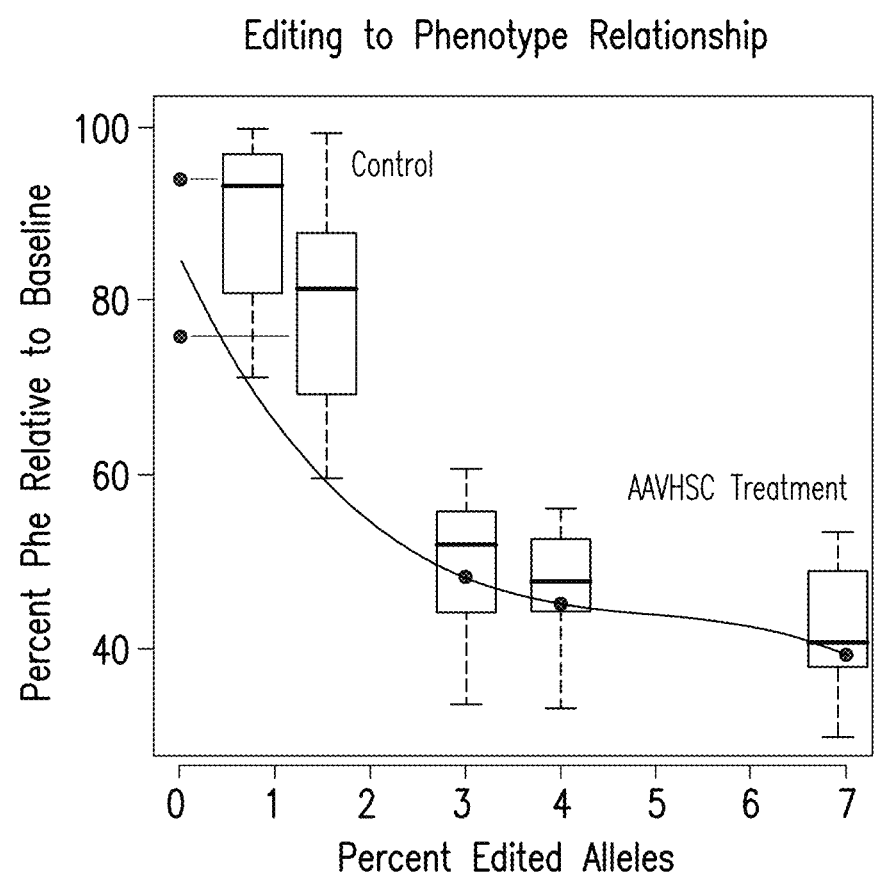
FIG. 7E is a graph showing the correlation between the percentage levels of serum phenylalanine relative to the baseline and the percentage editing efficiency.

The mice administered the hPAH-mAC-006 vector packaged in AAVHSC15 capsids showed a transduction efficiency of about 8 to 18 vector genomes per cell (FIG. 7A), and an average editing efficiency of about 4.4% relative to the number of alleles (FIG. 7B). This editing efficiency supported an expression level of PAH sufficient to reduce Phe levels in the serum of the mice by about 50% for at least 5 months (FIGS. 7C and 7D), and the phenotypic changes correlated with the editing efficiency (FIG. 7E). The correct homologous recombination of the vector at the Pah locus was verified by the length of the PCR product amplified from the edited genomic locus using a first primer that hybridized to the payload, and a second primer that hybridized to a genomic sequence downstream from the right homology arm (data not shown).

To determine whether the homologous recombination introduced any genomic alterations into the edited alleles, the DNA sequences in the genomic regions corresponding to the homology arms were further analyzed by deep sequencing (Illumina). The samples all had high quality sequence reads, and all the positions were sequenced with a depth of over 20,000 reads. Insertions and deletions (hereinafter "indels") were identified by Somatic Variant Callers with an indel quality filter and a strand bias filter. Specifically, a region in the right homology arm comprising 10 continuous G showed an elevated indel rate of about 0.02-0.05% in both control and treated animals. Indels at this locus, as well as several other loci, did not pass filters for bona fide changes, and were removed from further analysis. As shown in Table 8, the untreated control animals showed an indel rate of 0.002-0.006%. Treated animal 1 had an indel rate of 0.031%; treated animal 2 had no indels that passed the filters; treated animal 3 had an indel rate similar to those of the control animals. All the indels identified were located in untranslated regions.

TABLE 8

Deep sequencing data for individual animals

| Animal | Total reads | Average depth per base | Number of mutations passing filter | Accumulative mutations passing filter in % |
|---|---|---|---|---|
| Control animal 1 | 4,218,356 | 341,291 | 1 | 0.002% |
| Control animal 2 | 5,599,928 | 453,069 | 2 | 0.006% |
| Treated animal 1 | 4,785,826 | 387,203 | 9 | 0.031% |
| Treated animal 2 | 3,353,288 | 271,302 | 0 | 0.000% |
| Treated animal 3 | 9,514,938 | 769,817 | 9 | 0.006% |

The results above demonstrated the feasibility of reversing the phenotypes of PAH deficiency using correction vectors that insert a PAH coding sequence in a genome.

Figure 7F:
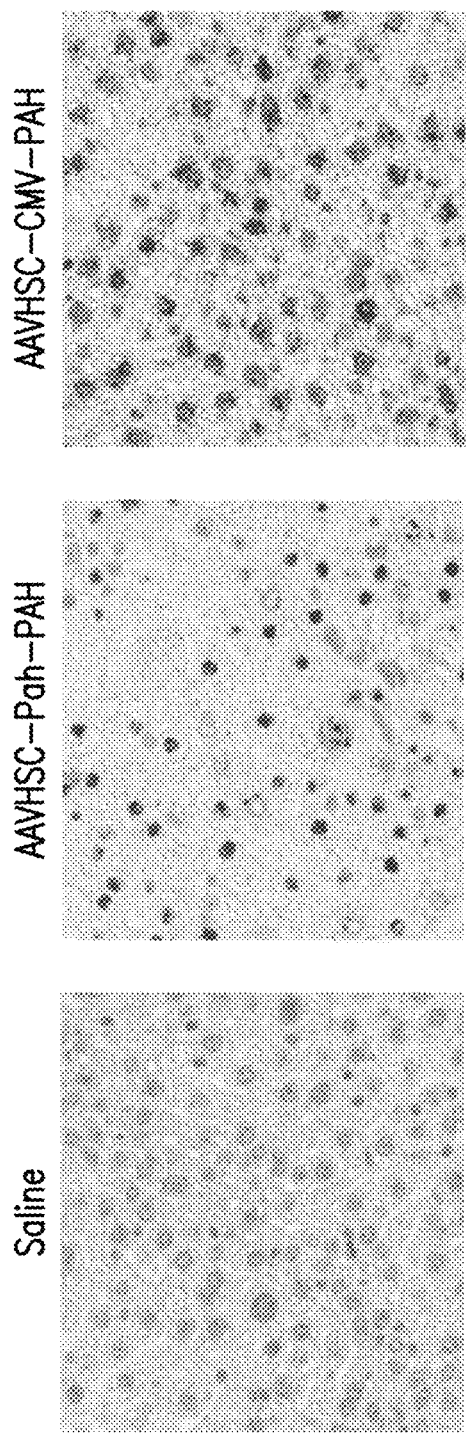
FIG. 7F is a set of images showing in situ hybridization (ISH) of Pah mRNA and possibly virus DNA comprising PAH sequence in liver samples of mice injected with the hPAH-mAC-006 vector (middle panel), a non-integrating Pah transgene vector (right panel), or saline control (left panel).

To detect expression of human PAH in individual mouse hepatocytes after the in vivo transduction, RNA in situ hybridization (ISH) was performed on liver tissue sections using a probe specific to >1kb of the human PAH RNA having the silent codon alteration as described above (Advanced Cell Diagnostics, Inc., Hayward, CA). As shown in FIG. 7F, this probe detected human PAH RNA and possibly virus DNA comprising PAH sequence in mouse hepatocytes transduced with the hPAH-mAC-006 vector, but did not cross-hybridize to endogenous mouse Pah RNA. A liver sample of a mouse transduced with a transgene construct comprising a CMV promoter driving the expression of a human Pah RNA having the same silent codon alteration was used as a positive control.

c) PAH Correction Vector pHMI-hPAH-mAC-006

The pHMI-hPAH-mAC-006 vector comprised 5' to 3' the following genetic elements: a 5' ITR element, a 5' homology arm, a silently altered human PAH coding sequence, an SV40 polyadenylation sequence, a 3' homology arm, and a 3' ITR element. The sequences of these elements are set forth in Table 9.

TABLE 9

Genetic elements in PAH correction vector pHMI-hPAH-mAC-006

| Genetic Element | SEQ ID NO |
|---|---|
| 5' ITR element | 18 |
| 5' homology arm | 111 |
| Silently altered human PAH coding sequence | 25 |
| SV40 polyadenylation sequence | 31 |
| Targeted integration restriction cassette | 71 |
| 3' homology arm | 112 |
| 3' ITR element | 19 |
| correction genome (5' HA to 3' HA) | 113 |
| correction genome (5' ITR to 3' ITR) | 114 | d) PAH Gene Editing Efficiency in Mice Administered pHMI-hPAH-mAC-006

Figure 9A:
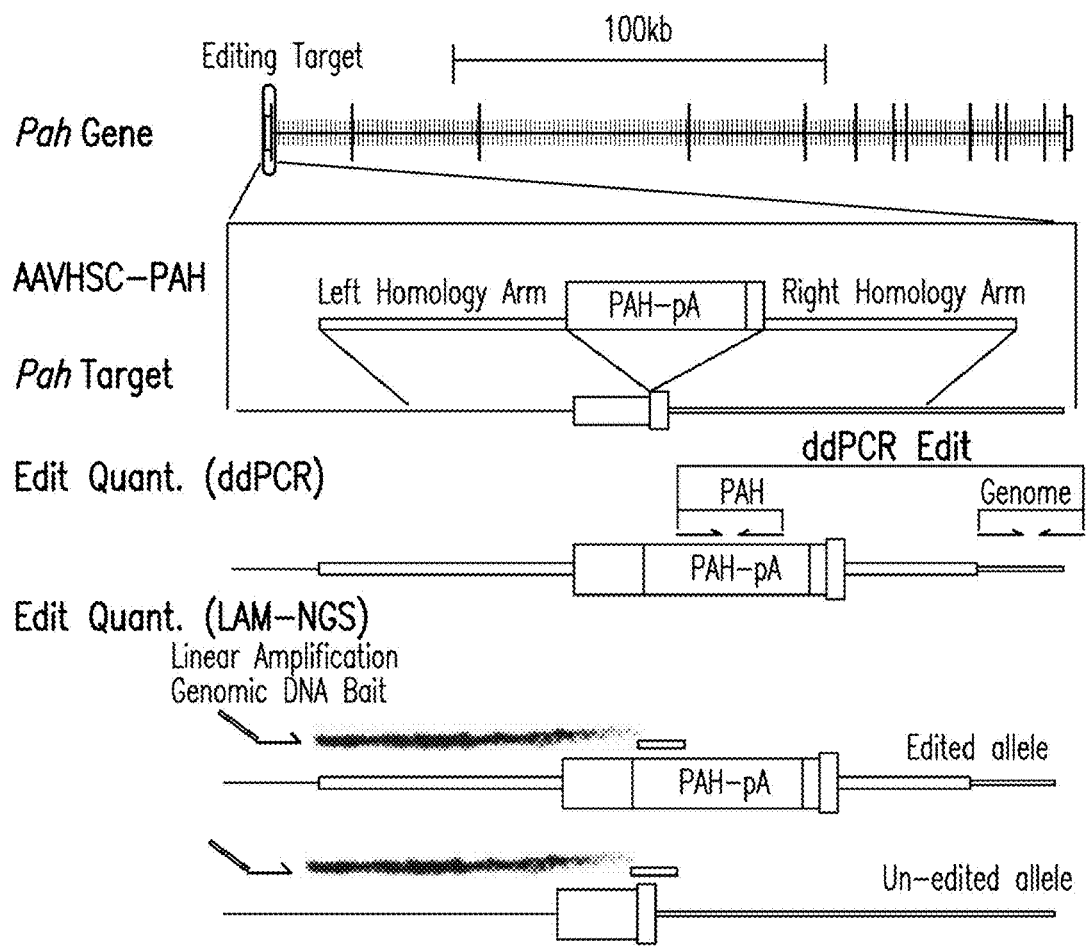
FIG. 9A depicts a schematic of the assay used to determine editing efficiency of the PAH gene in mice.
Figure 9B:
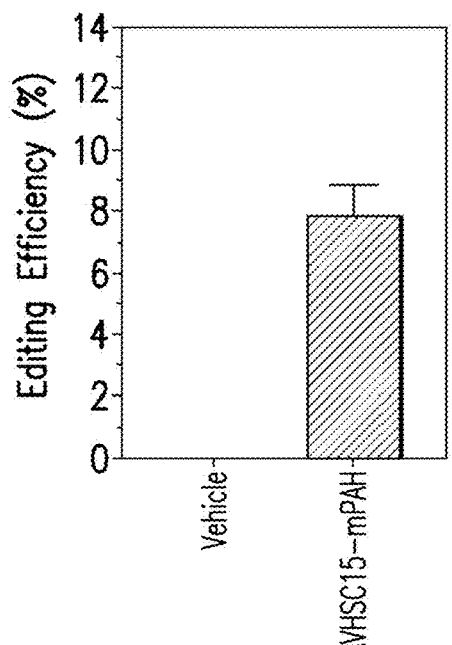
FIG. 9B is a graph showing the PAH gene editing efficiency in cells from mice that have been administered either the pHMI-hPAH-mAC-006 vector or vehicle control.

FIG. 9A depicts a schematic of the assay used to determine editing efficiency of the PAH gene in mice that received the pHMI-hPAH-mAC-006 vector. ddPCR and LAM-NGS (LAM-PCR followed by next generation sequencing (NGS)) was performed as described herein and as indicated in FIG. 9A. FIG. 9B shows a graph of PAH gene editing efficiency as determined in cells of mice administered either the pHMI-hPAH-mAC-006 vector or vehicle control. As shown in FIG. 9B, PAH gene editing efficiency in mice administered the HMI-hPAH-mAC-006 vector was determined to be about 8% relative to the number of alleles. No errors were detected in the edited regions.

e) Durable Phenotypic Correction of Hyperphenylalaninemia in Mouse Models

Figure 10A:
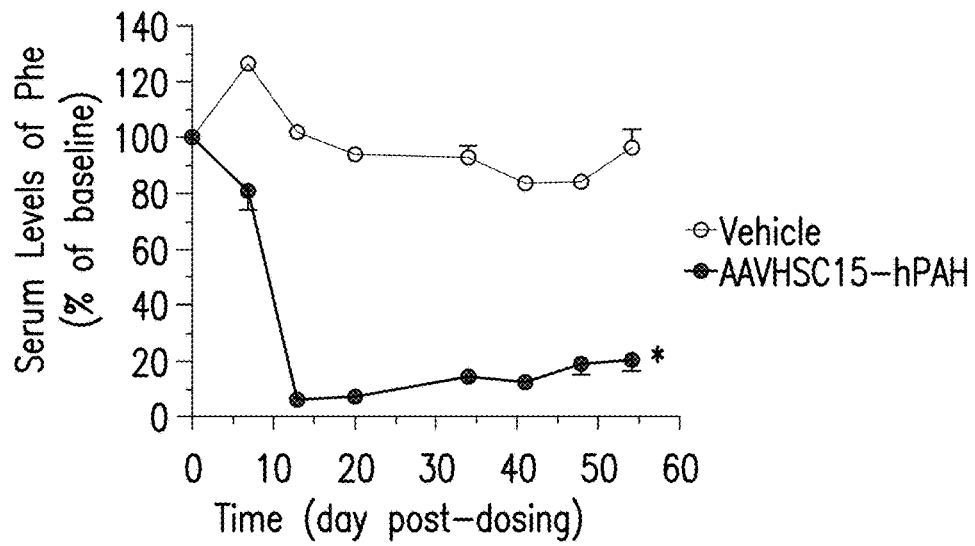
FIG. 10A is a graph showing the average percentage levels of serum phenylalanine relative to the baseline in mice after administration of either the pHMI-hPAH-mAC-006 vector packaged in AAVHSC15 capsids or a vehicle control.
Figure 10B:
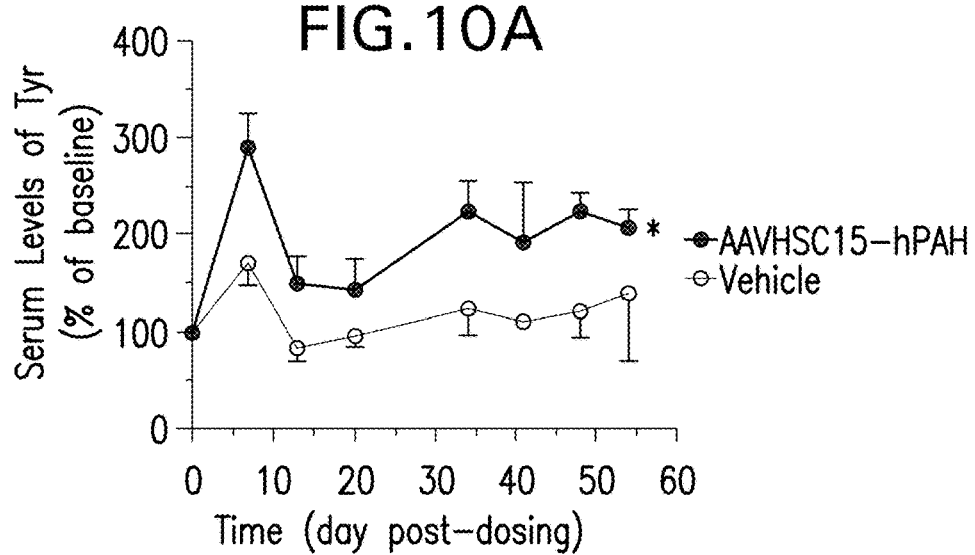
FIG. 10B is a graph showing the average percentage levels of serum tyrosine relative to the baseline in mice after administration of either the pHMI-hPAH-mAC-006 vector packaged in AAVHSC15 capsids or a vehicle control.
Figure 10C:
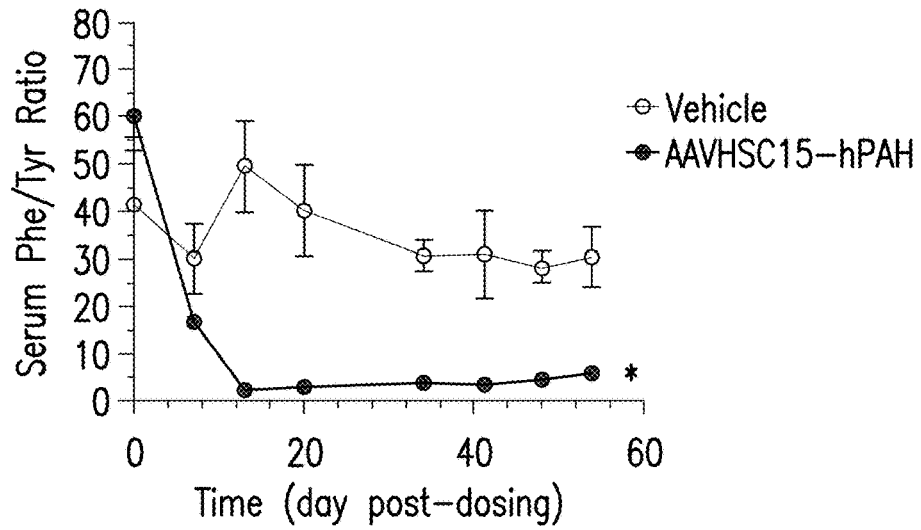
FIG. 10C is a graph showing the ratio between serum phenylalanine and serum tyrosine levels in mice that received either the pHMI-hPAH-mAC-006 vector packaged in AAVHSC15 capsids or a vehicle control.

In one experiment, the efficacy of the pHMI-hPAH-mAC-006 vector in phenotypic correction was determined using a PAH knock-out mouse model ($PAH^{ENU2}$). The pHMI-hPAH-mAC-006 vector was packaged in AAVHSC15 capsids and administered intravenously to mice at a dose of $1 \times 10^{14}$ vector genomes per kilogram of body weight. To examine phenotypic changes, the serum levels of phenylalanine (Phe) and tyrosine (Tyr) after administration of the pHMI-hPAH-mAC-006 vector packaged in AAVHSC15 capsids was measured weekly beyond 7 weeks, the percentage levels were calculated relative to the baseline at time zero, and the percentage levels were compared to the control mice that received a vehicle control. A total of 4 mice were administered the pHMI-hPAH-mAC-006 vector packaged in AAVHSC15 capsids, and 2 mice were administered vehicle control. As shown in FIG. 10, a significant reduction in serum levels of Phe (FIG. 10A; * indicates $p<0.0001$ by repeated measures 2-way ANOVA vs vehicle; $p<0.0001$ by repeated measures 2-way ANOVA vs time) and a significant increase in serum levels of Tyr (FIG. 10B; * indicates $p<0.05$ by repeated measures 2-way ANOVA vs vehicle; $p<0.0003$ by repeated measures 2-way ANOVA vs time) were observed in mice that received the vector. FIG. 10C shows the ratio between serum Phe and serum Tyr in mice that received the vector or a vehicle control (* indicates $p<0.002$ by repeated measures 2-way ANOVA vs vehicle; $p<0.0004$ by repeated measures 2-way ANOVA vs time).

Figure 11A:
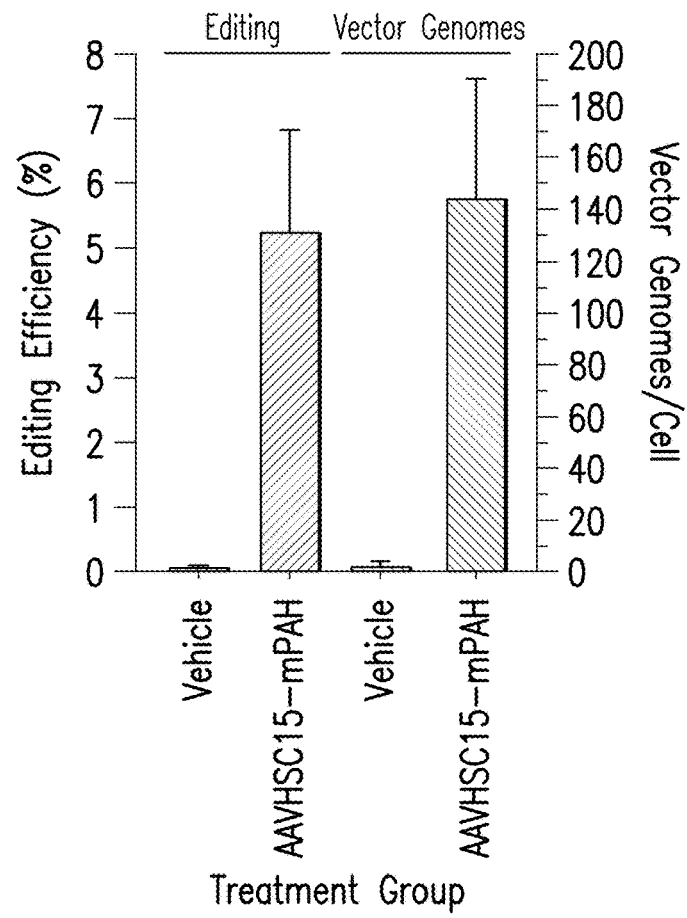
FIG. 11A is a graph showing the average PAH gene editing efficiency and transduction efficiency in cells obtained from mice administered either the pHMI-hPAH-mAC-006 vector or a vehicle control.

FIG. 11A depicts a graph showing the PAH gene editing efficiency and transduction efficiency of cells obtained from mice administered either the pHMI-hPAH-mAC-006 vector or a vehicle control. The left y-axis of FIG. 11A indicates the percentage of editing efficiency and shows that mice administered the pHMI-hPAH-mAC-006 vector (AAVHSC15-mPAH) had about 5% editing efficiency relative to the number of alleles. The right y-axis of FIG. 11A indicates the number of vector genomes per cell and shows that mice administered the pHMI-hPAH-mAC-006 vector (AAVHSC15-mPAH) had a transduction efficiency of about 140 vector genomes per cell.

Figure 11B:
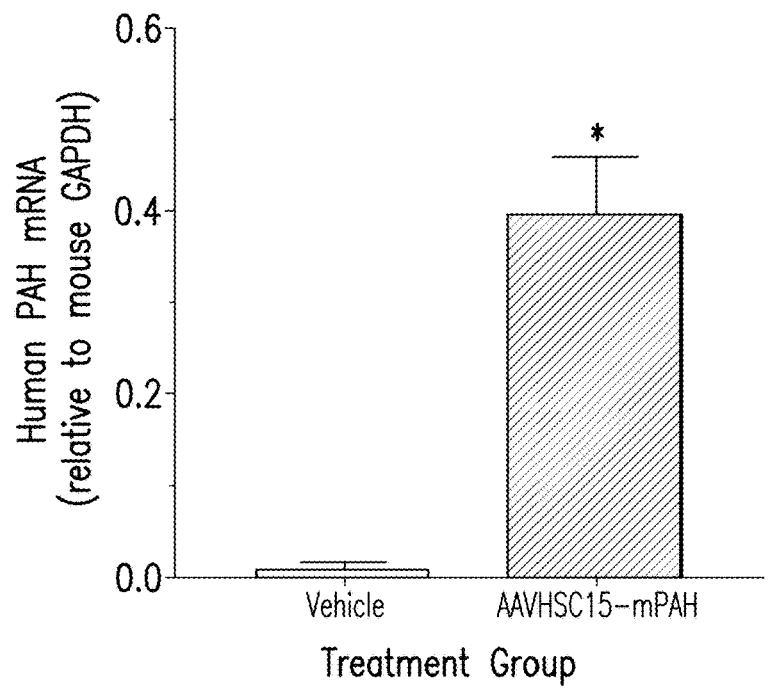
FIG. 11B depicts a graph showing the relative quantity of PAH mRNA expressed, normalized to the expression level of mouse GAPDH, in cells obtained from mice administered either the pHMI-hPAH-mAC-006 vector (AAVHSC15-mPAH) and or a vehicle control.

FIG. 11B depicts a graph showing the relative quantity of PAH mRNA expressed, normalized to the expression level of mouse GAPDH, of cells obtained from mice administered either the pHMI-hPAH-mAC-006 vector (AAVHSC15-mPAH) or a vehicle control. As shown, cells obtained from mice administered the pHMI-hPAH-mAC-006 vector (AAVHSC15-mPAH) had significant levels of human PAH mRNA, as compared mice administered a vehicle control (* indicates $p<0.005$ by two-tailed Mann Whitney test vs vehicle).

Example 5

In Vivo Editing of the Human PAH Gene in a Mouse Model

This example provides animal models for examining PAH correction vectors, such as those described in the previous examples, in the editing of the human PAH gene in a mouse model.

a) Editing of Human PAH in Human Blood Cells in a Mouse Model

Briefly, NOD.Cg-Prkdc$^{scid}$Il2rg$^{tm1Wjl}$/SzJ (NSG) mice were myeloblated through sublethal irradiation, and transplanted with human CD34$^+$hematopoietic stem cells. Engraftment levels were determined after 12 weeks by identifying the amounts of human and murine CD45$^+$ cells in the peripheral blood by flow cytometry, and the mice having more than 50% of circulating human CD45+ cells were selected. The hPAH-hAC-008 vector packaged with the AAVHSC17 capsid was administered intravenously to 12 such mice divided equally into four groups. The first and second groups of mice received a dose of $1.54\times10^{13}$ vector genomes per kilogram of body weight, and the third and fourth groups received a dose of $2.1\times10^{12}$ vector genomes per kilogram of body weight. The mice were euthanized 6 weeks after the injections. Samples of blood, bone marrow and spleen tissues were collected, and genomic DNA was extracted.

Editing frequency in mouse and human cells were measured by multiplexed droplet digital PCR (ddPCR) using primer probe sets to measure the frequency of the integrated DNA from the AAV vector ("payload") integrating into the mouse PAH locus and the human PAH locus. In short, single DNA strands were partitioned into oil droplets. Each droplet was tested for the presence of either human or mouse PAH DNA along with the presence or absence of the payload. Editing frequency was calculated based on the detected co-partitioning of a payload and a target DNA in a single droplet in excess of expected probability of co-partitioning of a payload and a target DNA in separate nucleic acid molecules.

As shown in Table 10, editing of human cells was detected in bone marrow samples in a dose-dependent manner. Notably, editing was specific to human genome, as no editing was detected in mouse cells.

TABLE 10

Editing efficiencies of hPAH-hAC-008 in mouse tissues

| Group | % Editing in bone marrow | % Editing in spleen | % Editing in blood |
|---|---|---|---|
| 1 | 0.16 | 0.0 | 0.0 |
| 2 | 0.25 | 0.01 | 0.0 |
| 3 | 0.09 | 0.09 | 0.0 |
| 4 | 0.02 | 0.013 | 0.001 |

Figure 8A:
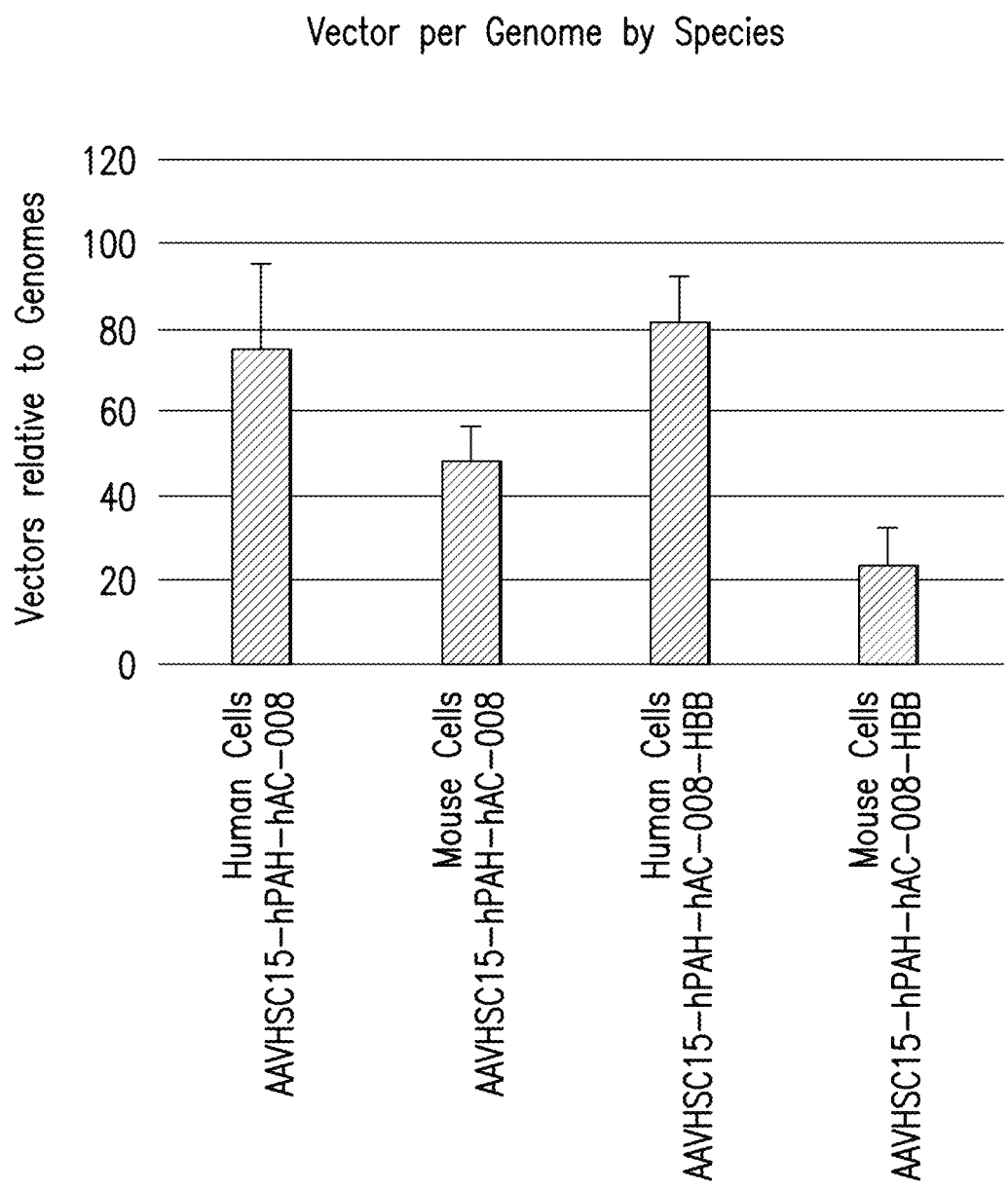
FIG. 8A is a graph showing the transduction efficiency of the hPAH-hAC-008 vector and hPAH-hAC-008-HBB vector in human and mouse hepatocytes in mice administered with the vector packaged in AAVHSC15 capsids, as measured by ddPCR using primers and probe sets specific for the vector. The y-axis represents the number of vectors measured relative to genomes of the mouse or human cells.

FIG. 8A shows the transduction efficiency of the hPAH-hAC-008 vector and hPAH-hAC-008-HBB vector in human and mouse hepatocytes in mice administered with the vector packaged in AAVHSC15 capsids.

b) Editing of Human PAH in Human Hepatocytes in a Mouse Model using a Vector Comprising an HBB Intron The hPAH-hAC-008 vector comprises a complete human PAH coding sequence without any intron. A modified vector hPAH-hAC-008-HBB, wherein the first intron of the human HBB gene (having the nucleotide sequence of SEQ ID NO: 28) is added between nucleotides 912 and 913 of the human PAH coding sequence, was generated for improving the nuclear export and stability of RNA molecules transcribed from the vector. The internucleotide bond between nucleotides 912 and 913 corresponds to the splicing site between exon 8 and exon 9 of the native PAH gene, which was not disrupted by the silent alteration of the codons.

Figure 8B:
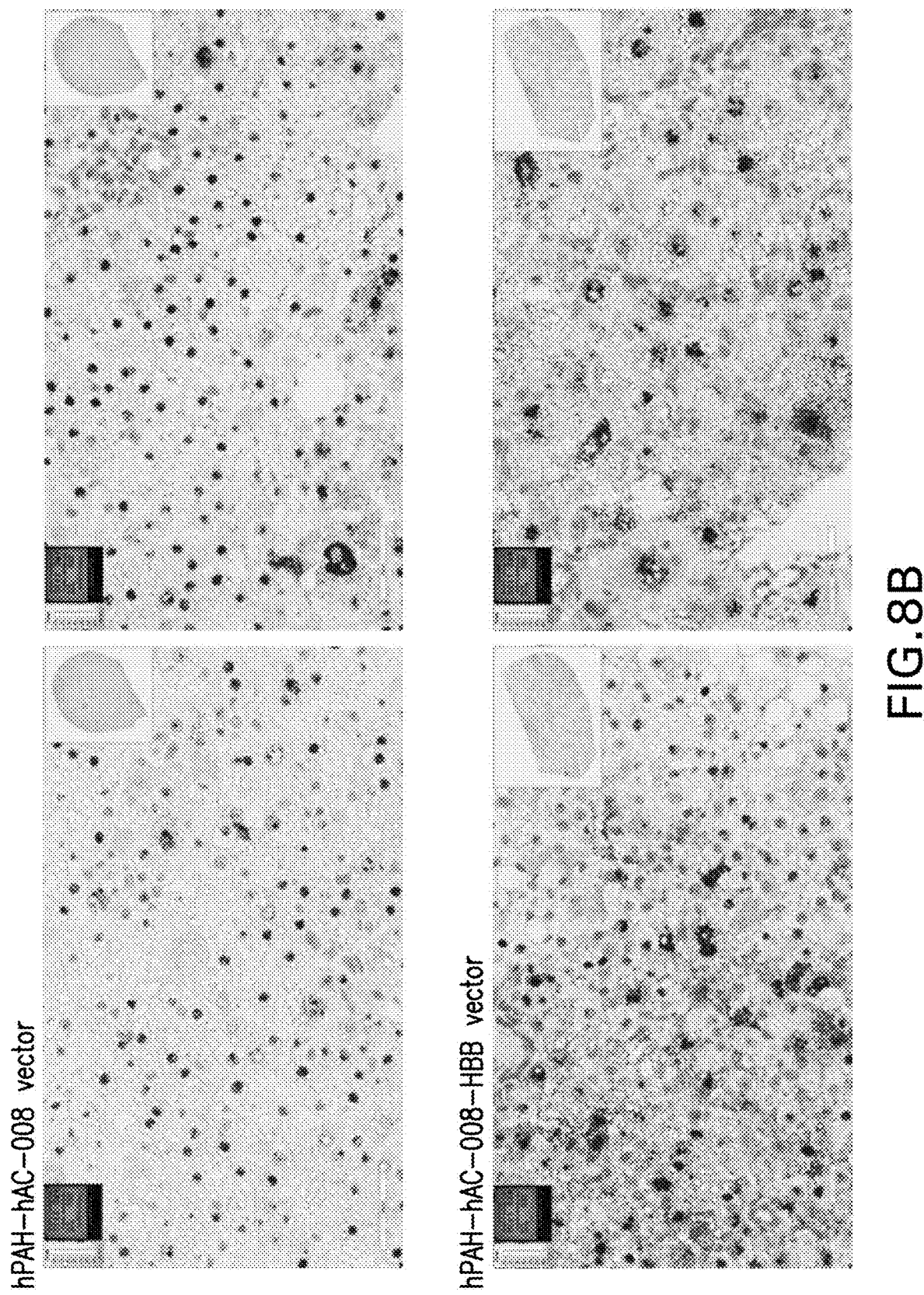
FIG. 8B is a series of photos showing in situ hybridization of human Pah mRNA and possibly virus DNA comprising PAH sequence with silent codon alteration in liver samples from mice administered an unmodified or a modified hPAH-hAC-008 vector. The probe detected only the mRNA transcribed from a gene locus edited by the unmodified or modified hPAH-hAC-008 vector.

The vectors were packages with AAVHSC15 capsids, and were administered into mice intravenously at a dose of $1\times10^{13}$ vector genomes per kilogram of body weight. Six weeks after the administration, liver samples were collected, and the localization of the silently altered human PAH mRNA and possibly virus DNA comprising PAH sequence was examined by in situ hybridization. As shown in FIG. 8B, the addition of the HBB intron substantially improved the nuclear export of the mRNA. This result demonstrated that addition of an intron in the PAH coding sequence could potentially increase the expression level of the PAH gene, and this feature can be included in the design of PAH correction vectors.

c) Editing of Human PAH in Human Hepatocytes in a Mouse Model

Briefly, Fah$^{-/-}$ Rag2$^{-/-}$ Il2rg$^{-/-}$ mice on the C57Bl/6 background, commonly referred to as the FRG® Knockout mice, were used as a model for liver humanization. The mice were immunodeficient and lacked the tyrosine catabolic enzyme fumarylacetoacetate hydrolase (Fah). Ablation of mouse hepatocytes was induced by the withdrawal of the protective drug 2-(2-nitro-4-trifluoromethylbenzoyl)-1,3-cyclohexanedione (NTBC). The mice were then engrafted with human hepatocytes, and a urokinase-expressing adenovirus was administered to enhance repopulation of the human hepatocytes. Engraftment was sustained over the life of the animal with an appropriate regimen of CuRx™ Nitisinone (20-0026) and prophylactic treatment of SMX/TMP antibiotics (20-0037). The animals weighed 22 grams on average and had a typical lifespan of 18-24 months.

The hPAH-hAC-008 or hPAH-hAC-008-HBB vector was packaged with AAVHSC15 capsids, and was administered into mice intravenously at a dose of $1\times10^{13}$ vector genomes per kilogram of body weight. Six weeks after the administration, liver samples were collected, the human and mouse hepatocytes were separated and purified using Miltenyi autoMACS columns following liver perfusion. DNA was extracted, and the efficiency of gene editing was measured using the same ddPCR method as described above.

Figure 8C:
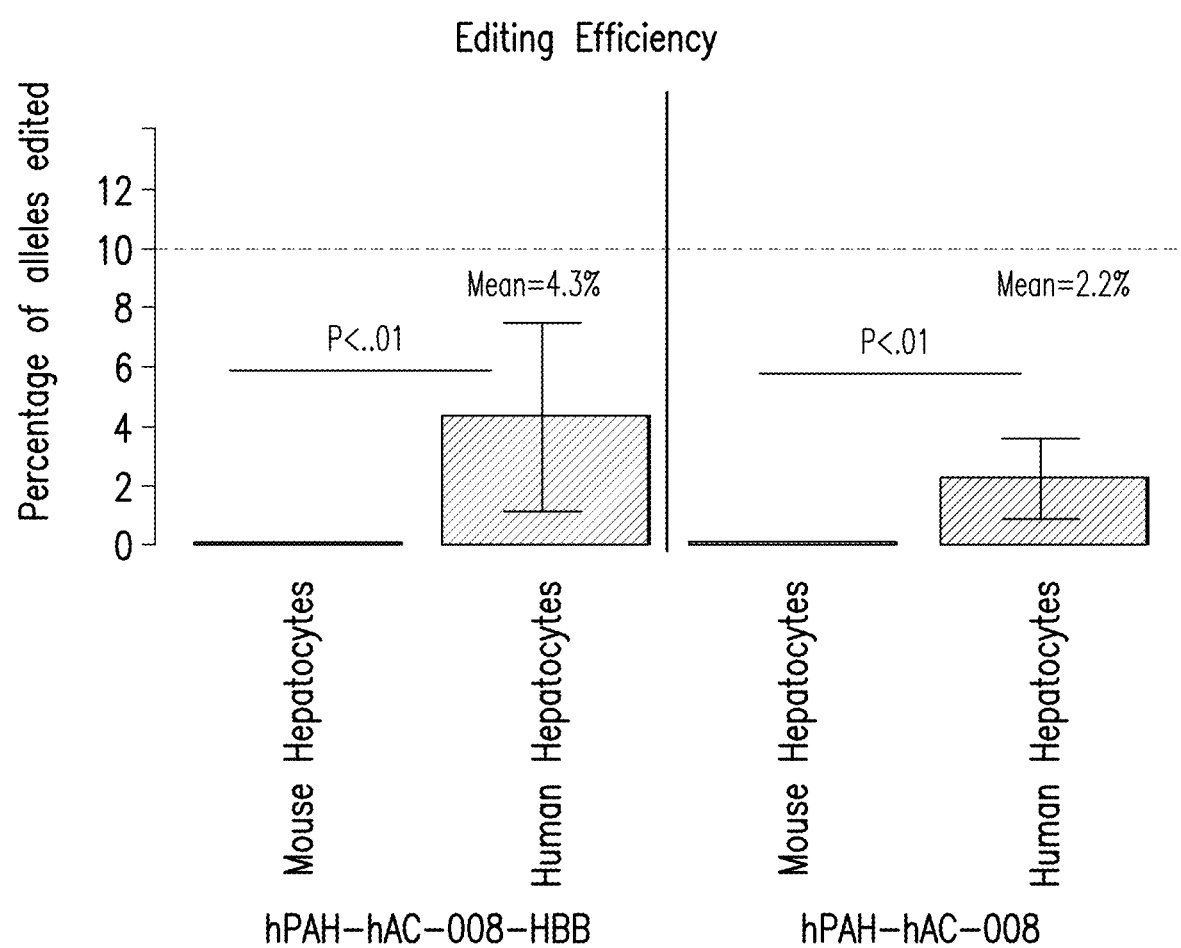
FIG. 8C is a graph showing the percentage editing efficiency of the hPAH-hAC-008 vector in mouse and human hepatocytes from mice transplanted with human hepatocytes, as measured by multiplexed ddPCR. The left half of the figure refers to the editing efficiency of an animal treated with the hPAH-hAC-008-HBB vector, and the right half refers to that of an animal treated with the hPAH-hAC-008 vector. The p values were calculated by ANOVA.

As shown in FIG. 8C, the percentage editing efficiency in human hepatocytes, measured as the percentage of edited alleles out of all alleles, was 2.2% in an animal treated with the hPAH-hAC-008 vector, and 4.3% in an animal treated with the hPAH-hAC-008-HBB vector. Editing was not detected in mouse hepatocytes from either animal. The lack of detection of editing in mouse hepatocytes from either animal is unlikely to be due to lack of transduction efficiency as mouse hepatocytes were transduced well (FIG. 8A). In a separate experiment, editing of the human genome by the hPAH-hAC-008 vector was detected at a rate of 2.131% relative to the number of alleles of human genome, whereas editing of the mouse genome in the liver sample was detected at a rate of 0.05% relative to the number of alleles of mouse genome. These results showed human-specific editing of the PAH gene by the hPAH-hAC-008 vector or a modified version thereof, and provided an in vivo model for examining the editing efficiency in hepatocytes.

d) Editing of Human PAH in Human Hepatocytes in a Mouse Model

Figure 12A:
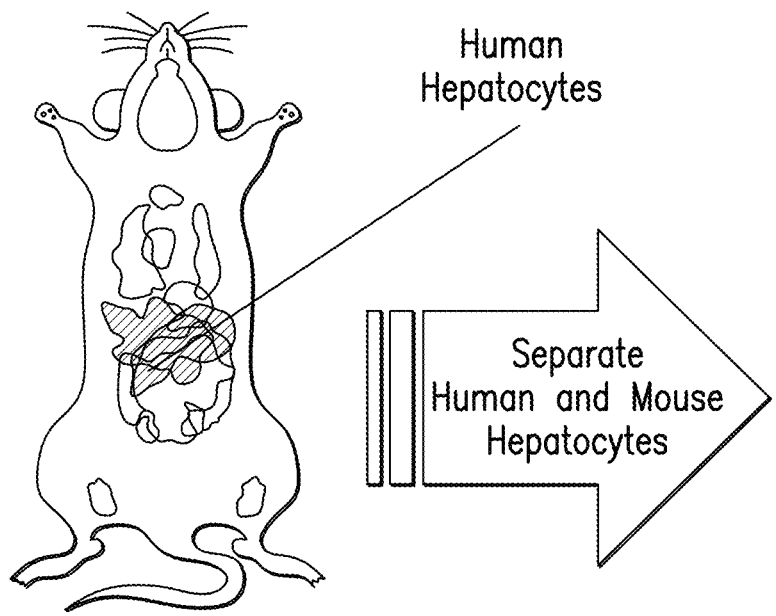
FIG. 12A is a schematic showing the HuLiv humanized liver mouse model.

In one experiment, $Fah^{-/-}$ $Rag2^{-/-}$ $Il2rg^{-/-}$ mice on the C57Bl/6 background, commonly referred to as the FRG® Knockout mice (also referred to herein as HuLiv mice), were used as a model for liver humanization, as described above (see FIG. 12A).

The pHMIK-hPAH-hI1C-032 vector comprised 5' to 3' the following genetic elements: a 5' ITR element, a 5' homology arm, a splicing acceptor, a 2A element, a silently altered human PAH coding sequence, an SV40 polyadenylation sequence, a 3' homology arm, and a 3' ITR element. The sequences of these elements are set forth in Table 11.

TABLE 11

Genetic elements in PAH correction vector pHMIK-hPAH-hI1C-032

| Genetic Element | SEQ ID NO |
| --- | --- |
| 5' ITR element | 18 |
| 5' homology arm | 115 |
| Splice acceptor | 14 |
| 2A element | 74 |
| Silently altered human PAH coding sequence | 116 |
| SV40 polyadenylation sequence | 31 |
| 3' homology arm | 117 |
| 3' ITR element | 19 |
| Correction genome (5' HA to 3' HA) | 118 |
| Correction genome (5' ITR to 3' ITR) | 119 |

The pHMIK-hPAH-hI1C032 vector was packaged with AAVHSC15 capsids, and was administered into mice intravenously at a dose of $1\times10^{14}$ vector genomes per kilogram of body weight. Liver samples from 3 mice that received the pHMIK-hPAH-hI1C-032 vector packaged with AAVHSC15 capsids were collected, the human and mouse hepatocytes were separated and purified, and DNA was extracted. The efficiency of gene editing was measured using the same ddPCR method as described above.

Figure 12B:
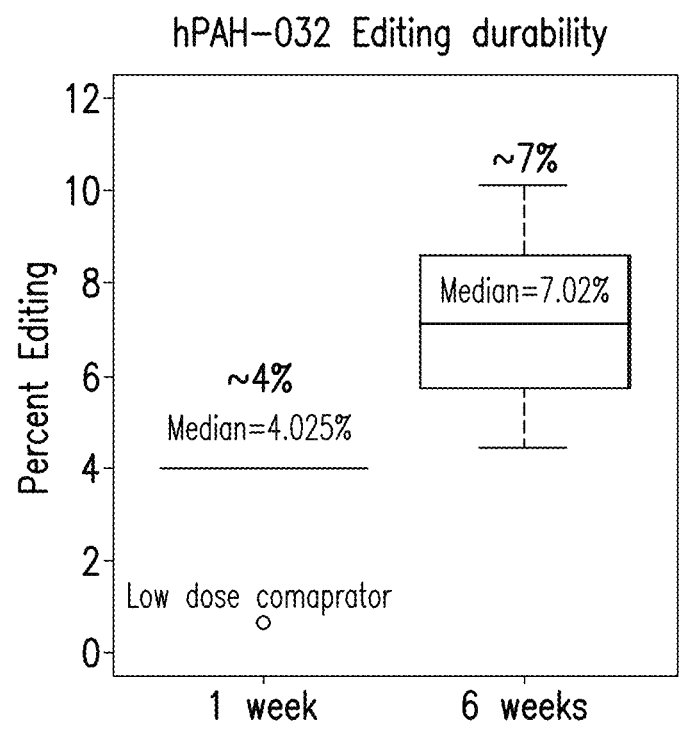
FIG. 12B depicts the average PAH gene editing efficiency in cells obtained from mice 1 week and 6 weeks after administration of the pHMIK-hPAH-hI1C-032 vector packaged in AAVHSC15 capsids.

The durability of PAH gene editing in human hepatocytes was measured by determining the percentage of edited alleles out of all alleles in cells obtained from treated mice 1 week and 6 weeks post-administration of vector. As shown in FIG. 12B, about 4% PAH gene editing was measured in cells obtained from mice 1 week after administration of the vector, and about 7% editing was measured in cells obtained from mice 6 weeks after administration of the vector.

Figure 13:
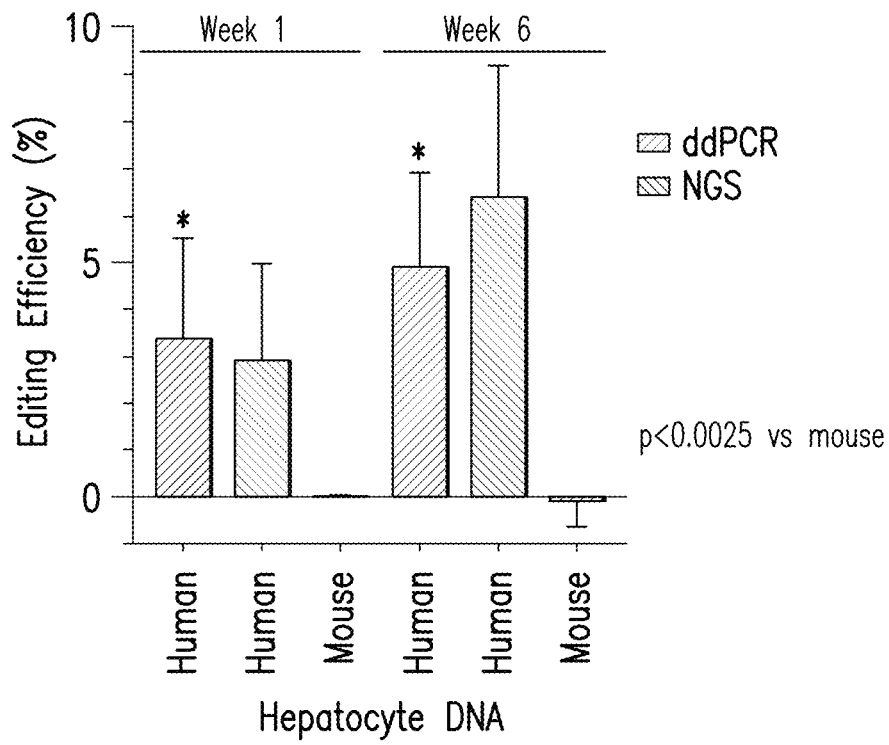
FIG. 13 is a graph showing the average PAH gene editing efficiency, as determined by ddPCR and next generation sequencing (NGS), in cells obtained from HuLiv mice administered the pHMIK-hPAH-hI1C-032 vector packaged in AAVHSC15 capsids.

Genome editing mediated by the pHMIK-hPAH-hI1C-032 vector was found to be specific for human hepatocytes in the HuLiv mice. As shown in FIG. 13, at 1 week after administration of the vector, PAH gene editing (as determined by ddPCR and NGS) was detected at a rate of about 3% to 3.5% relative to the number of alleles of human genome, whereas editing of the mouse genome in the liver sample was close to 0% relative to the number of alleles of mouse genome. At 6 weeks after administration of the vector, editing was detected at a rate of about 5% to 6.5% relative to the number of alleles of human genome. * indicates p<0.0025 compared to mouse values.

Figure 14:
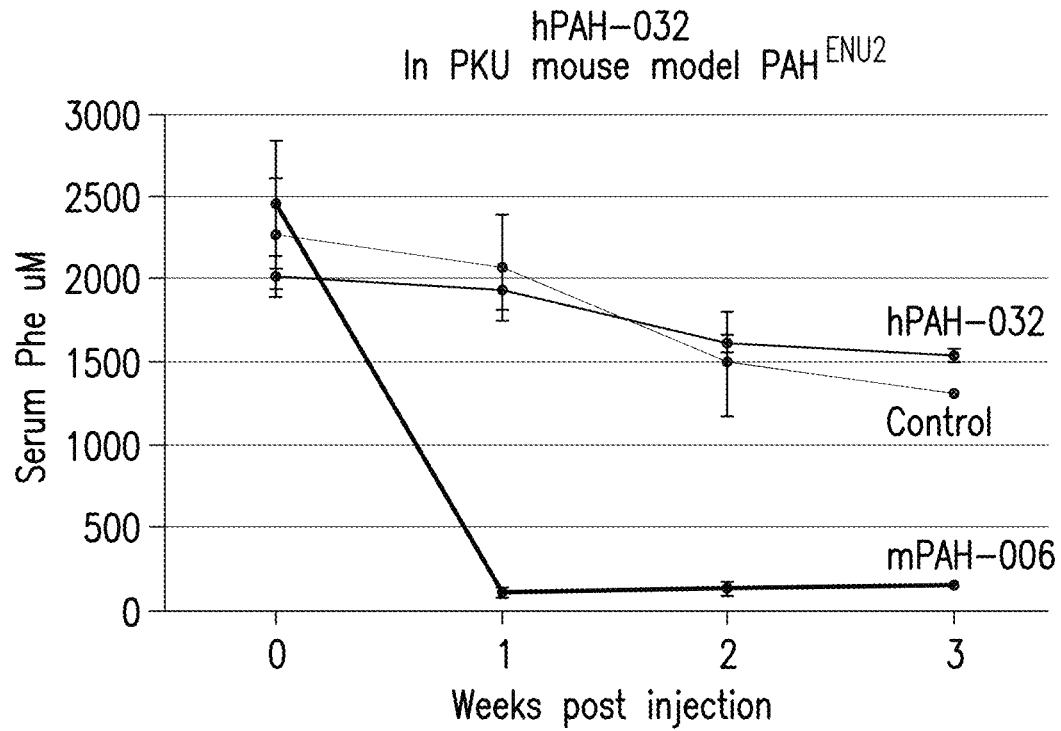
FIG. 14 is a graph showing the average serum phenylalanine levels of PAH knock-out mouse model ($PAH^{ENU2}$) mice administered intravenously with either the pHMIK-hPAH-hI1C-032 vector (hPAH-032) or the pHMI-hPAH-mAC-006 vector (mPAH-006), packaged in AAVHSC15 capsids, compared to control mice.

Further, the pHMIK-hPAH-hI1C-032 vector was found to be ineffective in non-human cells. As shown in FIG. 14, when PAH knock-out mouse ($PAH^{ENU2}$) mice were administered intravenously the pHMIK-hPAH-hI1C-032 vector (hPAH-032) packaged with AAVHSC15 capsids at a dose of $1\times10^{14}$ vector genomes per kilogram of body weight, the level of serum phenylalanine was similar to that of mice administered a control up to 3 weeks post-injection. In contrast, mice administered the pHMI-hPAH-mAC-006 vector (mPAH-006) showed reduction in serum Phe levels as soon as 1 week post-injection.

Figure 15A:
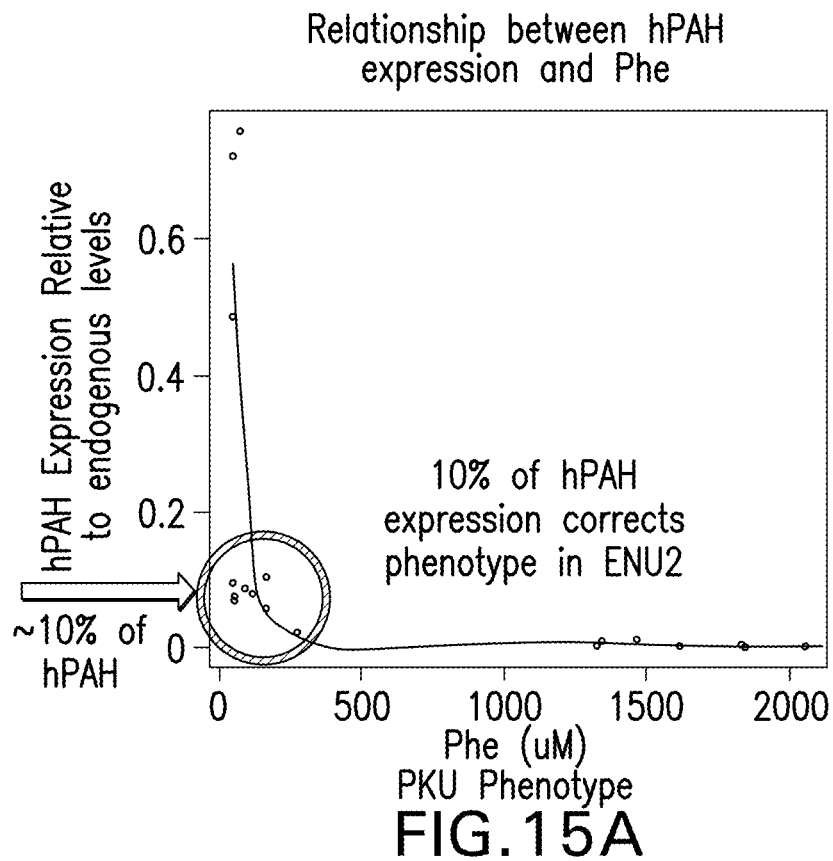
FIG. 15A is a graph showing the relationship between human PAH expression and serum Phe levels.

FIG. 15A shows the relationship between human PAH expression and serum Phe levels. As shown, in data gleaned from experiments using the pHMI-hPAH-mAC-006 vector in $PAH^{ENU2}$ mice, 10% of human PAH expression corrects the phenotype in $PAH^{ENU2}$ mice. Thus, 10% of human PAH expression relative to endogenous levels was determined to be the level required to correct phenylalaninemia (e.g., a therapeutic level).

Figure 15B:
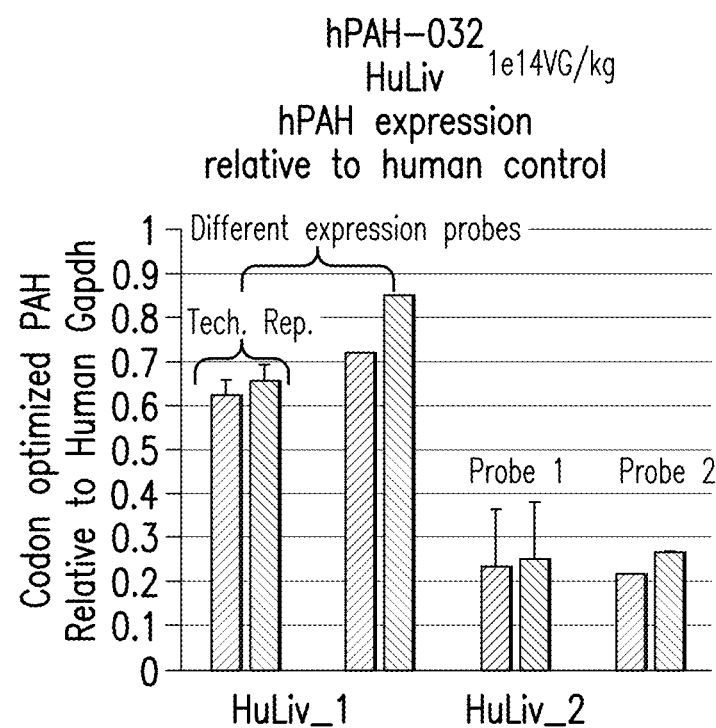
FIG. 15B is a plot showing the expression of human PAH relative to human GAPDH in two different HuLiv mice treated with pHMIK-hPAH-hI1C032 vector packaged in AAVHSC15 capsids.

Therapeutic levels of expression were detected with the pHMIK-hPAH-hI1C-032 vector. Human PAH expression in human hepatocytes was measured relative to human GAPDH in HuLiv mice administered the pHMIK-hPAH-hI1C-032 vector (hPAH-032) at a dose of $1\times10^{14}$ vector genomes per kilogram of body weight. As shown in FIG. 15B, using two different expression probes to measure expression of human PAH in two different HuLiv mice treated with the vector, human PAH expression was determined to be greater than 10% in human hepatocytes. The PAH gene editing range in human hepatocytes of HuLiv mice administered the vector was measured to be about 5% to about 11% in 13 different mice across 3 different experiments.

Figure 16:
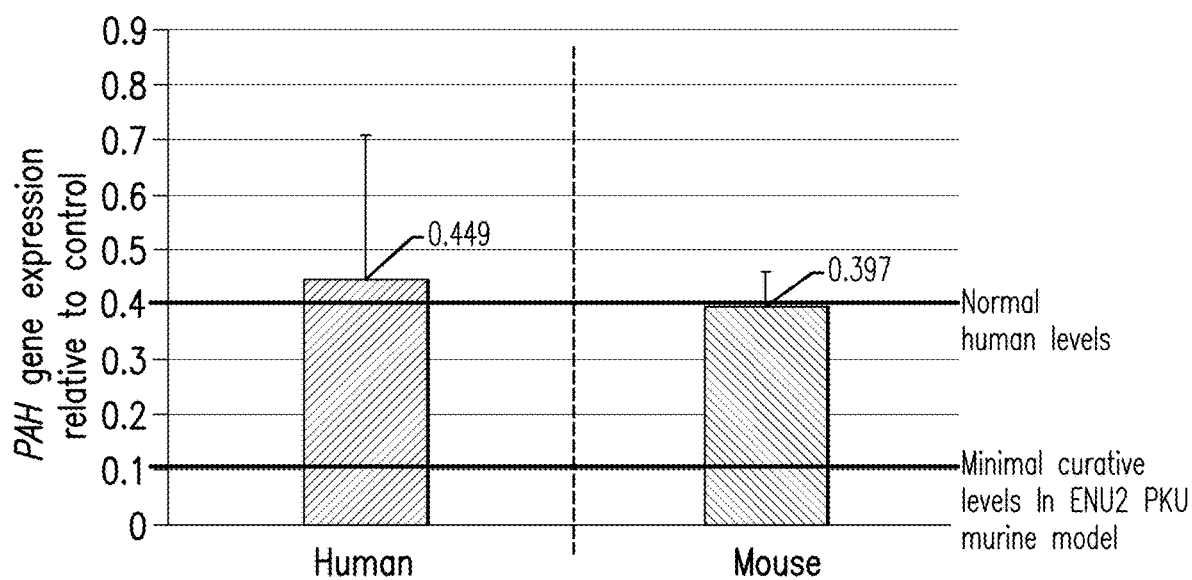
FIG. 16 is a plot showing human PAH gene expression in HuLiv mice treated with (left) and mouse PAH gene expression in $PAH^{ENU2}$ mice treated with pHMI-hPAH-mAC-006 vector (right) packaged in AAVHSC15 capsids.

The pHMIK-hPAH-hI1C-032 vector was found to target human PAH gene and resulted in corrected levels of edited mRNA in HuLiv mice. The PAH mRNA level required for phenotypic correction was first established in a murine model (using the PAH knock-out mouse model ($PAH^{ENU2}$)). This was determined to be about 10% of PAH expression relative to endogenous levels (see FIG. 15A). As shown in FIG. 16, human PAH gene expression relative to GAPDH expression was determined to be about 44.9% (left), and mouse PAH gene expression relative to GAPDH expression was determined to be about 39.7% (right).

Example 6

Human PAH Correction Vectors

This example provides the human PAH correction vectors pKITR-hPAH-mAC-006-HCR, pKITR-hPAH-hI1C-032-HCR, pKITR-hPAH-mAC-006-SD.3, pHMIA2-hPAH-hI1C-032-SD.3, and pHMIA2-hPAH-mAC-006-HBB1. Schematics of the vectors are depicted in FIGS. 17A, 17B, 17C, 17D, and 17E, respectively.

a) pKITR-hPAH-mAC-006-HCR, pKITR-hPAH-hI1C-032-HCR, and pHMIA2-hPAH-mAC-006-HBB1

Vectors pKITR-hPAH-mAC-006-HCR and pKITR-hPAH-hI1C-032-HCR were generated by inserting an HCR intron into the PAH coding sequence. Vector pHMIA2-hPAH-mAC-006-HBB1 was generated by inserting an HBB1 intron into the PAH coding sequence. The HCR and HBB1 introns were selected based on their performance in intron screening experiments using a luciferase reporter to determine introns that exhibit high expression in liver and blood cell lines. The introns used in the screen are set forth in Table 12.

TABLE 12

Intron sequences used in luciferase reporter screen

| Intron | SEQ ID NO |
| --- | --- |
| Chimeric MVM Intron (ChiMVM) | 120 |
| SV40 Intron | 121 |
| Adenovirus Tripartite Leader Intron (AdTPL) | 122 |
| Mini B-Globin Intron | 123 |
| AdV/Ig Chimeric Intron (AdVIgG) | 124 |
| B-Globin Ig Heavy Chain Intron (BGlobinIg) | 125 |
| Wu MVM Intron (Wu MVM) | 126 |
| HCR1 Intron (OptHCR) | 127 |
| B-Globin Intron | 128 |
| tFIX Intron (FIX) | 129 |
| ch2BLood Intron (BloodEnh) | 130 | pKITR-hPAH-mAC-006-HCR comprised 5' to 3' the following genetic elements: a 5' ITR element, a 5' homology arm, a silently altered human PAH coding sequence with HCR intron inserted therein, an SV40 polyadenylation sequence, a targeted integration restriction cassette ("TI RE"), a 3' homology arm, and a 3' ITR element. pKITR-hPAH-hI1C-032-HCR comprised 5' to 3' the following genetic elements: a 5' ITR element, a 5' homology arm, a splice acceptor, a 2A element, a silently altered human PAH coding sequence with HCR intron inserted therein, an SV40 polyadenylation sequence, a 3' homology arm, and a 3' ITR element. pHMIA2-hPAH-mAC-006-HBB1 comprised 5' to 3' the following genetic elements: a 5' ITR element, a 5' homology arm, a silently altered human PAH coding sequence with HBB1 intron inserted therein, an SV40 polyadenylation sequence, a targeted integration restriction cassette ("TI RE"), a 3' homology arm, and a 3' ITR element. The sequences of these elements are set forth in Table 13.

TABLE 13

Genetic elements in PAH correction vectors pKITR-hPAH-mAC-006-HCR, pKITR-hPAH-hI1C-032-HCR, and pHMIA2-hPAH-mAC-006-HBB1

Figure 17C:
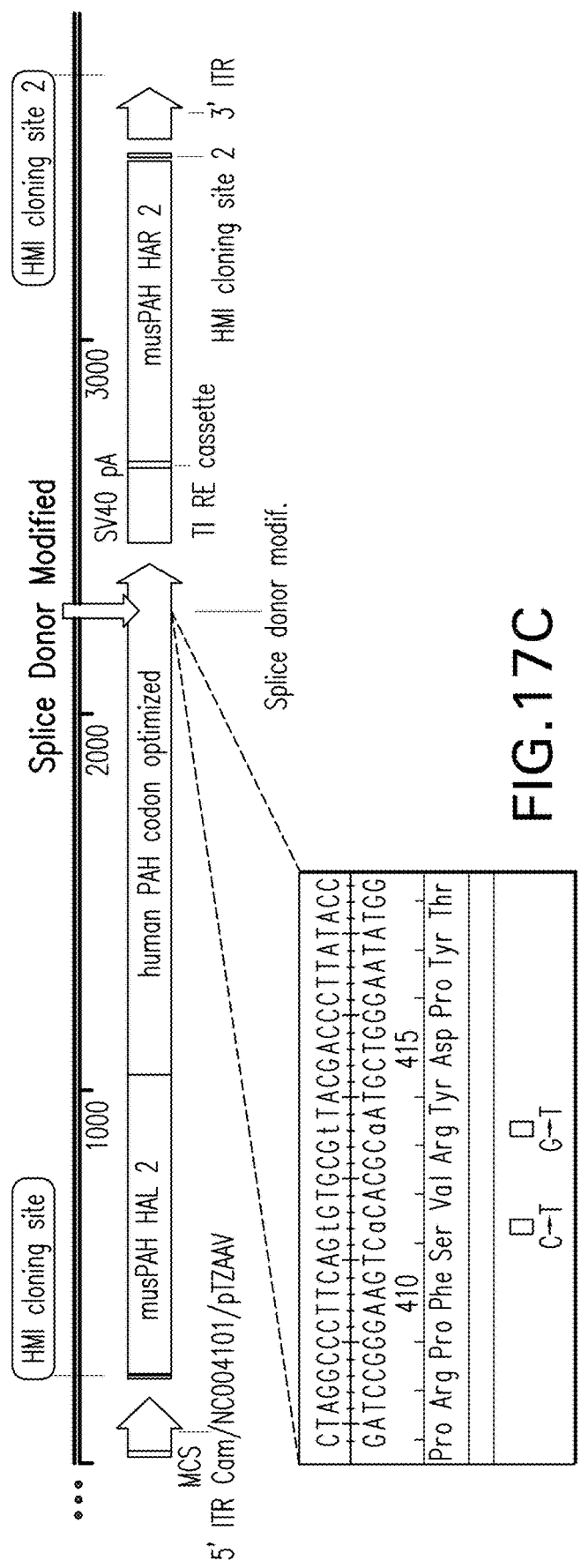
Figure 17D:
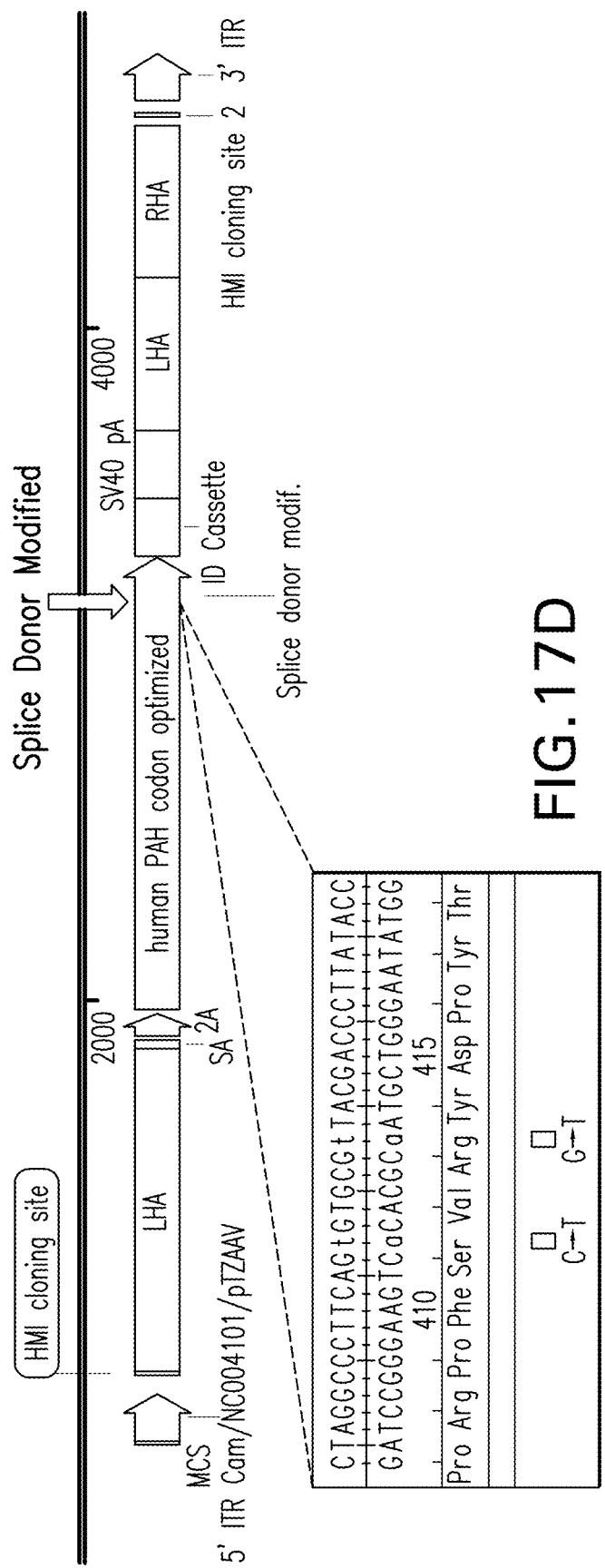
Figure 17E:
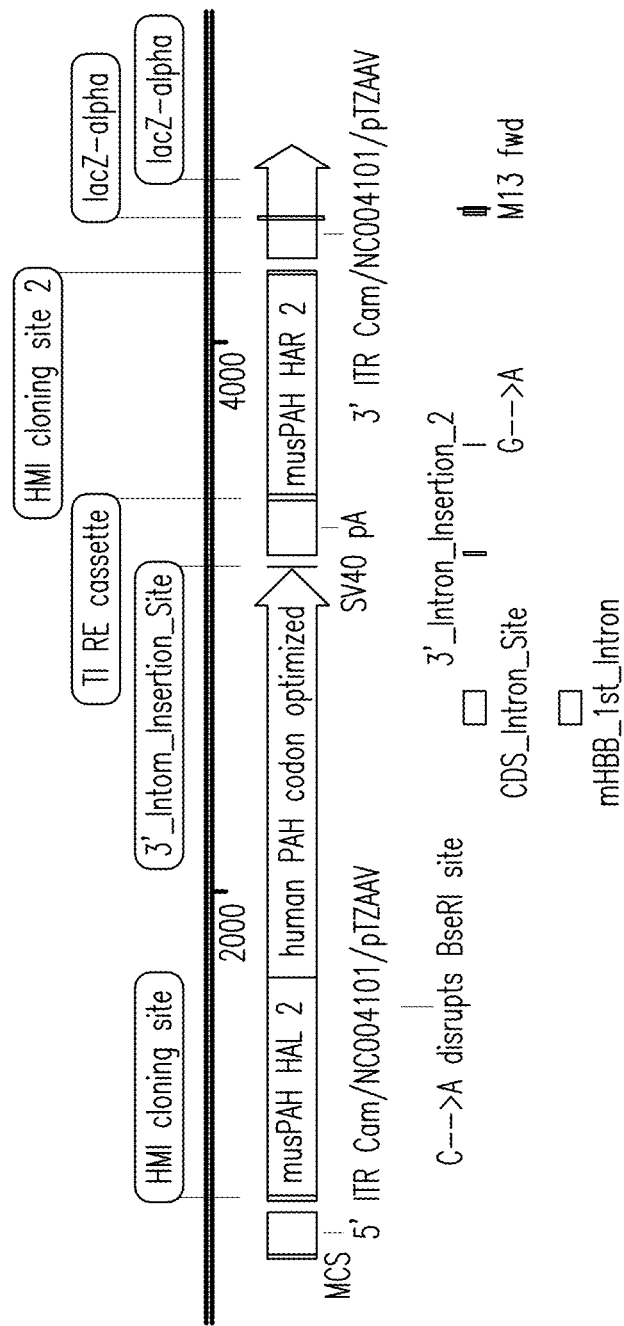

| Genetic Element | SEQ ID NO | | |
| --- | --- | --- | --- |
| | -006-HCR | -032-HCR | -006-HBB1 |
| 5' ITR element | 18 | 18 | 18 |
| 5' homology arm | 111 | 115 | 142 |
| Splice acceptor | N/A | 14 | N/A |
| 2A element | N/A | 74 | N/A |
| Human PAH coding sequence | 131 | 132 | 143 |
| SV40 polyadenylation sequence | 31 | 31 | 31 |
| Targeted integration restriction cassette | 71 | N/A | 71 |
| 3' homology arm | 112 | 117 | 144 |
| 3' ITR element | 19 | 19 | 19 |
| Correction genome (5' HA to 3' HA) | 134 | 136 | 145 |
| Correction genome (5' ITR to 3' ITR) | 135 | 137 | 146 | b) pKITR-hPAH-mAC-006-SD. 3 and pHMIA2-hPAH-hI1C-032-SD.3 Vectors pKITR-hPAH-mAC-006-SD.3 and pHMIA2-hPAH-hI1C-032-SD.3 were generated by modifying a splice donor site. The splice donor was modified as indicated in FIGS. 17C and 17D, respectively. pKITR-hPAH-mAC-006-SD.3 comprised 5' to 3' the following genetic elements: a 5' ITR element, a 5' homology arm, a silently altered human PAH coding sequence with splice donor modification, an SV40 polyadenylation sequence, a targeted integration restriction cassette ("TI RE"), a 3' homology arm, and a 3' ITR element. pHMIA2-hPAH-hI1C-032-SD.3 comprised 5' to 3' the following genetic elements: a 5' ITR element, a 5' homology arm, a splicing acceptor, a 2A element, a silently altered human PAH coding sequence with splice donor modification, an SV40 polyadenylation sequence, a 3' homology arm, and a 3' ITR element. The sequences of these elements are set forth in Table 14.

TABLE 14

Genetic elements in PAH correction vectors pKITR-hPAH-mAC-006-SD.3 and pHMIA2-hPAH-hI1C-032-SD.3

| Genetic Element | SEQ ID NO | |
| --- | --- | --- |
| | -006-SD.3 | -032-SD.3 |
| 5' ITR element | 18 | 18 |
| 5' homology arm | 111 | 115 |
| Splice acceptor | N/A | 14 |
| 2A element | N/A | 74 |
| Human PAH coding sequence | 138 | 139 |
| SV40 polyadenylation sequence | 31 | 31 |
| Targeted integration restriction cassette | 71 | N/A |
| 3' homology arm | 112 | 117 |
| 3' ITR element | 19 | 19 |

The invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

All references (e.g., publications or patents or patent applications) cited herein are incorporated herein by reference in their entirety and for all purposes to the same extent as if each individual reference (e.g., publication or patent or patent application) was specifically and individually indicated to be incorporated by reference in its entirety for all purposes. Other embodiments are within the following claims.

We claim:

1. A replication-defective adeno-associated virus (AAV) comprising:
   (a) an AAV capsid; and
   (b) a correction genome comprising:
      (i) an editing element for editing a target locus in a human phenylalanine hydroxylase (PAH) gene, wherein the editing element comprises a nucleotide sequence that is at least 90% identical to the nucleotide sequence set forth in SEQ ID NO: 35, 83, or 84;
      (ii) a 5' homology arm located 5' of the editing element, the 5' homology arm comprising a nucleotide sequence of at least 100 nucleotides in length, that is at least 90% identical to a nucleic acid sequence contained within the nucleic acid sequence set forth in SEQ ID NO: 36, 37, 38, 39, 40, 41, 42, 43, 44, or 115; and
      (iii) a 3' homology arm located 3' of the editing element, the 3' homology arm comprising a nucleotide sequence of at least 100 nucleotides in length, that is at least 90% identical to a nucleic acid sequence contained within the nucleic acid sequence set forth in SEQ ID NO: 45 or 117.

2. The AAV of claim 1, wherein each of the 5' and 3' homology arm nucleotide sequences independently has a length of about 100 to about 2000 nucleotides.

3. The AAV of claim 1, wherein: the 5' homology arm is at least 90% identical to the nucleotide sequence set forth in SEQ ID NO: 36, 37, 38, 39, 40, 41, 42, 43, 44, or 115; and/or the 3' homology arm is at least 90% identical to the nucleotide sequence set forth in SEQ ID NO: 45 or 117.

4. The AAV of claim 1, wherein:
   the 5' homology arm comprises:
      C corresponding to nucleotide-2 of the PAH gene, G corresponding to nucleotide 4 of the PAH gene, G corresponding to nucleotide 6 of the PAH gene, G corresponding to nucleotide 7 of the PAH gene, G corresponding to nucleotide 9 of the PAH gene, A corresponding to nucleotide-467 of the PAH gene, A corresponding to nucleotide-465 of the PAH gene, A corresponding to nucleotide-181 of the PAH gene, G corresponding to nucleotide-214 of the PAH gene, C corresponding to nucleotide-212 of the PAH gene, A corresponding to nucleotide-211 of the PAH gene, G corresponding to nucleotide 194 of the PAH gene, C corresponding to nucleotide-433 of the PAH gene, C corresponding to nucleotide-432 of the PAH gene, ACGCTGTTCTTCGCC (SEQ ID NO: 68) corresponding to nucleotides-394 to-388 of the PAH gene, A corresponding to nucleotide-341 of the PAH gene, A corresponding to nucleotide-339 of the PAH gene, A corresponding to nucleotide-225 of the PAH gene, A corresponding to nucleotide-211 of the PAH gene, and/or A corresponding to nucleotide-203 of the PAH gene;
   the 5' homology arm comprises:
      (a) C corresponding to nucleotide-2 of the PAH gene, G corresponding to nucleotide 4 of the PAH gene, G corresponding to nucleotide 6 of the PAH gene, G corresponding to nucleotide 7 of the PAH gene, and G corresponding to nucleotide 9 of the PAH gene;
      (b) A corresponding to nucleotide-467 of the PAH gene, and A corresponding to nucleotide-465 of the PAH gene;
      (c) A corresponding to nucleotide-181 of the PAH gene;
      (d) G corresponding to nucleotide-214 of the PAH gene, C corresponding to nucleotide -212 of the PAH gene, and A corresponding to nucleotide-211 of the PAH gene;
      (e) G corresponding to nucleotide 194 of the PAH gene;
      (f) C corresponding to nucleotide-433 of the PAH gene, and C corresponding to nucleotide-432 of the PAH gene;
      (g) ACGCTGTTCTTCGCC (SEQ ID NO: 68) corresponding to nucleotides-394 to -388 of the PAH gene; and/or
      (h) A corresponding to nucleotide-341 of the PAH gene, A corresponding to nucleotide -339 of the PAH gene, A corresponding to nucleotide-225 of the PAH gene, A corresponding to nucleotide-211 of the PAH gene, and A corresponding to nucleotide -203 of the PAH gene; or
   the 5' homology arm comprises the modifications of (c) and (d), (f) and (g), and/or (b) and (h).

5. The AAV of claim 1, wherein: the 5' homology arm comprises the nucleotide sequence set forth in SEQ ID NO: 36, 37, 38, 39, 40, 41, 42, 43, 44, or 115; and/or the 3' homology arm comprises the nucleotide sequence set forth in SEQ ID NO: 45 or 117.

6. The AAV claim 1, wherein: the nucleic acid sequence of the 5' homology arm consists of the sequence set forth in SEQ ID NO: 36, 37, 38, 39, 40, 41, 42, 43, 44, or 115; and/or the nucleic acid sequence of the 3' homology arm consists of the sequence set forth in SEQ ID NO: 45 or 117.

7. The AAV of claim 1, wherein the editing element comprises a PAH coding sequence, optionally wherein:
the PAH coding sequence encodes an amino acid sequence set forth in SEQ ID NO: 23;
the PAH coding sequence is silently altered, optionally wherein the PAH coding sequence comprises the sequence set forth in SEQ ID NO: 25, 116, 131, 132, 138, 139, or 143.

8. The AAV of claim 1, wherein the editing element comprises a PAH intron-inserted coding sequence, optionally wherein the PAH intron-inserted coding sequence comprises a nonnative intron inserted in a PAH coding sequence, optionally wherein:
the nonnative intron is selected from the group consisting of a first intron of a hemoglobin beta gene and a minute virus in mice (MVM) intron;
the nucleotide sequence of the nonnative intron consists of a nucleotide sequence at least 90% identical to the nucleotide sequence set forth in any one of SEQ ID NOs: 28-30, and 120-130;
the nucleotide sequence of the nonnative intron consists of the nucleotide sequence set forth in any one of SEQ ID NOs: 28-30, and 120-130; and/or
the PAH intron-inserted coding sequence encodes an amino acid sequence set forth in SEQ ID NO: 23.

9. The AAV of claim 8, wherein the PAH intron-inserted coding sequence comprises, from 5' to 3': a first portion of a PAH coding sequence, the intron, and a second portion of a PAH coding sequence, wherein the first portion and the second portion, when spliced together, form a complete PAH coding sequence, optionally wherein:
the PAH coding sequence is silently altered;
the PAH coding sequence comprises the nucleotide sequence set forth in SEQ ID NO: 25, 116, 131, 132, 138, 139, or 143;
the first portion of the PAH coding sequence comprises the nucleotide sequence set forth in
SEQ ID NO: 64 or 65, and/or the second portion of the PAH coding sequence comprises the nucleotide sequence set forth in SEQ ID NO: 66 or 67; and/or
the first portion of the PAH coding sequence consists of the nucleotide sequence set forth in SEQ ID NO: 64 or 65, and the second portion of the PAH coding sequence consists of the nucleotide sequence set forth in SEQ ID NO: 66 or 67.

10. The AAV of claim 1, wherein the editing element comprises, from 5' to 3': a ribosomal skipping element, and a PAH coding sequence or a PAH intron-inserted coding sequence, optionally wherein the editing element further comprises a polyadenylation sequence 3' to the PAH coding sequence or the PAH intron-inserted coding sequence, optionally wherein the polyadenylation sequence is an exogenous polyadenylation sequence, optionally wherein the exogenous polyadenylation sequence is an SV40 polyadenylation sequence, optionally wherein the SV40 polyadenylation sequence comprises a nucleotide sequence selected from the group consisting of SEQ ID NOs: 31-34.

11. The AAV of claim 1, wherein the nucleotide 5' to the target locus is in an intron of the PAH gene, optionally in intron 1 of the PAH gene.

12. The AAV of claim 1, wherein the editing element comprises a nucleotide sequence that is at least 99% identical to the nucleotide sequence set forth in SEQ ID NO: 35, 83, or 84.

13. The AAV of claim 1, wherein the correction genome comprises a nucleotide sequence that is at least 90% identical to the nucleotide sequence set forth in any one of SEQ ID NOs: 46-54, 118, 136, and 145.

14. The AAV of claim 1, wherein the correction genome further comprises a 5' inverted terminal repeat (5' ITR) nucleotide sequence 5' of the 5' homology arm nucleotide sequence, and a 3' inverted terminal repeat (3' ITR) nucleotide sequence 3' of the 3' homology arm nucleotide sequence, optionally wherein:
(a) the 5' ITR nucleotide sequence has at least 95% sequence identity to SEQ ID NO: 18, and the 3' ITR nucleotide sequence has at least 95% sequence identity to SEQ ID NO: 19;
(b) the 5' ITR nucleotide sequence has at least 95% sequence identity to SEQ ID NO: 20, and the 3' ITR nucleotide sequence has at least 95% sequence identity to SEQ ID NO: 21; or
(c) the 5' ITR nucleotide sequence has at least 95% sequence identity to SEQ ID NO: 26, and the 3' ITR nucleotide sequence has at least 95% sequence identity to SEQ ID NO: 27.

15. The AAV of claim 1, wherein the correction genome comprises a nucleotide sequence that is at least 90% identical to the nucleotide sequence set forth in any one of SEQ ID NOs: 55-63, 119, 135, 137, and 146.

16. The AAV of claim 1, wherein the AAV capsid comprises: an AAV capsid protein comprising an amino acid sequence having at least 95% sequence identity with the amino acid sequence of amino acids 203-736 of SEQ ID NO: 1, 2, 3, 4, 5, 6, 7, 8, 9, 10, 11, 12, 13, 15, 16, or 17, optionally wherein:
the amino acid in the capsid protein corresponding to amino acid 206 of SEQ ID NO: 2 is C; the amino acid in the capsid protein corresponding to amino acid 296 of SEQ ID NO: 2 is H; the amino acid in the capsid protein corresponding to amino acid 312 of SEQ ID NO: 2 is Q; the amino acid in the capsid protein corresponding to amino acid 346 of SEQ ID NO: 2 is A; the amino acid in the capsid protein corresponding to amino acid 464 of SEQ ID NO: 2 is N; the amino acid in the capsid protein corresponding to amino acid 468 of SEQ ID NO: 2 is S; the amino acid in the capsid protein corresponding to amino acid 501 of SEQ ID NO: 2 is I; the amino acid in the capsid protein corresponding to amino acid 505 of SEQ ID NO: 2 is R; the amino acid in the capsid protein corresponding to amino acid 590 of SEQ ID NO: 2 is R; the amino acid in the capsid protein corresponding to amino acid 626 of SEQ ID NO: 2 is G or Y; the amino acid in the capsid protein corresponding to amino acid 681 of SEQ ID NO: 2 is M; the amino acid in the capsid protein corresponding to amino acid 687 of SEQ ID NO: 2 is R; the amino acid in the capsid protein corresponding to amino acid 690 of SEQ ID NO: 2 is K; the amino acid in the capsid protein corresponding to amino acid 706 of SEQ ID NO: 2 is C; or, the amino acid in the capsid protein corresponding to amino acid 718 of SEQ ID NO: 2 is G;
(a) the amino acid in the capsid protein corresponding to amino acid 626 of SEQ ID NO: 2 is G, and the amino acid in the capsid protein corresponding to amino acid 718 of SEQ ID NO: 2 is G;

(b) the amino acid in the capsid protein corresponding to amino acid 296 of SEQ ID NO: 2 is H, the amino acid in the capsid protein corresponding to amino acid 464 of SEQ ID NO: 2 is N, the amino acid in the capsid protein corresponding to amino acid 505 of SEQ ID NO: 2 is R, and the amino acid in the capsid protein corresponding to amino acid 681 of SEQ ID NO: 2 is M;

(c) the amino acid in the capsid protein corresponding to amino acid 505 of SEQ ID NO: 2 is R, and the amino acid in the capsid protein corresponding to amino acid 687 of SEQ ID NO: 2 is R;

(d) the amino acid in the capsid protein corresponding to amino acid 346 of SEQ ID NO: 2 is A, and the amino acid in the capsid protein corresponding to amino acid 505 of SEQ ID NO: 2 is R;

(e) the amino acid in the capsid protein corresponding to amino acid 501 of SEQ ID NO: 2 is I, the amino acid in the capsid protein corresponding to amino acid 505 of SEQ ID NO: 2 is R, and the amino acid in the capsid protein corresponding to amino acid 706 of SEQ ID NO: 2 is C; and/or the AAV capsid protein comprises the amino acid sequence of amino acids 203-736 of SEQ ID NO: 1, 2, 3, 4, 5, 6, 7, 8, 9, 10, 11, 12, 13, 15, 16, or 17.

17. The AAV of claim 1, wherein the AAV capsid comprises: an AAV capsid protein comprising an amino acid sequence having at least 95% sequence identity with the amino acid sequence of amino acids 138-736 of SEQ ID NO: 1, 2, 3, 4, 5, 6, 7, 8, 9, 10, 11, 12, 13, 15, 16, or 17, optionally wherein:

the amino acid in the capsid protein corresponding to amino acid 151 of SEQ ID NO: 2 is R; the amino acid in the capsid protein corresponding to amino acid 160 of SEQ ID NO: 2 is D; the amino acid in the capsid protein corresponding to amino acid 206 of SEQ ID NO: 2 is C; the amino acid in the capsid protein corresponding to amino acid 296 of SEQ ID NO: 2 is H; the amino acid in the capsid protein corresponding to amino acid 312 of SEQ ID NO: 2 is Q; the amino acid in the capsid protein corresponding to amino acid 346 of SEQ ID NO: 2 is A; the amino acid in the capsid protein corresponding to amino acid 464 of SEQ ID NO: 2 is N; the amino acid in the capsid protein corresponding to amino acid 468 of SEQ ID NO: 2 is S; the amino acid in the capsid protein corresponding to amino acid 501 of SEQ ID NO: 2 is I; the amino acid in the capsid protein corresponding to amino acid 505 of SEQ ID NO: 2 is R; the amino acid in the capsid protein corresponding to amino acid 590 of SEQ ID NO: 2 is R; the amino acid in the capsid protein corresponding to amino acid 626 of SEQ ID NO: 2 is G or Y; the amino acid in the capsid protein corresponding to amino acid 681 of SEQ ID NO: 2 is M; the amino acid in the capsid protein corresponding to amino acid 687 of SEQ ID NO: 2 is R; the amino acid in the capsid protein corresponding to amino acid 690 of SEQ ID NO: 2 is K; the amino acid in the capsid protein corresponding to amino acid 706 of SEQ ID NO: 2 is C; or, the amino acid in the capsid protein corresponding to amino acid 718 of SEQ ID NO: 2 is G;

(a) the amino acid in the capsid protein corresponding to amino acid 626 of SEQ ID NO: 2 is G, and the amino acid in the capsid protein corresponding to amino acid 718 of SEQ ID NO: 2 is G;

(b) the amino acid in the capsid protein corresponding to amino acid 296 of SEQ ID NO: 2 is H, the amino acid in the capsid protein corresponding to amino acid 464 of SEQ ID NO: 2 is N, the amino acid in the capsid protein corresponding to amino acid 505 of SEQ ID NO: 2 is R, and the amino acid in the capsid protein corresponding to amino acid 681 of SEQ ID NO: 2 is M;

(c) the amino acid in the capsid protein corresponding to amino acid 505 of SEQ ID NO: 2 is R, and the amino acid in the capsid protein corresponding to amino acid 687 of SEQ ID NO: 2 is R;

(d) the amino acid in the capsid protein corresponding to amino acid 346 of SEQ ID NO: 2 is A, and the amino acid in the capsid protein corresponding to amino acid 505 of SEQ ID NO: 2 is R; or (e) the amino acid in the capsid protein corresponding to amino acid 501 of SEQ ID NO: 2 is I, the amino acid in the capsid protein corresponding to amino acid 505 of SEQ ID NO: 2 is R, and the amino acid in the capsid protein corresponding to amino acid 706 of SEQ ID NO: 2 is C; and/or the AAV capsid protein comprises the amino acid sequence of amino acids 138-736 of SEQ ID NO: 1, 2, 3, 4, 5, 6, 7, 8, 9, 10, 11, 12, 13, 15, 16, or 17.

18. The AAV of claim 1, wherein the AAV capsid comprises: an AAV capsid protein comprising an amino acid sequence having at least 95% sequence identity with the amino acid sequence of amino acids 1-736 of SEQ ID NO: 1, 2, 3, 4, 5, 6, 7, 8, 9, 10, 11, 12, 13, 15, 16, or 17, optionally wherein:

the amino acid in the capsid protein corresponding to amino acid 2 of SEQ ID NO: 2 is T; the amino acid in the capsid protein corresponding to amino acid 65 of SEQ ID NO: 2 is I; the amino acid in the capsid protein corresponding to amino acid 68 of SEQ ID NO: 2 is V; the amino acid in the capsid protein corresponding to amino acid 77 of SEQ ID NO: 2 is R; the amino acid in the capsid protein corresponding to amino acid 119 of SEQ ID NO: 2 is L; the amino acid in the capsid protein corresponding to amino acid 151 of SEQ ID NO: 2 is R; the amino acid in the capsid protein corresponding to amino acid 160 of SEQ ID NO: 2 is D; the amino acid in the capsid protein corresponding to amino acid 206 of SEQ ID NO: 2 is C; the amino acid in the capsid protein corresponding to amino acid 296 of SEQ ID NO: 2 is H; the amino acid in the capsid protein corresponding to amino acid 312 of SEQ ID NO: 2 is Q; the amino acid in the capsid protein corresponding to amino acid 346 of SEQ ID NO: 2 is A; the amino acid in the capsid protein corresponding to amino acid 464 of SEQ ID NO: 2 is N; the amino acid in the capsid protein corresponding to amino acid 468 of SEQ ID NO: 2 is S; the amino acid in the capsid protein corresponding to amino acid 501 of SEQ ID NO: 2 is I; the amino acid in the capsid protein corresponding to amino acid 505 of SEQ ID NO: 2 is R; the amino acid in the capsid protein corresponding to amino acid 590 of SEQ ID NO: 2 is R; the amino acid in the capsid protein corresponding to amino acid 626 of SEQ ID NO: 2 is G or Y; the amino acid in the capsid protein corresponding to amino acid 681 of SEQ ID NO: 2 is M; the amino acid in the capsid protein corresponding to amino acid 687 of SEQ ID NO: 2 is R; the amino acid in the capsid protein corresponding to amino acid 690 of SEQ ID NO: 2 is K; the amino acid in the capsid protein corresponding to amino acid 706 of SEQ ID NO: 2 is C; or, the amino acid in the capsid protein corresponding to amino acid 718 of SEQ ID NO: 2 is G;
(a) the amino acid in the capsid protein corresponding to amino acid 2 of SEQ ID NO: 2 is T, and the amino acid in the capsid protein corresponding to amino acid 312 of SEQ ID NO: 2 is Q;
(b) the amino acid in the capsid protein corresponding to amino acid 65 of SEQ ID NO: 2 is I, and the amino acid in the capsid protein corresponding to amino acid 626 of SEQ ID NO: 2 is Y;
(c) the amino acid in the capsid protein corresponding to amino acid 77 of SEQ ID NO: 2 is R, and the amino acid in the capsid protein corresponding to amino acid 690 of SEQ ID NO: 2 is K;
(d) the amino acid in the capsid protein corresponding to amino acid 119 of SEQ ID NO: 2 is L, and the amino acid in the capsid protein corresponding to amino acid 468 of SEQ ID NO: 2 is S;
(e) the amino acid in the capsid protein corresponding to amino acid 626 of SEQ ID NO: 2 is G, and the amino acid in the capsid protein corresponding to amino acid 718 of SEQ ID NO: 2 is G;
(f) the amino acid in the capsid protein corresponding to amino acid 296 of SEQ ID NO: 2 is H, the amino acid in the capsid protein corresponding to amino acid 464 of SEQ ID NO: 2 is N, the amino acid in the capsid protein corresponding to amino acid 505 of SEQ ID NO: 2 is R, and the amino acid in the capsid protein corresponding to amino acid 681 of SEQ ID NO: 2 is M;
(g) the amino acid in the capsid protein corresponding to amino acid 505 of SEQ ID NO: 2 is R, and the amino acid in the capsid protein corresponding to amino acid 687 of SEQ ID NO: 2 is R;
(h) the amino acid in the capsid protein corresponding to amino acid 346 of SEQ ID NO: 2 is A, and the amino acid in the capsid protein corresponding to amino acid 505 of SEQ ID NO: 2 is R; or
(i) the amino acid in the capsid protein corresponding to amino acid 501 of SEQ ID NO: 2 is I, the amino acid in the capsid protein corresponding to amino acid 505 of SEQ ID NO: 2 is R, and the amino acid in the capsid protein corresponding to amino acid 706 of SEQ ID NO: 2 is C; and/or
the AAV capsid protein comprises the amino acid sequence of amino acids 1-736 of SEQ ID NO: 1, 2, 3, 4, 5, 6, 7, 8, 9, 10, 11, 12, 13, 15, 16, or 17.

19. A pharmaceutical composition comprising the AAV of claim 1.

20. A polynucleotide comprising the nucleic acid sequence of any one of SEQ ID NO: 25, 46-63, 80-82, 116, 118, 119, 131, 132, 135-139, 143, 145, or 146, optionally wherein the polynucleotide is comprised within a vector or host cell.

\* \* \* \* \*